United States Patent
Strano et al.

(10) Patent No.: US 10,215,752 B2
(45) Date of Patent: Feb. 26, 2019

(54) NANOTUBE ARRAY FOR OPTICAL DETECTION OF PROTEIN-PROTEIN INTERACTIONS

(75) Inventors: Michael S. Strano, Lexington, MA (US); Jin-Ho Ahn, Youngin-Si (KR); Jong-Ho Kim, Ansan (KR); Paul W. Barone, Jamaica Plain, MA (US); Nigel F. Reuel, Cambridge, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 0 days.

(21) Appl. No.: 13/222,706

(22) Filed: Aug. 31, 2011

(65) Prior Publication Data
US 2012/0178640 A1   Jul. 12, 2012

Related U.S. Application Data

(60) Provisional application No. 61/378,622, filed on Aug. 31, 2010.

(51) Int. Cl.
*C40B 40/10* (2006.01)
*C40B 40/12* (2006.01)
*G01N 33/543* (2006.01)
*B82Y 5/00* (2011.01)
*B82Y 15/00* (2011.01)

(52) U.S. Cl.
CPC .......... *G01N 33/54373* (2013.01); *B82Y 5/00* (2013.01); *B82Y 15/00* (2013.01); *G01N 33/54353* (2013.01)

(58) Field of Classification Search
CPC .... B82Y 5/00; B82Y 15/00; G01N 33/54353; G01N 33/54373
See application file for complete search history.

(56) References Cited

FOREIGN PATENT DOCUMENTS

WO   WO2010/050439   5/2010

OTHER PUBLICATIONS

Chen et al. Gel-pad microarrays templated by patterned porous silicon for dual-mode detection of proteins. Lab Chip 2009, vol. 9, pp. 756-760.*
Zheng et al. Lectin arrays for profiling cell surface carbohydrate expression. J. Am. Chem. Soc. 2005, vol. 127, pp. 9982-9983.*
Yi et al. Biofabrication with Chitosan. Biomacromolecules 2005, vol. 6, No. 6, pp. 2881-2894.*
Chen et al. Protein microarrays with carbon nanotubes as multicolor raman labels. Nature Biotechnology 2008, vol. 26, No. 11, pp. 1285-1292.*
Carson et al. Synthesis and characterization of chitosan-carbon nanotube composites. Materials Letters 2009, vol. 63, pp. 617-620.*
Oyama et al. Photoluminescence intensity of single-wall carbon nanotubes. Carbon 2006, vol. 44, Issue 5, pp. 873-879.*

(Continued)

*Primary Examiner* — Shafiqul Haq
(74) *Attorney, Agent, or Firm* — Steptoe & Johnson LLP

(57) ABSTRACT

A composition can include a nanostructure, and a linker associated with the nanostructure, wherein the linker is configured to interact with a capture protein. The nanostructure can include a single-walled carbon nanotube. A plurality of the compositions can be configured in an array.

10 Claims, 61 Drawing Sheets

Specification includes a Sequence Listing.

(56) References Cited

OTHER PUBLICATIONS

Kim et al. Structural modificaitons of multiwalled carbon nanotubes and their effects on optical properties. J. Nanopart Res 2014, vol. 16, pp. 1-11.*
Palewdka et al. A photoluminescence study of Fullerenes: total luminescence spectroscopy of C60 and C70. J. Phys. Chem. 1993, 97, 12167-12172.*
Lefebvre et al. Photoluminescence from single-walled carbon nanotubes: a comparison between suspended and micelle-encapsulated nanotubes. Appl. Phys. A 2004, vol. 78, pp. 1107-1110.*
Wilchek et al. Introduction to avidin-biotin technology. Methods in Enzymology 1990, vol. 84, pp. 5-13.*
Riggs et al. Strong luminescence of solubilized carbon nanotubes. J. Am. Chem. Soc. 2000, vol. 122, pp. 5879-5880.*
Graff et al. Synthesis of nickel-nitrilotriacetic acid coupled single-walled carbon nanotubes for directed self-assembly with polyhistidine-tagged proteins. Chem. Mater. 2008, vol. 20, pp. 1824-1829.*
Zhang et al. Carbon nanotube-chitosan system for electrochemical sensing based on dehydrogenase enzymes. Anal. Chem. 2004, vol. 76, pp. 5045-5050.*
Gopalan, A.I. et al, "Development of a stable cholesterol biosensor based on multi-walled carbon nanotubes-gold nanoparticles composite covered with a layer of chitosan-room-temperature ionic liquid network," Biosensors and Bioelectronics, Elsevier BC, NL, vol. 24, No. 7, Mar. 15, 2009, pp. 2211-2217.
Star, A. et al, "Electronic Detection of Specific Protein Binding Using Nanotube FET Devices," Nano Letters, ACS, US, vol. 3, No. 4, Jan. 1, 2003, pp. 459-463.
Assali, M., et al., "Non-covalent functionalization of carbon nanotubes with glycolipids: Glyconanomaterials with specific lectin-affinity," Soft Matter, Royal Society of Chemistry, Cambridge, GB, vol. 5, No. 5, Jan. 1, 2009, pp. 948-950.
Jacobs, C.B. et al., "Review: Carbon nanotube based electrochemical sensors for biomolecules," Analytica Chimica Acta, Elsevier, Amsterdam, NL, vol. 662, No. 2, Mar. 10, 2010, pp. 105-127.
Nieba, L. et al., "Biacore Analysis of Histidine-Tagged Proteins Using a Chelating NTA Sensor Chip," Analytical Biochemistry, Academic Press Inc, New York, vol. 252, Jan. 1, 1997, pp. 217-228.
Ahn, Jin-Ho et al., "Label-Free, Single Protein Detection on a Near-Infrared Fluorescent Single-Walled Carbon Nanotube/Protein Microarray Fabricated by Cell-Free Synthesis," Nano Letters, vol. 11, No. 7, Jul. 13, 2011, pp. 2743-2752.
Reuel, N.F. et al, "Transduction of Glycan-Lectin Binding Using Near-Infrared Fluorescent Single-Walled Carbon Nanotubes for Glycan Profiling," Journal of the American Chemical Society, vol. 133, No. 44, Nov. 9, 2011, pp. 17923-17933.
International Search Report and Written Opinion dated Mar. 6, 2012 for PCT/US2011/049965.

* cited by examiner

C

T7 promoter
TCGATCCCGCGAAATTAATACGACTCACTATAGGGAGACCACA

RBS
ACGGTTTCCCTCTAGAAATAATTTTGTTTAACTTTAAGAAGGAG

Start codon                    6x His tag
ATATACATATG + gene of interest + CATCATCATCATCATCAT (SEQ ID 37)
(SEQ ID 35)

Stop codon
TAAGGATCCGAATTCGTCGACAAGCTTCTCGAGCTAGCATAAC

T7 terminator
CCCTTGGGGCCTCTAAACGGGTCTTGAGGGGTTTTTTG (SEQ ID 40)

NANOTUBE ARRAY FOR OPTICAL DETECTION OF PROTEIN-PROTEIN INTERACTIONS

CLAIM OF PRIORITY

This application claims priority to provisional U.S. Patent Application No. 61/378,622, filed Aug. 31, 2010, which is incorporated by reference in its entirety.

GOVERNMENT SPONSORSHIP

This invention was made with government support under Grant No. CBET 0753036, awarded by the National Science Foundation. The government has certain rights in this invention.

TECHNICAL FIELD

This invention relates to a nanotube array for optical detection of protein-protein interactions.

BACKGROUND

Advances in genomics and proteomics have created a demand for miniaturized, robust platforms for the high-throughput study of proteins. Microarrays, generated by spotting biomolecules on a solid surface at high spatial density, can offer these features by allowing investigators to query thousands of targets simultaneously. DNA microarrays including thousands of different DNA molecules or oligomeric sequences, for example, provide a snapshot of the transcriptional state of a biological sample. The widespread use of this technology for monitoring gene expression can provide valuable insight into various disease states. DNA microarrays can have particular value in analyzing clustered gene expression, revealing co-regulated gene networks; however, gene expression analysis does not readily predict protein abundance nor does it provide information about protein function.

Several properties of proteins make building protein microarrays more challenging than building their DNA counterparts. First, unlike the simple hybridization chemistry of nucleic acids, proteins demonstrate a staggering variety of chemistries, affinities and specificities. Moreover, proteins may require multimerization, partnership with other proteins or post-translational modification to demonstrate activity or binding. Second, there is no equivalent amplification process like PCR that can generate large quantities of protein. Third, expression and purification of proteins is a tedious task and does not guarantee the functional integrity of the protein. Lastly, many proteins are notoriously unstable, which raises concerns about microarray shelf life. Despite these challenges there has been a marked increase in the use of protein microarrays to map interactions of proteins with various other molecules, and to identify potential disease biomarkers, especially in the area of cancer biology.

SUMMARY

In one aspect, a composition can include a nanostructure, and a linker associated with the nanostructure, wherein the linker is configured to interact with a capture protein.

In another aspect, an array includes a plurality of analysis regions on a substrate, at least one analysis region including a composition including: a nanostructure; and a linker associated with the nanostructure, wherein the linker is configured to interact with a capture protein. Each analysis region can include a composition include a nanostructure; and a linker associated with the nanostructure, wherein the linker is configured to interact with a capture protein.

In some embodiments, the nanostructure can be a photoluminescent nanostructure. The photoluminescent nanostructure can be a nanotube. The nanotube can be a carbon nanotube. The carbon nanotube can be a single walled carbon nanotube.

In some embodiments, the linker can include a polymer. In some circumstances, at least a portion of the nanostructure is embedded in the polymer. In some circumstances, the polymer can be biocompatible. In certain circumstances, the polymer can have a protein adsorption of less than 5 µg/cm$^2$, less than 1 µg/cm$^2$, less than 0.5 µg/cm$^2$, less than 0.1 µg/cm$^2$, less than 0.05 µg/cm$^2$, or less than 0.01 µg/cm$^2$. In some circumstances, the polymer can include a polypeptide, a polynucleotide or a polysaccharide. Sometimes, the polysaccharide can be chitosan.

In some embodiments, the linker can further include a first binding partner and the capture protein can include a second binding partner, such that the first binding partner and second binding partner can bind together. The first binding partner can include an ion. The ion can be a metal ion. The metal ion can be a nickel, cobalt, zinc or copper ion (e.g. Ni$^{2+}$, Co$^{2+}$, Zi$^{2+}$ or Cu$^{2+}$).

In some embodiments, the linker can further include a chelating region.

In some embodiments, the linker can include a polydentate carboxylate (e.g. N$_\alpha$,N$_\alpha$-bis(carboxymethyl)-L-lysine) and the first binding partner can be a nickel ion (e.g. Ni$^{2+}$).

In some embodiments, the second binding partner can include a protein tag. The protein tag can be a histidine tag.

In some embodiments, a composition can further include a capture protein. The capture protein can be configured to specifically interact with at least one analyte.

In some embodiments, the capture protein can be a lectin and the analyte can include a glycan. In some embodiments, the analyte can be a glycoprotein.

In some embodiments, a linker can have a formula:

A-L-C, where A includes a polymer associated with the nanostructure,

L can be a linking moiety including a saturated or unsaturated C$_{4-10}$ hydrocarbon chain optionally containing at least two conjugated double bonds, at least one triple bond, or at least one double bond and one triple bond; said hydrocarbon chain being optionally substituted with C$_{1-4}$ alkyl, C$_{2-4}$ alkenyl, C$_{2-4}$ alkynyl, C$_{1-4}$ alkoxy, hydroxyl, halo, carboxyl, amino, nitro, cyano, C$_{3-6}$ cycloalkyl, 3-6 membered heterocycloalkyl, unsubstituted monocyclic aryl, 5-6 membered heteroaryl, C$_{1-4}$ alkylcarbonyloxy, C$_{1-4}$ alkyloxycarbonyl, C$_{1-4}$ alkylcarbonyl, or formyl and said hydrocarbon chain being optionally interrupted by O, S, N(R$^a$), C(O), N(R$^a$)C(O)O, OC(O)N(R$^a$), N(R$^a$)C(O)N(R$^b$), C(O)O, or OC(O)O; each of R$^a$ and R$^b$, independently, being hydrogen, alkyl, alkenyl, alkynyl, alkoxy, hydroxylalkyl, hydroxyl, or haloalkyl, or L can be a bond, and C can be a metal ion complexing moiety.

In some circumstances, A can include a polymer [(M)$_x$(N)$_y$(O)$_z$]$_q$, where each of M, N and Q, independently, can be selected from the group consisting of a linear or cyclic C$_3$-C$_8$ hydrocarbyl, heterocyclyl, cyclyl, or aryl including one or more amine, alcohol or carboxylic acid group, where each M-N, M-Q or N-Q can include O, S, N(R$^a$), C(O), N(R$^a$)C(O)O, OC(O)N(R$^a$), N(R$^a$)C(O)N(R$^b$), C(O)O, or OC(O)O, each of $R^a$ and $R^b$, independently, can be hydrogen, alkyl, alkenyl, alkynyl, alkoxy, hydroxylalkyl, hydroxyl, or haloalkyl, and where each of x, y and z can be integers between 0 and 50, 0 and 20 or 0 and 10 and q can be an integer between 1 and 1000, 5 and 500, or 10 and 100.

In some circumstances, L can have the formula:

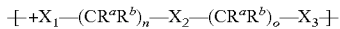

where each $X_1$, $X_2$ and $X_3$, can be O, S, $N(R^a)$, C(O), $N(R^a)C(O)O$, $OC(O)N(R^a)$, $N(R^a)C(O)N(R^b)$, C(O)O, or OC(O)O, each of $R^a$ and $R^b$, independently, can be hydrogen, alkyl, alkenyl, alkynyl, alkoxy, hydroxylalkyl, hydroxyl, or haloalkyl, and where the value of n added to o can be 4 to 10.

In some circumstances, C can have the formula, $H_zG((CH_2)_nCO_2H)_y$, and salts thereof, where G can be a bond, C, O, S, P, P=O or N; n is 0-6; and z and y can be selected to satisfy the valence requirements of G. In other preferred embodiments, the compound can have the formula,

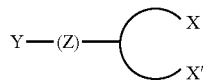

where X and X' can be the same or different and can be metal binding groups including atoms selected from the group of O, S, N, P or O=P, including carboxyl; Y can be bond, C, O, S, P, P=O or N; and Z can be a hydrocarbon having a backbone of one to six atoms, such as an alkyl group or alkenyl group. Each of X and X' can include other substituents in order to satisfy the valence requirements, such as for example, amine, thiol, phosphine or phosphine oxide, substituted by hydrogen or other organic moieties. In addition, the atoms bridging X and X' can be selected to form a 5-membered to 8-membered ring upon coordination to the metal ion. The bridging atoms can typically be carbon, but may be other elements, such as oxygen, nitrogen, or sulfur.

In yet another preferred embodiment, the compound can have the formula,

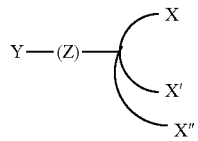

where X, X' and X" can be the same or different and can be metal binding groups including atoms selected from the group of O, S, N, P or O=P, including carboxyl; Y can be a bond, C, O, S, P, P=O or N; and Z can be a hydrocarbon having a backbone of one to six atoms, such as an alkyl group or alkenyl group. Each of X, X' and X" can include other substituents in order to satisfy the valence requirements, such as for example, amine, thiol, phosphine or phosphine oxide, substituted by hydrogen or other organic moieties. In addition, the atoms bridging X and X', X and X" or X' and X" can be selected to form a 5-membered to 8-membered ring upon coordination to the metal ion. The bridging atoms can typically be carbon, but may be other elements, such as oxygen, nitrogen, or sulfur. For example, C can be derived from $HSCH_2CH_2CH(SH)(CH_2)_nCOOH$, $H_2CH_2H_2CH(NH_2)(CH_2)_nCOOH$, $(HOOC(CH_2)_n)$ $HNCH_2CH_2NH((CH_2)_nCOOH)$, $(HOOC(CH_2)_n)_2$ $PCH_2CH_2P((CH_2)_nCOOH)_2$, $(HOOC(CH_2)_n)_2P(O)$ $CH_2CH_2P(O)((CH_2)_n COOH)_2$, $HSCH_2CH_2CH(SH)(CH_2)_4CONH(CH_2)_nCOOH$, where can is an integer between 1 and 10, or $N_\alpha,N_\alpha$-bis(carboxymethyl)-L-lysine.

In another aspect, an array can include a plurality of analysis regions on a substrate, at least one analysis region can include a composition, the composition can include a nanostructure and a linker associated with the nanostructure, where the linker can be configured to interact with a capture protein.

In some embodiments, the nanostructure can be a photoluminescent nanostructure. The photoluminescent nanostructure can be a nanotube. The nanotube can be a carbon nanotube. The carbon nanotube can be a single walled carbon nanotube.

In some embodiments, the linker can include a polymer. In some circumstances, at least a portion of the nanostructure is embedded in the polymer. In some circumstances, the polymer can be biocompatible. In certain circumstances, the polymer can have a protein adsorption of less than 5 µg/cm², less than 1 µg/cm², less than 0.5 µg/cm², less than 0.1 µg/cm², less than 0.05 µg/cm², or less than 0.01 µg/cm². In some circumstances, the polymer can include a polypeptide, a polynucleotide or a polysaccharide. Sometimes, the polysaccharide can be chitosan.

In some embodiments, the linker can further include a first binding partner and the capture protein can include a second binding partner, such that the first binding partner and second binding partner can bind together.

The metal ion can be a nickel, cobalt, zinc or copper ion (e.g. $Ni^{2+}$, $Co^{2+}$, $Zi^{2+}$ or $Cu^{2+}$).

In some embodiments, the linker can further include a chelating region.

In some embodiments, the linker can include a polydentate carboxylate (e.g. $N_\alpha,N_\alpha$-bis(carboxymethyl)-L-lysine) and the first binding partner can be a nickel ion (e.g. $Ni^{2+}$).

In some embodiments, the second binding partner can be a protein tag. The protein tag can be a histidine tag.

In some embodiments, the composition can further include a capture protein, where the capture protein can be configured to specifically interact with at least one analyte.

In some embodiments, at least one analysis region can further include a sample. The sample can include an analyte. The analyte can be a protein.

In some embodiments, at least one analysis region can further include a ribosome and the composition of the at least one analysis region can further include a capture protein, where the capture protein can be configured to specifically interact with at least one analyte.

In some embodiments, the plurality of analysis regions can include two or more subsets of analysis regions.

In some embodiments, an Nth subset of analysis regions can include an Nth composition which can include an Nth capture protein, where N can be an integer between 1 and 5000.

In some embodiments, the composition can further include a capture protein and an Nth subset of analysis regions can include an Nth sample, where N can be an integer between 1 and 5000.

In some embodiments, the composition can further include a capture protein and an Nth subset of analysis regions can include an Nth analyte, where N can be an integer between 1 and 5000.

In some embodiments, the capture protein can be a lectin and the analyte can include a glycan. In some embodiments, the analyte can be a glycoprotein.

In some embodiments, a linker can have a formula:

A-L-C, where A includes a polymer associated with the nanostructure,
L can be a linking moiety including a saturated or unsaturated $C_{4-10}$ hydrocarbon chain optionally containing at least two conjugated double bonds, at least one triple bond, or at least one double bond and one triple bond; said hydrocarbon chain being optionally substituted with $C_{1-4}$ alkyl, $C_{2-4}$ alkenyl, $C_{2-4}$ alkynyl, $C_{1-4}$ alkoxy, hydroxyl, halo, carboxyl, amino, nitro, cyano, $C_{3-6}$cycloalkyl, 3-6 membered heterocycloalkyl, unsubstituted monocyclic aryl, 5-6 membered heteroaryl, $C_{1-4}$ alkylcarbonyloxy, $C_{1-4}$ alkyloxycarbonyl, $C_{1-4}$ alkylcarbonyl, or formyl and said hydrocarbon chain being optionally interrupted by O, S, $N(R^a)$, C(O), $N(R^a)C(O)O$, $OC(O)N(R^a)$, $N(R^a)C(O)N(R^b)$, C(O)O, or OC(O)O; each of $R^a$ and $R^b$, independently, being hydrogen, alkyl, alkenyl, alkynyl, alkoxy, hydroxylalkyl, hydroxyl, or haloalkyl, or L can be a bond, and C can be a metal ion complexing moiety.

In some circumstances, A can include a polymer $[(M)_x(N)_y(O)_z]_q$, where each of M, N and Q, independently, can be selected from the group consisting of a linear or cyclic $C_3$-$C_8$ hydrocarbyl, heterocyclyl, cyclyl, or aryl including one or more amine, alcohol or carboxylic acid group, where each M-N, M-Q or N-Q can include O, S, $N(R^a)$, C(O), $N(R^a)C(O)O$, $OC(O)N(R^a)$, $N(R^a)C(O)N(R^b)$, C(O)O, or OC(O)O, each of $R^a$ and $R^b$, independently, can be hydrogen, alkyl, alkenyl, alkynyl, alkoxy, hydroxylalkyl, hydroxyl, or haloalkyl, and where each of x, y and z can be integers between 0 and 50, 0 and 20 or 0 and 10 and q can be an integer between 1 and 1000, 5 and 500, or 10 and 100.

In some circumstances, L can have the formula:

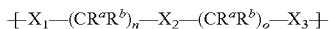

where each $X_1$, $X_2$ and $X_3$, can be O, S, $N(R^a)$, C(O), $N(R^a)C(O)O$, $OC(O)N(R^a)$, $N(R^a)C(O)N(R^b)$, C(O)O, or OC(O)O, each of $R^a$ and $R^b$, independently, can be hydrogen, alkyl, alkenyl, alkynyl, alkoxy, hydroxylalkyl, hydroxyl, or haloalkyl, and where the value of n added to o can be 4 to 10.

In some circumstances, C can have the formula, $H_zG((CH_2)_nCO_2H)_y$, and salts thereof, where G can be a bond, C, O, S, P, P=O or N; n is 0-6; and z and y can be selected to satisfy the valence requirements of G. In other preferred embodiments, the compound can have the formula,

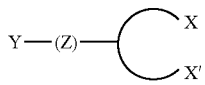

where X and X' can be the same or different and can be metal binding groups including atoms selected from the group of O, S, N, P or O=P, including carboxyl; Y can be bond, C, O, S, P, P=O or N; and Z can be a hydrocarbon having a backbone of one to six atoms, such as an alkyl group or alkenyl group. Each of X and X' can include other substituents in order to satisfy the valence requirements, such as for example, amine, thiol, phosphine or phosphine oxide, substituted by hydrogen or other organic moieties. In addition, the atoms bridging X and X' can be selected to form a 5-membered to 8-membered ring upon coordination to the metal ion. The bridging atoms can typically be carbon, but may be other elements, such as oxygen, nitrogen, or sulfur.

In yet another preferred embodiment, the compound can have the formula,

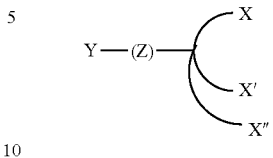

where X, X' and X" can be the same or different and can be metal binding groups including atoms selected from the group of O, S, N, P or O=P, including carboxyl; Y can be a bond, C, O, S, P, P=O or N; and Z can be a hydrocarbon having a backbone of one to six atoms, such as an alkyl group or alkenyl group. Each of X, X' and X" can include other substituents in order to satisfy the valence requirements, such as for example, amine, thiol, phosphine or phosphine oxide, substituted by hydrogen or other organic moieties. In addition, the atoms bridging X and X', X and X" or X' and X" can be selected to form a 5-membered to 8-membered ring upon coordination to the metal ion. The bridging atoms can typically be carbon, but may be other elements, such as oxygen, nitrogen, or sulfur. For example, C can be derived from $HSCH_2CH_2CH(SH)(CH_2)_nCOOH$, $H_2CH_2H_2CH(NH_2)(CH_2)_nCOOH$, $(HOOC(CH_2)_n)HNCH_2CH_2NH((CH_2)_nCOOH)$, $(HOOC(CH_2)_n)_2PCH_2CH_2P((CH_2)_nCOOH)_2$, $(HOOC(CH_2)_n)_2P(O)CH_2CH_2P(O)((CH_2)_n COOH)_2$, $HSCH_2CH_2CH(SH)(CH_2)_4CONH(CH_2)_nCOOH$, where can is an integer between 1 and 10, or $N_\alpha,N_\alpha$-bis(carboxymethyl)-L-lysine.

In another aspect, a method for detecting protein binding can include providing a composition, which can include a nanostructure, and a linker associated with the nanostructure, where the linker can be configured to interact with a capture protein, providing a capture protein capable of interacting with an analyte to the composition, such that the capture protein can interact with the linker, exposing the composition and capture protein to a sample, monitoring a property of the composition, and determining the presence of an analyte in the sample based on the monitored property.

In some embodiments, the nanostructure can be a photoluminescent nanostructure. The photoluminescent nanostructure can be a nanotube. The nanotube can be a carbon nanotube. The carbon nanotube can be a single walled carbon nanotube.

In some embodiments, the linker can include a polymer. In some circumstances, at least a portion of the nanostructure is embedded in the polymer. In some circumstances, the polymer can be biocompatible. In certain circumstances, the polymer can have a protein adsorption of less than 5 μg/cm$^2$, less than 1 μg/cm$^2$, less than 0.5 μg/cm$^2$, less than 0.1 μg/cm$^2$, less than 0.05 μg/cm$^2$, or less than 0.01 μg/cm$^2$. In some circumstances, the polymer can include a polypeptide, a polynucleotide or a polysaccharide. Sometimes, the polysaccharide can be chitosan.

In some embodiments, the linker can further include a first binding partner and the capture protein, which can include a second binding partner, such that the first binding partner and second binding partner can bind together.

In some embodiments, the first binding partner can include an ion. The ion can be a metal ion. The metal ion can be a nickel, cobalt, zinc or copper ion (e.g. $Ni^{2+}$, $Co^{2+}$, $Zi^{2+}$ or $Cu^{2+}$).

In some embodiments, the linker can further include a chelating region.

In some embodiments, the linker can include a polydentate carboxlate (e.g. $N_\alpha,N_\alpha$-bis(carboxymethyl)-L-lysine) and the first binding partner can be a nickel ion (e.g. $Ni^{2+}$).

In some embodiments, the second binding partner can be a protein tag. The protein tag can be a histidine tag.

In some embodiments, the sample can include an analyte. The analyte can be a protein.

In some embodiments, providing the capture protein can comprise synthesizing the capture protein.

In some embodiments, synthesizing the capture protein can include performing a cell-free protein synthesis reaction.

In some embodiments, the cell-free protein synthesis reaction can be performed at a location that can include the composition.

In some embodiments, the property can be an emission. In some circumstances, the property can be emission intensity. In some circumstances, the property can be an emission wavelength.

In some embodiments, determining the presence of an analyte can include determining the absence of the analyte. In some embodiments, the presence of an analyte can include determining the concentration of the analyte.

In some embodiments, the capture protein can be a lectin and the analyte can include a glycan. In some embodiments, the analyte can be a glycoprotein.

In some embodiments, a linker can have a formula:

A-L-C, where A includes a polymer associated with the nanostructure,

L can be a linking moiety including a saturated or unsaturated $C_{4-10}$ hydrocarbon chain optionally containing at least two conjugated double bonds, at least one triple bond, or at least one double bond and one triple bond; said hydrocarbon chain being optionally substituted with $C_{1-4}$ alkyl, $C_{2-4}$ alkenyl, $C_{2-4}$ alkynyl, $C_{1-4}$ alkoxy, hydroxyl, halo, carboxyl, amino, nitro, cyano, $C_{3-6}$ cycloalkyl, 3-6 membered heterocycloalkyl, unsubstituted monocyclic aryl, 5-6 membered heteroaryl, $C_{1-4}$ alkylcarbonyloxy, $C_{1-4}$ alkyloxycarbonyl, $C_{1-4}$ alkylcarbonyl, or formyl and said hydrocarbon chain being optionally interrupted by O, S, $N(R^a)$, C(O), $N(R^a)C(O)O$, $OC(O)N(R^a)$, $N(R^a)C(O)N(R^b)$, C(O)O, or OC(O)O; each of $R^a$ and $R^b$, independently, being hydrogen, alkyl, alkenyl, alkynyl, alkoxy, hydroxylalkyl, hydroxyl, or haloalkyl, or L can be a bond, and C can be a metal ion complexing moiety.

In some circumstances, A can include a polymer $[(M)_x(N)_y(O)_z]_q$, where each of M, N and Q, independently, can be selected from the group consisting of a linear or cyclic $C_3$-$C_8$ hydrocarbyl, heterocyclyl, cyclyl, or aryl including one or more amine, alcohol or carboxylic acid group, where each M-N, M-Q or N-Q can include O, S, $N(R^a)$, C(O), $N(R^a)C(O)O$, $OC(O)N(R^a)$, $N(R^a)C(O)N(R^b)$, C(O)O, or OC(O)O, each of $R^a$ and $R^b$, independently, can be hydrogen, alkyl, alkenyl, alkynyl, alkoxy, hydroxylalkyl, hydroxyl, or haloalkyl, and where each of x, y and z can be integers between 0 and 50, 0 and 20 or 0 and 10 and q can be an integer between 1 and 1000, 5 and 500, or 10 and 100.

In some circumstances, L can have the formula:

$\{X_1-(CR^aR^b)_n-X_2-(CR^aR^b)_o-X_3\}$ where each $X_1$, $X_2$ and $X_3$, can be O, S, $N(R^a)$, C(O), $N(R^a)C(O)O$, $OC(O)N(R^a)$, $N(R^a)C(O)N(R^b)$, C(O)O, or OC(O)O, each of $R^a$ and $R^b$, independently, can be hydrogen, alkyl, alkenyl, alkynyl, alkoxy, hydroxylalkyl, hydroxyl, or haloalkyl, and where the value of n added to o can be 4 to 10.

In some circumstances, C can have the formula, $H_zG((CH_2)_nCO_2H)_y$ and salts thereof, where G can be a bond, C, O, S, P, P=O or N; n is 0-6; and z and y can be selected to satisfy the valence requirements of G. In other preferred embodiments, the compound can have the formula,

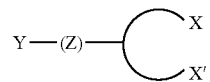

where X and X' can be the same or different and can be metal binding groups including atoms selected from the group of O, S, N, P or O=P, including carboxyl; Y can be bond, C, O, S, P, P=O or N; and Z can be a hydrocarbon having a backbone of one to six atoms, such as an alkyl group or alkenyl group. Each of X and X' can include other substituents in order to satisfy the valence requirements, such as for example, amine, thiol, phosphine or phosphine oxide, substituted by hydrogen or other organic moieties. In addition, the atoms bridging X and X' can be selected to form a 5-membered to 8-membered ring upon coordination to the metal ion. The bridging atoms can typically be carbon, but may be other elements, such as oxygen, nitrogen, or sulfur.

In yet another preferred embodiment, the compound can have the formula,

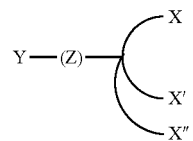

where X, X' and X" can be the same or different and can be metal binding groups including atoms selected from the group of O, S, N, P or O=P, including carboxyl; Y can be a bond, C, O, S, P, P=O or N; and Z can be a hydrocarbon having a backbone of one to six atoms, such as an alkyl group or alkenyl group. Each of X, X' and X" can include other substituents in order to satisfy the valence requirements, such as for example, amine, thiol, phosphine or phosphine oxide, substituted by hydrogen or other organic moieties. In addition, the atoms bridging X and X', X and X" or X' and X" can be selected to form a 5-membered to 8-membered ring upon coordination to the metal ion. The bridging atoms can typically be carbon, but may be other elements, such as oxygen, nitrogen, or sulfur. For example, C can be derived from $HSCH_2CH_2CH(SH)(CH_2)_nCOOH$, $H_2CH_2H_2CH(NH_2)(CH_2)_nCOOH$, $(HOOC(CH_2)_n)HNCH_2CH_2NH((CH_2)_nCOOH)$, $(HOOC(CH_2)_n)_2PCH_2CH_2P((CH_2)_nCOOH)_2$, $(HOOC(CH_2)_n)_2P(O)CH_2CH_2P(O)((CH_2)_n COOH)_2$, $HSCH_2CH_2CH(SH)(CH_2)_4CONH(CH_2)_nCOOH$, where can is an integer between 1 and 10, or $N_\alpha,N_\alpha$-bis(carboxymethyl)-L-lysine.

In another aspect, the composition can include a nanostructure and a linker having a formula:

A-L-C, where A includes a polymer associated with the nanostructure,

L can be a linking moiety including a saturated or unsaturated $C_{4-10}$ hydrocarbon chain optionally containing at least two conjugated double bonds, at least one triple bond, or at least one double bond and one triple bond; said hydrocarbon chain being optionally substituted with $C_{1-4}$ alkyl, $C_{2-4}$ alkenyl, $C_{2-4}$ alkynyl, $C_{1-4}$ alkoxy, hydroxyl, halo, carboxyl, amino, nitro, cyano, $C_{3-6}$cycloalkyl, 3-6 membered heterocycloalkyl, unsubstituted monocyclic aryl, 5-6 membered heteroaryl, $C_{1-4}$ alkylcarbonyloxy, $C_{1-4}$ alkyloxycarbonyl, $C_{1-4}$alkylcarbonyl, or formyl and said hydrocarbon chain being optionally interrupted by O, S, $N(R^a)$, C(O), $N(R^a)C(O)O$, $OC(O)N(R^a)$, $N(R^a)C(O)N(R^b)$, C(O)O, or OC(O)O; each of $R^a$ and $R^b$, independently, being hydrogen, alkyl, alkenyl, alkynyl, alkoxy, hydroxylalkyl, hydroxyl, or haloalkyl, or L can be a bond, and C can be a metal ion complexing moiety.

In some circumstances, A can include a polymer $[(M)_x(N)_y(O)_z]q$, where each of M, N and Q, independently, can be selected from the group consisting of a linear or cyclic $C_3$-$C_8$ hydrocarbyl, heterocyclyl, cyclyl, or aryl including one or more amine, alcohol or carboxylic acid group, where each M-N, M-Q or N-Q can include O, S, $N(R^a)$, C(O), $N(R^a)C(O)O$, $OC(O)N(R^a)$, $N(R^a)C(O)N(R^b)$, C(O)O, or OC(O)O, each of $R^a$ and $R^b$, independently, can be hydrogen, alkyl, alkenyl, alkynyl, alkoxy, hydroxylalkyl, hydroxyl, or haloalkyl, and where each of x, y and z can be integers between 0 and 50, 0 and 20 or 0 and 10 and q can be an integer between 1 and 1000, 5 and 500, or 10 and 100.

In some circumstances, L can have the formula:

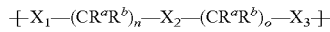

where each $X_1$, $X_2$ and $X_3$, can be O, S, $N(R^a)$, C(O), $N(R^a)C(O)O$, $OC(O)N(R^a)$, $N(R^a)C(O)N(R^b)$, C(O)O, or OC(O)O, each of $R^a$ and $R^b$, independently, can be hydrogen, alkyl, alkenyl, alkynyl, alkoxy, hydroxylalkyl, hydroxyl, or haloalkyl, and where the value of n added to o can be 4 to 10.

In some circumstances, C can have the formula, $H_zG((CH_2)_nCO_2H)_y$ and salts thereof, where G can be a bond, C, O, S, P, P=O or N; n is 0-6; and z and y can be selected to satisfy the valence requirements of G. In other preferred embodiments, the compound can have the formula,

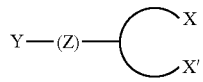

where X and X' can be the same or different and can be metal binding groups including atoms selected from the group of O, S, N, P or O=P, including carboxyl; Y can be bond, C, O, S, P, P=O or N; and Z can be a hydrocarbon having a backbone of one to six atoms, such as an alkyl group or alkenyl group. Each of X and X' can include other substituents in order to satisfy the valence requirements, such as for example, amine, thiol, phosphine or phosphine oxide, substituted by hydrogen or other organic moieties. In addition, the atoms bridging X and X' can be selected to form a 5-membered to 8-membered ring upon coordination to the metal ion. The bridging atoms can typically be carbon, but may be other elements, such as oxygen, nitrogen, or sulfur.

In yet another preferred embodiment, the compound can have the formula,

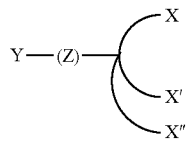

where X, X' and X" can be the same or different and can be metal binding groups including atoms selected from the group of O, S, N, P or O=P, including carboxyl; Y can be a bond, C, O, S, P, P=O or N; and Z can be a hydrocarbon having a backbone of one to six atoms, such as an alkyl group or alkenyl group. Each of X, X' and X" can include other substituents in order to satisfy the valence requirements, such as for example, amine, thiol, phosphine or phosphine oxide, substituted by hydrogen or other organic moieties. In addition, the atoms bridging X and X', X and X" or X' and X" can be selected to form a 5-membered to 8-membered ring upon coordination to the metal ion. The bridging atoms can typically be carbon, but may be other elements, such as oxygen, nitrogen, or sulfur. For example, C can be derived from $HSCH_2CH_2CH(SH)(CH_2)_nCOOH$, $H_2CH_2H_2CH(NH_2)(CH_2)_nCOOH$, $(HOOC(CH_2)_n)$ $HNCH_2CH_2NH((CH_2)_nCOOH)$, $(HOOC(CH_2)_n)_2$ $PCH_2CH_2P((CH_2)_n COOH)_2$, $(HOOC(CH_2)_n)_2P(O)$ $CH_2CH_2P(O)((CH_2)_n COOH)_2$, $HSCH_2CH_2CH(SH)(CH_2)_4$ $CONH(CH_2)_nCOOH$, where can is an integer between 1 and 10, or $N_\alpha,N_\alpha$-bis(carboxymethyl)-L-lysine.

It should be recognized that a compound of the invention can contain chiral carbon atoms. In other words, it may have optical isomers or diastereoisomers.

Alkyl is a straight or branched hydrocarbon chain containing 1 to 10 (preferably, 1 to 6; more preferably 1 to 4) carbon atoms. Examples of alkyl include, but are not limited to, methyl, ethyl, propyl, isopropyl, butyl, isobutyl, sec-butyl, tert-butyl, n-pentyl, 2-methylhexyl, and 3-ethyloctyl.

The terms "alkenyl" and "alkynyl" refer to a straight or branched hydrocarbon chain containing 2 to 10 carbon atoms and one or more (preferably, 1-4 or more preferably 1-2) double or triple bonds, respectively. Some examples of alkenyl and alkynyl are allyl, 2-butenyl, 2-pentenyl, 2-hexenyl, 2-butynyl, 2-pentynyl, and 2-hexynyl.

Cycloalkyl is a monocyclic, bicyclic or tricyclic alkyl group containing 3 to 14 carbon atoms. Some examples of cycloalkyl are cyclopropyl, cyclopentyl, cyclohexyl, cycloheptyl, adamantyl, and norbornyl. Heterocycloalkyl is a cycloalkyl group containing at least one heteroatom (e.g., 1-3) such as nitrogen, oxygen, or sulfur. The nitrogen or sulfur may optionally be oxidized and the nitrogen may optionally be quaternized. Examples of heterocycloalkyl include piperidinyl, piperazinyl, tetrahydropyranyl, tetrahydrofuryl, and morpholinyl. Cycloalkenyl is a cycloalkyl group containing at least one (e.g., 1-3) double bond. Examples of such a group include cyclopentenyl, 1,4-cyclohexa-di-enyl, cycloheptenyl, and cyclooctenyl groups. By the same token, heterocycloalkenyl is a cycloalkenyl group containing at least one heteroatom selected from the group of oxygen, nitrogen or sulfur.

Aryl is an aromatic group containing a 5-14 ring and can contain fused rings, which may be saturated, unsaturated, or aromatic. Examples of an aryl group include phenyl, naphthyl, biphenyl, phenanthryl, and anthracyl. If the aryl is specified as "monocyclic aryl," if refers to an aromatic group containing only a single ring, i.e., not a fused ring.

Heteroaryl is aryl containing at least one (e.g., 1-3) heteroatom such as nitrogen, oxygen, or sulfur and can contain fused rings. Some examples of heteroaryl are pyridyl, furanyl, pyrrolyl, thienyl, thiazolyl, oxazolyl, imidazolyl, indolyl, benzofuranyl, and benzthiazolyl.

A cyclic moiety can be a fused ring formed from two or more of the just-mentioned groups.

Amino protecting groups and hydroxy protecting groups are well-known to those in the art. In general, the species of protecting group is not critical, provided that it is stable to the conditions of any subsequent reaction(s) on other positions of the compound and can be removed without adversely affecting the remainder of the molecule. In addition, a protecting group may be substituted for another after substantive synthetic transformations are complete. Examples of an amino protecting group include, but not limited to, carbamates such as 2,2,2-trichloroethylcarbamate or tertbutylcarbamate. Examples of a hydroxyl protecting group include, but not limited to, ethers such as methyl, t-butyl, benzyl, p-methoxybenzyl, p-nitrobenzyl, allyl, trityl, methoxymethyl, 2-methoxypropyl, methoxyethoxymethyl, ethoxyethyl, tetrahydropyranyl, tetrahydrothiopyranyl, and trialkylsilyl ethers such as trimethylsilyl ether, triethylsilyl ether, dimethylarylsilyl ether, triisopropylsilyl ether and t-butyldimethylsilyl ether; esters such as benzoyl, acetyl, phenylacetyl, formyl, mono-, di-, and trihaloacetyl such as chloroacetyl, dichloroacetyl, trichloroacetyl, trifluoroacetyl; and carbonates including but not limited to alkyl carbonates having from one to six carbon atoms such as methyl, ethyl, n-propyl, isopropyl, n-butyl, t-butyl; isobutyl, and n-pentyl; alkyl carbonates having from one to six carbon atoms and substituted with one or more halogen atoms such as 2,2,2-trichloroethoxymethyl and 2,2,2-trichloro-ethyl; alkenyl carbonates having from two to six carbon atoms such as vinyl and allyl; cycloalkyl carbonates having from three to six carbon atoms such as cyclopropyl, cyclobutyl, cyclopentyl and cyclohexyl; and phenyl or benzyl carbonates optionally substituted on the ring with one or more $C_{1-6}$ alkoxy, or nitro. Other protecting groups and reaction conditions can be found in T. W. Greene, *Protective Groups in Organic Synthesis*, (3rd, 1999, John Wiley & Sons, New York, N.Y.).

Note that an amino group can be unsubstituted (i.e., —$NH_2$), mono-substituted (i.e., —NHR), or di-substituted (i.e., —$NR_2$). It can be substituted with groups (R) such as alkyl, cycloalkyl, heterocycloalkyl, aryl, heteroaryl, aralkyl, or heteroaralkyl. Halo refers to fluoro, chloro, bromo, or iodo.

Other features or advantages will be apparent from the following detailed description of several embodiments, and also from the appended claims.

BRIEF DESCRIPTION OF THE DRAWINGS

FIG. 32a: Experimental setup: a thin film of chitosan-SWNT was spin-coated on the glass chip and excited by a 660 nM crystal laser, the resulting emission was analyzed by an InGaAs array. FIG. 32b: The array produced a tiff image per time frame where each pixel value denoted the fluorescent intensity, in this manner single SWNT were visualized. FIG. 32c: By binning 2×2 pixel regions for the brightest 1000 SWNT, individual traces of fluorescence intensity versus time were created for each SWNT sensor. These traces were then noise-reduced and fitted to determine kinetic parameters (--- denotes addition of GlcNAc-Streptavidin at 10 μM to GafD). FIG. 32d: An ensemble average of the individual SWNT sensors were approximated by adding the signals of 150 SWNT sensors (--- denotes addition of GlcNAc-Streptavidin at 10 μM to GafD).

FIG. 37a: a thin film of CHI-SWNT was imaged by the single sensor setup showing a field of sensors on the glass surface. FIG. 37b: The sensors were evaluated individually to find which ones gave maximum signal modulation. Shown are curves from eight of the most responsive with their positions marked by red circles in FIG. 37a. Vertical dotted lines denote the time of analyte addition. FIG. 37c: 289 SWNT sensors had signals strong enough to determine $K_D$ values, these are plotted versus starting intensity. Four sensors were found to have strong $K_D$ values (<10 μM) and their locations are denoted by green circles on FIG. 37a. FIG. 37d: The population of $K_D$ values yielded a single Gaussian distribution when plotted as a histogram of $\log_{10}$ ($K_D$) values with a mean $K_D$ of 250 μM.

DETAILED DESCRIPTION

Figure 1:
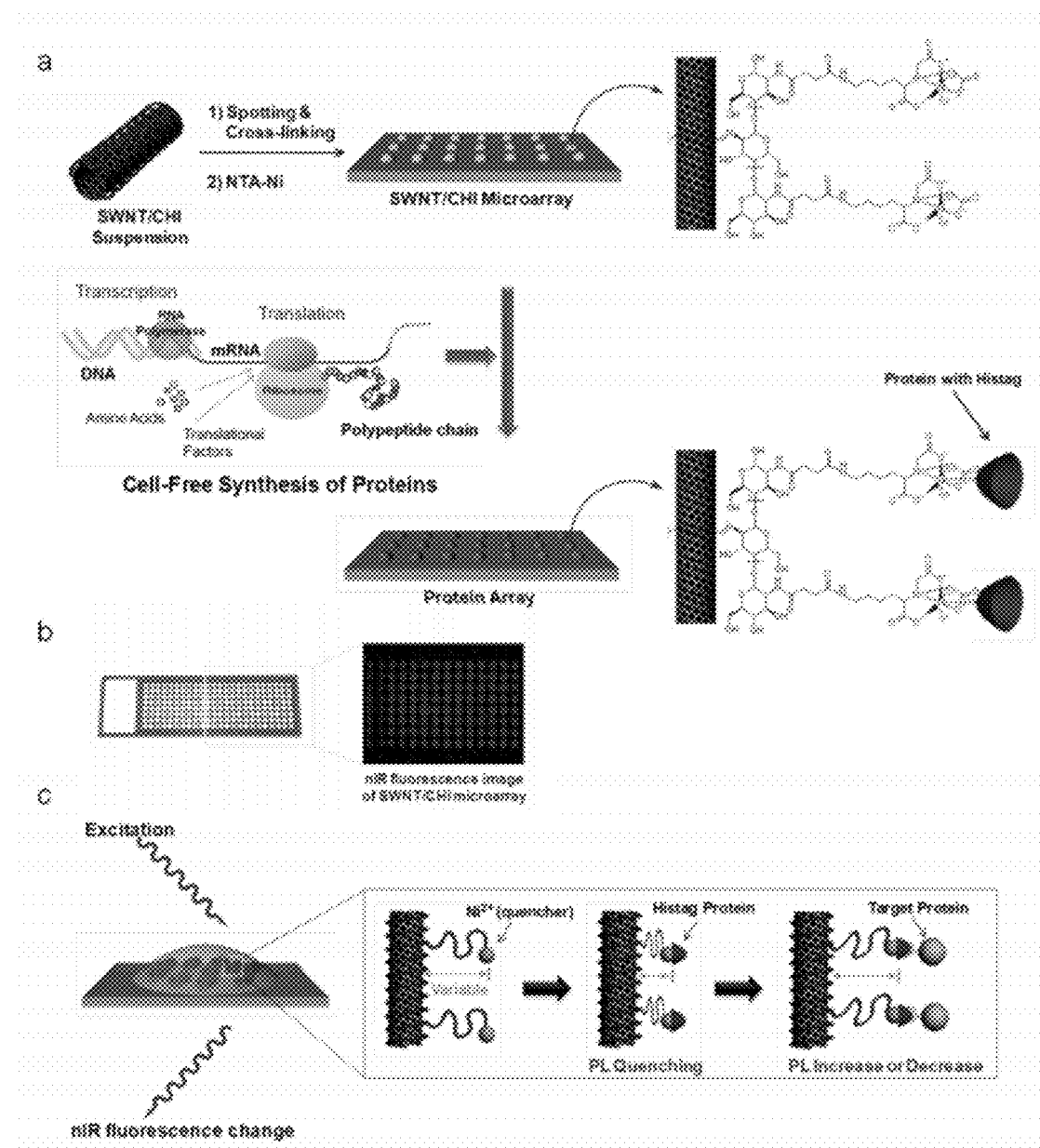
FIG. 1 is a schematic of a label-free protein array based upon fluorescent single-walled carbon nanotubes.

The ability to measure protein-protein binding in a label-free and high-throughput manner can allow for the testing of protein-protein interactions, measuring the selectivity of small molecule drug binding, screening of enzyme substrates and determination of novel cancer biomarkers. Label-free detection can have a number of advantages over conventional methods, such as simple operational procedures and lack of conjugated labels. Label-free detection methods employed in protein arrays can form a vital tool for the study and analysis of biomolecular interactions.

However, despite significant progress, protein microarrays remain limited by protein availability and minimum sample requirements, which can be dictated by pre-labeling protocols and the detection limits of fluorometric analysis. The labor associated with the creation of protein libraries to create such arrays can also limit their widespread application. Protein stability during array storage can also attenuate a robust response. (MacBeath, G. & Schreiber, S. L. Printing proteins as microarrays for high-throughput function determination. Science 289, 1760-1763 (2000); Zhu, H. et al. Global analysis of protein activities using proteome chips. Science 293, 2101-2105 (2001); Ramachandran, N., Srivastava, S. & LaBaer, J. Applications of protein microarrays for biomarker discovery. Proteomics Clinical Applications 2, 1444-1459 (2008), each of which is incorporated by reference in its entirety). This may have motivated the development of technologies capable of directly transducing protein binding, therefore eliminating the need for intensive sample preparation, labeling and pre-treatment, and consequently, reducing sample volume requirements. While the DNA microarray may be largely successful in terms of economic deployment and widespread usage, the protein equilivalent seems to have lagged behind. (LaBaer, J. & Ramachandran, N. Protein microarrays as tools for functional proteomics. Curr Opin Chem Biol 9, 14-19 (2005), which is incorporated by reference in its entirety).

Progress has been made in label-free detection methods applied to protein microarrays. One motivating factor for such progress may have been avoidance of conjugated labels or radioactive materials, both of which can be perturbative. (Ramachandran, N., et al (2008)). Success has been demonstrated using novel photonic approaches, including fiber-optic waveguides, surface plasmon resonance imaging and optical microcavities. (Burg, T. P. et al. Weighing of biomolecules, single cells and single nanoparticles in fluid. Nature 446, 1066-1069 (2007); O'Connell, M. J. et al. Band gap fluorescence from individual single-walled carbon nanotubes. Science 297, 593 (2002); Li, Q. et al. Sustained Growth of Ultralong Carbon Nanotube Arrays for Fiber Spinning. Adv. Mater 18, 3160-3163 (2006), each of which has been incorporated by reference in its entirety). As an alternative to less economical optical components, non-optical methods can include electrical transduction using nanowires and resonant mechanical cantilevers. (Heller, D. A., Baik, S., Eurell, T. E. & Strano, M. S. Single-walled carbon nanotube spectroscopy in live cells: Towards long-term labels and optical sensors. Advanced Materials 17, 2793-2798 (2005); Barone, P. W., Baik, S., Heller, D. A. & Strano, M. S, Near-infrared optical sensors based on single-walled carbon nanotubes. Nature Materials 4, 86-92 (2005); Kim, J. et al. The rational design of nitric oxide selectivity in single-walled carbon nanotube near-infrared fluorescence sensors for biological detection. Nature Chemistry (2009), each of which is incorporated by reference in its entirety). Novel nanoparticle probes can replace conventional labels, allowing for increased multiplexing and lower detection limits for detection. (Satishkumar, B. C. et al. Reversible fluorescence quenching in carbon nanotubes for biomolecular sensing. Nature Nanotechnology 2, 560-564 (2007), which is incorporated by reference in its entirety). While promising, many of these approaches cannot be scaled down to single protein detection limits, and to date none of these approaches has demonstrated the capability to detect a single protein molecule.

Transduction technology can be an important component of future label free microarray technologies; however, protein library production can be significantly more complex and costly in comparison to its DNA equivalent. The creation of label free technologies compatible with cell-free protein expression can offer significant advantages over conventional protein synthesis, in which individual proteins are synthesized, purified, and spotted in segregated processes. In situ immobilization of proteins during synthesis directly on the array can eliminate the need for separate protein preparation and purification. Several protein array systems using cell-free protein synthesis have been reported to overcome the limitations of conventional protein synthesis. (Perebeinos, V., Tersoff, J. & Avouris, P. Scaling of excitons in carbon nanotubes. Physical Review Letters 92, 257402 (2004); Walsh, A. G. et al. Screening of excitons in single, suspended carbon nanotubes. Nano Lett 7, 1485-1488 (2007); Heller, D. A. et al. Optical detection of DNA conformational polymorphism on single-walled carbon nanotubes. Science 311, 508 (2006); Jeng, E. S., Moll, A. E., Roy, A. C., Gastala, J. B. & Strano, M. S. Detection of DNA hybridization using the near-infrared band-gap fluorescence of single-walled carbon nanotubes. *Nano Letters* 6, 371-375 (2006); Heller, D. A. et al. Multimodal optical sensing and analyte specificity using single-walled carbon nanotubes. *Nature Nanotechnology* (2008), each of which can be incorporated by reference in its entirety). For example, Ramachandran, et al. developed nucleic acid programmable protein arrays (NAPPA) in which protein arrays can be generated from plasmid DNA arrays by cell-free synthesis with capture of tagged proteins onto the same array surface by an immobilized antibody to fusion tag. (Walsh, A. G. et al. (2007); Heller, D. A. et al. (2006)). He, et al. developed the concept of the DNA array to protein array (DAPA) procedure in which an immobilized DNA array can be the re-usable template for printing multiple copies of protein arrays on separate slides as and when required. (Jeng, E. S., et al (2006)). In addition, with an adaption of mRNA display technology, Tao and Zhu reported a protein array from modified cell-free transcription and translation on the chip surface. (Perebeinos, V., (2004)). These cell free approaches to protein microarray synthesis have not yet been applied to label free technologies despite obvious advantages.

Single-walled carbon nanotubes, which can be rolled cylinders of graphene, can have several advantages as potential fluorometric detectors of protein binding. They can possess band-gap photoluminescence (PL) in the near infra-red (nIR) and have not demonstrated a photo-bleaching threshold, thus permitting long exposure/integration times. (Hall, D. A., Ptacek, J. & Snyder, M. Protein microarray technology. *Mech Ageing Dev* 128, 161-167 (2007); Joos, T. Protein microarray technology. *Expert Rev* Proteomic 1, 1-3 (2004); Wolf-Yadlin, A., Sevecka, M. & MacBeath, G. Dissecting protein function and signaling using protein microarrays. *Curr Opin Chem Biol* 13, 398-405 (2009), each of which is incorporated by reference in its entirety). The photoemission can be sensitive to electron-donating or -withdrawing analytes or those that change the local dielectric constant, causing solvatochromism. (Stoevesandt, O., Taussig, M. J. & He, M. Y. Protein microarrays: high-throughput tools for proteomics. *Expert Rev Proteomic* 6, 145-157 (2009); Ramachandran, N. et al. Self-assembling protein microarrays. *Science* 305, 86-90 (2004); He, M. et al. Printing protein arrays from DNA arrays. *Nature Methods* 5, 175-177 (2008); Tao, S. C. & Zhu, H. Protein chip fabrication by capture of nascent polypeptides. *Nature Biotechnology* 24, 1253-1254 (2006); Chen, Z. et al. Protein microarrays with carbon nanotubes as multicolor Raman labels. *Nature Biotechnology* 26, 1285-1292 (2008); Hughes, R. C., Ricco, A. J., Butler, M. A. & Martin, S. J. Chemical Microsensors. *Science* 254, 74-80 (1991); Lokate, A. M. C., Beusink, J. B., Besselink, G. A. J., Pruijn, G. J. M. & Schasfoort, R. B. M. Biomolecular interaction monitoring of autoantibodies by scanning surface plasmon resonance microarray imaging. *J Am Chem Soc* 129, 14013-14018 (2007), each of which is incorporated by reference in its entirety). While SWNT PL sensors have been developed for detecting β-D-glucose, DNA hybridization, divalent metal cations, assorted genotoxins, nitric oxide, pH and avidin, a generic scheme for detecting protein-protein interactions has not been previously developed. Such a mechanism can enable SWNT PL sensor application to label-free protein microarrays. (Stoevesandt, O., et al, (2009); Lokate, A. M. C., et al, (2007); Hughes, R. C., et al (1991); Armani, A. M., Kulkarni, R. P., Fraser, S. E., Flagan, R. C. & Vahala, K. J. Label-free, single-molecule detection with optical microcavities. *Science* 317, 783-787 (2007); Ramachandran, N. et al. (2004); Zheng, G. F., Patolsky, F., Cui, Y., Wang, W. U. & Lieber, C. M. Multiplexed electrical detection of cancer markers with nanowire sensor arrays. *Nature Biotechnology* 23, 1294-1301 (2005); He, M. et al. (2008), each of which is incorporated by reference in it entirety). Using SWNT PL sensors, the binding of small molecules, which can quench the nanotube emission, can be detected even at the single molecule level. (Zheng, G. F., et al (2005); Thong, Z. H., Wang, D. L., Cui, Y., Bockrath, M. W. & Lieber, C. M. Nanowire crossbar arrays as address decoders for integrated nanosystems. *Science* 302, 1377-1379 (2003), each of which is incorporated by reference in its entirety).

A nanotube/polymer microarray can be capable of optically reporting the binding of an analyte to a tagged capture protein docked to a metal ion complex interacting with the nanotube and polymer. This microarray arrangement can enable the resolution of single protein binding events, which is the lowest detection limit of any protein array demonstrated to date. A nanotube can detect the stochastic fluctuations of single quenching molecules that adsorb or desorb in real time, which can allow the measurement of both forward and reverse binding rate constants, the ratio of which can be the inverse equilibrium or affinity constant.

One binding event that can be detected is the binding of a lectin and a glycan. Glycans can participate in protein signaling, interaction, structure, and folding. (Ohtsubo and Marth "Glycosylation in Cellular Mechanisms of Health and Disease" Cell 2006; Gamblin et al., "Glycoprotein Synthesis: An Update. Chem. Rev. 2009, each of which is incorporated by reference in its entirety). Thus knowledge of the structure of the attached glycans can help characterize a protein. This can be applicable to protein therapeutics, where over two thirds of the rapidly-growing market may be composed of glycoproteins (Li and d'Anjou, "Pharmacological Significance of Glycosylation in Therapeutic Proteins. Curr. Opin. Biotech. 2009, which is incorporated by reference in its entirety). Expression of these therapies in non-native cell lines can yield a highly heterogeneous mixture of glycosylated proteins. Additionally, there have been recent studies showing the production of homogenous glycoproteins using eukaryotic cells (Hamilton et al., "Production of Complex Human Glycoproteins in Yeast" Science 2003; Rich and Withers, "Emerging methods for the production of homogenous human glycoproteins" Nat. Chem. Biol. 2009; Schwarz et al., "A combined method for producing homogeneous glycoproteins with eukaryotic N-glycosylation, Nat. Chem. Biol. 2010, each of which is incorporated by reference in its entirety). The heterogeneity can be unacceptable for highly-specific therapies, as well as passing any stringent drug review process (Li and d'Anjou 2009). As a result, various profiling systems have been proposed: magnetic nanoparticles (Zhou et al., "Facile synthesis of aminophenylboronic acid-functionalized magnetic nanoparticles for selective separation of glycopeptides and glycoproteins" Chem. Comm. 2008, which is incorporated by reference in its entirety), reverse-phase chromatography tandem mass spectrometry (Prater et al., "High-throughput immunoglobin G N-glycan characterization using rapid resolution reverse-phase chromatography tandem mass spectrometry," Anal. Biochem. 2009, which is incorporated by reference in its entirety), nanoflow liquid chromatography coupled with Fourier-transform, ion-cyclotron, resonance mass spectrometry (Bereman et al., "Development of a Robust and High Throughput Method for Profiling N-Linked Glycans Derived from Plasma Glycoproteins by NanoLC-FTICR Mass Spectrometry, J. Proteome Res. 2009, which is incorporated by reference in its entirety), and magnetic resonance imaging (El-Boubbou et al., "Magnetic Glyco-Nanoparticles: A Tool to Detect, Differentiate, and Unlock the Glyco-Codes of Cancer via Magnetic Resonance Imaging, J. Am. Chem. Soc. 2010, which is incorporated by reference in its entirety). Lectin arrays have recently been proposed; however, current platforms may be limited to detection of more strongly affined ligands. (Pilobello et al., "Development of a lectin microarray for the rapid analysis of protein glycopatterns," ChemBioChem 2005; Zheng et al., "Lectin arrays for profiling cell surface carbohydrate expression," J. Am. Chem. Soc. 2005; Rosenfeld et al., "A lectin array-based methodology for the analysis of protein glycosylation," J. Biochel Biophys Methods, 2007; Tao et al., "Lectin microarrays identify cell-specific and functionally significant cell surface glycan markers," Glycobiology 2008; Hirabayashi, "Concept, Strategy and Realization of Lectin-based Glycan Profiling, J. Biochem. 2008, each of which is incorporated by reference in its entirety). A Weak Affinity Dynamic Microarray (WADM) may overcome these limitations by monitoring single-molecule adsorption and desorption dynamics in real time, as opposed to equilibrium binding only. A full spectrum of affinities, with an emphasis in the weakly binding regime, can be resolved, thereby reducing the number of lectin types needed for glycoprotein profiling.

Figure 16:
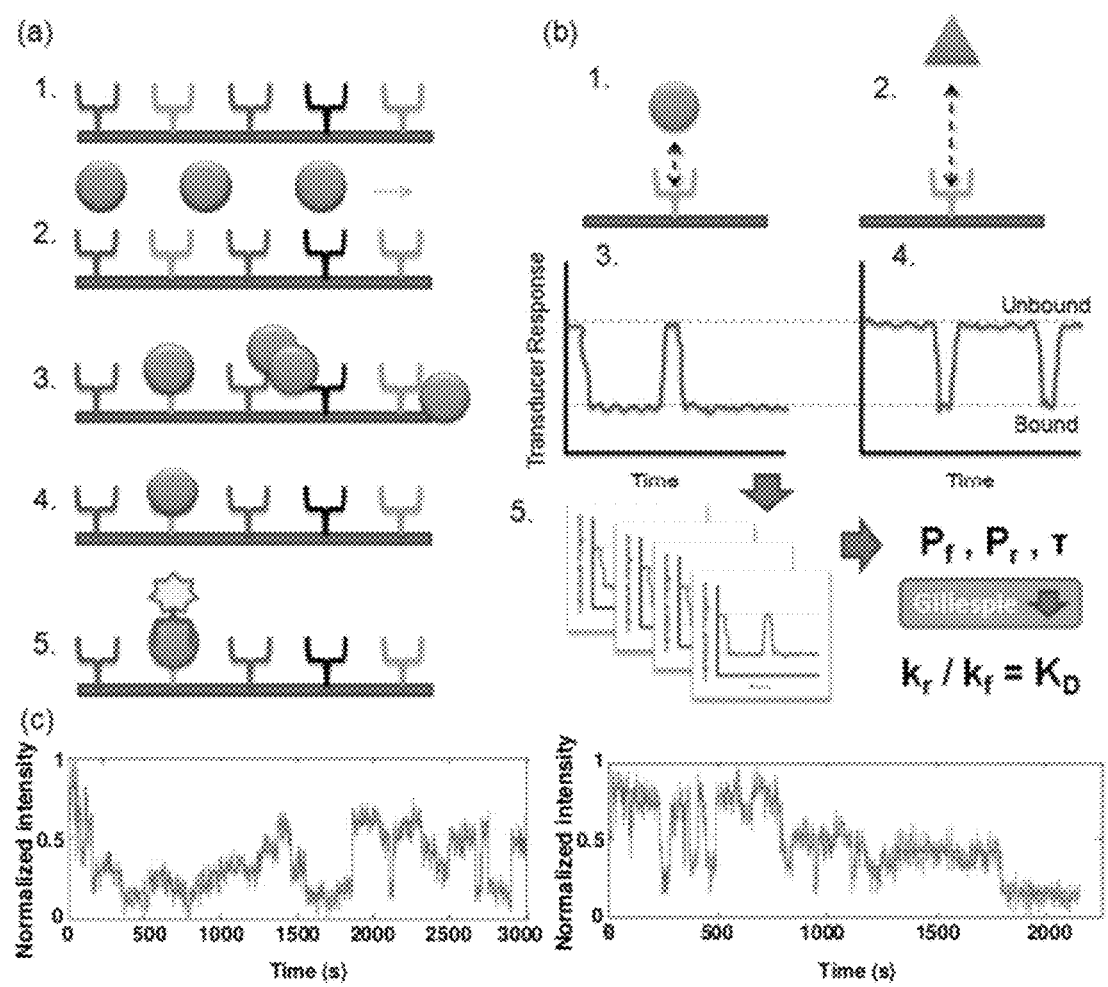
FIG. 16a includes schematics of detection steps.
FIG. 16b is a schematic showing detection of strong and weak interactions.
FIG. 16c includes two graphs representing the fluorescence response to a single analyte molecule of a composition.

Lectins, unlike other proteins, for example antibodies, can have a wider range of binding affinities, but their affinities can be weaker than typical protein-protein interactions (e.g. antibody-antigen pairs) (Hirabayashi 2008—showing experimental values of KD ranged from 10-3 to 10-7). A carefully selected array of stronger binding lectins might be able to profile glycoproteins (Pilobello et al. 2005; Zheng et al. 2005; Rosenfeld et al. 2007; Tao et al. 2008; Hirabayashi 2008). An array of four lectins can exhibit characteristic, fluorescent binding patterns to four different glycans (Tateno et al., "How to Determine Specificity: From Lectin Profiling to Glycan Mapping and Arrays, 2009, which is incorporated by reference in its entirety). One possible limitation to this approach may be that it relies on strong associations between glycan lectin pairs to obtain a unique fluorescent signal. The weakly binding pairs can be lost in the typical processing steps of conventional arrays (FIG. 16a). Because of the vast number of natural structures that may be in the glycome and the infinitely varied synthetic structures, such a platform could require a substantial set of unique lectins to provide a clear fluorescent signature from bound-pairs. (Tateno et al. 2009). However, a full spectrum of affinities, from weak to strong, may provide a clear readout signature, and consequently, may reduce the set of unique lectins required in a microarray.

As an alternative to current microarray technology which uses strong-binding, ligand receptor pairs for differentiation, the transient binding behavior of weakly-affined lectins (FIG. 16b) can be utilized to identify the glycan. By monitoring the statistical behavior of a glycoprotein binding on and off the lectin receptor, the full spectrum of the affinities of lectins can be used to profile the glycoprotein in solution. Nanosensor platforms can allow for single molecule adsorption/desorption dynamics to be recorded in real time (Cognet et al., "Stepwise Quenching of Exciton Fluorescence in Carbon Nanotubes by Single-Molecule Reactions," Science 2007; Jin et al., "Stochastic Analysis of Stepwise Fluorescence Quenching Reactions on Single-Walled Carbon Nanotubes: Single Molecule Sensors," Nano Lett 2008; Jin et al., "Detection of single-molecule H2O2 signalling from epidermal growth factor receptor using fluorescent single-walled carbon nanotubes," Nat Nanotech 2010; Goldsmith et al., "Monitoring Single Molecule Reactivity on a Carbon Nanotube," Nano Lett 2007; Goldsmith et al., "Conductance-Controlled Point Functionalization of Single-Walled Carbon Nanotubes," Science, 2008, each of which is incorporated by reference in its entirety). The response of such nanosensors (FIG. 1c) can be used to determine the kinetic parameters between glycan-lectin pairs. These parameters, in turn, can help differentiate between glycans present on the protein surface. By carefully choosing the right lectin types and running the experiment under optimal conditions the profiling accuracy can be greatly improved.

A composition can include a nanostructure and a linker (FIGS. 13a and 14a). A nanostructure can be an article having at least one cross-sectional dimension between opposed boundaries of less than about 1 micron. In some embodiments, a nanostructure can have at least one cross-sectional dimension between opposed boundaries of less than about 500 nm, less than about 250 nm, less than about 100 nm, less than about 75 nm, less than about 50 nm, less than about 25 nm, less than about 10 nm, or in some cases, less than about 1 nm.

Examples of a nanostructure can include a nanotube (including a carbon nanotube), a nanowire (including a carbon nanowire), a nanorod, a nanofiber, graphene or a quantum dot, among others. A nanostructure can include a fullerene, for example, a carbon nanotube, a buckyball, a buckytube or a fullerene ring. A nanostructure can also include a nanocrystal. A nanostructure can include a metal, a nonmetal, or semiconductor.

A nanostructure can be a photoluminescent nanostructure, which can exhibit photoluminescence. In some instances, photoluminescent nanostructures can exhibit fluorescence. For example, a photoluminescent nanostructure can emit fluorescence with a wavelength in the near infrared spectrum. In some instances, photoluminescent nanostructures can exhibit phosphorescence. A photoluminescent nanostructure can be a nanotube. A nanotube can be a carbon nanotube. A carbon nanotube can be a single walled carbon nanotube. In some embodiments, a photoluminescent nanostructure can be a semi-conductive single-walled carbon nanotube. Additional examples of photoluminescent nanostructures can include, but are not limited to, double-walled carbon nanotubes, multi-walled carbon nanotubes, semiconductor quantum dots, semi-conductor nanowires, or graphene, among others.

A nanostructure can have a property that can be altered by changes in the environment of the nanostructure. The property can be detectable or observable. The property can also be measurable so that changes in the property can be described or quantified. The property can be photoluminescence, conductivity, polarity, or resonance. Photoluminescence can be fluorescence or phosphorescence. The photoluminescence can be fluorescence with a wavelength within the near infrared spectrum. A property can be an emission wavelength, an emission intensity, a conductance, an electromagnetic absorbance or an emittance.

If the nanostructure is a carbon nanotube, the carbon nanotube can be classified by its chiral vector (n,m), which can indicate the orientation of the carbon hexagons. The orientation of carbon hexagons can affect interactions of the nanotube with other molecules, which in turn, can affect a property of the nanostructure.

A nanostructure can exhibit solvatochromism. Analytes that change the local dielectric constant can change the photoluminescence of the nanostructure. An interaction of an electron-donating or -withdrawing molecule with a nanostructure can alter a property, for example photoluminescence, of the nanostructure. An interaction with a nanostructure can be direct or indirect. Additionally, more than one electron-donating or -withdrawing molecule can interact with a nanostructure and each molecule can alter a property of the nanostructure. A second molecule can also interact with an electron-donating or -withdrawing molecule and change the relationship of the electron-donating or -withdrawing molecule to the nanostructure. This can also alter a nanostructure property. For example, a first molecule can interact with the nanostructure and alter a property (e.g. the photoluminescence) of the nanostructure, and then a second molecule can interact with either the nanostructure or the first molecule and further alter a property (e.g. the photoluminescence) of the nanostructure.

A linker can be associated with the nanostructure. The association can be a bond, for example, a covalent, ionic, van der Waals, dipolar or hydrogen bond. The association can be a physical association. For example, at least a portion of the nanostructure can be embedded in the polymer or a portion of the polymer can encompass the nanostructure.

Figure 13:
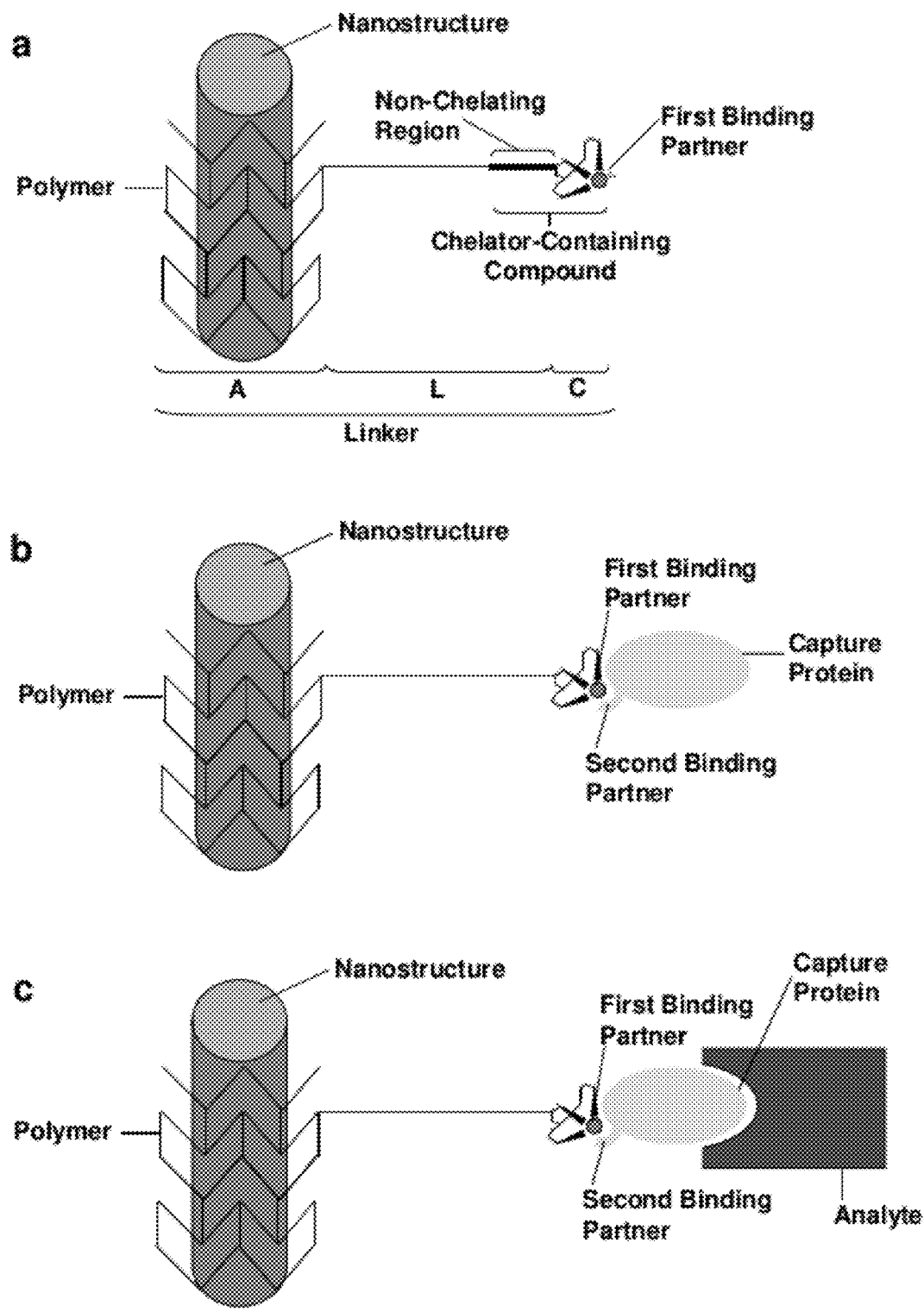
FIG. 13 is a schematic of a composition.
Figure 14:
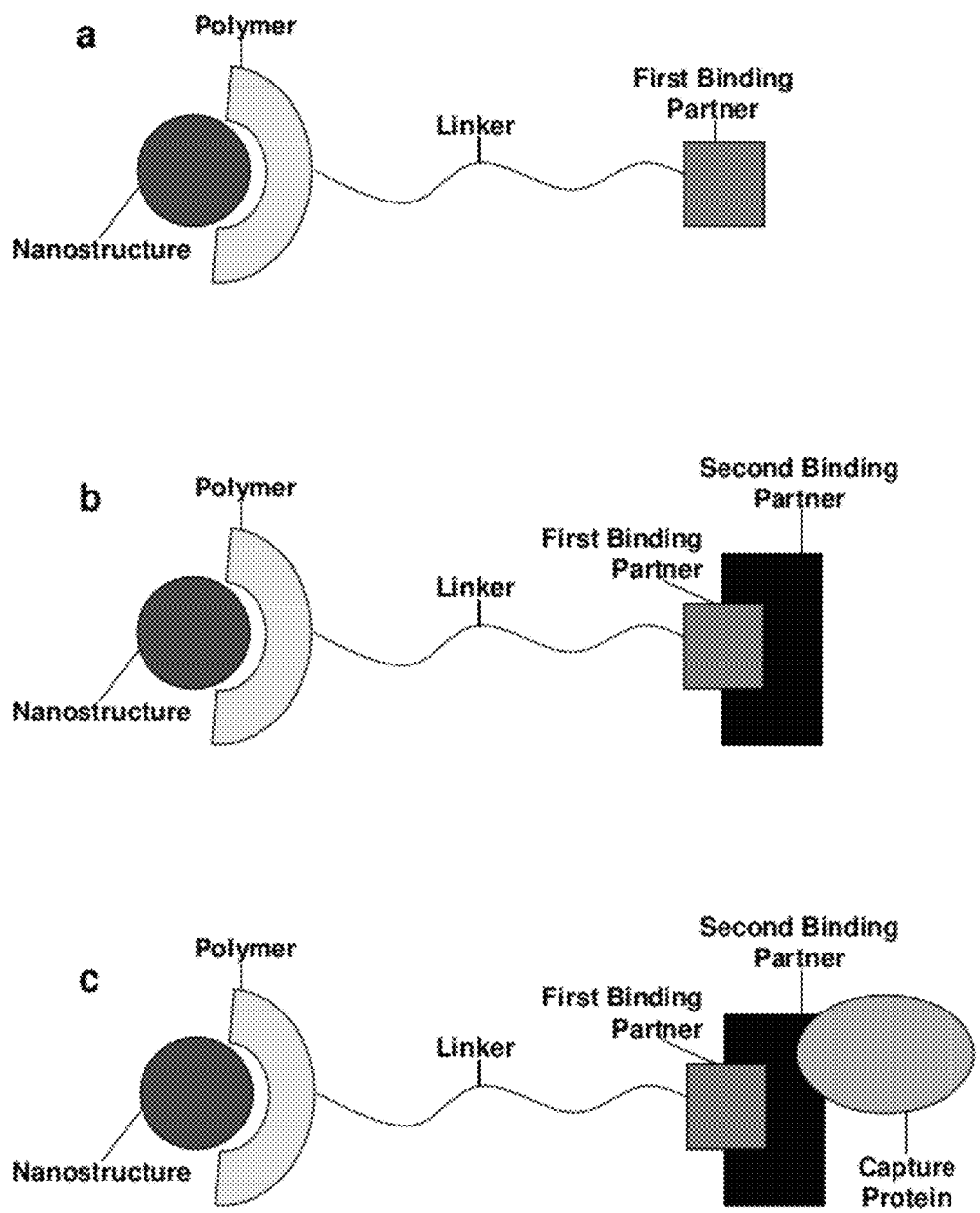
FIG. 14 is a schematic of a composition.
Figure 15:
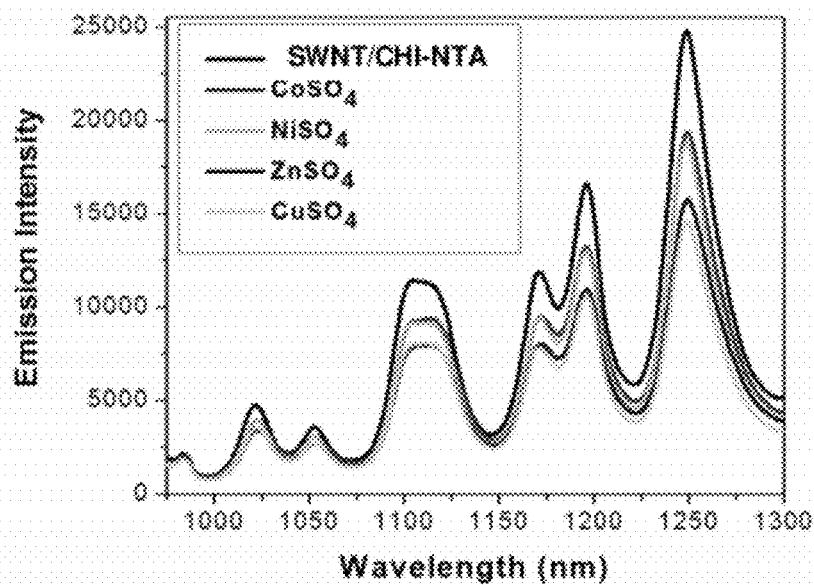
FIG. 15a is a graph showing that copper significantly quenches nIR fluorescence.
FIG. 15b is a bar graph demonstrating that copper is effective for discriminating a protein-protein interaction.
Figure 15:
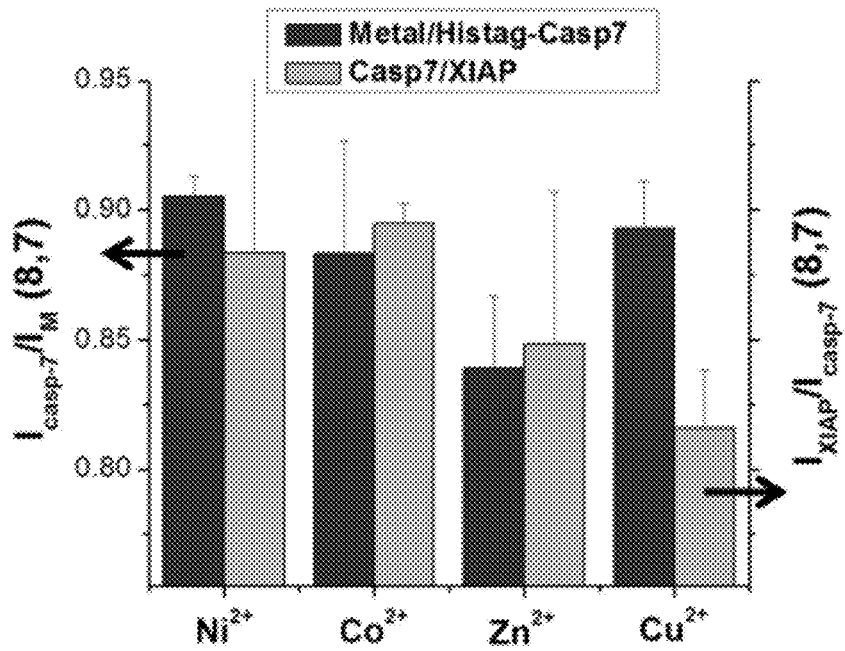

A linker can include a polymer (FIGS. 13 and 14). A polymer can include a polypeptide, a polynucleotide or a polysaccharide. A polysaccharide can include chitosan. A polymer can include a plastic, for example, polystyrene, polyamide, polyvinyl chloride, polyethylene, polyester, polypropylene, polycarbonate, polyacrylamide or polyvinyl alcohol.

A polymer can be biocompatible, which can mean that the polymer is well tolerated by an organism. More specifically, biocompatibility can mean that a polymer does not elicit an immune response when it is brought in contact with an organism. It can also mean that a polymer can integrate into cell structures, cells, tissues or organs of an organism. The organism can be mammal, in particular, a human.

An exemplary polymer can exhibit minimal binding with other molecules. In certain circumstances, a polymer can have a protein adsorption of less than 5 $\mu g/cm^2$, less than 1 $\mu g/cm^2$, less than 0.5 $\mu g/cm^2$, less than 0.1 $\mu g/cm^2$, less than 0.05 $\mu g/cm^2$, or less than 0.01 $\mu g/cm^2$.

The association of a linker with a nanostructure can change a property of the nanostructure. The property can be conductivity, polarity, or resonance. The property can be photoluminescence, including fluorescence or phosphorescence. More specifically, the property can be fluorescence with a wavelength in the near infrared spectrum. The property can be an emission wavelength, an emission intensity, a conductance, an electromagnetic absorbance or an emittance.

A linker can be configured to interact with a capture protein (FIGS. 13b and 14b). A capture protein can include a protein, a polypeptide or a peptide. In some cases, a capture protein can be a complex of proteins. A capture protein can also include a full length protein, a fragment of a protein or a protein domain. A capture protein can be a fusion protein, which can include portions originating from one protein or portions originating from more than one protein. A capture protein can include a protein tag or marker. A capture protein can also be modified, for example, by glycosylation, ubiquitination, PEGylation, SUMOylation or biotinylation. A capture protein can be synthesized from a nucleic acid sequence that was amplified from a cDNA library, genomic DNA, a DNA vector or plasmid, or a DNA fragment.

The interaction between the linker and the capture protein can be binding to a capture protein. The linker can be configured to interact with a capture protein by including a first binding partner in the linker that can interact with the capture protein (FIG. 13a, shown as an ion). The first binding partner can be known binding partner of the capture protein or a portion thereof. The first binding partner can include an ion. The ion can be a metal ion. The metal ion can be a nickel, iron, cadmium, copper, magnesium, calcium, arsenic, lead, mercury or cobalt ion (e.g. $Ni^{2+}$, $Fe^{2+}$, $Cd^{2+}$, $Cu^{2+}$, $Mg^{2+}$, $Ca^{2+}$, $As^{2+}$, $Pb^{2+}$, $Hg^{2+}$ or $Co^{2+}$). The first binding partner can include a protein, a nucleotide, a saccharide, a lipid or combinations thereof.

A linker can further include a chelating region (FIG. 13a). A chelating region can include a chelator, which can be a polydentate ligand capable of forming two or more bonds with a single central atom. A chelator can include one or more carboxylate ions. For example, a linker can include $N_\alpha,N_\alpha$-bis(carboxymethyl)-L-lysine. A chelator can bind to a first binding partner (e.g. a metal ion) in order to incorporate the first binding partner into a linker.

The ion can act a proximity quencher of photoluminescent nanostructure. In particular, the ion can quench near infrared fluorescence. The quenching can be reversible. The quenching can also depend on the distance between the nanostructure and the ion. In other words, as the distance between the nanostructure and the ion changes, the photoluminescence from the nanostructure can also change. Generally, as the distance between the ion and the nanostructure decreases, the amount of photoluminescence quenching can increase.

In some embodiments, the capture protein can include a second binding partner, such that the first binding partner and second binding partner can bind together (FIGS. 13b and 14b). The second binding partner can be an endogenous motif or endogenous domain within a capture protein. Alternatively, the second binding partner can be added to a capture protein. In some embodiments, the second binding partner can be a protein tag. A protein tag can be a peptide sequence grafted onto a protein, which can be used for separating (e.g. using tag affinity techniques), increasing solubility, immobilizing, localizing or detecting a protein. The protein tag can be a histidine tag, chitin binding protein tag, maltose binding protein tag, glutathione-S-transferase tag, c-myc tag, FLAG-tag, V5-tag or HA-tag. One method for adding a second binding partner to a capture protein can include using primers including the sequence encoding for the second binding partner to PCR amplify DNA encoding for the capture protein. A second method can include cloning DNA encoding for the capture protein into an expression vector designed to produce a fusion of the capture protein and the second binding partner.

Binding of a first and a second binding partner can be selective binding, which can provide the selectivity needed to bind to the corresponding binding partner (or relatively small group of related molecules or proteins) in a complex mixture. The degree of binding can be less than 100%, less than 90%, less than 80%, less than 70%, less than 60%, less than 50%, less than 40%, less than 30%, less than 20% or less than 10% of a second binding partner present binding to a first binding partner. The degree of binding can be more than 10%, more than 20%, more than 30%, more than 40%, more than 50%, more than 60%, more than 70%, more than 80% or more than 90% of a second binding partner present binding to a first binding partner. A first binding partner and a second binding partner can bind with a dissociation constant less than 1 mM, less than 0.1 mM, less than 0.01 mM, less than 1 µM, less than 0.1 µM, or less than 0.01 µM. A first binding partner and a second binding partner can bind with a dissociation constant greater than 1 nm, greater than 0.01 µM, greater than 0.1 µM, greater than 1 µM, greater than 0.01 mM, or greater than 0.1 mM.

The linker can also be configured to interact with a capture protein by including a region capable of chemically reacting with the capture protein. The chemical reaction can form a covalent, ionic, van der Waals, dipolar or hydrogen bond between the linker and the capture protein.

The interaction of a capture protein with a linker associated with a nanostructure can change a property of the nanostructure. The property can be conductivity, polarity, or resonance. The property can be photoluminescence, including fluorescence or phosphorescence. The photoluminescence can be fluorescence with a wavelength within the near infrared spectrum. The property can be an emission wavelength, an emission intensity, a conductance, an electromagnetic absorbance or an emittance.

The change in the property can be caused by a change in the distance between an ion in the first binding partner and the nanostructure. As the distance between the nanostructure and the ion changes, a nanostructure property can also change. For example, as the distance between the nanostructure and the ion changes, nanostructure photoluminescence can also change. When the capture protein binds to the linker, the distance between the ion and nanostructure can change, which can alter the nanostructure photoluminescence. Generally, as the distance between the ion and the nanostructure decreases, the amount of photoluminescence quenching can increase.

In some embodiments, a composition can further include a capture protein, which can be configured to specifically interact with at least one analyte (FIGS. 13c and 14c). In particular, the capture protein can be configured to specifically bind to at least one analyte. Specific binding can be more limited than selective binding. Specific binding can be used to distinguish a binding partner from most other chemical species except optical isomers, isotopic variants and perhaps certain structural isomers. The degree of binding can be less than 100%, less than 90%, less than 80%, less than 70%, less than 60%, less than 50%, less than 40%, less than 30%, less than 20% or less than 10% of an analyte present binding to a capture protein. The degree of binding can be more than 10%, more than 20%, more than 30%, more than 40%, more than 50%, more than 60%, more than 70%, more than 80% or more than 90% of an analyte present binding to a capture protein. An analyte and a capture protein can bind with a dissociation constant less than 1 mM, less than 0.1 mM, less than 0.01 mM, less than 1 μM, less than 0.1 μM, or less than 0.01 μM. An analyte and a capture protein can bind with a dissociation constant greater than 1 nm, greater than 0.01 μM, greater than 0.1 μM, greater than 1 μM, greater than 0.01 mM, or greater than 0.1 mM.

The interaction of an analyte with a capture protein that is interacting with a linker associated with a nanostructure can change a property of the nanostructure. The property can be conductivity, polarity, or resonance. The property can be photoluminescence, including fluorescence or phosphorescence. More specifically, the property can be a fluorescent emission within the near infrared spectrum. The property can be an emission wavelength, an emission intensity, a conductance, an electromagnetic absorbance or an emittance.

The interaction of an analyte with a capture protein can be reversible (FIG. 7), meaning that the analyte can bind to the capture protein and then release and be free of binding. The change in a property of the nanostructure due to the interaction of an analyte with a capture protein can also be reversible. For example, the property of a nanostructure can have a first value, the analyte can bind to the capture protein and alter the property to a second value, then the analyte can release from the capture protein and the property can return to the first value.

The analyte can be a small molecule, protein, biomolecule, drug, biologic, or a metabolite thereof. For example, the analyte can be monosaccharide, a polysaccharide, an amino acid, peptide, polypeptide, protein, a nucleotide, an oligonucleotide, a lipid, a polylipid, or a combination thereof. Specifically, the capture protein can be a lectin and the analyte can include a glycan (e.g. the analyte can be a glycoprotein).

A linker can have a formula:

A-L-C, where A can include a polymer, where at least a portion of the nanostructure is embedded in the polymer, L can be a linking moiety including a saturated or unsaturated $C_{4-10}$ hydrocarbon chain optionally containing at least two conjugated double bonds, at least one triple bond, or at least one double bond and one triple bond; said hydrocarbon chain being optionally substituted with $C_{1-4}$ alkyl, $C_{2-4}$ alkenyl, $C_{2-4}$ alkynyl, $C_{1-4}$ alkoxy, hydroxyl, halo, carboxyl, amino, nitro, cyano, $C_{3-6}$ cycloalkyl, 3-6 membered heterocycloalkyl, unsubstituted monocyclic aryl, 5-6 membered heteroaryl, $C_{1-4}$ alkylcarbonyloxy, $C_{1-4}$ alkyloxycarbonyl, $C_{1-4}$ alkylcarbonyl, or formyl and said hydrocarbon chain being optionally interrupted by O, S, $N(R^a)$, C(O), $N(R^a)C(O)O$, $OC(O)N(R^a)$, $N(R^a)C(O)N(R^b)$, C(O)O, or OC(O)O; each of $R^a$ and $R^b$, independently, being hydrogen, alkyl, alkenyl, alkynyl, alkoxy, hydroxylalkyl, hydroxyl, or haloalkyl, or L can be a bond, and C can be a metal ion complexing moiety (FIG. 13a).

The composition can include a chelator-containing compound, which can include a chelator region and a non-chelator region. C can be the chelator region. L can include the non-chelator region (FIG. 13a).

In some circumstances, A can include a polymer $[(M)_x(N)_y(O)_z]_q$, where each of M, N and Q, independently, can be selected from the group consisting of a linear or cyclic $C_3$-$C_8$ hydrocarbyl, heterocyclyl, cyclyl, or aryl including one or more amine, alcohol or carboxylic acid group, where each M-N, M-Q or N-Q can include O, S, $N(R^a)$, C(O), $N(R^a)C(O)O$, $OC(O)N(R^a)$, $N(R^a)C(O)N(R^b)$, C(O)O, or OC(O)O, each of $R^a$ and $R^b$, independently, can be hydrogen, alkyl, alkenyl, alkynyl, alkoxy, hydroxylalkyl, hydroxyl, or haloalkyl, and where each of x, y and z can be integers between 0 and 50, 0 and 20 or 0 and 10 and q can be an integer between 1 and 1000, 5 and 500, or 10 and 100.

In some circumstances, L can have the formula:

$$=X_1-(CR^aR^b)_n-X_2-(CR^aR^b)_o-X_3+$$

where each $X_1$, $X_2$ and $X_3$, can be O, S, $N(R^a)$, C(O), $N(R^a)C(O)O$, $OC(O)N(R^a)$, $N(R^a)C(O)N(R^b)$, C(O)O, or OC(O)O, each of $R^a$ and $R^b$, independently, can be hydrogen, alkyl, alkenyl, alkynyl, alkoxy, hydroxylalkyl, hydroxyl, or haloalkyl, and where the value of n added to o can be 4 to 10.

In some circumstances, C can have the formula, $H_zG((CH_2)_nCO_2H)_y$, and salts thereof, where G can be a bond, C, O, S, P, P=O or N; n is 0-6; and z and y can be selected to satisfy the valence requirements of G. In other preferred embodiments, the compound can have the formula,

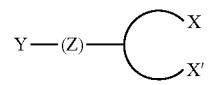

where X and X' can be the same or different and can be metal binding groups including atoms selected from the group of O, S, N, P or O=P, including carboxyl; Y can be bond, C, O, S, P, P=O or N; and Z can be a hydrocarbon having a backbone of one to six atoms, such as an alkyl group or alkenyl group. Each of X and X' can include other substituents in order to satisfy the valence requirements, such as for example, amine, thiol, phosphine or phosphine oxide, substituted by hydrogen or other organic moieties. In addition, the atoms bridging X and X' can be selected to form a 5-membered to 8-membered ring upon coordination to the metal ion. The bridging atoms can typically be carbon, but may be other elements, such as oxygen, nitrogen, or sulfur.

In yet another preferred embodiment, the compound can have the formula,

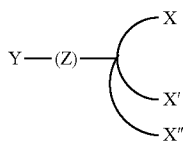

where X, X' and X" can be the same or different and can be metal binding groups including atoms selected from the group of O, S, N, P or O=P, including carboxyl; Y can be a bond, C, O, S, P, P=O or N; and Z can be a hydrocarbon having a backbone of one to six atoms, such as an alkyl group or alkenyl group. Each of X, X' and X" can include other substituents in order to satisfy the valence requirements, such as for example, amine, thiol, phosphine or phosphine oxide, substituted by hydrogen or other organic moieties. In addition, the atoms bridging X and X', X and X" or X' and X" can be selected to form a 5-membered to 8-membered ring upon coordination to the metal ion. The bridging atoms can typically be carbon, but may be other elements, such as oxygen, nitrogen, or sulfur. For example, C can be derived from $HSCH_2CH_2CH(SH)(CH_2)_nCOOH$, $H_2CH_2H_2CH(NH_2)(CH_2)_nCOOH$, $(HOOC(CH_2)_n)HNCH_2CH_2NH((CH_2)_nCOOH)$, $(HOOC(CH_2)_n)_2PCH_2CH_2P((CH_2)_nCOOH)_2$, $(HOOC(CH_2)_n)_2P(O)CH_2CH_2P(O)((CH_2)_nCOOH)_2$, $HSCH_2CH_2CH(SH)(CH_2)_4CONH(CH_2)_nCOOH$, where can is an integer between 1 and 10, or $N_\alpha,N_\alpha$-bis(carboxymethyl)-L-lysine.

In some embodiments, the composition can include a nanostructure and a linker having a formula:

 A-L-C, where A can include the polymer covalently bonded to a portion of the nanostructure, L can be a linking moiety including a saturated or unsaturated $C_{4-10}$ hydrocarbon chain optionally containing at least two conjugated double bonds, at least one triple bond, or at least one double bond and one triple bond; said hydrocarbon chain being optionally substituted with $C_{1-4}$ alkyl, $C_{2-4}$ alkenyl, $C_{2-4}$ alkynyl, $C_{1-4}$ alkoxy, hydroxyl, halo, carboxyl, amino, nitro, cyano, $C_{3-6}$cycloalkyl, 3-6 membered heterocycloalkyl, unsubstituted monocyclic aryl, 5-6 membered heteroaryl, $C_{1-4}$ alkylcarbonyloxy, $C_{1-4}$ alkyloxycarbonyl, $C_{1-4}$ alkylcarbonyl, or formyl and said hydrocarbon chain being optionally interrupted by O, S, $N(R^a)$, C(O), $N(R^a)C(O)O$, $OC(O)N(R^a)$, $N(R^a)C(O)N(R^b)$, C(O)O, or OC(O)O; each of $R^a$ and $R^b$, independently, being hydrogen, alkyl, alkenyl, alkynyl, alkoxy, hydroxylalkyl, hydroxyl, or haloalkyl, or L can be a bond, and C can be a metal ion complexing moiety (FIG. 13a).

The composition can include a chelator-containing compound, which can include a chelator region and a non-chelator region. C can be the chelator region. L can include the non-chelator region (FIG. 13a).

In some circumstances, A can include a polymer $[(M)_x(N)_y(O)_z]_q$, where each of M, N and Q, independently, can be selected from the group consisting of a linear or cyclic $C_3-C_8$ hydrocarbyl, heterocyclyl, cyclyl, or aryl including one or more amine, alcohol or carboxylic acid group, where each M-N, M-Q or N-Q can include O, S, $N(R^a)$, C(O), $N(R^a)C(O)O$, $OC(O)N(R^a)$, $N(R^a)C(O)N(R^b)$, C(O)O, or OC(O)O, each of $R^a$ and $R^b$, independently, can be hydrogen, alkyl, alkenyl, alkynyl, alkoxy, hydroxylalkyl, hydroxyl, or haloalkyl, and where each of x, y and z can be integers between 0 and 50, 0 and 20 or 0 and 10 and q can be an integer between 1 and 1000, 5 and 500, or 10 and 100.

In some circumstances, L can have the formula:

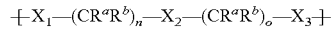 $+X_1-(CR^aR^b)_n-X_2-(CR^aR^b)_o-X_3+$ where each $X_1$, $X_2$ and $X_3$, can be O, S, $N(R^a)$, C(O), $N(R^a)C(O)O$, $OC(O)N(R^a)$, $N(R^a)C(O)N(R^b)$, C(O)O, or OC(O)O, each of $R^a$ and $R^b$, independently, can be hydrogen, alkyl, alkenyl, alkynyl, alkoxy, hydroxylalkyl, hydroxyl, or haloalkyl, and where the value of n added to o can be 4 to 10.

In some circumstances, C can have the formula, $H_zG((CH_2)_nCO_2H)_y$, and salts thereof, where G can be a bond, C, O, S, P, P=O or N; n is 0-6; and z and y can be selected to satisfy the valence requirements of G. In other preferred embodiments, the compound can have the formula,

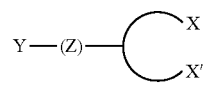

where X and X' can be the same or different and can be metal binding groups including atoms selected from the group of O, S, N, P or O=P, including carboxyl; Y can be bond, C, O, S, P, P=O or N; and Z can be a hydrocarbon having a backbone of one to six atoms, such as an alkyl group or alkenyl group. Each of X and X' can include other substituents in order to satisfy the valence requirements, such as for example, amine, thiol, phosphine or phosphine oxide, substituted by hydrogen or other organic moieties. In addition, the atoms bridging X and X' can be selected to form a 5-membered to 8-membered ring upon coordination to the metal ion. The bridging atoms can typically be carbon, but may be other elements, such as oxygen, nitrogen, or sulfur.

In yet another preferred embodiment, the compound can have the formula,

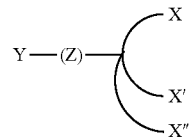

where X, X' and X" can be the same or different and can be metal binding groups including atoms selected from the group of O, S, N, P or O=P, including carboxyl; Y can be a bond, C, O, S, P, P=O or N; and Z can be a hydrocarbon having a backbone of one to six atoms, such as an alkyl group or alkenyl group. Each of X, X' and X" can include other substituents in order to satisfy the valence requirements, such as for example, amine, thiol, phosphine or phosphine oxide, substituted by hydrogen or other organic moieties. In addition, the atoms bridging X and X', X and X" or X' and X" can be selected to form a 5-membered to 8-membered ring upon coordination to the metal ion. The bridging atoms can typically be carbon, but may be other elements, such as oxygen, nitrogen, or sulfur. For example, C can be derived from $HSCH_2CH_2CH(SH)(CH_2)_nCOOH$, $H_2CH_2H_2CH(NH_2)(CH_2)_nCOOH$, $(HOOC(CH_2)_n)$ $HNCH_2CH_2NH((CH_2)_nCOOH)$, $(HOOC(CH_2)_n)_2$ $PCH_2CH_2P((CH_2)_n\ COOH)_2$, $(HOOC(CH_2)_n)_2P(O)$ $CH_2CH_2P(O)((CH_2)_nCOOH)_2$, $HSCH_2CH_2CH(SH)(CH_2)_4$ $CONH(CH_2)_nCOOH$, where can is an integer between 1 and 10, or $N_\alpha,N_\alpha$-bis(carboxymethyl)-L-lysine.

Compounds can be prepared according to published procedures such as those described, for example, in Parameswara et al., Synthesis, 815-818 (1980) and Denny et al., J. Org. Chem., 27, 3404 (1962).

In another aspect, an array can include a plurality of analysis regions on a substrate (FIG. 1b). A substrate can be glass or plastic.

An analysis region can be a divot, a tube, a tray, a well or a similar compartment for suitable for containing a liquid sample. In some cases, an analysis region can include a droplet or spot on the surface of a substrate. In those cases, an analysis region can be formed by spotting the composition on a substrate. A plurality of analysis regions can be in a pattern on a substrate. A pattern can include concentric circles, a spiral, a row, a column or a grid.

In some embodiments, the plurality of analysis regions can include two or more subsets of analysis regions. For example, a first subset of analysis regions can differ from a second subset of analysis regions by including a different nanostructure, a different linker, a different binding partner, a different capture protein, a different analyte or a different sample. Additionally, a first subset of analysis regions can differ from a second subset of analysis regions by including a different environmental factor including a buffer, a reagent, a nutrient, a serum, an exposure to light, an oxygen concentration, a temperature or a pH.

At least one analysis region can include a composition (FIGS. 1a and 1b). A composition can include a nanostructure and a linker. A nanostructure can be an article having at least one cross-sectional dimension between opposed boundaries of less than about 1 micron. In some embodiments, a nanostructure can have at least one cross-sectional dimension between opposed boundaries of less than about 500 nm, less than about 250 nm, less than about 100 nm, less than about 75 nm, less than about 50 nm, less than about 25 nm, less than about 10 nm, or in some cases, less than about 1 nm.

Examples of a nanostructure can include a nanotube (including a carbon nanotube), a nanowire (including a carbon nanowire), a nanorod, a nanofiber, graphene or a quantum dot, among others. A nanostructure can include a fullerene, for example, a carbon nanotube, a buckyball, a buckytube or a fullerene ring. A nanostructure can also include a nanocrystal. A nanostructure can include a metal, a nonmetal, or semiconductor.

A nanostructure can be a photoluminescent nanostructure, which can exhibit photoluminescence. In some instances, photoluminescent nanostructures can exhibit fluorescence. For example, a photoluminescent nanostructure can emit fluorescence with a wavelength in the near infrared spectrum. In some instances, photoluminescent nanostructures can exhibit phosphorescence. A photoluminescent nanostructure can be a nanotube. A nanotube can be a carbon nanotube. A carbon nanotube can be a single walled carbon nanotube. In some embodiments, a photoluminescent nanostructure can be a semi-conductive single-walled carbon nanotube. Additional examples of photoluminescent nanostructures can include, but are not limited to, double-walled carbon nanotubes, multi-walled carbon nanotubes, semi-conductor quantum dots, semi-conductor nanowires, or graphene, among others.

A nanostructure can have a property that can be altered by changes in the environment of the nanostructure. The property can be detectable or observable. The property can also be measurable so that changes in the property can be described or quantified. The property can be photoluminescence, conductivity, polarity, or resonance. Photoluminescence can be fluorescence or phosphorescence. The photoluminescence can be fluorescence with a wavelength within the near infrared spectrum. The property can be an emission wavelength, an emission intensity, a conductance, an electromagnetic absorbance or an emittance.

If the nanostructure is a carbon nanotube, the carbon nanotube can be classified by its chiral vector (n,m), which can indicate the orientation of the carbon hexagons. The orientation of carbon hexagons can affect interactions of the nanotube with other molecules, which in turn, can affect a property of the nanostructure.

A nanostructure can exhibit solvatochromism. Analytes that change the local dielectric constant can change the photoluminescence of the nanostructure. An interaction of an electron-donating or -withdrawing molecule with a nanostructure can alter a property, for example photoluminescence, of the nanostructure. An interaction with a nanostructure can be direct or indirect. Additionally, more than one electron-donating or -withdrawing molecule can interact with a nanostructure and each molecule can alter a property of the nanostructure. A second molecule can also interact with an electron-donating or -withdrawing molecule and change the relationship of the electron-donating or -withdrawing molecule to the nanostructure. This can also alter a nanostructure property. For example, a first molecule can interact with the nanostructure and alter a property (e.g. the photoluminescence) of the nanostructure, and then a second molecule can interact with either the nanostructure or the first molecule and further alter a property (e.g. the photoluminescence) of the nanostructure.

A linker can be associated with the nanostructure. The association can be a bond, for example, a covalent, ionic, van der Waals, dipolar or hydrogen bond. The association can be a physical association. For example, at least a portion of the nanostructure can be embedded in the polymer or a portion of the polymer can encompass the nanostructure.

A linker can include a polymer (FIGS. 13 and 14). The polymer can include a polypeptide, a polynucleotide or a polysaccharide. The polysaccharide can include chitosan. The polymer can include a plastic, for example, polystyrene, polyamide, polyvinyl chloride, polyethylene, polyester, polypropylene, polycarbonate, polyacrylamide or polyvinyl alcohol.

A polymer can be biocompatible, which can mean that the polymer is well tolerated by an organism. More specifically, biocompatibility can mean that a polymer does not elicit an immune response when it is brought in contact with an organism. It can also mean that a polymer can integrate into cell structures, cells, tissues or organs of an organism. The organism can be mammal, in particular, a human.

An exemplary polymer can exhibit minimal binding with other molecules. In certain circumstances, a polymer can have a protein adsorption of less than 5 $\mu g/cm^2$, less than 1 $\mu g/cm^2$, less than 0.5 $\mu g/cm^2$, less than 0.1 $\mu g/cm^2$, less than 0.05 $\mu g/cm^2$, or less than 0.01 $\mu g/cm^2$.

The association of a linker with a nanostructure can change a property of the nanostructure. The property can be conductivity, polarity, or resonance. The property can be photoluminescence, including fluorescence or phosphorescence. The photoluminescence can be fluorescence with a wavelength within the near infrared spectrum. The property can be an emission wavelength, an emission intensity, a conductance, an electromagnetic absorbance or an emittance.

A linker can be configured to interact with a capture protein (FIGS. 13b and 14b). A capture protein can include a protein, a polypeptide or a peptide. In some cases, a capture protein can be a complex of proteins. A capture protein can also include a full length protein, a fragment of a protein or a protein domain. A capture protein can be a fusion protein, which can include portions originating from one protein or portions originating from more than one protein. A capture protein can include a protein tag or marker. A capture protein can also be modified, for example, by glycosylation, ubiquitination, PEGylation, SUMOylation or biotinylation. A capture protein can be synthesized from a nucleic acid sequence that was amplified from a cDNA library, genomic DNA, a DNA vector or plasmid, or a DNA fragment.

The number of linkers associated with the nanostructure present in the analysis region can exceed the number of capture proteins. More specifically, the number of capture protein binding sites on linkers associated with a nanostructure can exceed the number of capture proteins. The ratio of capture protein binding sites on linkers associated with a nanostructure to capture proteins can be greater than 1.1 to 1, greater than 1.5 to 1, greater than 2 to 1, greater than 5 to 1, or greater than 10 to 1. Having an excess of capture protein binding sites on linkers associated with a nanostructure can minimize the amount of unbound capture protein in a sample. Unbound capture proteins within the sample can compete with capture proteins bound to the composition for binding to the analyte. This can affect the accuracy and/or precision of the analyte detection. Having an excess of capture protein binding sites on linkers associated with a nanostructure can also increase the analyte concentration range over which analyte can be accurately detected because the saturation limit of the binding sites is increased.

The interaction between the linker and the capture protein can be binding to a capture protein. The linker can be configured to interact with a capture protein by including a first binding partner in the linker that can interact with the capture protein (FIG. 13, shown as an ion). The first binding partner can be known binding partner of the capture protein or a portion thereof. The first binding partner can include an ion. The ion can be a metal ion. The metal ion can be nickel, iron, cadmium, copper, magnesium, calcium, arsenic, lead, mercury or cobalt (e.g. $Ni^{2+}$, $Fe^{2+}$, $Cd^{2+}$, $Cu^{2+}$, $Mg^{2+}$, $Ca^{2+}$, $As^{2+}$, $Pb^{2+}$, $Hg^{2+}$ or $Co^{2+}$). The first binding partner can include a protein, a nucleotide, a saccharide, a lipid or combinations thereof.

A linker can further include a chelating region (FIG. 13). A chelating region can include a chelator, which can be a polydentate ligand capable of forming two or more bonds with a single central atom. A chelator can include one or more carboxylate ions. For example, a linker can include $N_\alpha,N_\alpha$-bis(carboxymethyl)-L-lysine. A chelator can bind to a first binding partner (e.g. a metal ion) in order to incorporate the first binding partner into a linker.

The ion can act a proximity quencher of photoluminescent nanostructure. In particular, the ion can quench near infrared fluorescence. The quenching can be reversible. The quenching can also depend on the distance between the nanostructure and the ion. In other words, as the distance between the nanostructure and the ion changes, the photoluminescence from the nanostructure can also change. Generally, as the distance between the ion and the nanostructure decreases, the amount of photoluminescence quenching can increase.

In some embodiments, the capture protein can include a second binding partner, such that the first binding partner and second binding partner can bind together (FIGS. 13b and 14b). The second binding partner can be an endogenous motif or endogenous domain within a capture protein. Alternatively, the second binding partner can be added to a capture protein. In some embodiments, the second binding partner can be a protein tag. A protein tag can be a peptide sequence grafted onto a protein. The protein tag can be a histidine tag, chitin binding protein tag, maltose binding protein tag, glutathione-S-transferase tag, c-myc tag, FLAG-tag, V5-tag or HA-tag. One method for adding a second binding partner to a capture protein can include using primers including the sequence encoding for the second binding partner to PCR amplify DNA encoding for the capture protein. A second method can include cloning DNA encoding for the capture protein into an expression vector designed to produce a fusion of the capture protein and the second binding partner.

Binding of a first and a second binding partner can be selective binding, which can provide the selectivity needed to detect a given analyte (or relatively small group of related analytes) in a complex mixture. The degree of binding can be less than 100%, less than 90%, less than 80%, less than 70%, less than 60%, less than 50%, less than 40%, less than 30%, less than 20% or less than 10% of a second binding partner present binding to a first binding partner. The degree of binding can be more than 10%, more than 20%, more than 30%, more than 40%, more than 50%, more than 60%, more than 70%, more than 80% or more than 90% of a second binding partner present binding to a first binding partner. A first binding partner and a second binding partner can bind with a dissociation constant less than 1 mM, less than 0.1 mM, less than 0.01 mM, less than 1 µM, less than 0.1 µM, or less than 0.01 µM. A first binding partner and a second binding partner can bind with a dissociation constant greater than 1 nm, greater than 0.01 µM, greater than 0.1 µM, greater than 1 µM, greater than 0.01 mM, or greater than 0.1 mM.

The linker can also be configured to interact with a capture protein by including a region capable of chemically reacting with the capture protein. The chemical reaction can form a covalent, ionic, van der Waals, dipolar or hydrogen bond between the linker and the capture protein.

The interaction of a capture protein with a linker associated with a nanostructure can change a property of the nanostructure. The property can be conductivity, polarity, or resonance. The property can be photoluminescence, including fluorescence or phosphorescence. The photoluminescence can be fluorescence with a wavelength within the near infrared spectrum. The property can be an emission wavelength, an emission intensity, a conductance, an electromagnetic absorbance or an emittance.

The change in the property can be caused by a change in the distance between an ion in the first binding partner and the nanostructure. As the distance between the nanostructure and the ion changes, a nanostructure property can also change. For example, as the distance between the nanostructure and the ion changes, nanostructure photoluminescence can also change. When the capture protein binds to the linker, the distance between the ion and nanostructure can change, which can alter the nanostructure photoluminescence. Generally, as the distance between the ion and the nanostructure decreases, the amount of photoluminescence quenching can increase.

Capture proteins can be synthesized in situ by performing in vitro transcription followed by in vitro translation in an analysis region. In vitro transcription can produce RNA encoding for a capture protein from the DNA sequence encoding for the capture protein. DNA encoding for a capture protein can be added to an analysis region. An in vitro transcription reaction mixture can also be added to an analysis region. The in vitro transcription reaction mixture can include nucleic acids, RNA polymerase, cell extract, salts or buffers.

A first subset of analysis regions can differ from a second subset of analysis regions by the DNA present in each. For example, different pairs of primers can be used to PCR amplify different DNA sequences from a cDNA library. A second set of primers that can overlap a portion of the sequence of the first set of primers can be used to add transcription and/or translation regulatory elements to the amplified DNA. The amplified DNA can be added to an analysis region. A first subset of analysis regions can include a first DNA sequence encoding for a first capture protein. A second subset of analysis regions can include a second DNA sequence encoding for a second capture protein, and an Nth subset of analysis regions can include an Nth DNA sequence encoding for an Nth capture protein. N can be an integer between 1 and 10.

In some embodiments, at least one analysis region can further include a ribosome and the composition of the at least one analysis region can further include a capture protein (FIG. 1a). The capture protein can be configured to specifically interact with at least one analyte. In vitro translation can produce a capture protein from an RNA sequence encoding for the capture protein. An RNA sequence can be in vitro transcribed within an analysis region from a DNA sequence. A ribosome can then translate the RNA into a protein, for example, the capture protein. A ribosome can include ribosomal RNA and ribosomal proteins. The ribosome can be a component of a cellular extract, for example S30 extract. The ribosome can be added to the analysis region as part of an in vitro translation reaction mixture. Other components of an in vitro translation reaction mixture can include amino acids, cell extract, tRNA, salts or buffers. The in vitro translation reaction mixture can be used to synthesize the capture protein in situ.

A first subset of analysis regions can differ from a second subset of analysis regions by the RNA present in each. For example, a first subset of analysis regions can include a first RNA sequence encoding for a first capture protein. A second subset of analysis regions can include a second RNA sequence encoding for a second capture protein, and an Nth subset of analysis regions can include an Nth RNA sequence encoding for an Nth capture protein. N can be an integer between 1 and 10.

Additionally, a first subset of analysis regions can differ from a second subset of analysis regions by the capture protein within the analysis regions. A first subset of analysis regions can include a first composition, which can include first capture protein. A second subset of analysis regions can include a second composition, which can include a second capture protein, and an Nth subset of analysis regions can include an Nth composition which can include an Nth capture protein. N can be an integer between 1 and 5000. Changing the capture proteins can allow experiments involving an analyte with multiple natural binding partners or different analytes to take place at the same time. It can also allow for the development of a capture protein library against which an analyte can be tested for binding.

In situ synthesis of capture proteins can allow for the capture proteins to interact with a linker shortly after being synthesized. This can, in turn, allow for the capture proteins to be directly immobilized in the analysis region. An advantage of in situ synthesis can be the elimination of purification steps required by other techniques. Elimination of purification steps can be beneficial for proteins that are difficult to purify, aggregate during purification, or produce a low yield following purification.

In some embodiments, a composition can further include a capture protein, which can be configured to specifically interact with at least one analyte (FIGS. 13c and 14c). In particular, the capture protein can be configured to specifically bind to at least one analyte. Specific binding can describe a more limited than selective binding. Specific binding can be used to distinguish a binding partner from most other chemical species except optical isomers, isotopic variants and perhaps certain structural isomers. The degree of binding can be less than 100%, less than 90%, less than 80%, less than 70%, less than 60%, less than 50%, less than 40%, less than 30%, less than 20% or less than 10% of an analyte present binding to a capture protein. The degree of binding can be more than 10%, more than 20%, more than 30%, more than 40%, more than 50%, more than 60%, more than 70%, more than 80% or more than 90% of an analyte present binding to a capture protein. An analyte and a capture protein can bind with a dissociation constant less than 1 mM, less than 0.1 mM, less than 0.01 mM, less than 1 µM, less than 0.1 µM, or less than 0.01 µM. An analyte and a capture protein can bind with a dissociation constant greater than 1 nm, greater than 0.01 µM, greater than 0.1 µM, greater than 1 µM, greater than 0.01 mM, or greater than 0.1 mM.

The interaction of an analyte with a capture protein that is interacting with a linker associated with a nanostructure can change a property of the nanostructure. The property can be conductivity, polarity, or resonance. The property can be photoluminescence, including fluorescence or phosphorescence. The property can be an emission wavelength, an emission intensity, a conductance, an electromagnetic absorbance or an emittance.

The interaction of an analyte with a capture protein can be reversible (FIG. 7), meaning that the analyte can bind to the capture protein and then release and be free of binding. The change in a property of the nanostructure due to the interaction of an analyte with a capture protein can also be reversible. For example, the property of a nanostructure can have a first value, the analyte can bind to the capture protein and alter the property to a second value, then the analyte can release from the capture protein and the property can return to the first value.

In some embodiments, at least one analysis region can further include a sample. The sample can include a gas, a liquid or a solid. In other embodiments, the sample can be a biological fluid or cell lysate. The sample can include an analyte. The analyte can be a small molecule, protein, biomolecule, drug, biologic, or a metabolite thereof. For example, the analyte can be monosaccharide, a polysaccharide, an amino acid, peptide, polypeptide, protein, a nucleotide, an oligonucleotide, a lipid, a polylipid, or a combination thereof. Specifically, the capture protein can be a lectin and the analyte can include a glycan (e.g. the analyte can be a glycoprotein).

The number of capture proteins interacting with the composition can exceed the number of analyte molecules present in a sample. More specifically, the number of analyte binding sites on capture proteins interacting with the composition can exceed the number of analyte molecules present in a sample. The ratio of analyte binding sites on capture proteins interacting with the composition to analyte can be greater than 1.1 to 1, greater than 1.5 to 1, greater than 2 to 1, greater than 5 to 1, or greater than 10 to 1. The number of binding sites on capture proteins interacting with the composition can limit detection of analyte if the number of analyte molecules is about or exceeds the number binding sites. Because detection of the analyte can be dependent on a change in a property of a nanostructure due to analyte binding, if a binding site is not available for the analyte, the analyte cannot bind and change a property of the nanostructure, and consequently, can go undetected. In other words, when the composition is saturated with analyte, unbound analyte can go undetected.

A first subset of analysis regions can differ from a second subset of analysis regions by the sample within the analysis regions. A first subset of analysis regions can include a first sample. A second subset of analysis regions can include a second sample, and an Nth subset of analysis regions can include an Nth sample. N can be an integer between 1 and 5000. Changing the samples can allow experiments involving one analyte present in different samples or two or more analytes each present in a different sample. For example, a first sample can include a first analyte and a second sample can include a second analyte. Said another way, an Nth subset of analysis regions can include an Nth sample which can include an Nth analyte, where N can be an integer between 1 and 5000. Alternatively, a first sample can include a first analyte and a second sample can include a first analyte. In other words, an Nth subset of analysis regions can include an Nth sample which can include first analyte, where N can be an integer between 1 and 10.

A linker can have a formula:

A-L-C, where A can include a polymer, where at least a portion of the nanostructure is embedded in the polymer,
L can be a linking moiety including a saturated or unsaturated $C_{4-10}$ hydrocarbon chain optionally containing at least two conjugated double bonds, at least one triple bond, or at least one double bond and one triple bond; said hydrocarbon chain being optionally substituted with $C_{1-4}$ alkyl, $C_{2-4}$ alkenyl, $C_{2-4}$ alkynyl, $C_{1-4}$ alkoxy, hydroxyl, halo, carboxyl, amino, nitro, cyano, $C_{3-6}$ cycloalkyl, 3-6 membered heterocycloalkyl, unsubstituted monocyclic aryl, 5-6 membered heteroaryl, $C_{1-4}$ alkylcarbonyloxy, $C_{1-4}$ alkyloxycarbonyl, $C_{1-4}$ alkylcarbonyl, or formyl and said hydrocarbon chain being optionally interrupted by O, S, N($R^a$), C(O), N($R^a$)C(O)O, OC(O)N($R^a$), N($R^a$)C(O)N($R^b$), C(O)O, or OC(O)O; each of $R^a$ and $R^b$, independently, being hydrogen, alkyl, alkenyl, alkynyl, alkoxy, hydroxylalkyl, hydroxyl, or haloalkyl, or L can be a bond, and C can be a metal ion complexing moiety.

The composition can include a chelator-containing compound, which can include a chelator region and a non-chelator region. C can be the chelator region. L can include the non-chelator region (FIG. 13a).

In some circumstances, A can include a polymer $[(M)_x(N)_y(O)_z]_q$, where each of M, N and Q, independently, can be selected from the group consisting of a linear or cyclic $C_3$-$C_8$ hydrocarbyl, heterocyclyl, cyclyl, or aryl including one or more amine, alcohol or carboxylic acid group, where each M-N, M-Q or N-Q can include O, S, N($R^a$), C(O), N($R^a$)C(O)O, OC(O)N($R^a$), N($R^a$)C(O)N($R^b$), C(O)O, or OC(O)O, each of $R^a$ and $R^b$, independently, can be hydrogen, alkyl, alkenyl, alkynyl, alkoxy, hydroxylalkyl, hydroxyl, or haloalkyl, and where each of x, y and z can be integers between 0 and 50, 0 and 20 or 0 and 10 and q can be an integer between 1 and 1000, 5 and 500, or 10 and 100.

In some circumstances, L can have the formula:

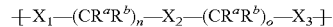

where each $X_1$, $X_2$ and $X_3$, can be O, S, N($R^a$), C(O), N($R^a$)C(O)O, OC(O)N($R^a$), N($R^a$)C(O)N($R^b$), C(O)O, or OC(O)O, each of $R^a$ and $R^b$, independently, can be hydrogen, alkyl, alkenyl, alkynyl, alkoxy, hydroxylalkyl, hydroxyl, or haloalkyl, and where the value of n added to o can be 4 to 10.

In some circumstances, C can have the formula, $H_zG((CH_2)_nCO_2H)_y$ and salts thereof, where G can be a bond, C, O, S, P, P=O or N; n is 0-6; and z and y can be selected to satisfy the valence requirements of G. In other preferred embodiments, the compound can have the formula,

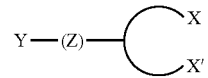

where X and X' can be the same or different and can be metal binding groups including atoms selected from the group of O, S, N, P or O=P, including carboxyl; Y can be bond, C, O, S, P, P=O or N; and Z can be a hydrocarbon having a backbone of one to six atoms, such as an alkyl group or alkenyl group. Each of X and X' can include other substituents in order to satisfy the valence requirements, such as for example, amine, thiol, phosphine or phosphine oxide, substituted by hydrogen or other organic moieties. In addition, the atoms bridging X and X' can be selected to form a 5-membered to 8-membered ring upon coordination to the metal ion. The bridging atoms can typically be carbon, but may be other elements, such as oxygen, nitrogen, or sulfur.

In yet another preferred embodiment, the compound can have the formula,

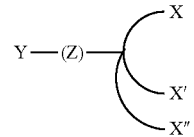

where X, X' and X" can be the same or different and can be metal binding groups including atoms selected from the group of O, S, N, P or O=P, including carboxyl; Y can be a bond, C, O, S, P, P=O or N; and Z can be a hydrocarbon having a backbone of one to six atoms, such as an alkyl group or alkenyl group. Each of X, X' and X" can include other substituents in order to satisfy the valence requirements, such as for example, amine, thiol, phosphine or phosphine oxide, substituted by hydrogen or other organic moieties. In addition, the atoms bridging X and X', X and X" or X' and X" can be selected to form a 5-membered to 8-membered ring upon coordination to the metal ion. The bridging atoms can typically be carbon, but may be other elements, such as oxygen, nitrogen, or sulfur. For example, C can be derived from $HSCH_2CH_2CH(SH)(CH_2)_nCOOH$, $H_2CH_2H_2CH(NH_2)(CH_2)_nCOOH$, $(HOOC(CH_2)_n)$ $HNCH_2CH_2NH((CH_2)_nCOOH)$, $(HOOC(CH_2)_n)_2$ $PCH_2CH_2P((CH_2)_n COOH)_2$, $(HOOC(CH_2)_n)_2P(O)$ $CH_2CH_2P(O)((CH_2)_n COOH)_2$, $HSCH_2CH_2CH(SH)(CH_2)_4CONH(CH_2)_nCOOH$, where can is an integer between 1 and 10, or $N_\alpha,N_\alpha$-bis(carboxymethyl)-L-lysine.

In another aspect, a method for detecting protein binding can include providing a composition. The composition can include a nanostructure and a linker.

A nanostructure can be an article having at least one cross-sectional dimension between opposed boundaries of less than about 1 micron. In some embodiments, a nanostructure can have at least one cross-sectional dimension between opposed boundaries of less than about 500 nm, less than about 250 nm, less than about 100 nm, less than about 75 nm, less than about 50 nm, less than about 25 nm, less than about 10 nm, or in some cases, less than about 1 nm.

Examples of a nanostructure can include a nanotube (including a carbon nanotube), a nanowire (including a carbon nanowire), a nanorod, a nanofiber, graphene or a quantum dot, among others. A nanostructure can include a fullerene, for example, a carbon nanotube, a buckyball, a buckytube or a fullerene ring. A nanostructure can also include a nanocrystal. A nanostructure can include a metal, a nonmetal, or semiconductor.

A nanostructure can be a photoluminescent nanostructure, which can exhibit photoluminescence. In some instances, photoluminescent nanostructures can exhibit fluorescence. For example, a photoluminescent nanostructure can emit fluorescence with a wavelength in the near infrared spectrum. In some instances, photoluminescent nanostructures can exhibit phosphorescence. A photoluminescent nanostructure can be a nanotube. A nanotube can be a carbon nanotube. A carbon nanotube can be a single walled carbon nanotube. In some embodiments, a photoluminescent nanostructure can be a semi-conductive single-walled carbon nanotube. Additional examples of photoluminescent nanostructures can include, but are not limited to, double-walled carbon nanotubes, multi-walled carbon nanotubes, semi-conductor quantum dots, semi-conductor nanowires, or graphene, among others.

A nanostructure can have a property that can be altered by changes in the environment of the nanostructure. The property can be detectable or observable. The property can also be measurable so that changes in the property can be described or quantified. The property can be photoluminescence, conductivity, polarity, or resonance. Photoluminescence can be fluorescence or phosphorescence. The photoluminescence can be fluorescence with a wavelength within the near infrared spectrum. The property can be an emission wavelength, an emission intensity, a conductance, an electromagnetic absorbance or an emittance.

If the nanostructure is a carbon nanotube, the carbon nanotube can be classified by its chiral vector (n,m), which can indicate the orientation of the carbon hexagons. The orientation of carbon hexagons can affect interactions of the nanotube with other molecules, which in turn, can affect a property of the nanostructure.

A nanostructure can exhibit solvatochromism. Analytes that change the local dielectric constant can change the photoluminescence of the nanostructure. An interaction of an electron-donating or -withdrawing molecule with a nanostructure can alter a property, for example photoluminescence, of the nanostructure. An interaction with a nanostructure can be direct or indirect. Additionally, more than one electron-donating or -withdrawing molecule can interact with a nanostructure and each molecule can alter a property of the nanostructure. A second molecule can also interact with an electron-donating or -withdrawing molecule and change the relationship of the electron-donating or -withdrawing molecule to the nanostructure. This can also alter a nanostructure property. For example, a first molecule can interact with the nanostructure and alter a property (e.g. the photoluminescence) of the nanostructure, and then a second molecule can interact with either the nanostructure or the first molecule and further alter a property (e.g. the photoluminescence) of the nanostructure.

A linker can be associated with the nanostructure. The association can be a bond, for example, a covalent, ionic, van der Waals, dipolar or hydrogen bond. The association can be a physical association. For example, at least a portion of the nanostructure can be embedded in the polymer or a portion of the polymer can encompass the nanostructure.

The association of a linker with a nanostructure can change a property of the nanostructure. The property can be conductivity, polarity, or resonance. The property can be photoluminescence, including fluorescence or phosphorescence. More specifically, the property can be fluorescence with a wavelength in the near infrared spectrum. The property can be an emission wavelength, an emission intensity, a conductance, an electromagnetic absorbance or an emittance.

A linker can include a polymer (FIGS. 13 and 14). The polymer can include a polypeptide, a polynucleotide or a polysaccharide. The polysaccharide can include chitosan. The polymer can include a plastic, for example, polystyrene, polyamide, polyvinyl chloride, polyethylene, polyester, polypropylene, polycarbonate, polyacrylamide or polyvinyl alcohol.

A polymer can be biocompatible, which can mean that the polymer is well tolerated by an organism. More specifically, biocompatibility can mean that a polymer does not elicit an immune response when it is brought in contact with an organism. It can also mean that a polymer can integrate into cell structures, cells, tissues or organs of an organism. The organism can be mammal, in particular, a human.

An exemplary polymer can exhibit minimal binding with other molecules. In certain circumstances, a polymer can have a protein adsorption of less than 5 µg/cm², less than 1 µg/cm², less than 0.5 µg/cm², less than 0.1 µg/cm², less than 0.05 µg/cm², or less than 0.01 µg/cm².

Providing a composition can include making the composition or obtaining the composition. Making the composition can include creating the nanostructure and/or the linker or obtaining the nanostructure and/or the linker. Making the composition can include sonicating a solution including a nanostructure and a linker. The solution can be chilled during sonication, for example, the solution can be put on ice. Making the composition can also include mixing a solution including a nanostructure and a linker.

Providing a composition can include providing an array. An array can include a plurality of analysis regions on a substrate. At least one analysis region can include a composition (FIGS. 1a and 1b).

An analysis region can be a divot, a tube, a tray, a well or a similar compartment for suitable for containing a liquid sample. In some cases, an analysis region can include a droplet or spot on the surface of a substrate. In those cases, an analysis region can be formed by spotting the composition on a substrate. A plurality of analysis regions can be in a pattern on a substrate. A pattern can include concentric circles, a spiral, a row, a column or a grid.

In some embodiments, the plurality of analysis regions can include two or more subsets of analysis regions. For example, a first subset of analysis regions can differ from a second subset of analysis regions by including a different nanostructure, a different linker, a different binding partner, a different capture protein, a different analyte or a different sample. Additionally, a first subset of analysis regions can differ from a second subset of analysis regions by including a different environmental factor including a buffer, a reagent, a nutrient, a serum, an exposure to light, an oxygen concentration, a temperature or a pH.

A method of detecting protein binding can be a high-throughput screening assay. An array can be used for the method. The compositions in different analysis regions can include different components, be exposed to different conditions or be exposed to different samples and/or analytes, including different analyte concentrations.

A method for detecting protein binding can include providing a capture protein to the composition. The capture protein can be capable of interacting with an analyte. The capture protein also can interact with the linker.

A capture protein can include a protein, a polypeptide or a peptide. In some cases, a capture protein can be a complex of proteins. A capture protein can also include a full length protein, a fragment of a protein or a protein domain. A capture protein can be a fusion protein, which can include portions originating from one protein or portions originating from more than one protein. A capture protein can include a protein tag or marker. A capture protein can also be modified, for example, by glycosylation, ubiquitination, PEGylation, SUMOylation or biotinylation. A capture protein can be synthesized from a nucleic acid sequence that was amplified from a cDNA library, genomic DNA, a DNA vector or plasmid, or a DNA fragment.

Providing a capture protein can include synthesizing protein, for example, in cells or in a cell-free protein synthesis reaction (i.e. in vitro). Synthesizing a capture protein can include in situ protein synthesis performed at the location that can include the composition. In vitro capture protein synthesis can include in vitro transcription and/or in vitro translation.

Synthesizing a capture protein in vitro can include performing in vitro transcription and in vitro translation simultaneously by providing DNA encoding for a capture protein, providing an in vitro transcription/translation reaction mixture, and incubating the DNA with the transcription/translation reaction mixture.

Alternatively, synthesizing a capture protein in vitro can include performing in vitro transcription and in vitro translation sequentially. Synthesizing a capture protein can include providing DNA encoding for the capture protein, providing an in vitro transcription reaction mixture, incubating the reaction mixture with the DNA encoding for the capture protein, thereby synthesizing RNA encoding for the capture protein. Synthesizing a capture protein can further include providing an in vitro translation reaction mixture, incubating the translation reaction mixture with the RNA encoding for the capture protein, thereby synthesizing capture protein.

The in vitro transcription reaction mixture can include nucleic acids, RNA polymerase, cell extract, salts or buffers. An in vitro translation reaction mixture can include amino acids, cell extract, tRNA, salts or buffers. A ribosome can also be part of an in vitro translation reaction mixture and can translate the RNA into a protein, for example, the capture protein. A ribosome can include ribosomal RNA and ribosomal proteins. The ribosome can be a component of a cellular extract, for example S30 extract, rabbit reticulosyte lysate, wheat germ extract, or E. coli extract.

In situ synthesis of capture proteins can allow for the capture proteins to interact with a linker shortly after being synthesized. This can, in turn, allow for the capture proteins to be directly immobilized. An advantage of in situ synthesis can be the elimination of purification steps required by other techniques. Elimination of purification steps can be beneficial for proteins that are difficult to purify, aggregate during purification, or produce a low yield following purification.

A linker can be configured to interact with a capture protein. The interaction can be binding to a capture protein. The interaction of a capture protein with a linker associated with a nanostructure can change a property of the nanostructure. The property can be conductivity, polarity, or resonance. The property can be photoluminescence, including fluorescence or phosphorescence. The photoluminescence can be fluorescence with a wavelength within the near infrared spectrum. The property can be an emission wavelength, an emission intensity, a conductance, an electromagnetic absorbance or an emittance.

The change in the property can be caused by a change in the distance between an ion in the first binding partner and the nanostructure. As the distance between the nanostructure and the ion changes, a nanostructure property can also change. For example, as the distance between the nanostructure and the ion changes, nanostructure photoluminescence can also change. When the capture protein binds to the linker, the distance between the ion and nanostructure can change, which can alter the nanostructure photoluminescence. Generally, as the distance between the ion and the nanostructure decreases, the amount of photoluminescence quenching can increase.

In some embodiments, the linker can be configured to interact with a capture protein by including a first binding partner in the linker that can interact with the capture protein. The first binding partner can be known binding partner of the capture protein or a portion thereof. The first binding partner can include an ion. The ion can be a metal ion. The metal ion can be nickel, iron, cadmium, copper, magnesium, calcium, arsenic, lead, mercury or cobalt (e.g. $Ni^{2+}$, $Fe^{2+}$, $Cd^{2+}$, $Cu^{2+}$, $Mg^{2+}$, $Ca^{2+}$, $As^{2+}$, $Pb^{2+}$, $Hg^{2+}$ or $Co^{2+}$). The first binding partner can include a protein, a nucleotide, a saccharide, a lipid or combinations thereof.

A linker can further include a chelating region (FIG. 13). A chelating region can include a chelator, which can be a polydentate ligand capable of forming two or more bonds with a single central atom. A chelator can include one or more carboxylate ions. For example, a linker can include $N_\alpha,N_\alpha$-bis(carboxymethyl)-L-lysine. A chelator can bind to a first binding partner (e.g. a metal ion) in order to incorporate the first binding partner into a linker.

The ion can act a proximity quencher of photoluminescent nanostructure. In particular, the ion can quench near infrared fluorescence. The quenching can be reversible. The quenching can also depend on the distance between the nanostructure and the ion. In other words, as the distance between the nanostructure and the ion changes, the photoluminescence from the nanostructure can also change. Generally, as the distance between the ion and the nanostructure decreases, the amount of photoluminescence quenching can increase.

In some embodiments, the capture protein can include a second binding partner, such that the first binding partner and second binding partner can bind together (FIGS. 13b and 14b). The second binding partner can be an endogenous motif or endogenous domain within a capture protein. Alternatively, the second binding partner can be added to a capture protein. In some embodiments, the second binding partner can be a protein tag. A protein tag can be a peptide sequence grafted onto a protein. A protein tag can be a histidine tag, chitin binding protein tag, maltose binding protein tag, glutathione-S-transferase tag, c-myc tag, FLAG-tag, V5-tag or HA-tag. One method for adding a second binding partner to a capture protein can include using primers including the sequence encoding for the second binding partner to PCR amplify DNA encoding for the capture protein. A second method can include cloning DNA encoding for the capture protein into an expression vector designed to produce a fusion of the capture protein and the second binding partner.

Binding of a first and a second binding partner can be selective binding, which can provide the selectivity needed to detect a given analyte (or relatively small group of related analytes) in a complex mixture. The degree of binding can be less than 100%, less than 90%, less than 80%, less than 70%, less than 60%, less than 50%, less than 40%, less than 30%, less than 20% or less than 10% of a second binding partner present binding to a first binding partner. The degree of binding can be more than 10%, more than 20%, more than 30%, more than 40%, more than 50%, more than 60%, more than 70%, more than 80% or more than 90% of a second binding partner present binding to a first binding partner. A first binding partner and a second binding partner can bind with a dissociation constant less than 1 mM, less than 0.1 mM, less than 0.01 mM, less than 1 µM, less than 0.1 µM, or less than 0.01 µM. A first binding partner and a second binding partner can bind with a dissociation constant greater than 1 nm, greater than 0.01 µM, greater than 0.1 µM, greater than 1 µM, greater than 0.01 mM, or greater than 0.1 mM.

The linker can also be configured to interact with a capture protein by including a region capable of chemically reacting with the capture protein. The chemical reaction can form a covalent, ionic, van der Waals, dipolar or hydrogen bond.

The number of linkers associated with the nanostructure present in the analysis region can exceed the number of capture proteins. More specifically, the number of capture protein binding sites on linkers associated with a nanostructure can exceed the number of capture proteins. The ratio of capture protein binding sites on linkers associated with a nanostructure to capture proteins can be greater than 1.1 to 1, greater than 1.5 to 1, greater than 2 to 1, greater than 5 to 1, or greater than 10 to 1. Having an excess of capture protein binding sites on linkers associated with a nanostructure can minimize the amount of unbound capture protein in a sample. Unbound capture proteins within the sample can compete with capture proteins bound to the composition for binding to the analyte. This can affect the accuracy and/or precision of the analyte detection. Having an excess of capture protein binding sites on linkers associated with a nanostructure can also increase the analyte concentration range over which analyte can be accurately detected because the saturation limit of the binding sites is increased.

The interaction of a capture protein with a linker associated with a nanostructure can change a property of the nanostructure. The property can be conductivity, polarity, or resonance. The property can be photoluminescence, including fluorescence or phosphorescence. The photoluminescence can be fluorescence with a wavelength within the near infrared spectrum. The property can be an emission wavelength, an emission intensity, a conductance, an electromagnetic absorbance or an emittance.

The change in the property can be caused by a change in the distance between an ion in the first binding partner and the nanostructure. As the distance between the nanostructure and the ion changes, a nanostructure property can also change. For example, as the distance between the nanostructure and the ion changes, nanostructure photoluminescence can also change. When the capture protein binds to the linker, the distance between the ion and nanostructure can change, which can alter the nanostructure photoluminescence. Generally, as the distance between the ion and the nanostructure decreases, the amount of photoluminescence quenching can increase.

In some embodiments, a composition can further include a capture protein, which can be configured to specifically interact with at least one analyte (FIGS. 13c and 14c). In particular, the capture protein can be configured to specifically bind to at least one analyte. Specific binding can describe a more limited than selective binding. Specific binding can be used to distinguish a binding partner from most other chemical species except optical isomers, isotopic variants and perhaps certain structural isomers. The degree of binding can be less than 100%, less than 90%, less than 80%, less than 70%, less than 60%, less than 50%, less than 40%, less than 30%, less than 20% or less than 10% of an analyte present binding to a capture protein. The degree of binding can be more than 10%, more than 20%, more than 30%, more than 40%, more than 50%, more than 60%, more than 70%, more than 80% or more than 90% of an analyte present binding to a capture protein. An analyte and a capture protein can bind with a dissociation constant less than 1 mM, less than 0.1 mM, less than 0.01 mM, less than 1 µM, less than 0.1 µM, or less than 0.01 µM. An analyte and a capture protein can bind with a dissociation constant greater than 1 nm, greater than 0.01 µM, greater than 0.1 µM, greater than 1 µM, greater than 0.01 mM, or greater than 0.1 mM.

The interaction of an analyte with a capture protein that is interacting with a linker associated with a nanostructure can change a property of the nanostructure. The property can be conductivity, polarity, or resonance. The property can be photoluminescence, including fluorescence or phosphorescence. The property can be an emission wavelength, an emission intensity, a conductance, an electromagnetic absorbance or an emittance.

The interaction of an analyte with a capture protein can be reversible (FIG. 7), meaning that the analyte can bind to the capture protein and then release and be free of binding. The change in a property of the nanostructure due to the interaction of an analyte with a capture protein can also be reversible. For example, the property of a nanostructure can have a first value, the analyte can bind to the capture protein and alter the property to a second value, then the analyte can release from the capture protein and the property can return to the first value.

A method for detecting protein binding can further include exposing the composition and capture protein to a sample. Exposing can include adding the sample to the location of the composition and the capture protein, for example, an analysis region.

The sample can include a gas, a liquid or a solid. In other embodiments, the sample can be a biological fluid or cell lysate. The sample can include an analyte. The analyte can be a small molecule, protein, biomolecule, drug, biologic, or a metabolite thereof. For example, the analyte can be monosaccharide, a polysaccharide, an amino acid, peptide, polypeptide, protein, a nucleotide, an oligonucleotide, a lipid, a polylipid, or a combination thereof. Specifically, the capture protein can be a lectin and the analyte can include a glycan (e.g. the analyte can be a glycoprotein).

The number of capture proteins interacting with the composition can exceed the number of analyte molecules present in a sample. More specifically, the number of analyte binding sites on capture proteins interacting with the composition can exceed the number of analyte molecules present in a sample. The ratio of analyte binding sites on capture proteins interacting with the composition to analyte can be greater than 1.1 to 1, greater than 1.5 to 1, greater than 2 to 1, greater than 5 to 1, or greater than 10 to 1. The number of binding sites on capture proteins interacting with the composition can limit detection of analyte if the number of analyte molecules is about or exceeds the number binding sites. Because detection of the analyte can be dependent on a change in a property of a nanostructure due to analyte binding, if a binding site is not available for the analyte, the analyte cannot bind and change a property of the nanostructure, and consequently, can go undetected. In other words, when the composition is saturated with analyte, unbound analyte can go undetected.

A method for detecting protein binding can include monitoring a property of the composition. A property can be conductivity, polarity, or resonance. A property can be photoluminescence, including fluorescence or phosphorescence. The property can be an emission wavelength, an emission intensity, a conductance, an electromagnetic absorbance or an emittance.

Monitoring the property can include observing the property of the composition alone. Monitoring the property can include monitoring the property after the composition has been exposed to a sample. Monitoring the property can include monitoring the property after the composition has been exposed to an analyte. Monitoring the property can include monitoring the property after the composition has been exposed to known concentrations of an analyte.

Monitoring a property of the composition can include observing the property through a microscope. The microscope can be an optical or a fluorescence microscope. In particular, the microscope can detect near infrared fluorescence. Monitoring a property of the composition can include measuring the property using a microscope. Monitoring a property of the composition can include monitoring the property using still photography or movies. The photography or movies can be on film media or digital form.

Monitoring a property can include taking a data point reflecting a value of a property. This can be repeated. A representation of the data points, for example, a chart or graph, can be created from the data points.

Monitoring a property can occur in real-time and allow for real-time detection of analyte binding. Real-time detection can allow in situ identification of a wide dynamic range of molecular interactions.

A method of detecting protein binding can include determining the presence of an analyte in the sample based on the monitored property. Determining the presence of an analyte can include determining the absence of the analyte. In some embodiments, determining the presence of an analyte can include determining the concentration of the analyte, determining the purity of the analyte or determining the quantity of the analyte. In some embodiments, relatively low concentrations or quantities of an analyte can be determined. The ability to determine low concentrations of an analyte may be useful, for example, in detecting trace pollutants or trace amounts of toxins within a subject. In some embodiments, analyte concentrations of less than about 100 micromolar, less than about 10 micromolar, less than about 1 micromolar, less than about 100 nanomolar, less than about 10 nanomolar, or less than about 1 nanomolar can be determined. The quantity of the analyte that can be determined can be less than 1 mole, less than 1 millimole, less than 1 micromole, less than 1 nanomole, less than 1 picomole, less than 1 femtomole, less than 1 attomole or less than 1 zeptomole. In some cases, a single molecule of an analyte can be determined. The purity of the analyte can be greater than 25% pure, greater than 50%, greater than 75% pure, greater than 80%, greater than 85% pure, greater than 90% pure, greater than 95% pure, greater than 99% pure or greater than 99.9% pure.

A linker can have a formula:

A-L-C, where A can include a polymer, where at least a portion of the nanostructure is embedded in the polymer, L can be a linking moiety including a saturated or unsaturated $C_{4-10}$ hydrocarbon chain optionally containing at least two conjugated double bonds, at least one triple bond, or at least one double bond and one triple bond; said hydrocarbon chain being optionally substituted with $C_{1-4}$ alkyl, $C_{2-4}$ alkenyl, $C_{2-4}$ alkynyl, $C_{1-4}$ alkoxy, hydroxyl, halo, carboxyl, amino, nitro, cyano, $C_{3-6}$ cycloalkyl, 3-6 membered heterocycloalkyl, unsubstituted monocyclic aryl, 5-6 membered heteroaryl, $C_{1-4}$ alkylcarbonyloxy, $C_{1-4}$ alkyloxycarbonyl, $C_{1-4}$ alkylcarbonyl, or formyl and said hydrocarbon chain being optionally interrupted by O, S, $N(R^a)$, $C(O)$, $N(R^a)C(O)O$, $OC(O)N(R^a)$, $N(R^a)C(O)N(R^b)$, $C(O)O$, or $OC(O)O$; each of $R^a$ and $R^b$, independently, being hydrogen, alkyl, alkenyl, alkynyl, alkoxy, hydroxylalkyl, hydroxyl, or haloalkyl, or L can be a bond, and C can be a metal ion complexing moiety.

The composition can include a chelator-containing compound, which can include a chelator region and a non-chelator region. C can be the chelator region. L can include the non-chelator region (FIG. 13a).

In some circumstances, A can include a polymer $[(M)_x(N)_y(O)_z]_q$, where each of M, N and Q, independently, can be selected from the group consisting of a linear or cyclic $C_3$-$C_8$ hydrocarbyl, heterocyclyl, cyclyl, or aryl including one or more amine, alcohol or carboxylic acid group, where each M-N, M-Q or N-Q can include O, S, $N(R^a)$, $C(O)$, $N(R^a)C(O)O$, $OC(O)N(R^a)$, $N(R^a)C(O)N(R^b)$, $C(O)O$, or $OC(O)O$, each of $R^a$ and $R^b$, independently, can be hydrogen, alkyl, alkenyl, alkynyl, alkoxy, hydroxylalkyl, hydroxyl, or haloalkyl, and where each of x, y and z can be integers between 0 and 50, 0 and 20 or 0 and 10 and q can be an integer between 1 and 1000, 5 and 500, or 10 and 100.

In some circumstances, L can have the formula:

$$\{X_1-(CR^aR^b)_n-X_2-(CR^aR^b)_o-X_3\}$$

where each $X_1$, $X_2$ and $X_3$, can be O, S, $N(R^a)$, $C(O)$, $N(R^a)C(O)O$, $OC(O)N(R^a)$, $N(R^a)C(O)N(R^b)$, $C(O)O$, or $OC(O)O$, each of $R^a$ and $R^b$, independently, can be hydrogen, alkyl, alkenyl, alkynyl, alkoxy, hydroxylalkyl, hydroxyl, or haloalkyl, and where the value of n added to o can be 4 to 10.

In some circumstances, C can have the formula, $H_zG((CH_2)_nCO_2H)_y$ and salts thereof, where G can be a bond, C, O, S, P, P=O or N; n is 0-6; and z and y can be selected to satisfy the valence requirements of G. In other preferred embodiments, the compound can have the formula,

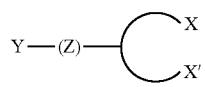

where X and X' can be the same or different and can be metal binding groups including atoms selected from the group of O, S, N, P or O=P, including carboxyl; Y can be bond, C, O, S, P, P=O or N; and Z can be a hydrocarbon having a backbone of one to six atoms, such as an alkyl group or alkenyl group. Each of X and X' can include other substituents in order to satisfy the valence requirements, such as for example, amine, thiol, phosphine or phosphine oxide, substituted by hydrogen or other organic moieties. In addition, the atoms bridging X and X' can be selected to form a 5-membered to 8-membered ring upon coordination to the metal ion. The bridging atoms can typically be carbon, but may be other elements, such as oxygen, nitrogen, or sulfur.

In yet another preferred embodiment, the compound can have the formula,

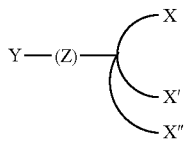

where X, X' and X" can be the same or different and can be metal binding groups including atoms selected from the group of O, S, N, P or O=P, including carboxyl; Y can be a bond, C, O, S, P, P=O or N; and Z can be a hydrocarbon having a backbone of one to six atoms, such as an alkyl group or alkenyl group. Each of X, X' and X" can include other substituents in order to satisfy the valence requirements, such as for example, amine, thiol, phosphine or phosphine oxide, substituted by hydrogen or other organic moieties. In addition, the atoms bridging X and X', X and X" or X' and X" can be selected to form a 5-membered to 8-membered ring upon coordination to the metal ion. The bridging atoms can typically be carbon, but may be other elements, such as oxygen, nitrogen, or sulfur. For example, C can be derived from $HSCH_2CH_2CH(SH)(CH_2)_nCOOH$, $H_2CH_2H_2CH(NH_2)(CH_2)_nCOOH$, $(HOOC(CH_2)_n)$ $HNCH_2CH_2NH((CH_2)_nCOOH)$, $(HOOC(CH_2)_n)_2$ $PCH_2CH_2P((CH_2)_n\ COOH)_2$, $(HOOC(CH_2)_n)_2P(O)$ $CH_2CH_2P(O)((CH_2)_n\ COOH)_2$, $HSCH_2CH_2CH(SH)(CH_2)_4$ $CONH(CH_2)_nCOOH$, where can is an integer between 1 and 10, or $N_\alpha,N_\alpha$-bis(carboxymethyl)-L-lysine.

In some embodiments, the capture protein can be a lectin and the analyte can include a glycan. An analyte can include more than one glycan. A lectin can have a weaker affinity for the glycan. A lectin may or may not have selective binding for a glycan. For example, a lectin can bind to a single glycan or multiple glycans. Sometimes, microarrays can include selected lectins, which can be used as high-throughput platforms for profiling glycoproteins. Each glycan group can have a highly-specific lectin pair. It may be possible to profile using a smaller set of lectins, if the entire affinity spectrum can be utilized. A Weak Affinity Dynamic Microarray (WADM) can utilize transducers that allow for single molecule adsorption and desorption dynamics to be measured in real time, as opposed to equilibrium binding only. Lectins, can have much weaker affinities yet larger numbers of binding partners compared to other proteins, for example, antibodies. Lectins can potentially fingerprint glycosylated proteins with higher resolution by dynamically monitoring the on and off binding rates of a target glycan. This can reduce the complexity and increase the robustness of lectin microarrays.

The composition, array and/or the method for detecting protein binding can have a number of advantages over other protein detection technologies. First, neither the composition nor the array require labeling of the target analyte protein, which can be perturbative to a protein—protein interaction of interest. Second, the composition and/or array can be suitable for the detection of any protein—protein interaction, not just antigen—antibody pairs. Third, the composition and/or the array can be capable of detecting single protein binding events, which has not been demonstrated using other detection techniques.

The composition, array and/or the method for detecting protein binding can have a number of advantages over existing label-free protein-protein detection methods. First, fabrication of the array can be simple and fairly cheap as in situ immobilization of proteins during synthesis directly on the array can eliminate the need for separate protein preparation and purification. Second, the array and the method for detecting protein binding can allow for high-throughput detection of protein-protein interactions.

The method for detecting protein binding can also have a number of advantages over existing glycan profiling methodologies. First, the method for detecting protein binding can be performed in a multiplexed manner, unlike conventional methods such as liquid chromatography and mass spectrometry. Second, the method for detecting protein binding does not require labeling as does current lectin microarray.

EXAMPLES

Preparation of Cell Extract

The S30 cell extracts were prepared from *E. coli* strain BL21 (DE3) (Novagen, Madison, Wis.) according to the method reported elsewhere (Kim, T. W., Oh, I. S., Ahn, J. H., Choi, C. Y. & Kim, D. M. Cell-free synthesis and in situ isolation of recombinant proteins. *Protein Expres Purif* 45, 249-254 (2006); Ahn, J. H., et al. Cell-free synthesis of recombinant proteins from PCR-amplified genes at a comparable productivity to that of plasmid-based reactions. *Biochem Biophys REs Co* 338, 1246-1352 (2005); Ahn, J. H., Keum, J. W. & Kim, D. M. High-throughput, combinatorial engineering of initial codons for tunable expression of recombinant proteins. *J Proteome Res* 7, 2107-2113 (2008).) The cells were grown at 37° C. in 4 L of 2xYT medium with agitation and aeration. When the cell density (OD600) reached 0.5, isopropyl-thiogalactopyranoside (IPTG, 0.5 mM) was added to the culture media to induce T7 RNA polymerase expression. The cells were harvested when the $OD_{600}$ reached 4.0 and cells were washed trice by suspending them in 20 mL of S30 buffer per gram of wet cells and then centrifuged. S30 buffer contained 10 mM Tris-acetate buffer (pH 8.2), 14 mM magnesium acetate, 60 mM potassium glutamate, and 1 mM dithiothreitol (DTT) containing 0.05% (v/v) 2-mercaptoethanol (2-ME). The resulting cell pellets were weighed and then suspended with 12.7 mL of S30 buffer without 2-ME and disrupted in a French press cell (Thermo Scientific) at a constant pressure of 20,000 psi. The crude lysate was then centrifuged at 12,000 RCF for 10 min, and the recovered supernatant was briefly incubated at 37° C. The resulting extract was divided into small aliquots and stored at −80° C. before use for cell-free expression.

Synthesis of Ni-NTA Functionalized SWNT-CHI Array

SWNT (10 mg) was added into 10 mL of the CHI solution (0.25 wt %), and the solution was sonicated for 20 min in an ice bath. The SWNT dispersion was centrifuged for 3 h at 13,000 g and the supernatant was decanted to the reservoir. A 150 μL portion of SWNT suspension was well mixed with 1 mL of the CHI solution (2 wt %), and followed by glutaraldehyde (0.25%, vol/vol). The resulting mixture (1 μL/spot) was spotted on the patterned glass functionalized with poly-L-lysine (Tekdon Inc.), and allowed to stand for 6 h at 25° C. After washing the SWNT/CHI array with H₂O, the array was dipped in the succinic anhydride solution (0.1 M, NMP) containing N,N-diisopropyethylamine (DIEA, 0.1 M) for 2 h at 25° C. After washing the array with NMP and H₂O, the carboxylic acid on CHI was activated with EDC-HCl and NHS (0.1 M) for 1.5 h, and the SWNT/CHI array was washed with H₂O several times. The array was then treated with the NTA solution (0.1 M, in PBS pH 8.0) for 3 h at 25° C. Nickel sulfate (100 mM) was added to the SWNT/CHI array for 1 h at 25° C., and washed it with H₂O several times.

Gene Preparation

Target ORF (Ack, DnaK, FbaA, GlyA, LpdA, RpoA, RplB, RspB, Tsf, Ada, Cdd) were amplified using primers P1s and P2s (Table 1). The first PCR products were purified by gel extraction and used for the second-round PCR, in which the full expression templates were synthesized using the P3 and P4. After amplification, the PCR products were used in cell-free protein synthesis reaction without purification. (Kim, T. W., Oh, I. S., Ahn, J. H., Choi, C. Y. & Kim, D. M. Cell-free synthesis and in situ isolation of recombinant proteins. *Protein Expres Purif* 45, 249-254 (2006); Scholz, C. et al. SlyD proteins from different species exhibit high prolyl isomerase and chaperone activities. *Biochemistry* 45, 20-33 (2006); Swartz, J. R., Jewett, M. C. & Woodrow, K. A. Cell-free protein synthesis with prokaryotic combined transcription-translation. *Methods Mol Biol* 267, 169-182 (2004), each of which is incorporated by reference in its entirety). The temperature and time settings for PCR were as follows: 5 min at 95° C., 30 s at 95° C., 1 min at 55° C., 1 min at 72° C. for 30 cycles for amplification, and 7 min for work-up extension.

Cell-Free Protein Synthesis and on Chip Protein Expression

The standard reaction mixture for cell-free protein synthesis reactions consisted of the following components in a total volume of 10 μl; 57 mM of Hepes-KOH (pH 8.2), 1.2 mM of ATP, 0.85 mM each of CTP, GTP and UTP, 0.64 mM of cAMP, 90 mM of potassium glutamate, 80 mM of ammonium acetate, 12 mM of magnesium acetate, 34 μg/ml of L-5-formyl-5,6,7,8-tetrahydrofolic acid (folinic acid), 1 mM each of 20 amino acids, 0.17 mg/ml of *E. coli* total tRNA mixture (from strain MRE600), 2% PEG (8000), 67 mM of creatine phosphate (CP), 5.6 μg/ml of creatine kinase, 4 μl of the S30 extract and 1 μl of PCR products.

TABLE 1

Target ORF Primers

| Protein[a] | P1 | P2 |
|---|---|---|
| Ack (P0A6A3) | aagaaggagatatacatatgtcgagtaagttagtactggtttaatgatgatgatgatgatgggcagtcaggcggctcgcgt (SEQ ID NO: 1) | (SEQ ID NO: 2) |
| Dnak (P0A6Y8) | aagaaggagatatacatatgggtaaaataattggtatcgattaatgatgatgatgatgatgttttttgtctttgacttctt (SEQ ID NO: 3) | (SEQ ID NO: 4) |
| FbaA (P0AB71) | aagaaggagatatacatatgtctaagattttgatttcgtttaatgatgatgatgatgatgcagaacgtcgatcgcgttca (SEQ ID NO: 5) | (SEQ ID NO: 6) |
| GlyA (P0A825) | aagaaggagatatacatatgttaaagcgtgaaatgaacatttaatgatgatgatgatgatgtgcgtaaaccgggtaacgtg (SEQ ID NO: 7) | (SEQ ID NO: 8) |
| LpdA (P0A9P0) | aagaaggagatatacatatgagtactgaaatcaaaactcattaatgatgatgatgatgatgcttcttcttcgctttcgggt (SEQ ID NO: 9) | (SEQ ID NO: 10) |
| RpoA (P0A7Z4) | aagaaggagatatacatatgcagggttctgtgacagagttttaatgatgatgatgatgatgctcgtcagcgatgcttgccg (SEQ ID NO: 11) | (SEQ ID NO: 12) |
| RplB (P60422) | aagaaggagatatacatatggcagttgttaaatgtaaaccttaatgatgatgatgatgatgtttgctacggcgacgtacga (SEQ ID NO: 13) | (SEQ ID NO: 14) |
| RpsB (P0A7V0) | aagaaggagatatacatatggcaactgtttccatgcgcgattaatgatgatgatgatgatgctcagcttctacgaagcttt (SEQ ID NO: 15) | (SEQ ID NO: 16) |
| Tsf (P0A6P1) | aagaaggagatatacatatggctgaaattaccgcatccctttaatgatgatgatgatgatgagactgcttggacatcgcag (SEQ ID NO: 17) | (SEQ ID NO: 18) |
| Ada (P06134) | aagaaggagatatacatatgaaaaaagccacatgcttaacttaatgatgatgatgatgatgcctctcctcattttcagctt (SEQ ID NO: 19) | (SEQ ID NO: 20) |
| Cdd (P0ABF6) | aagaaggagatatacatatgcatccacgttttcaaaccgcttaatgatgatgatgatgatgagcgagaagcactcggtcga (SEQ ID NO: 21) | (SEQ ID NO: 22) |
| CDK4 (P11802) | aagaaggagatatacatatggctacctctcgatatga (SEQ ID NO: 23) | ttaatgatgatgatgatgatgcaactccggattaccttcat (SEQ ID NO: 24)<br>atgatgatgatgatgatgttacaactccggattaccttcat (noHis) (SEQ ID NO: 25) |
| p16 (P42771) | aagaaggagatatacatatggtgcgcaggttcttggt (SEQ ID NO: 26) | ttaatgatgatgatgatgatgcaagccaggtccacgggcag (SEQ ID NO: 27)<br>atgatgatgatgatgatgttacaagccaggtccacgggcag (noHis) (SEQ ID NO: 28) |

TABLE 1-continued

Target ORF Primers

| Protein[a] | P1 | P2 |
|---|---|---|
| Jun (P05412) | aagaaggagatatacatatgactgcaaagatggaaac (SEQ ID NO: 29) | ttaatgatgatgatgatgatggtcaaatgtttgcaactgct (SEQ ID NO: 30)<br>atgatgatgatgatgatgttagtcaaatgtttgcaactgct (noHis) (SEQ ID NO: 31) |
| Fos (P01100) | aagaaggagatatacatatgatgttctcgggcttcaa (SEQ ID NO: 32) | ttaatgatgatgatgatgcaacagggccagcagcgtgg (SEQ ID NO: 33)<br>atgatgatgatgatgttacaacagggccagcagcgtgg (noHis) (SEQ ID NO: 34) |
| P3: Mega-F | TCGATCCCGCGAAATTAATACGACTCACTATAGGGAGACCACAACGGTTTCCCTCTAGAAATAATTTTGTTTAACTTTAAGAAGGAGATATACATATG (SEQ ID NO: 35) | |
| P4: Mega-R | CAAAAAACCCCTCAAGACCCGTTTAGAGGCCCCAAGGGGTTATGCTAGCTCGAGAAGCTTGTCGACGAATTCGGATCCTTAATGATGATGATGATGATG (SEQ ID NO: 36) | |

[a]ExPASy accession ID in parenthesis

Protein Binding and Protein-Protein Interaction Measurements

Reaction mixtures for cell-free protein expression were added to each array wells. The fluorescent intensities of each SWNT/CHI well were taken to track the intensity changes. To initiate protein synthesis, 1 µl PCR-amplified DNAs were added to each well a humidified chamber at 37° C. for 2 hours. The arrays were washed three times for 10 min each with PBS buffer (pH 7.4, 100 mM) at RT and then PL spectra were taken. To analyze protein-protein interaction on SWNT/XHI array, anti-Histag antibody or cell-free expressed protein mixtures were added to each well and then PL spectra were taken to compare the intensity change.

Spectroscopy and Microscopy

Near-infrared photoluminescence spectra were acquired using 785 nm excitation and an Acton SP-150 spectrograph coupled to a Princeton instruments OMA V InGaAs detector or with Kaiser Holospec f/1.8 Imaging Spectrograph (Kaiser Optical). Absorption measurements were taken with a Shimadzu UV-3101 PC UV-VIS-NIR scanning spectrophotometer.

Microscopy and Data Analysis for Single Molecule Detection of Protein

After SWNT/CHI film was functionalized with Ni-NTA, the nIR fluorescence response of SWNT to His-tagged EGFP as a capture protein and anti-His-tag antibody as a target was imaged and monitored in real-time for 25 min through a 100×TIRF objective using an inverted microscope (Carl Zeiss, Axiovert 200) attached with a 2D InGaAs array (Princeton Instruments OMA 2D) with a 658 nm laser excitation (LDM-OPT-A6-13, Newport Corp., 35 mW). The nIR fluorescence response movies were acquired at 1.0 sec/frame using the WinSpec data acquisition program (Princeton Instruments). Before the experiment, a control movie was taken for 25 min to ensure a stable baseline. A 20 µL portion of His-tagged EGFP (final concentration: 100 µg/ml) was added into the SWNT/CHI film bearing Ni-NTA 5 min after taking the movie in PBS (pH 7.4, 100 mM) without addition of proteins, and the fluorescence response was further imaged and monitored for 10 min. Then, a 10 µL portion of anti-His-tag antibody (final concentration: 200 µg/ml) was added into EGFP-immobilized SWNT/CHI film, and the fluorescence response was monitored for 10 min. The fluorescence response within a 2×2 pixel spatial binning region in the movie images was examined, and the analysis algorithm used was similar to that reported before. (Yabuki, T. et al. A robust two-step PCR method of template DNA production for high-throughput cell-free protein synthesis. *J Struct Funct Genomics* 8, 173-191 (2007), which is incorporated by reference in its entirety). The four-pixel area in the image corresponded to a 600×600 nm$^2$ region in the real sample, representing the PL from a single SWNT, which was determined by the diffraction limit in the nIR range. (Ahn, J. H. et al. Cell-free synthesis of recombinant proteins from PCR-amplified genes at a comparable productivity to that of plasmid-based reactions. *Biochem Bioph Res Co* 338, 1346-1352 (2005), which is incorporated by reference in its entirety). Hidden Markov Modeling (HMM) was employed to correlate the rate constants of immobilization of His-tagged EGFP to Ni-NTA and binding of anti-His-tag antibody to EGFP on the SWNT/CHI film.

Lectin Array

This dynamic array was modeled with a Kinetic Monte Carlo simulation of a Langmuir surface reaction. The Gillespie algorithm was used to find an ensemble average of occupied lectin sites for a given glycoprotein in solution. (Gillespie, "Exact Stochastic Simulation of Coupled Chemical Reactions," J. Phys. Chem. 1977, which is incorporated by reference in its entirety). To make the simulation tractable, the modeled glycoprotein was significantly reduced. The natural occurrence of heterogeneous mixtures of glycoproteins (glycoforms) was neglected in the current model. Only homogenous solutions of glycoproteins were considered, although a system for profiling heterogeneous mixtures is discussed below. In the first three examples, each glycan group on the surface of the simulated glycoprotein was assumed as equally accessible; but in the fourth example, profiling a glycoprotein was modeled while taking into account spatial arrangement. As multivalent interactions would lead to obvious, non-dynamic responses (the glycoprotein would simply adhere strongly to the lectin transducer), these events were omitted in the dynamic model. These events were also rarer between a wide range of glycans and lectins due to the required, close-matched spacing of carbohydrate recognition domains and surface ligands needed for a multivalent interaction (Carlsson et al., "Affinity of galectin-8 and its carbohydrate recognition domains for ligands in solution and at the cell surface," Glycobiology, 2007, which is incorporated by reference in its entirety). However, the dynamic array could be used to measure more accurate mono- and multivalent kinetic parameters. Interactions between the protein surfaces (charge, Van der Waals, and sterics) were assumed to be minimal. This must be a holding assumption or all the laboriously collected kinetic parameters between lectins and glycans would have little application to real glycoproteins, as each unique protein would need its own set of parameters.

The kinetic parameters for this model were supplied in the form of dissociation constants between 75 unique lectins and 442 glycans, approximated from the only public database of lectin-glycan interaction values (Consortium for Functional Glycomics, "Primary Screen," 2010). This database is much smaller than the number of naturally occurring glycans (Cummings, "The repertoire of glycan determinants in the human glycome," Mol. BioSyste, 2009, which is incorporated by reference in its entirety) and the kinetic estimates from the fluorescent data were approximate. Notwithstanding these assumptions and limitations, the model still provided valuable insight into the working parameters of a dynamic array.

To demonstrate how a dynamic microarray could be used for screening and profiling the reduced glycoprotein model was applied to three pertinent areas of glycoprotein research: 1) screening of protein therapeutics, 2) differentiating arthritic disease, and 3) complete profiling of unknown glycoproteins. A fourth example explored profiling glycoproteins while taking into account spatial arrangement, or accessibility.

Screening of Protein Therapeutics—Galactose-α1,3-Galactose

Figure 17:
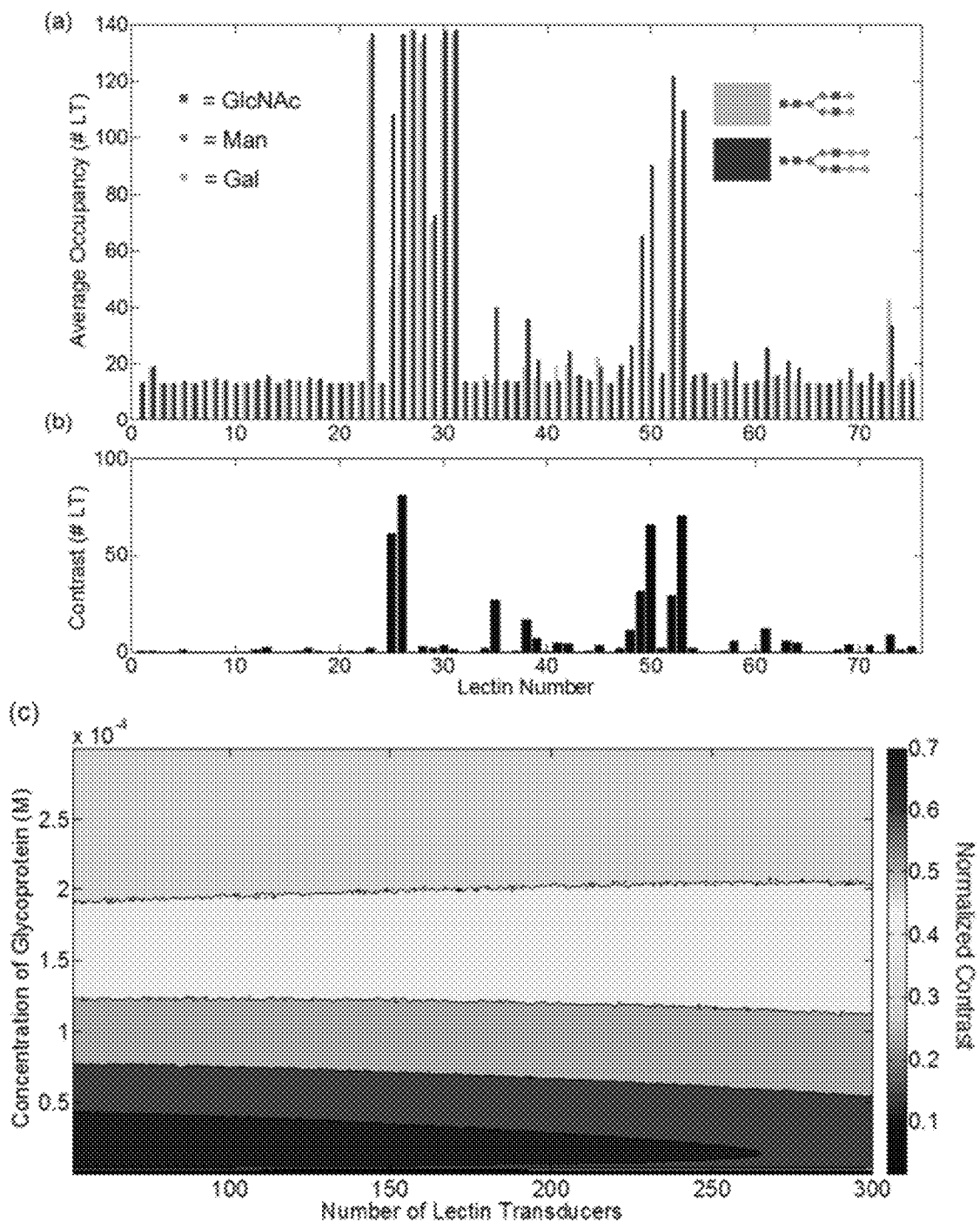
FIG. 17a is a graph showing the average occupancy for two glycoproteins on different lectin types.
FIG. 17b is a graph showing two protein profiles using different lectins.
FIG. 17c illustrates the effect of lectin transducer number and concentration of glycoprotein on contrast of a lectin for glycoprotein therapeutic screening.

A recent example of recombinant glycoprotein therapeutics being expressed with harmful glycans is the drug Cetuximab used for colorectal cancer and squamous cell carcinoma. Chung et al. found that this murine-expressed, monoclonal antibody occasionally contained a glycan, Galactose-α1,3-Galactose, which caused hypersensitivity in a third of the treated patients (Chung, et al. "Cetuximab-Induced Anaphylaxis and IgE Specific for Galactose-α-1,3-Galactose, N Engl J Med, 2008, which is incorporated by reference in its entirety). Another study found that this therapeutic had 21 unique glycan candidates (Qian et al., "Structural characteristization of N-linked oligosaccharides on monoclonal antibody cetuximab by the combination of orthogonal matrix-assisted laser desorption/ionization hybrid quadrupole-quadrupole time-of-flight tandem mass spectrometry and sequential enzymatic digestion," Anal Biochem, 2007, which is incorporated by reference in its entirety). Most of these glycans were not yet part of the kinetic parameter database; however two of the candidates, biatternary glycans were included: one benign and one with two deleterious Galactose-α1,3-Galactose groups (FIG. 17a). A dynamic microarray could be used to screen between these two and determine if a cell line is producing harmful strains of the drug. This first case study was the simplest form of screening: differentiation of one glycoprotein from one other.

The kinetic model simulated the dynamic response of the unique glycoprotein in solution to find optimal conditions for screening. Utilizing the user-supplied kinetic parameters (in the form of dissociation constants), it determined the ensemble average of bound lectins over time. The responses of both glycoproteins were then determined for each lectin type (150 ensemble averages generated for the current 75-lectin database). The responses of the two glycoproteins were then compared for each lectin type to determine the number of lectin types needed for screening and optimal lectin types. Once the optimal lectin type has been found, the best operating conditions were determined by running the model at various concentrations and number of lectin binding sties (or lectin transducers). The resulting contrast values were normalized by the total number of lectin transducers used in the simulations. This yielded an operating space to find the optimal number of transducers and concentration of glycoproteins in solution. This predictive process was illustrated with the current approximate database for the Cetuximab problem.

The model predicted that a single lectin type was sufficient for clear differentiation between two homogenous solutions of Cetuximab therapeutics and provided the practical operating conditions for the screen. By looking at the average number of bound species over time of both proteins on each lectin (FIG. 17a), it was found that a single lectin was needed to show contrast between these two glycoproteins. Lectin 26 (Antibody BD6 made to rat basophilic leukemia cells (RBL-2H3)) was found to show maximum contrast (difference between the average number of bound species over time of the two proteins) (FIG. 17b). By varying both number of lectin transducers and concentration of glycoprotein, an operating space was generated to help maximize contrast in the screen (FIG. 17c).

There existed an optimal protein concentration and number of transducers as too few of the latter did not yield a measurable response above the noise and too many proteins in solution saturated the binding sites. At saturation, both protein types would be in excess and bind to the limited number of transducers, thus decreasing the ability to differentiate between the two solutions. For this example, glycoprotein concentrations less than 5 μM and greater than 100 μM inhibited differentiation. It was found that a glycoprotein concentration of 20 μM and 150 lectin transducers exhibited a normalized contrast of 0.74; the protein with the benign group occupied 111 less (out of the 150) lectin transducer sites than the protein with the harmful glycan. In this particular example, the range of allowable glycoprotein concentrations and number of lectin transducer sites was wide. In other situations where the affinities were weaker or the two glycoproteins were very similar there was a much tighter optimal range. Galactose-α1,3-Galactose was just one of many potentially harmful or simply unwanted glycans that can be expressed on therapeutics or other laboratory glycoproteins. For each case of differentiation between two known glycoprofiles there was be a unique, optimized lectin and operating space. However, the generalized method described above held for all differentiation-screen scenarios and the predictive power was increased with the quality of available kinetic data.

Differentiating Arthritic Disease—Glycosylation of IgG

Arthritis has been linked with changes to the single glycosylation site in the constant domain of the IgG Fc region (Alavi and Axford, "Glyco-biomarkers" Potential determinants of cellular physiology and pathology," Dis. Markers, 2008, which is incorporated by reference in its entirety). It has been hypothesized that by screening the glycan group on these proteins, clinicians would be able to tell what type of Arthritis an individual has. Healthy individuals have a large glycan group in this region, yet as the arthritis severity increases, this glycan group loses many of its terminal sugars (Alavi and Axford 2008). When an increased count of the IgG proteins contain only the base glycan structure ((GlcNAc2Man6)-Man4GlcNAc-4GlcNAc also known as IgG-G0), the individual can be suffering from Rheumatoid Arthritis (RA) (Watson et al., "Sugar printing rheumatic diseases: a potential method for disease differentiation using immunoglobulin G oligosaccharides." Arthritis Rheum, 1999, which is incorporated by reference in its entirety). In a clinical setting, it would be advantageous to create a rapid screening tool for this prescient glycan group from all the other possible IgG variants.

This second case study represented a more difficult situation of screening than the proceeding example (differentiation of one "desired" profile from 49 other "undesired"), yet the basic method outlined in the previous case study remained the same. The ensemble average of occupied sites was generated for each of the glycoproteins to each lectin type (50 glycoproteins with the 75-lectin database yields 3750 simulations). The response of the "desired" protein for screening was then subtracted from all the "undesired" for each lectin type. These contrast values were then normalized by dividing by the total number of lectin transducers in the simulation. An algorithm was then written that sorted the lectin database types by contrast response (best contrasting lectin to worst) for each of the "undesired" glycan types. Finally, the algorithm searched through the best contrasting lectin types for each of the "undesired" glycans to find which minimal subset of lectins could achieve clear profiling between the "desired" glycan and all the other "undesired" groups. This expanded algorithm was demonstrated for the case of IgG-G0 screening using the approximate 75-lectin database.

Figure 18:
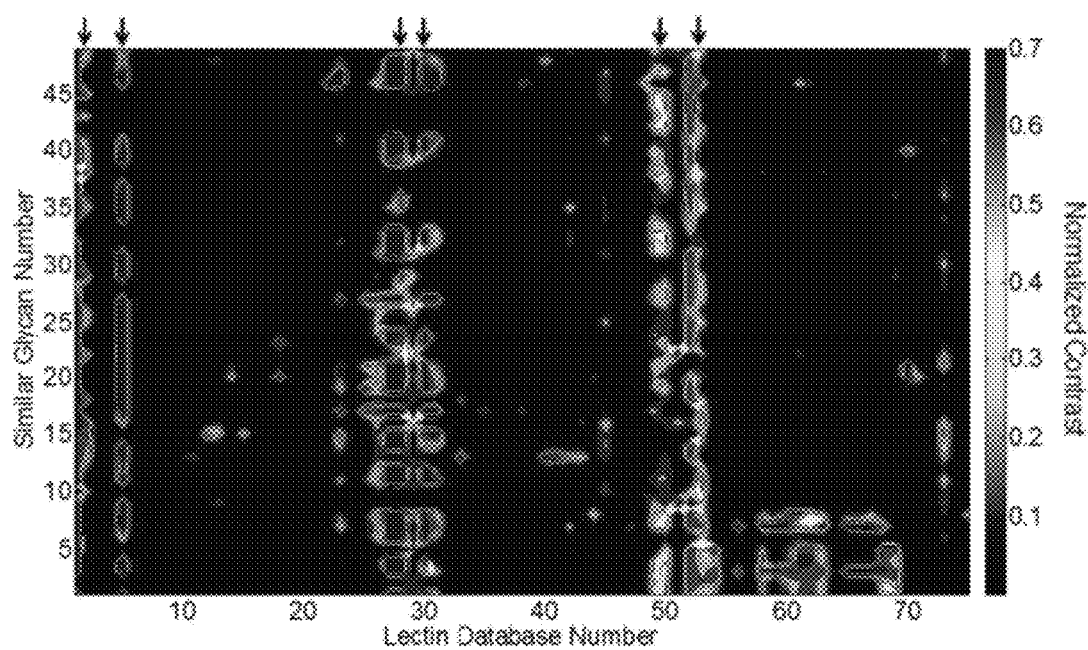
FIG. 18 shows a normalized contrast of a glycan from other similar glycans.

The model predicted that two types of lectins would be sufficient to differentiate the RA glycan group (IgG-G0) from other similar glycans. The glycan group was identified in the database as glycan #301 and the database was then searched for other glycans with similar base structures; this yielded 49 similar glycans. The contrast between glycan #301 and the other 49 glycans were generated for each lectin type and normalized by the total number of lectin transducers (FIG. 18). The algorithm described above then sorted the lectin database numbers by contrast response (best contrasting lectin to worst) and found which subset of lectin types where among the top-ten contrasting lectin types for each of the similar glycans. It was found that by using both Lectin #1 (LSECtin:Mouse LSectin 0.5) and #52 (Nictaba:Nictaba, wild type) high contrast was shown between Glycan #301 and each of the other similar glycans. Used together, the two lectins exhibited high contrast over the entire range of glycans. However, these predictions were based on approximate kinetic data. As better kinetic parameters between glycans and lectins are obtained, these predictions can be further refined by the described model and method.

Complete Profiling of Unknown Glycoprotein

One difficult differentiation scheme to imagine for this platform would be full profiling of an unknown glycoprotein. This could be advantageous in many Glycobiology applications, such as the detection of known biomarkers and discovery of new. Glycoprotein biomarkers have been found for general inflammatory problems (Gornik and Lauc, "Glycosylation of serum proteins in inflammatory diseases," Dis Markers, 2008, which is incorporated by reference in its entirety), prostate cancer (Leoz M L, An H J, Kronewitter S, Kim J, Beecroft S, Vinall R, et al. 2008. *Dis Markers* 25(4-5):243-258, 2008), ovarian cancer (Saldovaa R, et al. *Dis Markers* 25(4-5):219-232), and a host of other diseases (Peracaulaa R, et al. *Dis Markers* 25(4-5):207-218), each of which is incorporated by reference in its entirety. The stochastic model provides an estimate of the number of lectin types would be needed for clear profiling.

Profiling is a monumentally harder problem than the previous screening examples, as there are more unknowns to differentiate. For a model protein with a single glycosylation site, there are 442 unique possibilities in the current database (442 different glycans on the current CFG array, many more groups naturally exist (Cummings R D. 2009. *Mol BioSyst* 5:1087-1104), which is incorporated by reference in its entirety). For a protein with two glycans there are 97,903 unique combinations (442 choose 2), for three groups there are 14,294,280 combinations (442 choose 3), and upward to an average biological limit of 5 glycosylation sites with an astounding number of 137 billion unique combinations (442 choose 5). The possibilities are further compounded when more glycans are added to the model and when spatial considerations are taken into account (as seen in the next example). Finding a unique, strong binding ligand for each of these glycoproteins is an impossible task, but with dynamic observation of lectins a much smaller number of lectin types could be used to make an effectual bar-code for reading each glycoprofile.

Due to computational limits, only the cases of proteins with one and two glycosylation sites have been currently simulated, but the process holds for glycoproteins with more glycans. A response matrix (average number of occupied transducers) for each glycan lectin pair was generated with the conditions of 200 lectin transducers and a glycoprotein concentration of 300 µM. An algorithm then sorted the lectin response vectors in order of uniqueness (most unique to least). Uniqueness was measured by scoring how many glycan responses on the given lectin were outside a tolerance of four occupied sites from the other glycan responses on the same lectin (this indicates a glycan group that could be readily differentiated from the others on the lectin). A second algorithm then searched down the resorted matrix to determine how many lectins it would take to create a unique response "bar code" for each possible glycan profile (again using the tolerance of at least four occupied site difference). For a protein with a single glycosylation site and the 75 lectins now available in the database it was found that 6 lectin types were needed for full profiling, and for a two glycosylation site protein 37 lectin types are needed.

Adding Accessibility to Profiling Algorithm

Figure 19:
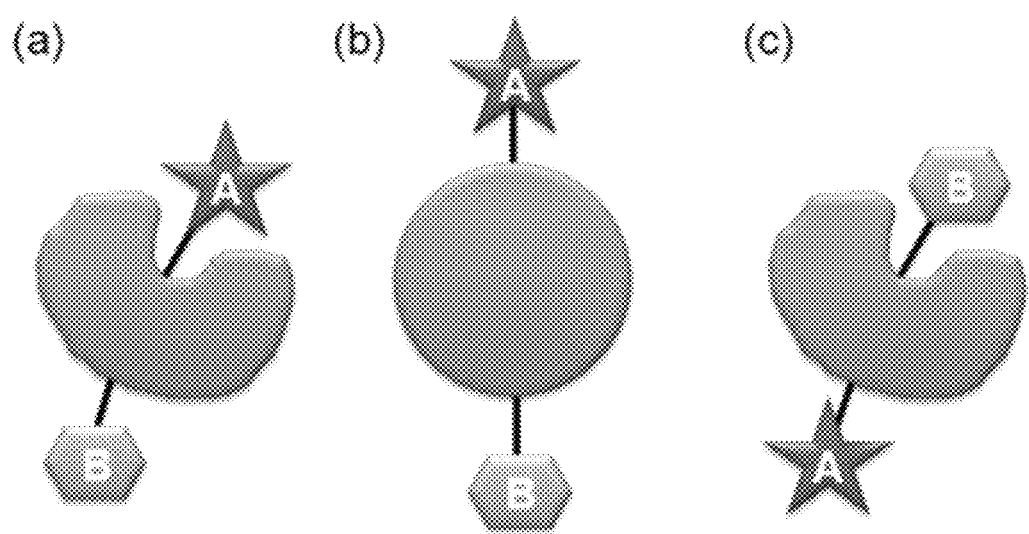
FIG. 19 is a schematic of spatial conformations of a glycoprotein.

In the preceding profiling example, spatial arrangement of the glycans was neglected. If considerations are made for the accessibility of the glycans to the lectin transducer, the number of possible profiles is greatly increased as is the required number of lectin types for clear profiling. Consider a simple case where the two-site glycoprotein model has been modified to include three different spatial arrangements: 25% accessible in glycan A—75% accessible in glycan B, 50% in both, and 75% in glycan A—25% in glycan B (FIG. 19). If the same profiling algorithm as above is used, the number of unique profiles increases three-fold (293,709 response profiles) and the number of lectin types required for clear profiling is not met with the current database of lectins. A much larger set of unique lectins is needed to both profile and determine the spatial arrangement of glycans on a homogenous solution of glycoproteins. The number depends on the uniqueness of the lectin, and as more lectins and other sugar-binding proteins are explored this required number will decrease.

The predictions of this stochastic model are promising but they are only as good as the affinity parameters supplied to the model. As discussed in the Methods section, a comprehensive, public database of lectin-glycan binding affinities does not yet exist. In order to make better predictions of which lectin types will be best for specific situations such a database should first be obtained. The WADM can be used to obtain more accurate kinetic parameters of glycans to lectin transducers. These in turn could be cycled back to the model for clearer predictions of which lectins to use for specific applications. Also, by expanding the library of lectins there is a greater possibility of finding lectin types with more unique binding affinities to glycans. This will reduce the total number of lectin types needed for profiling.

Although the affinity parameters are not exact and may lead to different optimal lectin types, they are on the correct experimental order and the operating conditions found herein will hold for any lectin dynamic array system. Such an experimental system would require the ability to monitor single protein binding events via electrical or florescent transduction at a very high frame rate. In order to capture the correct statistics, or ensemble average, of occupied transducers, the system would need to be sampled on the order of the binding event time scale.

Figure 20:
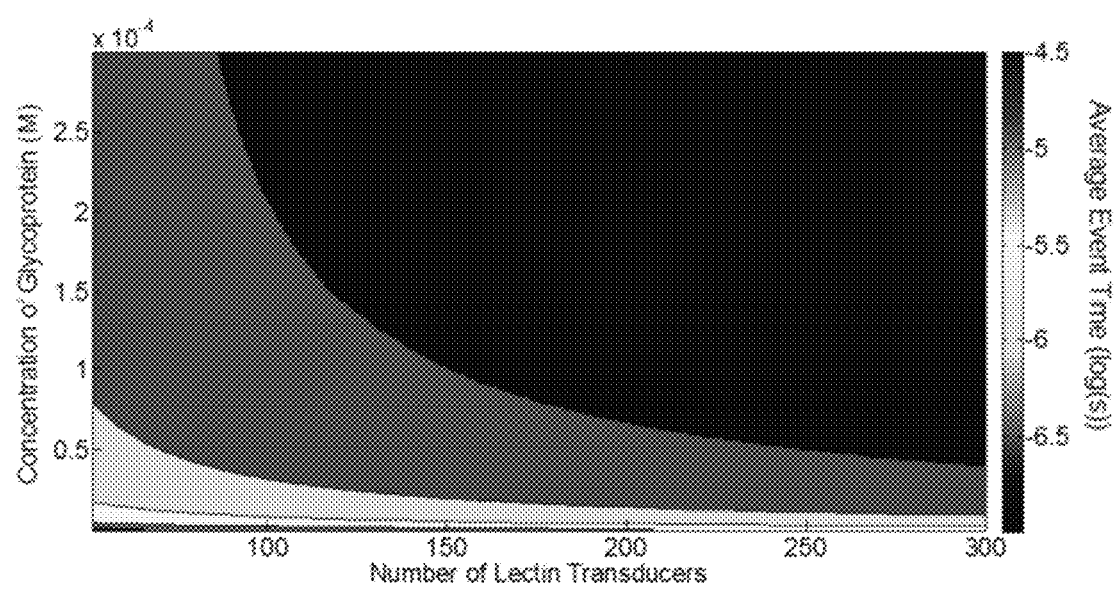
FIG. 20 is a graph showing the average time scale of binding or release events in a glycoprotein therapeutic case study.

This time scale changes depending on the concentration of glycoproteins and number of lectin transducers used. Consider the hypothetical therapeutic screening of the first case study. The average event time scale (for binding or release) is on the order of 100 nanoseconds (FIG. 20). This corresponds to a frame capture rate of 10 MHz. This is on the cusp of current single molecule detection schemes using highly sensitive nano-mechanical cantilevers (Waggoner P S, Craighead H G. 2007. *Lab Chip* 7:1238-1255), nanowire electronic sensors (Zheng G, et al. *Nat Biotechnol* 23:1294-1301), or carbon nanotube fluorescence (Jin H, et al. *Nano Lett* 8(12):4299-4304), each of which is incorporated by reference in its entirety. It would be possible to operate at a lower frame rate for situations where the contrast is greater or with lectins that have higher affinities. Because of the extremely high frame rate, enough data could be gathered in a fraction of a second to determine what glycoprotein is present in solution, hence making this an extremely rapid profiling platform.

Figure 21:
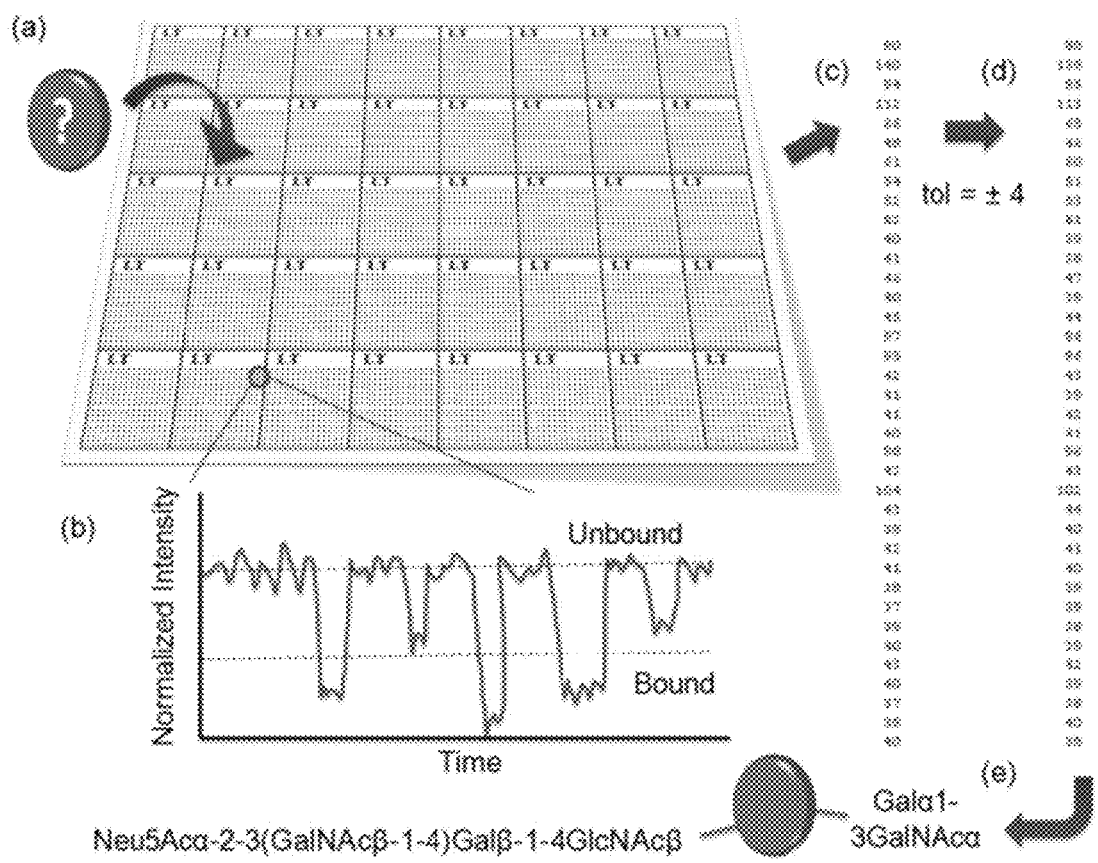
FIG. 21 is a schematic of a proposed experimental set up for profiling unknown glycoproteins with two glycosylation sites.

The experimental setup for profiling homogenous solutions of unknown glycoproteins would consist of a greater array of WADMs (FIG. 21a). The stochastic model currently predicts the number of lectin types that are required for clear profiling (37 lectin types for 2 site glycosylation). If the lectin transducer response is a fluorescent signal, these arrays could be micro-printed onto a single glass slide. The glycoprotein solution would then be added on top of the large array assembly. Each lectin type would be monitored for a fraction of a second to determine the average site occupancy numbers. Expected response traces (FIG. 21b) will be similar to those found in an emerging class of stochastic sensors based on nanoscale transducers that allow for single molecule dynamics to be resolved (Jin H, et al. *Nano Lett* 8(12):4299-4304, which is incorporated by reference in its entirety). The stepwise signal can be translated to both kinetic parameters (forward and reverse rates) as well as an ensemble average of bound lectin sites (FIG. 21c). The ensemble averages could then be fed to the response database which is searched (within the given tolerance) for a profile match FIG. 21d). If a successful match is found, the profile is supplied to the user (FIG. 21e). This simple experimental setup could be expanded for a larger number of glycosylation sites. Again, the number of required lectin types will be reduced as more lectins are screened for unique glycan binding characteristics.

Figure 22:
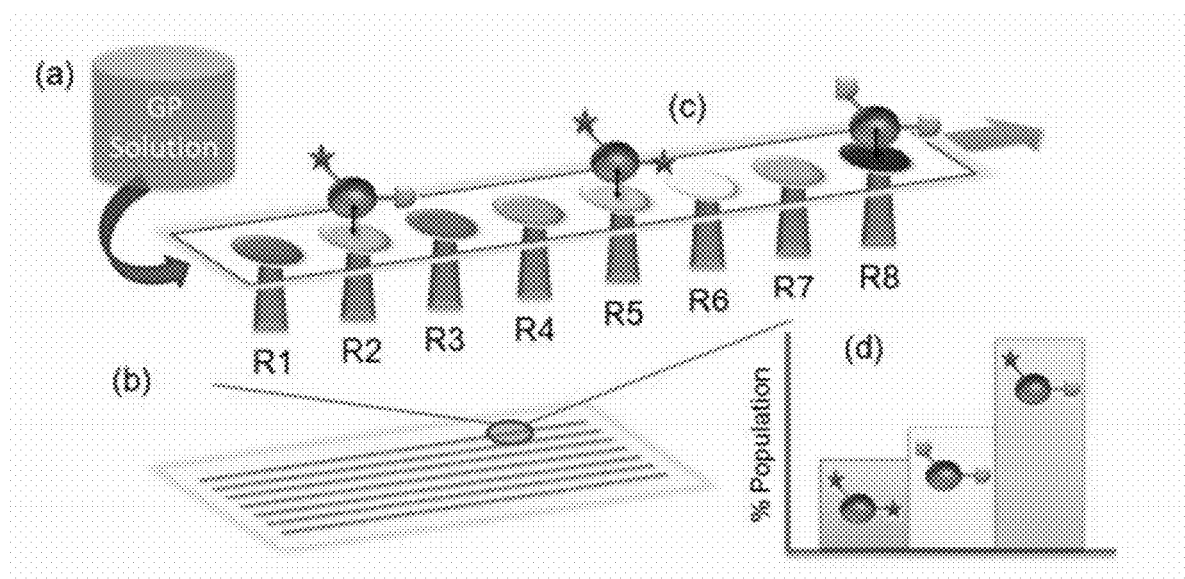
FIG. 22 is a schematic of a proposed experimental set up for profiling heterogeneous solution of glycoproteins in an array.

Rapid profiling of a heterogeneous solution of glycoproteins (the estimable goal of the field) would require a more elaborate setup for the dynamic array (FIG. 22a). It could be realized with emerging nanofluidic platforms (Daiguji H. 2010 *Chem Soc Rev* 39:901-911; Kim S J, et al. *Chem Soc Rev* 39:912-922; and Napoli M, et al. *Lab Chip* 10:957-985, each of which is incorporated by reference in its entirety). The setup would consist of a series of nanochannels with patterned lectin transducers along the bottoms, in which glycoproteins are induced to flow in single-file (FIG. 22b). The glycoproteins would flow at a rate that would allow dynamic interaction with the lectins. The response of the transducers would be recorded for each protein as it drifts over the different types of lectins (FIG. 22c). After a sufficient sample of proteins has been profiled, a histogram of the glycoprotein types could be generated (FIG. 22d). The number of unique lectin types would depend greatly on the desired fidelity of the profile and on the application. However, hundreds of lectin types could easily be patterned on a single chip with existing micro and nanofabrication techniques. The stochastic model herein promotes the WADM as a valuable potential avenue for glycan screening and profiling. The platform would require less experimental time and does not require a unique, strong-binding site for every glycan combination. With carefully selected lectins the dynamic array could monitor the average occupancy via nanoscale transducers and accurately translate this into a glycan profile. Such transducers could be made with emerging mechanical, electronic, and florescent nanotechnology. It is hoped that this article stimulates further interest in the area of glycoprotein profiling and encourages an open database of accurate, kinetic data for lectin-glycan pairs. The concept of a WADM might also be useful in other fields of molecular screening and profiling where finding strong-binding partners for each analyte is an insurmountable task.

Figure 23:
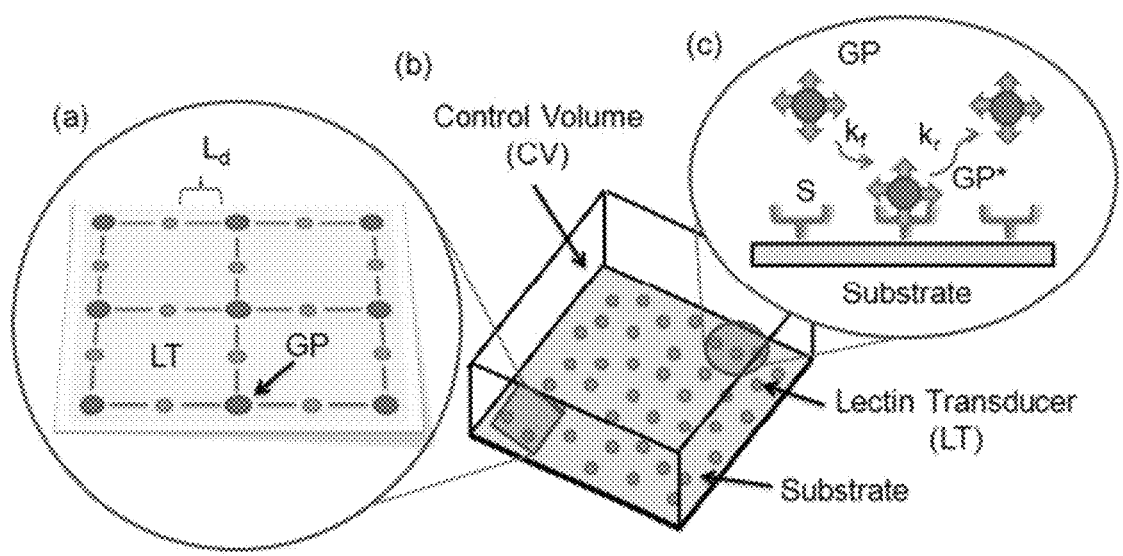
FIG. 23 is a schematic of a proposed setup of a stochastic model.

The stochastic model is based on a Langmuir association/disassociation surface reaction (FIG. 23). The glycoproteins in solution (GP) bind to free lectin sites (S) to form a glycoprotein-lectin pair (GP*). The pair can then dissociate back to a free site and a glycoprotein in solution. Association and dissociation are governed by the forward and reverse rates (kf and kr) respectively. The ratio of these rates (kr/kf) is the disassociation constant (KD). These interaction values can be determined experimentally from liquid chromatography (LC), mass spectrometry (MS), capillary electrophoresis (CE), and frontal affinity chromatography (FAC) (Hirabayashi J. 2008. *J. Biochem* 144(2):139-147, which is incorporated by reference in its entirety). Due to growing importance of glycoproteins, databases of these affinity values are continually expanding, but access for general researchers is still limited. Hirabayashi's mini-review presents the "Hect-by-Hect" project (Hirabayashi 2008) in which a hundred glycans were screened against a hundred lectins. These affinity results are open to the public in a large database from the Lectin Application and Analysis Team of AIST, (National Institute of Advanced Industrial Science and Technology (AIST). 2008. *Lectin FrontierDataBase*. Retrieved Mar. 11, 2010, from riodb.ibase.aist.go.jp/rcmg/glycodb/LectinSearch) but the results are inconveniently imbedded in small, electronic graphs and mostly given in terms of (V−V0) which is only proportional to KD. Another database available to the public is provided by the Consortium for Functional Glycomics (CFG) (Consortium for Functional Glycomics, 2010, *Primary Screen*. Retrieved from CFG Gateway: www.functionalglycomics.org/glycomics/publicdata/primaryscreen.jsp).

Figure 24:
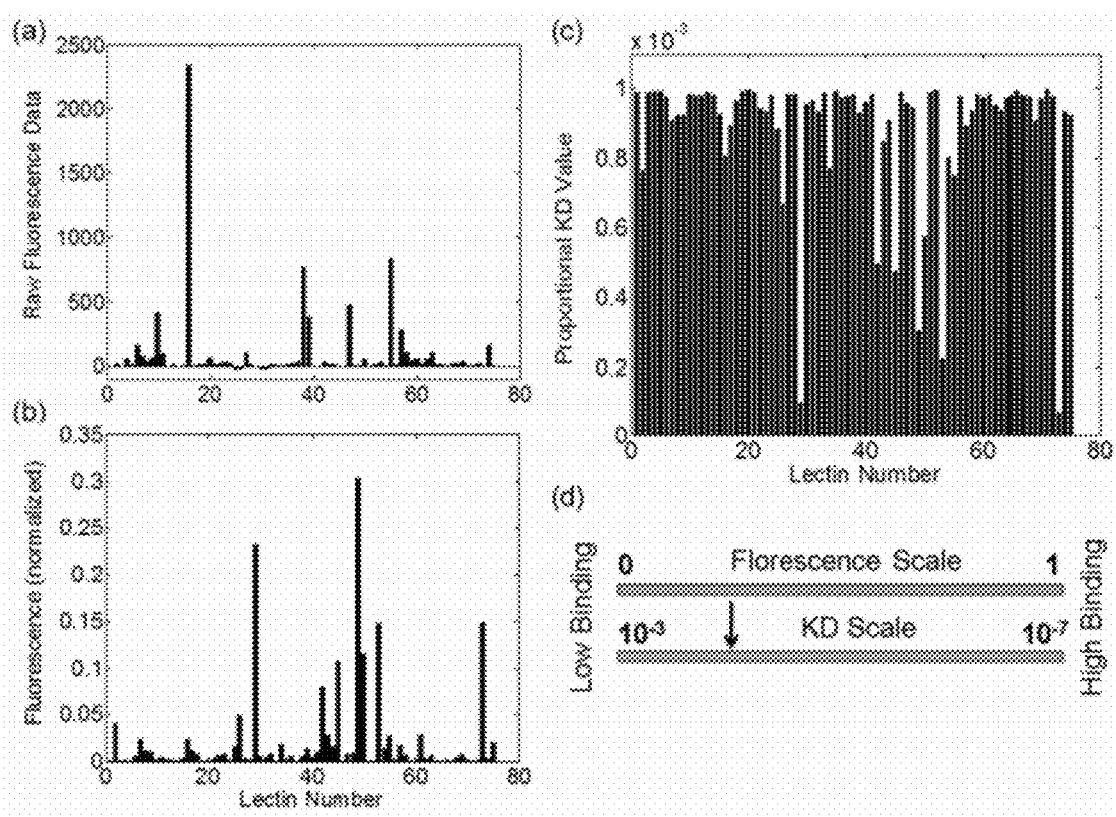
FIG. 24 includes three graphs showing the approximation of dissociation constants from a glycomics fluorescent database.

The CFG typically collects lectin proteins submitted by consortium investigators and the CFG core staff assay the proteins. Occasionally they provide their standardized, printed glycan arrays to participating glycobiologists who then follow the set procedure in adding fluorescently labeled lectins to the array. Affinity of lectin-glycan pairs are measured by relative florescence. The most current printed array (Version 4.1) has 442 glycans. To date over a hundred lectin submissions have been made by CFG members on this current array, with 75 of them being unique lectin types at varying low concentrations. Carefully measured dissociation values of lectin-glycan pairs collected by a single organization would yield the most accurate predictions from the stochastic model. As these are not currently, freely available, the KD interaction matrix for this model was made by combining the experimentally known KD range from Hirabayashi's work (Hirabayashi 2008) with the florescent data given by the CFG (Consortium for Functional Glycomics, 2010). Hirabayashi found that glycan-lectin KD values range from 10-3 to 10-7. It is assumed that the 442 glycans present on the CFG array span this interaction range. By normalizing the relative florescence data of each CFG lectin submission to its respective florescence range, and then finding the proportional distance in the KD range, a full matrix of Glycan-Lectin approximated KD values can be formed for the 75 unique lectin entries (FIG. 24). Again, these interaction parameters are approximated to illustrate how the WADM would operate and the method of using the model for optimal predictions. More accurate parameters could be obtained from the dynamic array itself and fed into the model to provide more accurate predictions of lectin subsets for specific screening and profiling problems.

Stochastics were invoked in this model due to the very small species concentrations and simulated control volume. Treating the species as concentrations would yield faulty contrast values between lectin binding species. Thus a stochastic Kinetic Monte Carlo method was employed for this system. It was solved using the Gillespie algorithm (Gillespie D T. 1977. Exact Stochastic Simulation of Coupled Chemical Reactions. *J Phys Chem.* 81(25):2340-2360, which is incorporated by reference in its entirety). First the forward and reverse rate expressions were transformed into probability functions:

$$P(R_f) = \frac{k_f \cdot N_S \cdot N_{GP}}{A_N \cdot V} \quad (1)$$

$$P(R_r) = k_r \cdot N_{GP*} \quad (2)$$

The concentration of glycoproteins in solution and the number of lectin sites (NS) were specified by the user. The control volume (V) was dynamically solved for using the diffusion length ($L_d$) of protein in solution and the event time step (ts) predicted by the Gillespie algorithm:

$$L_D = \sqrt{4 \cdot D \cdot t_s} \quad (3)$$

The diffusion length was used to space the lectin transducers into a regular grid and the resulting area was multiplied by the reactive depth (again the diffusion length) to produce the control volume (V) (FIG. 8b). The number of free glycoproteins in solution (NGP) was calculated from the specified protein concentration and the control volume. To ensure that both reactive probabilities have the units of molecular event per second, Equation 1 also includes Avogadro's number (AN). The forward reaction rate was assumed to be diffusion limited. The diffusion constants for glycoproteins vary by a small degree so an average protein kf value of 2E8 (M·s)$^{-1}$ was used (Creighton T E. 1993. *Proteins.* 2nd ed. New York (NY): W.H. Freeman and Company. p. 345, which is incorporated by reference in its entirety).

The glycoprotein in solution was simplified in the stochastic simulation to save on computation time. Glycoproteins have a distinct number of glycosylation sites where oligosaccharides can be attached. N-linked glycans attach to accessible asparagine residues and O-linked to serine or threonine. (Li H, d'Anjou M. 2009. Pharmacological significance of glycosylation in therapeutic proteins. *Curr Opin Biotechnol* 20(6):678-684) For example, an important physiologic glycoprotein, α1—acid glycoprotein (Orosomucoid), has five, N-linked glycosylation sites (FIG. 25a) (Schonfeld D, et al. *J Mol Biol* 384(2):393-405, which is incorporated by reference in its entirety). To simplify the multi-site glycosylated protein, probability was again employed. In the stochastic simulation, if a binding event occurs an additional random number was generated to determine which of the glycans would be presented to the lectin. Thus the protein was effectively reduced to a sphere with glycan sites that each has an equal probability of being presented in a binding event (FIG. 25b). In this study, multiple glycosylation sites were equally distributed on the surface of the protein, but the model can be adapted to accommodate irregular spacing as well, as shown in the accessibility consideration of the fourth case study above.

The Gillespie algorithm uses an ensemble average of probabilistic binding/dissociation events over a given simulation time to predict frequency of events and average occupancy number. Each experimental "run" is for 1000 binding events, and the ensemble average is composed of 1000 runs. The code loops through each of the lectins to determine which types provide the greatest contrast for screening/profiling purposes. The general algorithm goes as follows: 1) read in glycan profile for protein in solution (either user specified or randomly generated—numbers should correspond to the glycan rows in the interaction KD matrix, 2) generate a random number to determine which glycan site is presented on the glycoprotein, 3) generate a random number to determine which of the reactions occur, 4) adjust count of GP, S, and GP*, 5) generate next time step according to Equation 4, 6) Add time step to time count, 7) loop through steps 2-6 until 1000 binding events are achieved, 8) conduct 1000 runs of the stochastic simulation to create ensemble average, and 9) perform an ensemble average for each of the lectins to determine which would be best for screening purposes. This algorithm was compiled for MATLAB.

$$\Delta Time = -\left(\frac{1}{R_f + R_r}\right) \cdot \log(rand) \quad (4)$$

Figure 2:
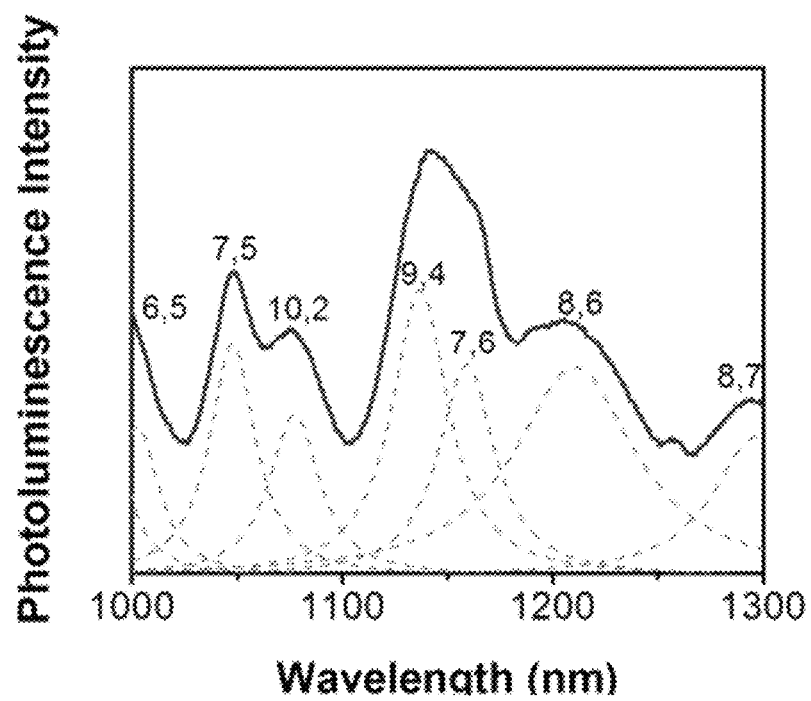
FIG. 2 is a graph showing the deconvolution of photoluminescence of a nanostructre in response to capture protein binding.
Figure 3:
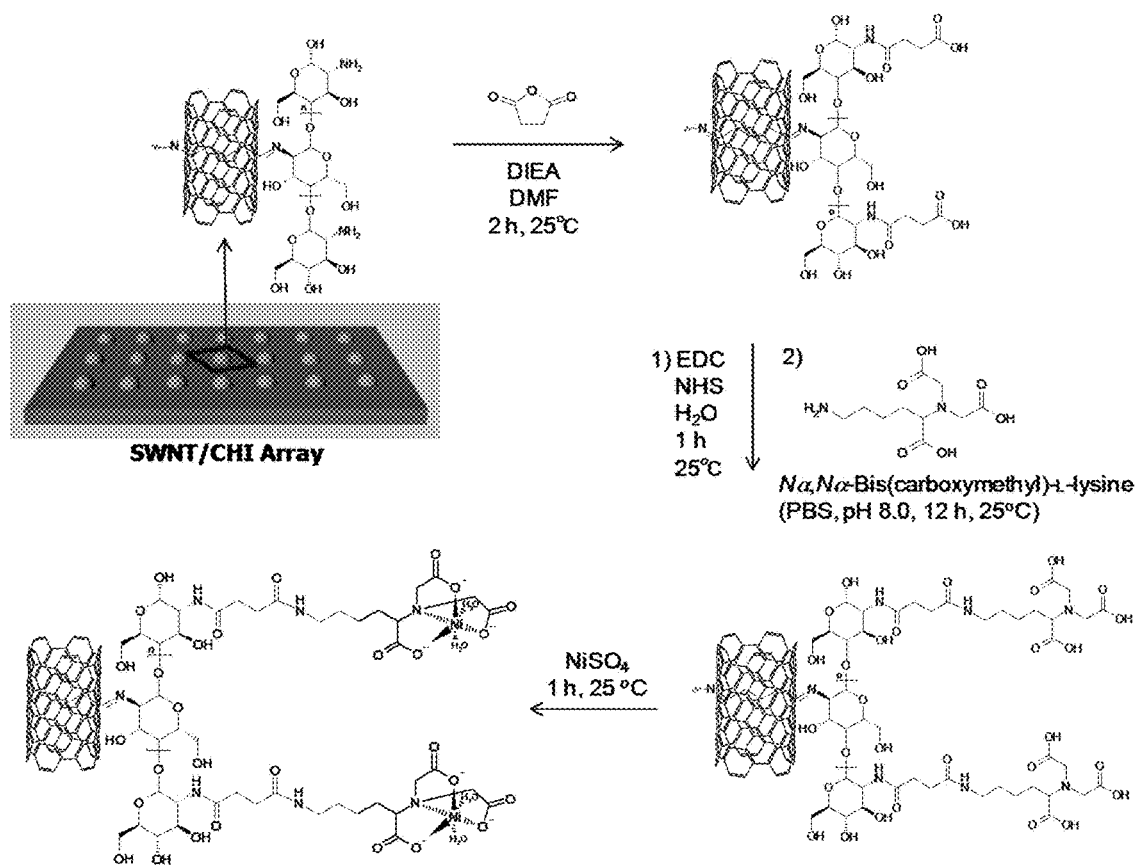
FIG. 3 is a schematic of the functionalization of a single walled nanotube/chitosan array with Ni—$N_\alpha,N_\alpha$-bis(carboxymethyl)-L-lysine.

In order to achieve a label-free sensing platform for protein-protein interactions (FIG. 1a), SWNT were first suspended with CHI (0.25 wt % in 1% acetic acid), which was selected for its chemical resistance, low tendency for non-specific adsorption of proteins, and biocompatibility. (Yan, L. Y., Poon, Y. F., Chan-Park, M. B., Chen, Y. & Zhang, Q. Individually dispersing single-walled carbon nanotubes with novel neutral pH water-soluble chitosan derivatives. *Journal of Physical Chemistry C* 112, 7579-7587 (2008), which is incorporated by reference in its entirety). The SWNT were directly ultra-sonicated, and the resulting solution was centrifuged for 3 h at 16,000 g. The supernatant was mixed with a CHI solution (2 wt % in 1% acetic acid) containing glutaraldehyde (0.25%, vol/vol), the SWNT/CHI suspension was then spotted on a patterned glass slide. In order for cross-linking to occur, the spotted SWNT/CHI solution was allowed to stand for 6 h at 25° C. in a humidified chamber. FIG. 1b shows an optical micrograph of the SWNT/CHI array and its corresponding nIR fluorescence image obtained with a Si CCD imaging camera, showing bright and homogeneous fluorescence. The SWNT/CHI array exhibited intense and discrete nIR fluorescent spectra, as shown in FIG. 2, and spectral properties were highly uniform across the entire array. The SWNT/CHI array was then carboxylated with succinic anhydride in N,N-dimethylformamide (DMF) for 2 h at 25° C. After activation of carboxylic acid on the SWNT/CHI array with N-(3-dimethylamino-propyl)-N'-ethylcarbodiimide hydrochloride (EDC•HCl) and N-hydroxysuccinimide (NHS), NTA was coupled in PBS (pH 8.0) for 12 h at 25° C. Nickel sulfate ($NiSO_4$) was added on each spot of the array, and incubated for 1 h at 25° C. (FIG. 3).

Figure 4:
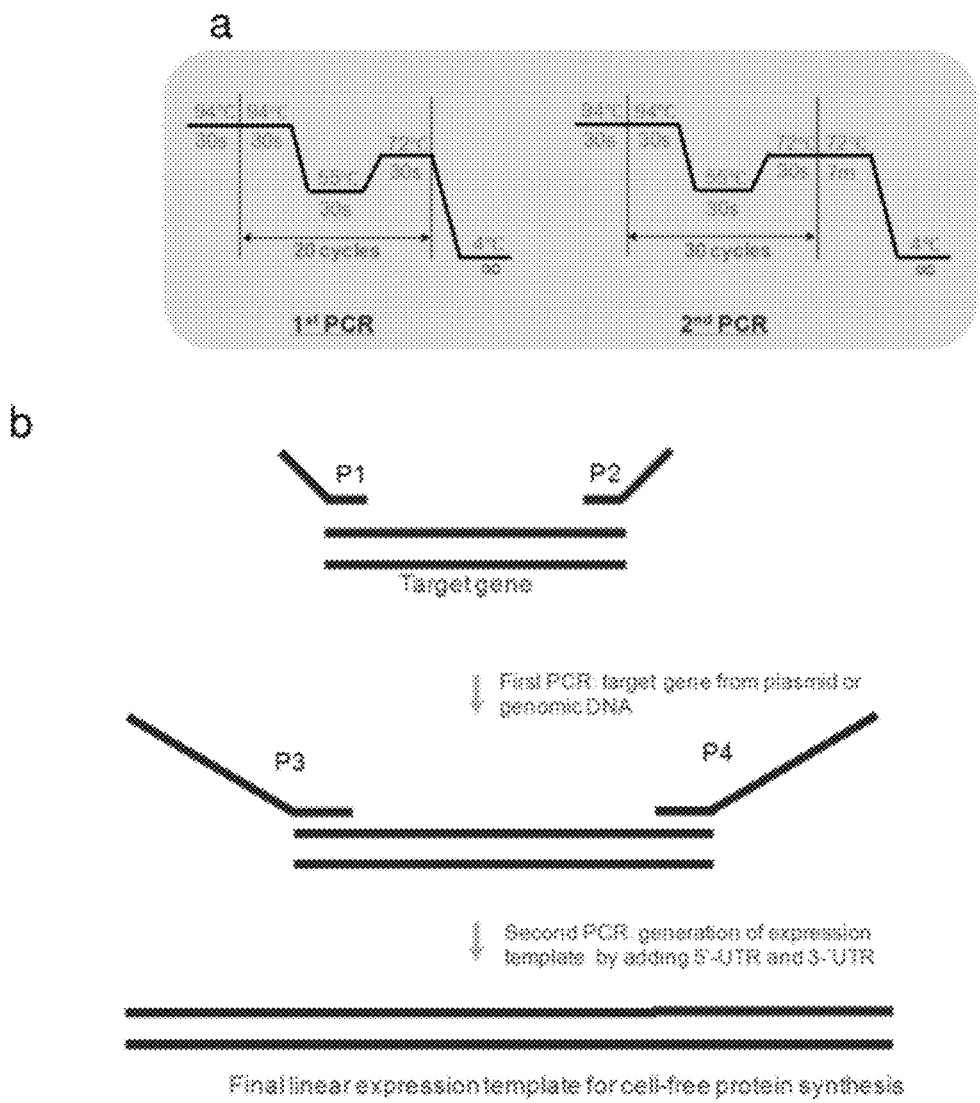
FIG. 4a illustrates the generation of a capture protein expression template by PCR.
FIG. 4b discloses SEQ ID NOS 38-39 and 35-36, respectively, in order of appearance, and FIG. 4c discloses SEQ ID NOS 35 and 40, respectively, in order of appearance, and the "6xHistag" as SEQ ID NO: 37.
Figure 5:
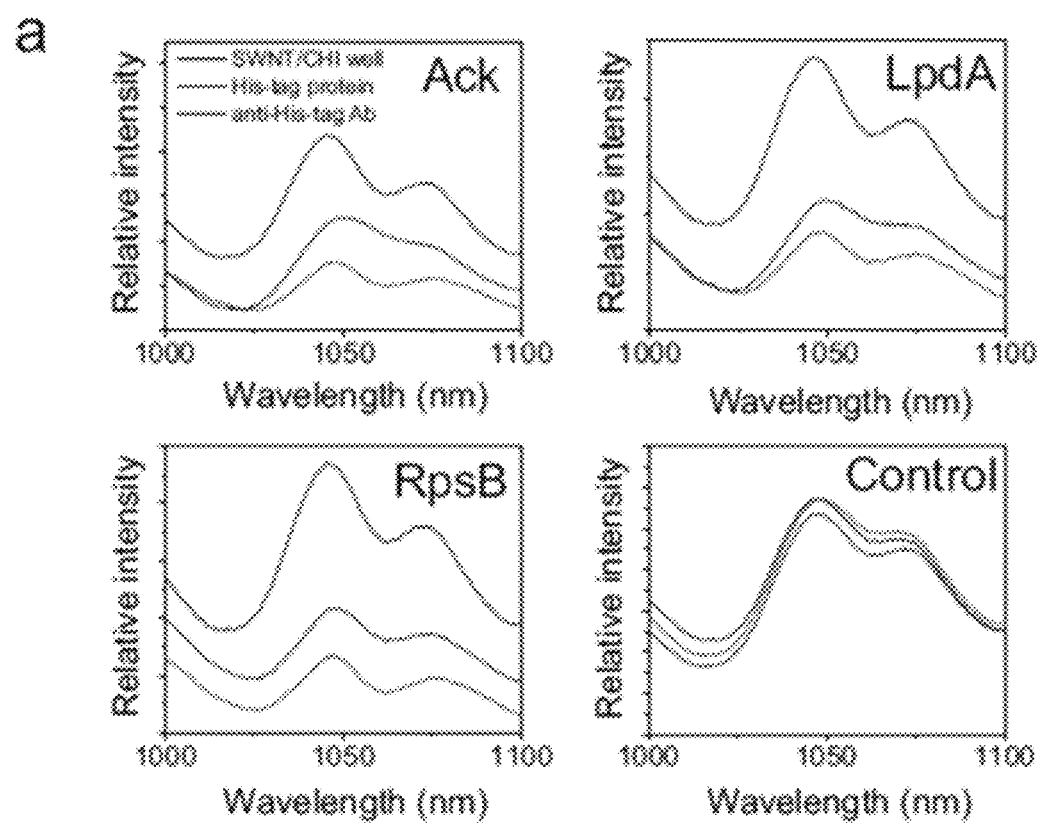
FIG. 5 includes graphs showing selective recognition of protein-protein interactions on an array.
Figure 5:
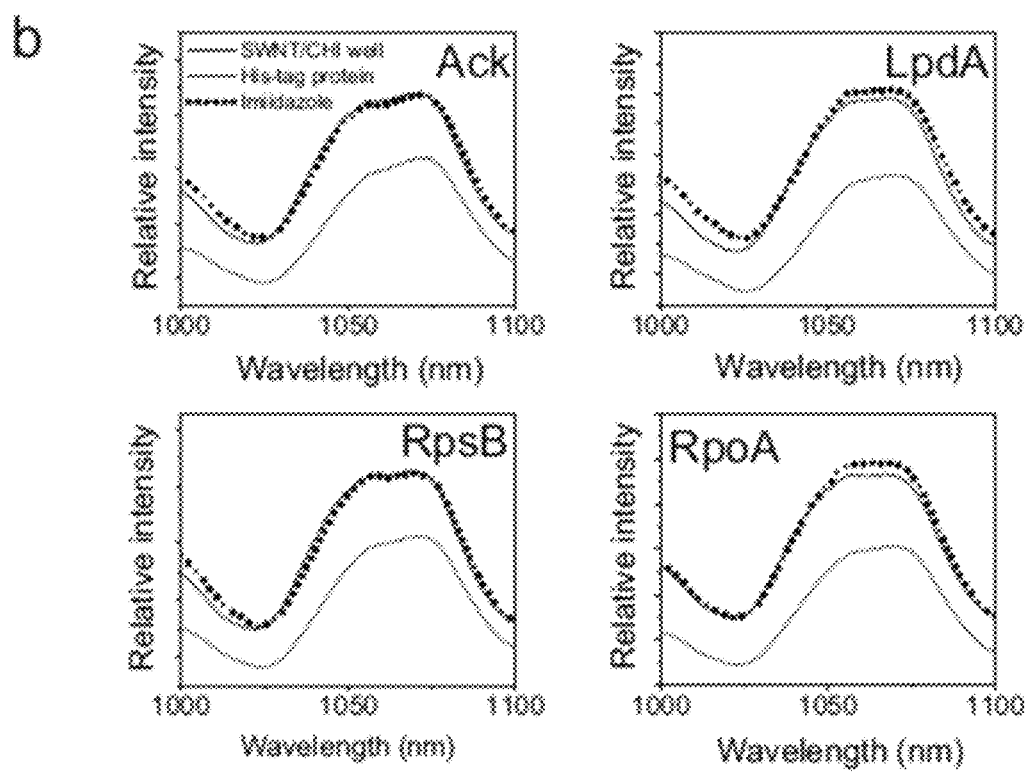
Figure 5:
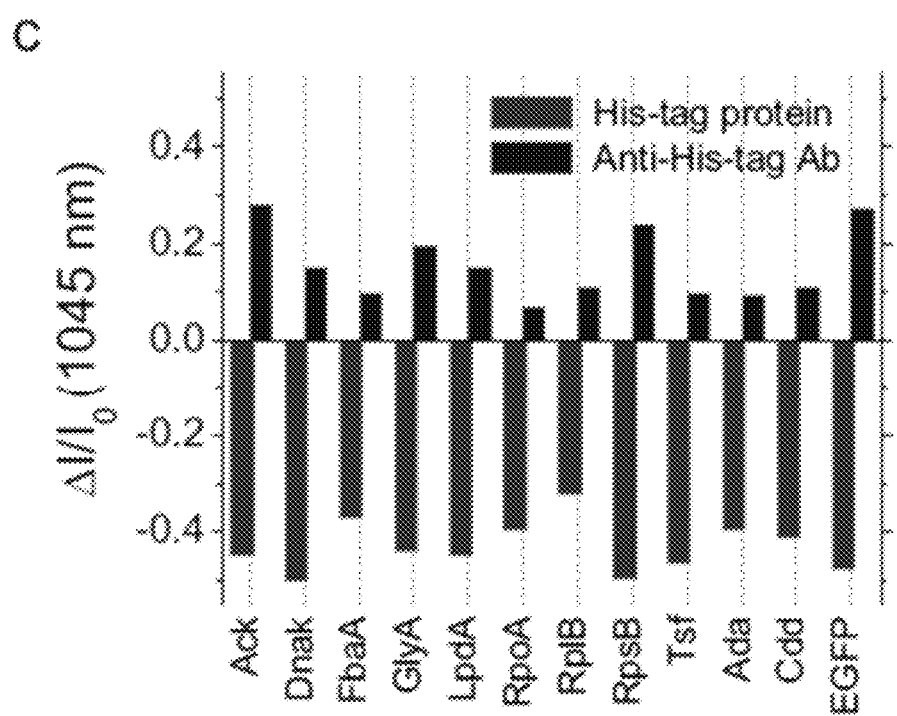
Figure 5:
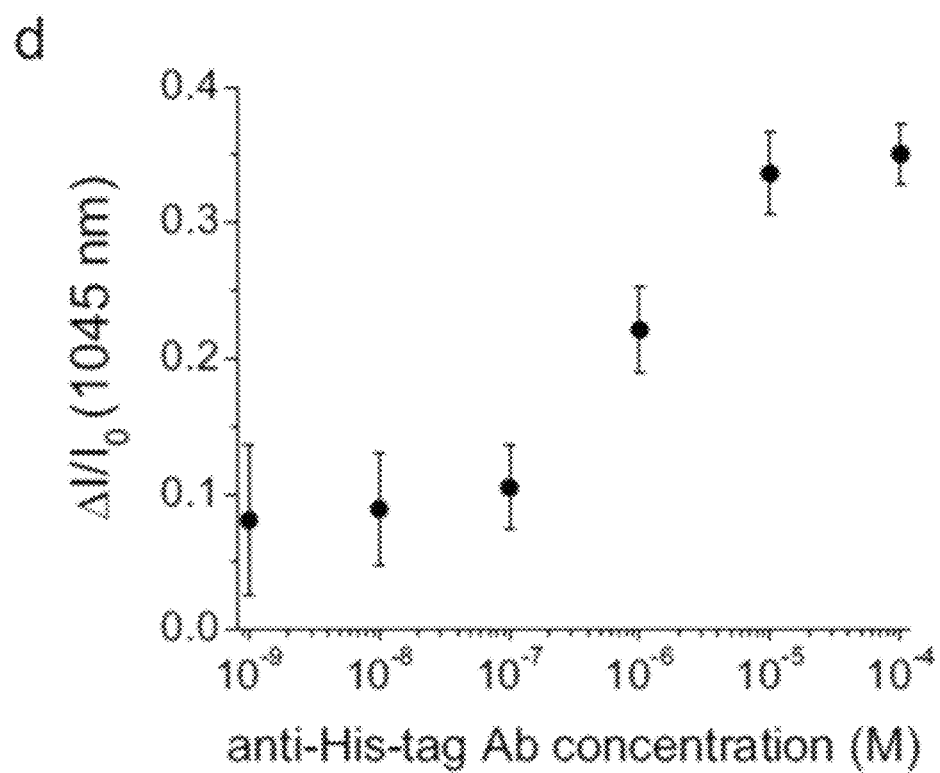
Figure 6A:
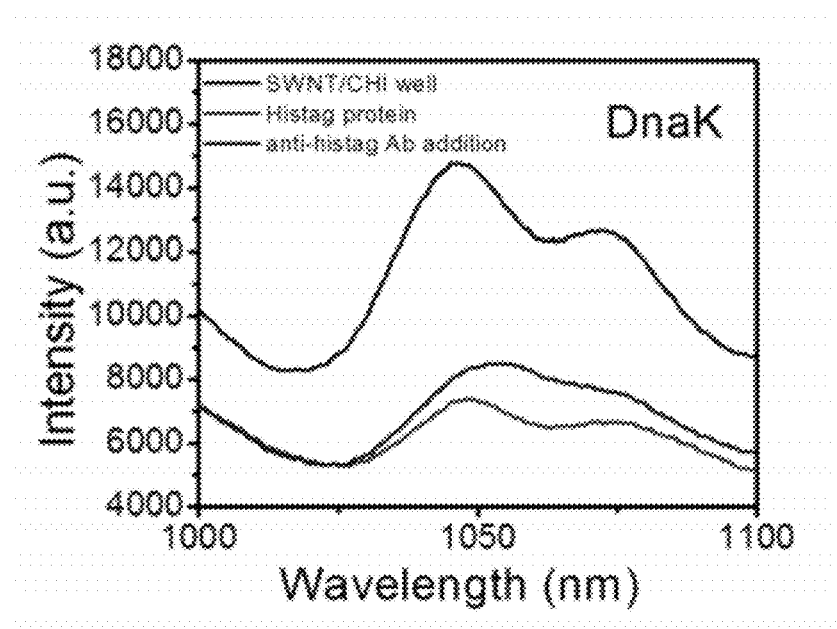
FIG. 6 includes graphs showing changes in nanostructure photoluminescence in response to selective recognition of protein-protein interactions on an array.
Figure 6B:
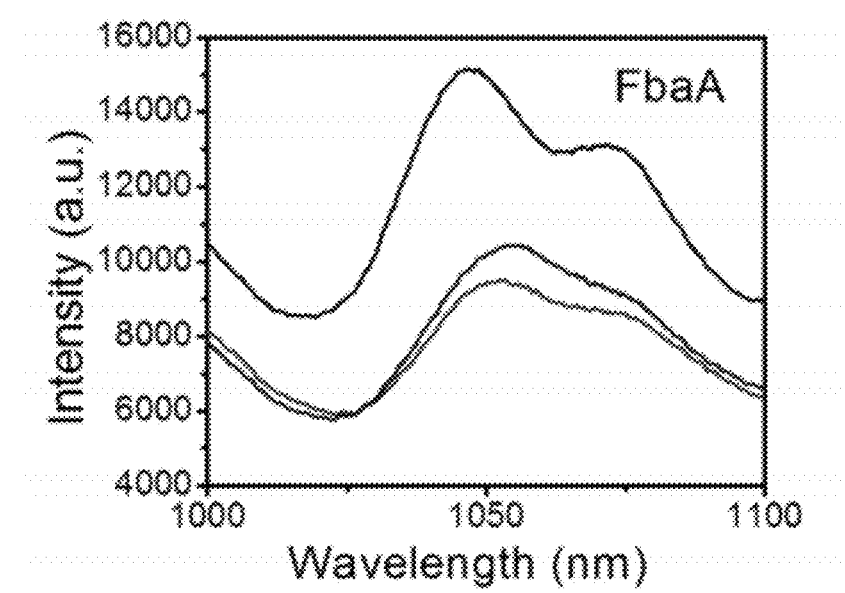
Figure 6C:
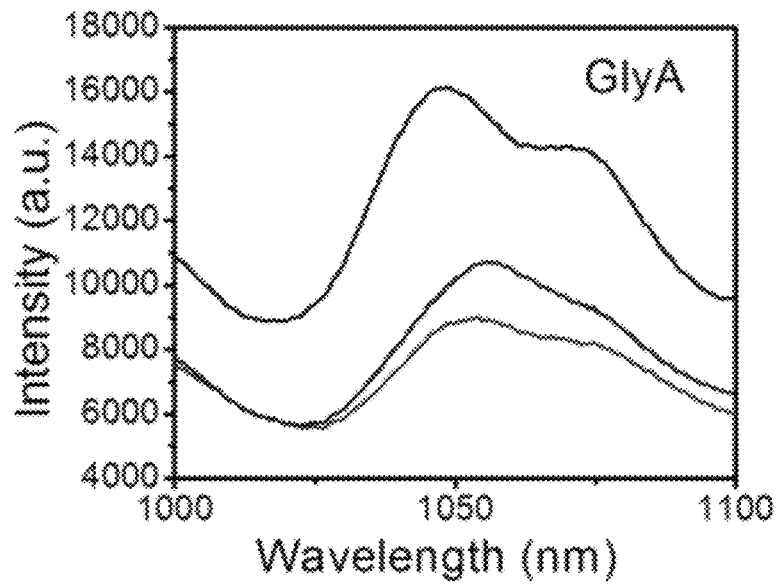
Figure 6D:
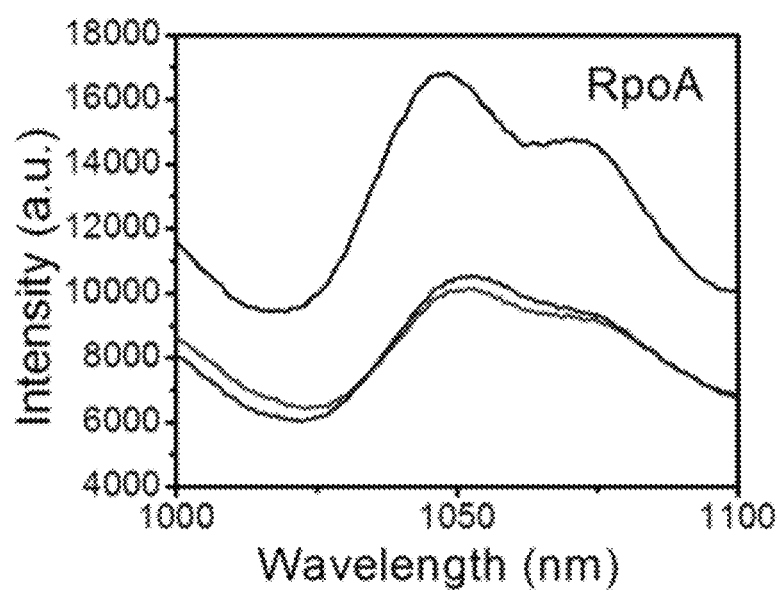
Figure 6E:
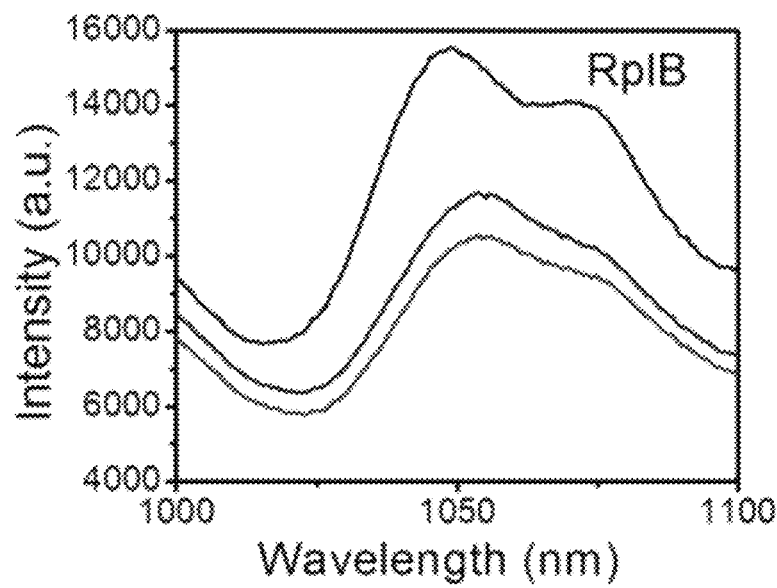
Figure 6F:
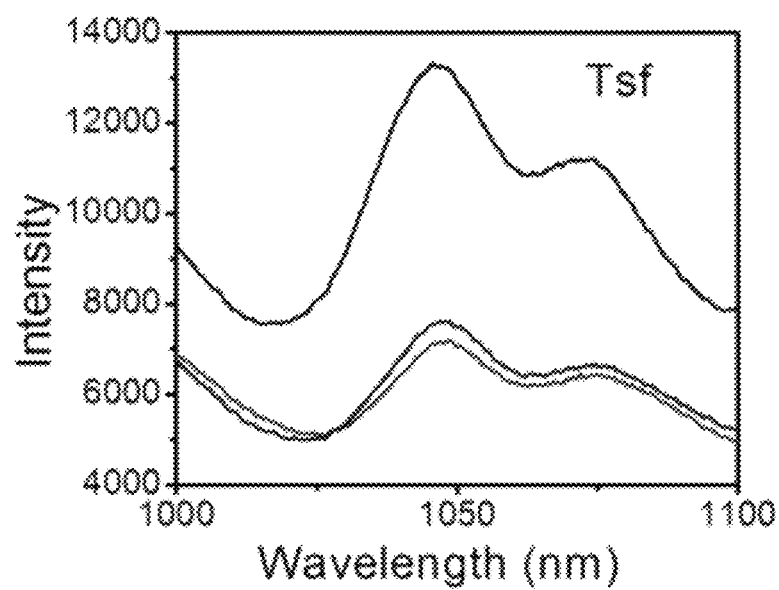
Figure 6G:
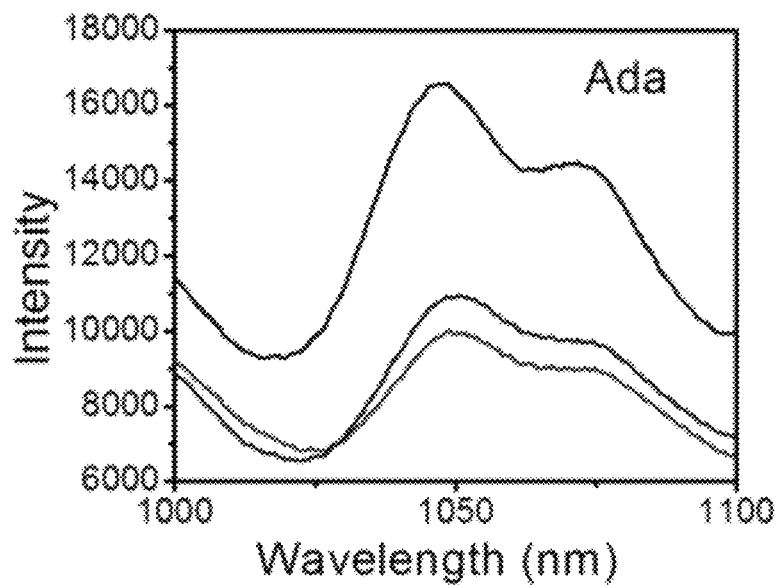
Figure 6H:
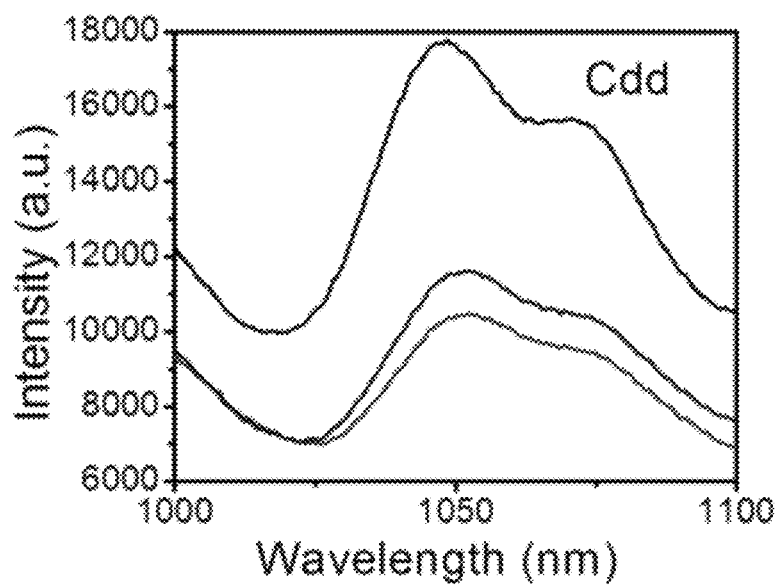

The addition of the chelating $Ni^{2+}$ ion to the grafted NTA on SWNT/CHI array resulted in a partial fluorescence quenching as expected from studies of excited state quenching from divalent ions. (Brege, J. J., Gallaway, C. & Barron, A. R. Fluorescence Quenching of Single-Walled Carbon Nanotubes with Transition-Metal Ions. *Journal of Physical Chemistry C* 113, 4270-4276 (2009), which is incorporated by reference in its entirety). Binding proteins can dock in such a way as to alter the distance between the $Ni^{2+}$ and the SWNT, thereby allowing for their detection. The S30 extract for cell-free protein expression was added to each spot of the SWNT/CHI array containing the Ni-NTA group, followed by the addition of PCR-amplified DNA coding for each protein to initiate protein synthesis. Since each in vitro synthesized protein has a C-terminal His-tag, nascent proteins can be in situ immobilized directly on the SWNT/CHI array with Ni-NTA. To reduce nonspecific binding onto the array, proteins known to bind to the Ni-NTA group were removed from the *E. coli* S30 extract. (Kim, T. W., Oh, I. S., Ahn, J. H., Choi, C. Y. & Kim, D. M. Cell-free synthesis and in situ isolation of recombinant proteins. *Protein Expres Purif* 45, 249-254 (2006), which is incorporated by reference in its entirety). Significant contamination of wondrous histidine-rich protein (WHP), such as SlyD (29 kDa) can frequently observed when using immobilized metal affinity chromatography (IMAC). (Scholz, C. et al. SlyD proteins from different species exhibit high prolyl isomerase and chaperone activities. *Biochemistry* 45, 20-33 (2006); Mitterauer, T., Nanoff, C., Ahorn, H., Freissmuth, M. & Hohenegger, M. Metal-dependent nucleotide binding to the *Escherichia coli* rotamase SlyD. *Biochem. J.* 342, 33-39 (1999), each of which is incorporated by reference in its entirety). To eliminate nonspecific binding that could cause background optical changes, the *E. coli* S30 extract was pretreated with Ni-NTA resin prior to protein expression to eliminate WHP. Eleven *E. coli* proteins, spanning a range of molecular weights were chosen as model proteins for the proof of concept of this SWNT-based protein array. Instead of cloning each of the fusion constructs in the expression vector, the PCR-amplified DNAs were used directly as the expression templates for protein synthesis, thereby eliminating the time- and labor-intensive cloning steps. PCR-amplified linear genes can be used as expression templates in a cell-free protein synthesis system, which facilitates the rapid preparation of expressible genes for high-throughput protein synthesis. (Yabuki, T. et al. A robust two-step PCR method of template DNA production for high-throughput cell-free protein synthesis. *J Struct Funct Genomics* 8, 173-191 (2007); Swartz, J. R., Jewett, M. C. & Woodrow, K. A. Cell-free protein synthesis with prokaryotic combined transcription-translation. *Methods Mol Biol* 267, 169-182 (2004); Ahn, J. H. et al. Cell-free synthesis of recombinant proteins from PCR-amplified genes at a comparable productivity to that of plasmid-based reactions. *Biochem Bioph Res Co* 338, 1346-1352 (2005); Ahn, J. H., Keum, J. W. & Kim, D. M. High-throughput, combinatorial engineering of initial codons for tunable expression of recombinant proteins. *J Proteome Res* 7, 2107-2113 (2008); Woodrow, K. A. & Swartz, J. R. A sequential expression system for high-throughput functional genomic analysis. *Proteomics* 7, 3870-3879 (2007), each of which is incorporated by reference in its entirety). The genes coding for each of the eleven proteins were prepared by a two-step PCR method (FIG. 4a). In the first-round PCR, target ORFs were amplified from *E. coli* K12 genomic DNA with gene specific primers flanked with overlapping region (Table 1, see above). The PCR products were purified by gel extraction and used for the second-round PCR, in which the full-length expression templates were synthesized by fusing ORF with regulatory elements including T7 promoter, ribosomal binding site, T7 terminator, and stop codon (FIG. 4b,c). As shown in FIG. 1, cell-free protein synthesis was performed on the SWNT/CHI array in a humidified chamber at 37° C. After the expression reaction for 2 h, the array was washed three times with PBS buffer (10 mM, pH 7.4). The nIR fluorescence spectra of each spot were measured before and after cell-free translation. The fluorescence intensity of SWNT decreased up to 40% as the His-tag proteins were expressed on the SWNT/CHI array (FIG. 5a). However, no significant fluorescence change was observed in the absence of DNA (FIG. 5a, control). These results indicated that the proteins were expressed by cell-free synthesis on each spot of the SWNT/CHI array and immobilized by the Ni-NTA group. Immobilization can occur through complexation between $Ni^{2+}$ and the His-tag residue of proteins. The other eight proteins tested showed the same pattern with slight intensity variations that depend upon the specific protein (FIG. 6). In order to further confirm that the fluorescence quenching of SWNT was caused by selective immobilization of the expressed His-tag proteins to the Ni-NTA group on the SWNT/CHI array, each spot was treated with imidazole (250 mM) to dissociate them from the Ni-NTA functionalized surface. As shown in FIG. 5b, the quenched fluorescence was completely restored after imidazole treatment. This suggested that the Ni-NTA group can allow the SWNT to report the binding and unbinding of the capture protein.

To determine whether the SWNT/CHI array system is able to detect protein-protein interactions using the capture proteins, the anti-His-tag antibody was added to each spot containing immobilized His-tag proteins, and the subsequent fluorescence response was monitored. As shown in FIG. 5a,c, the fluorescence intensity increased after addition of anti-His-tag antibody while no significant intensity change was observed in the SWNT/CHI spot without the His-tag protein, which indicated that the SWNT/CHI array system was capable of optically reporting the selective protein interaction. This SWNT/CHI array was the first label-free sensing platform utilizing nIR fluorescence of SWNT for detecting protein-protein interactions.

To evaluate the detection limit of capture proteins on the SWNT/CHI array, the PL response was analyzed as a function of protein concentration using an entire array spot (FIG. 5d). When the anti-His-tag antibody was added to each well on which His-tag EGFP was immobilized, up to 1 nM protein concentration is detected ($K_{eg}$=1.8 $\mu M^{-1}$). FIG. 5d shows the fluorescent response of SWNT after binding of anti-His-tag antibody added in various concentrations from 100 μM to 1 nM to His-tag EGFP. The curve exhibited the sigmoidal shape characteristic of equilibrium binding.

Single SWNT fluorescence spectroscopy has been previously demonstrated and can be quite robust with essentially an infinite photo-bleaching lifetime. SWNT do not intrinsically blink, as can be the case with quantum dots. In previous work, it was shown that when monitored at the single SWNT level, the photoemission will stochastically quench and dequench only in the presence of specific quenching molecules. (Cognet, L. et al. Stepwise quenching of exciton fluorescence in carbon nanotubes by single-molecule reactions. *Science* 316, 1465-1468 (2007); Tin, H., Heller, D. A., Kim, T. H. & Strano, M. S. Stochastic Analysis of Stepwise Fluorescence Quenching Reactions on Single-Walled Carbon Nanotubes: Single Molecule Sensors. *Nano Lett* 8, 4299-4304 (2008), each of which is incorporated by reference in its entirety). These fluctuations were shown to correlate with the adsorption and desorption of individual quenching molecules, allowing one to calculate forward and reverse rates, and therefore, affinity constants from this ratio. The fluctuations were quantized according to the exciton diffusion length of approximately 90 nm. (Cognet, L. et al. (2007)). For example, a 1 μm long SWNT may have up to 1000 nm/90 nm~11 quenching states per diffraction limited spot, each distinguishable in a histogram of fluorescence intensities.

Figure 7:
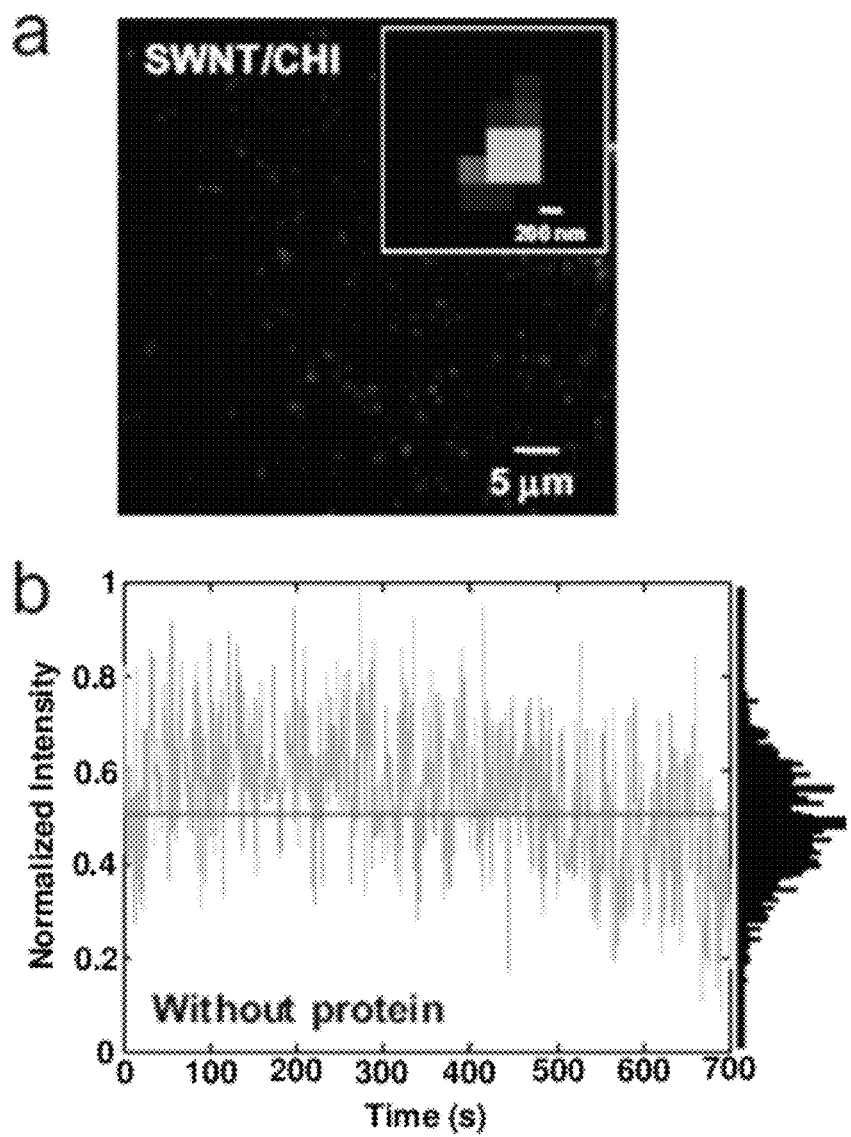
FIG. 7 includes graphs showing single molecule detection of protein-protein interactions on an array.
Figure 7:
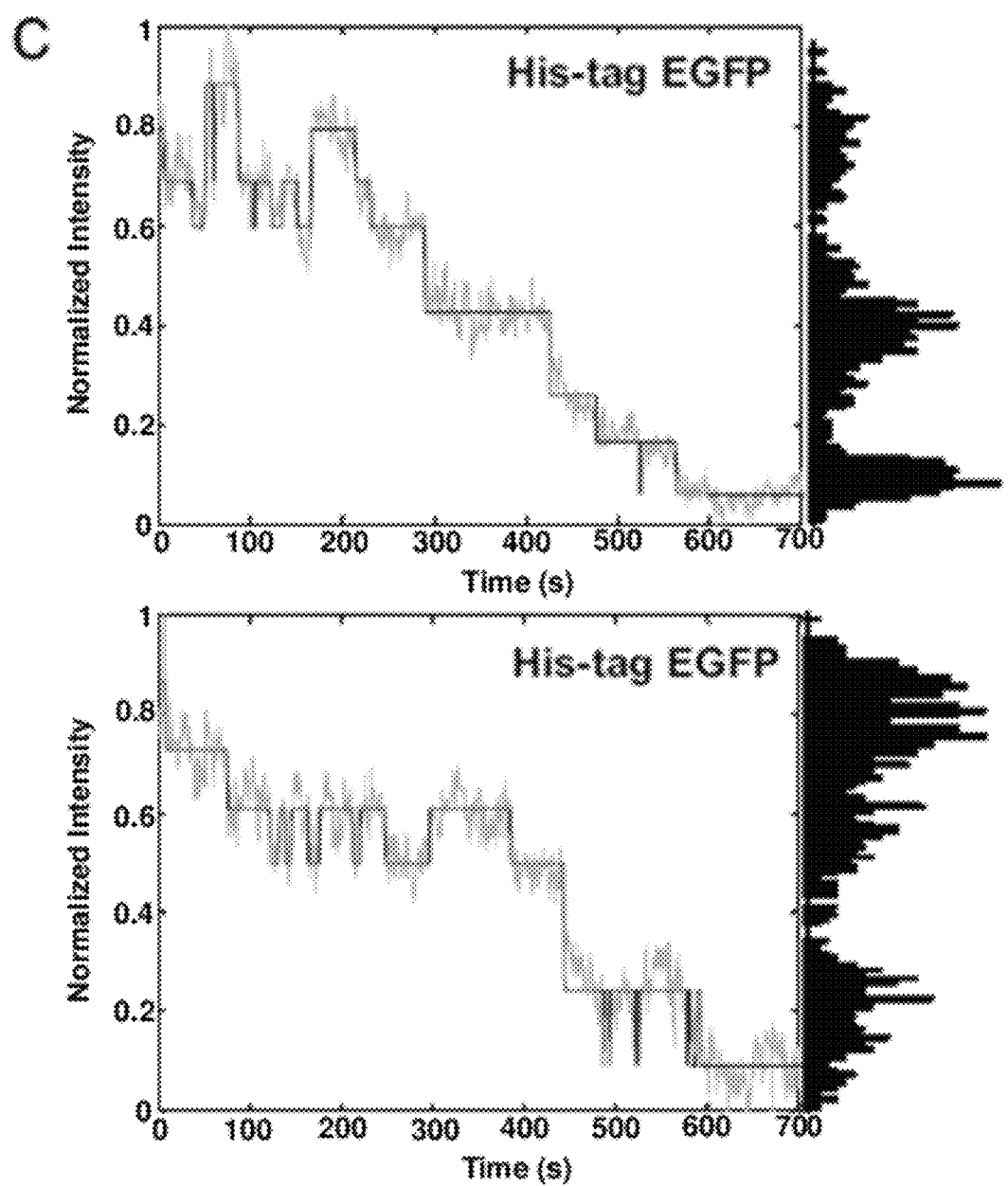
Figure 7:
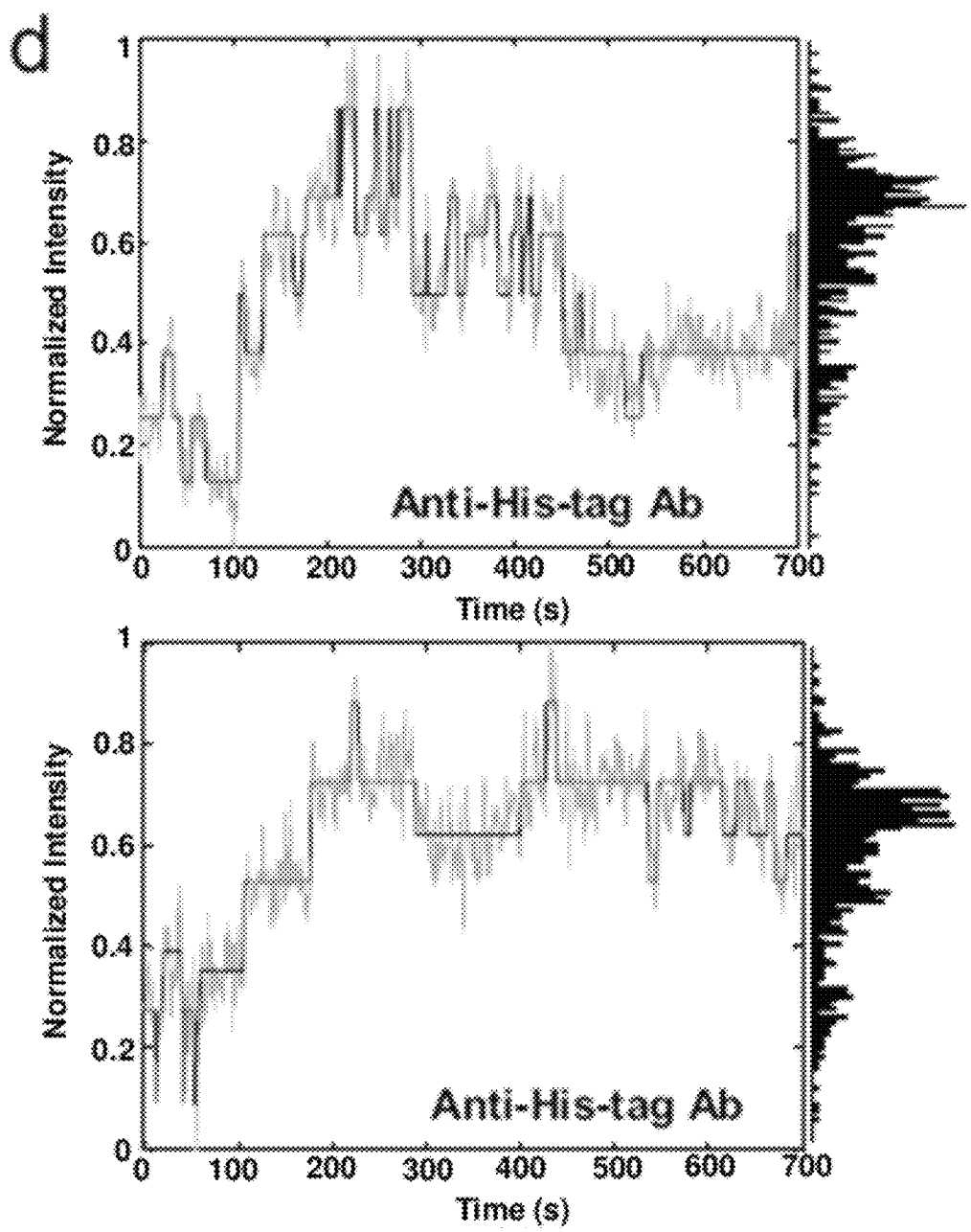
Figure 8:
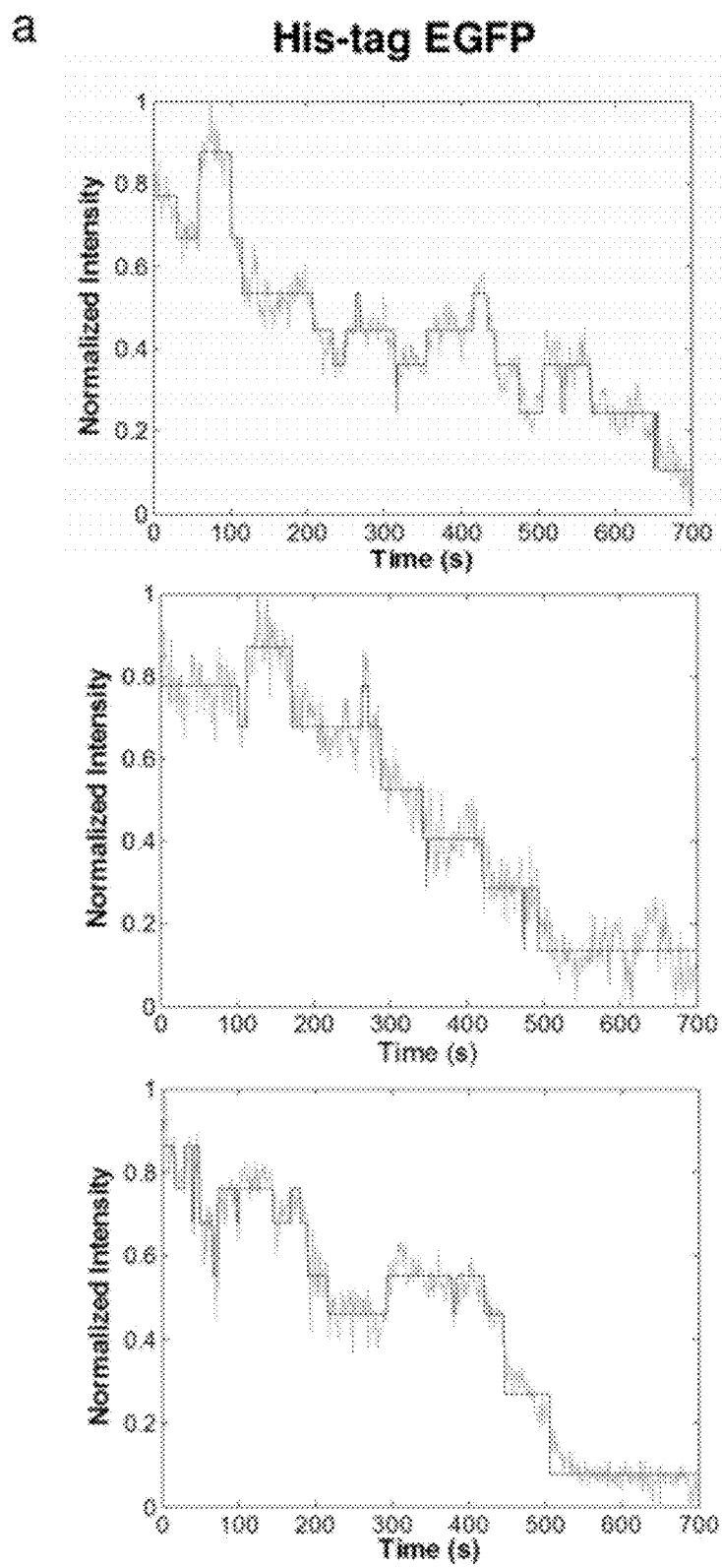
FIG. 8 includes graphs showing single molecule detection of protein-protein interactions on an array.
Figure 8:
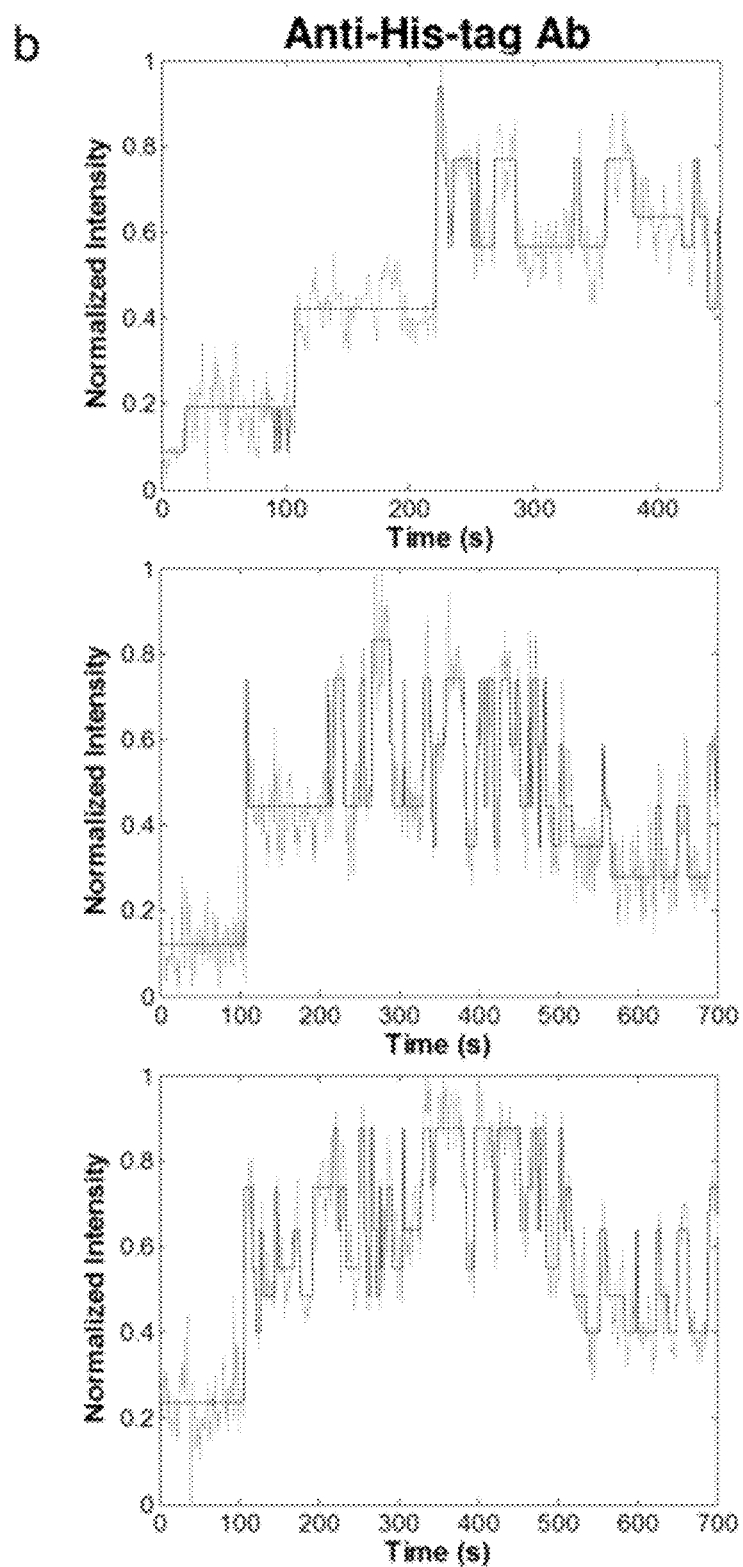

To examine whether this single molecule detection scheme can extend to our mechanism of protein detection, nIR imaging of the CHI/SWNT spots was conducted, allowing us to record in parallel the emission of single SWNT in response to protein binding. As shown in FIG. 7, stepwise nIR fluorescence quenching of the SWNT/CHI array occurred in response to capture protein addition with partial restoration occurring upon addition of the antibody. After the His-tag EGFP was added to SWNT/CHI bearing Ni-NTA (FIG. 7c), time traces of the SWNT fluorescence response were obtained by measuring the intensity of four pixel spots in movies recorded at 1 frame per second. This resulted in multiple traces that exhibit single-step fluorescence variations, which may arise from the quenching of excitons by $Ni^{2+}$. Each trace yielded a narrow histogram of normalized intensity changes after a hidden Markov algorithm was applied to each SWNT signal, indicating that binding of single His-tag EGFP to the Ni-NTA group in the SWNT/CHI array can be detected. (Tin, H., et al (2008)). The forward and reverse quenching rate constants for His-tag EGFP were 7.24 $nM^{-1}s^{-1}$ and 0.0184 $s^{-1}$, respectively. Then, single molecule detection of protein-protein binding was investigated by adding anti-His-tag antibody to His-tag EGFP in the SWNT/CHI array. As shown in FIG. 7d, stepwise fluorescence increase was observed upon addition of the antibody to His-tag EGFP, in agreement with the results shown in FIG. 5. In addition, the histograms of the normalized intensity for all points of each trace appeared narrow and distinct, which may confirm the detection of single quenching states upon protein-protein interaction. Rate constants ($k_f$=4.0×10⁻⁶ $nM^{-1}s^{-1}$ and $k_r$=4.023×10⁻⁴ $s^{-1}$) for His tag EGFP/antibody interactions were obtained after applying a stochastic step-fitting algorithm. (Tin, H., et al (2008); McKinney, S. A., Too, C. & Ha, T. Analysis of single-molecule FRET trajectories using hidden Markov modeling. *Biophys J* 91, 1941-1951 (2006), which is incorporated by reference in its entirety). Without addition of protein, the fluorescence remained invariant (FIG. 7b). SWNT emission was stable with zero mean deflection. The all points histogram showed a single Gaussian distribution. This may indicate that the stepwise fluorescence response of SWNT was caused by the protein-protein interaction (FIG. 7 and FIG. 8).

TABLE 2

Distances between the $Ni^{2+}$ ion and the SWNT

| Receptor protein | $\Delta d_1$ (nm) | $\Delta d_2$ | Analyte Protein for $\Delta d_2$ calculation |
| --- | --- | --- | --- |
| ACK | 0.17863 | −0.06980 | antiHis Ab |
| Dnak | 0.21011 | −0.03993 | antiHis Ab |
| FbaA | 0.13853 | −0.02607 | antiHis Ab |
| GlvA | 0.17494 | −0.05045 | antiHis Ab |
| LpdA | 0.17908 | −0.03964 | antiHis Ab |
| RpoA | 0.15028 | −0.01080 | antiHis Ab |
| RplB | 0.11432 | −0.02945 | antiHis Ab |
| RpsB | 0.20878 | −0.06084 | antiHis Ab |
| Tsf | 0.18831 | −0.01899 | antiHis Ab |
| Ada | 0.15081 | −0.02568 | antiHis Ab |
| Cdd | 0.15809 | −0.02948 | antiHis Ab |
| CDK4 | 0.07655 | 0.06338 | p16 |
| p16 | 0.08120 | 0.05174 | CDK4 |
| JUN | 0.07671 | 0.04646 | FOS |
| FOS | 0.09560 | 0.02362 | JUN |

*$\Delta d_1$ and $\Delta d_2$ were calculated using the Förster resonance energy transfer equation.

Extension of the single molecule detection results into a concerted assay with single protein detection limits required several improvements such as: (1) a software/hardware interface that could quickly capture a series of images over the CHI spot from which single channel traces can be extracted, (2) a film synthesis method that could result in a higher fraction of responsive nanotube elements, and (3) the use of existing placement methods that could localize with uniform pitch, each single SWNT sensor, in a diffraction limited spot at 900 nm pitch. (Sharma, R., Lee, C. Y., Choi, J. H., Chen, K. & Strano, M. S, Nanometer positioning, parallel alignment, and placement of single anisotropic nanoparticles using hydrodynamic forces in cylindrical droplets. *Nano Lett* 7, 2693-2700 (2007); Sharma, R. & Strano, M. S. Centerline Placement and Alignment of Anisotropic Nanotubes in High Aspect Ratio Cylindrical Droplets of Nanometer Diameter. *Adv Mater* 21, 60-65 (2009), each of which is incorporated by reference in its entirety).

Figure 9:
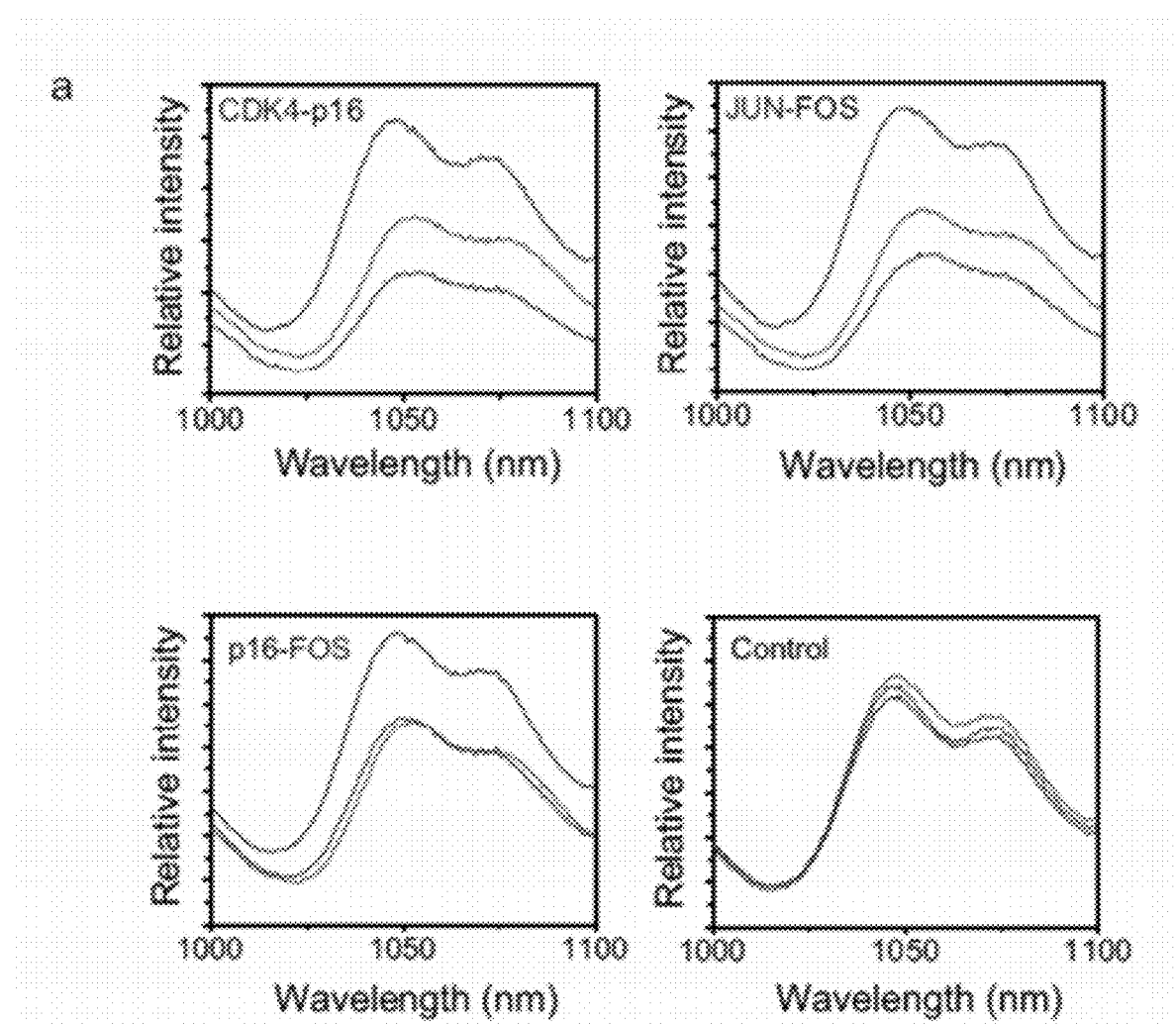
FIG. 9 includes graphs demonstrating detection of protein-protein interactions.
Figure 9:
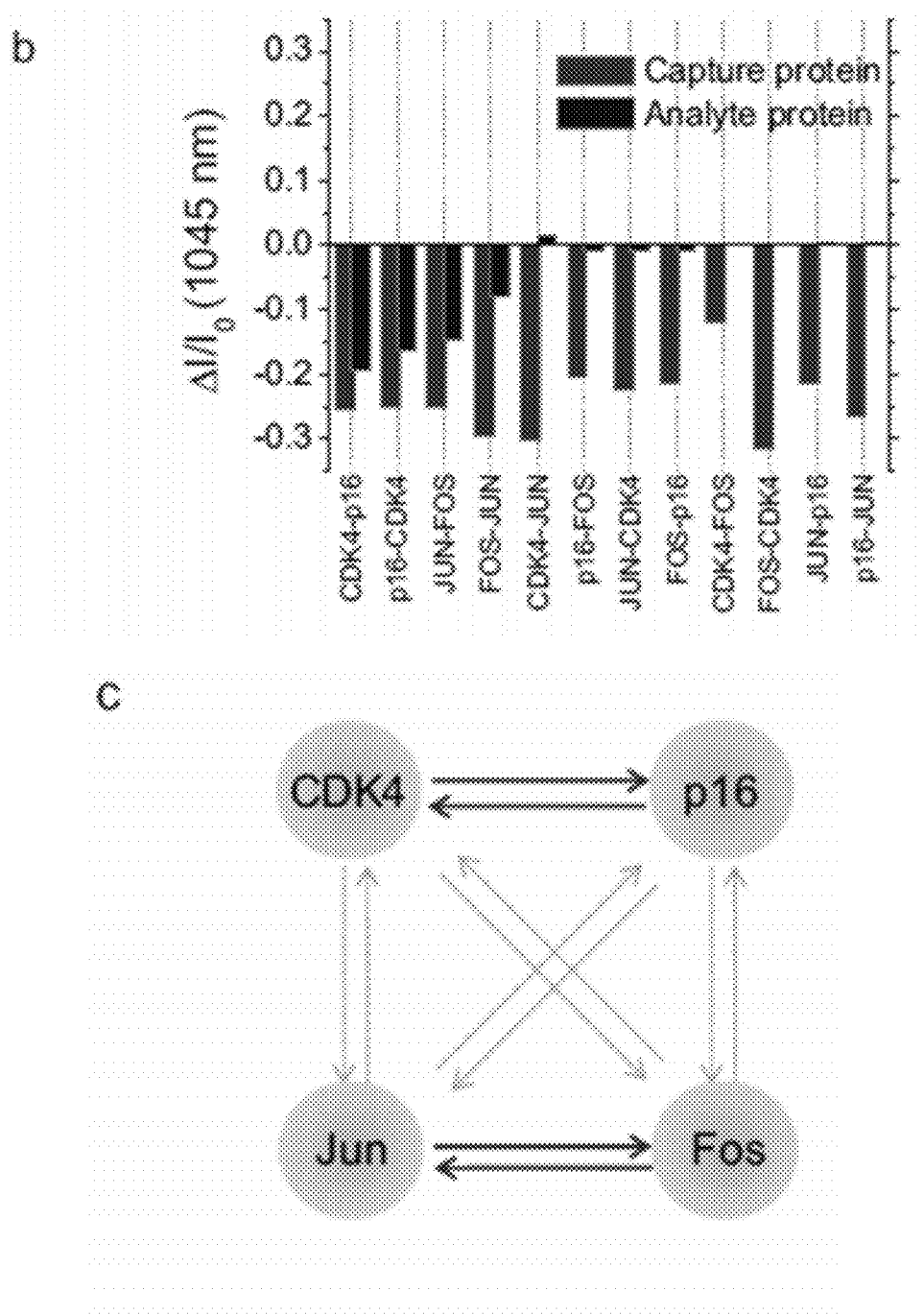
Figure 9:
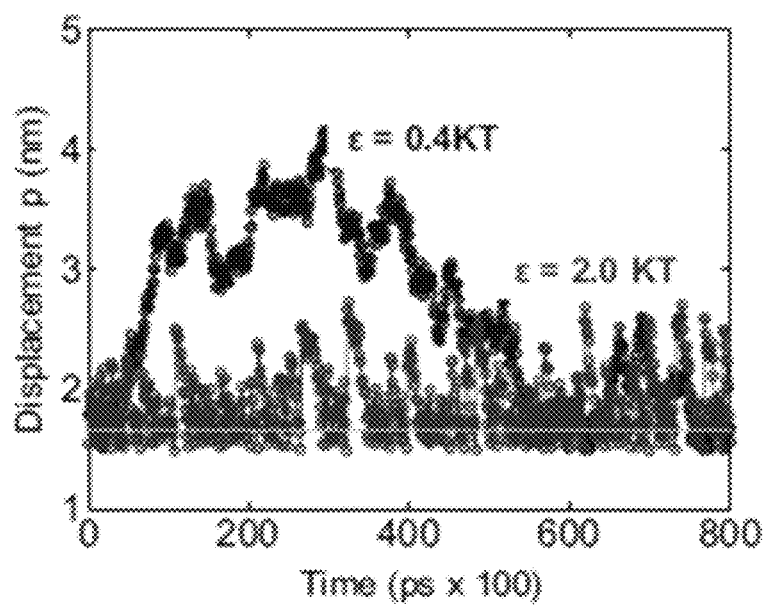
Figure 9:
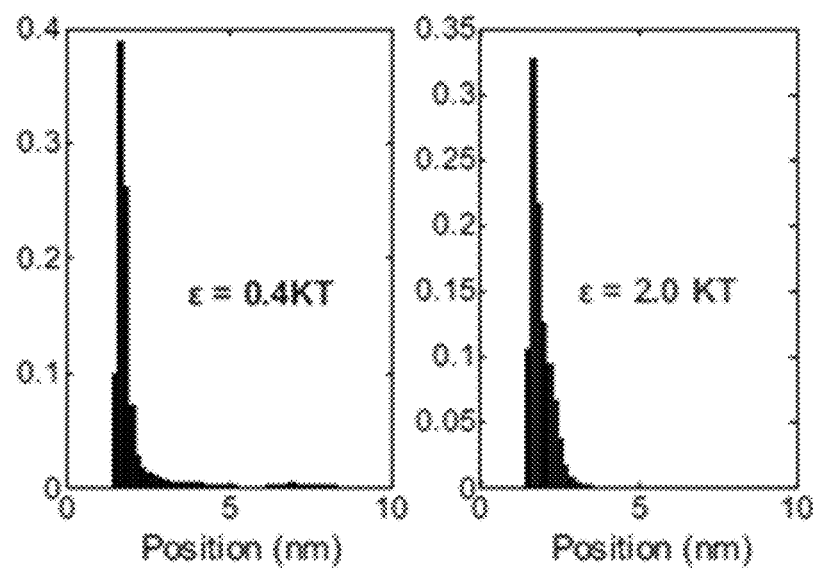
Figure 9:
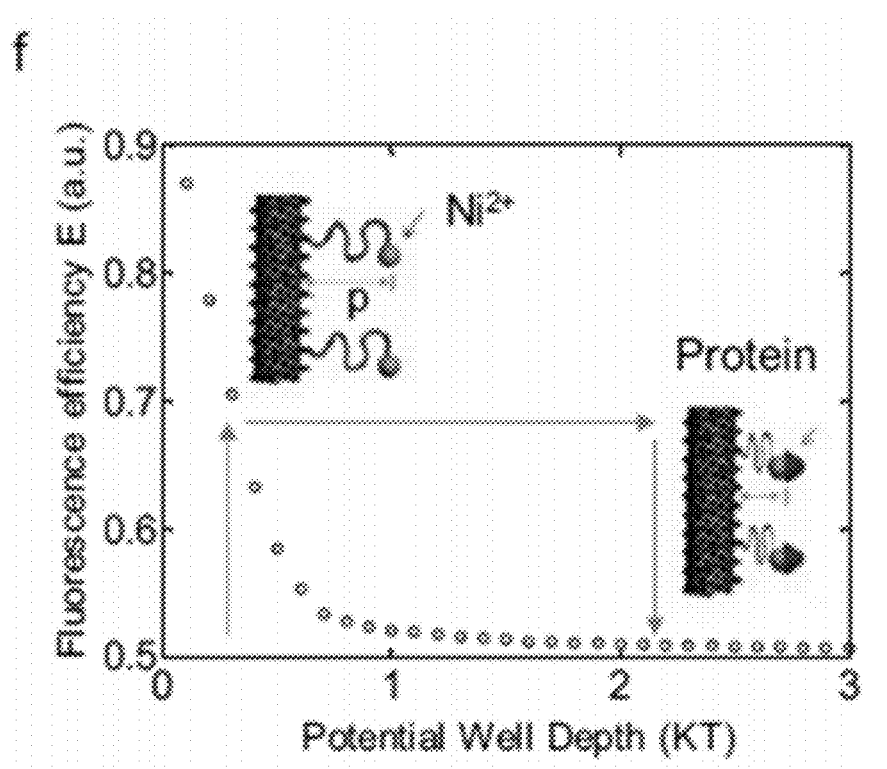
Figure 10A:
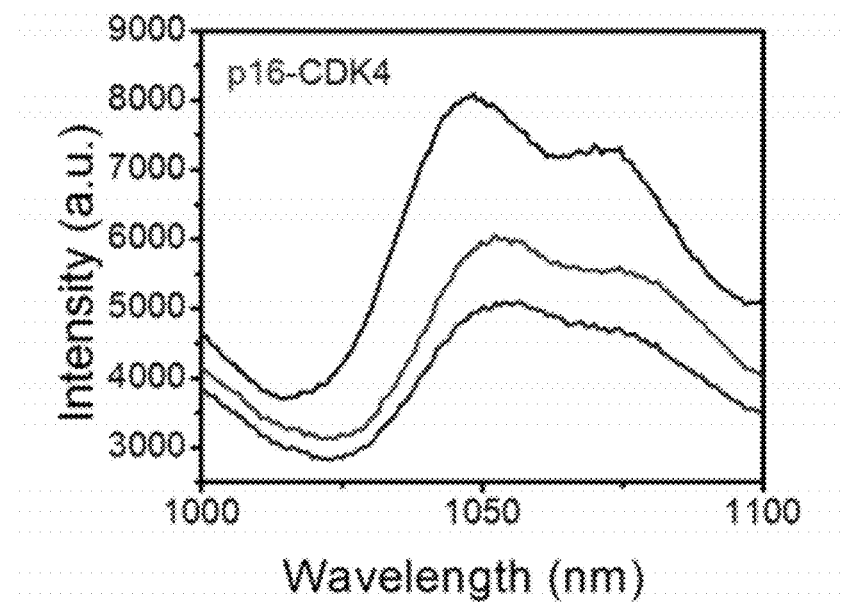
FIG. 10 includes graphs showing changes in nanostructure photoluminescence in response to selective recognition of protein-protein interactions on an array.
Figure 10B:
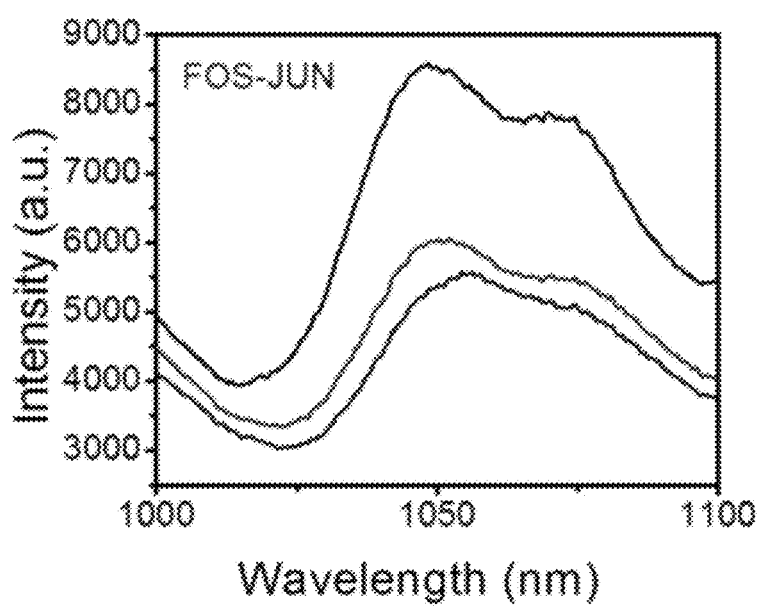
Figure 10C:
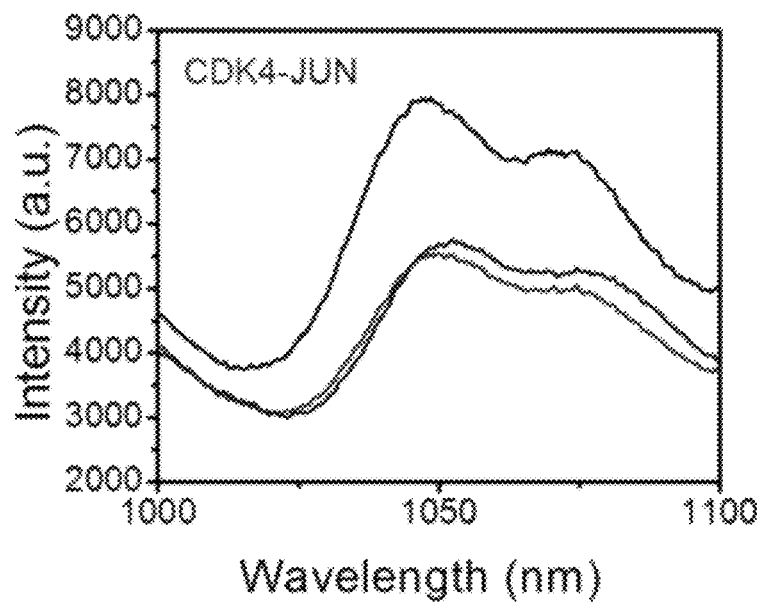
Figure 10D:
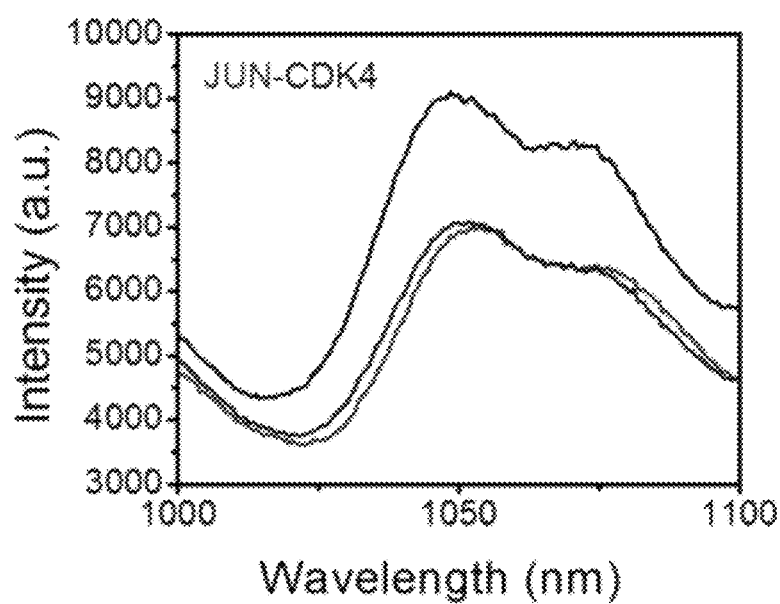
Figure 10E:
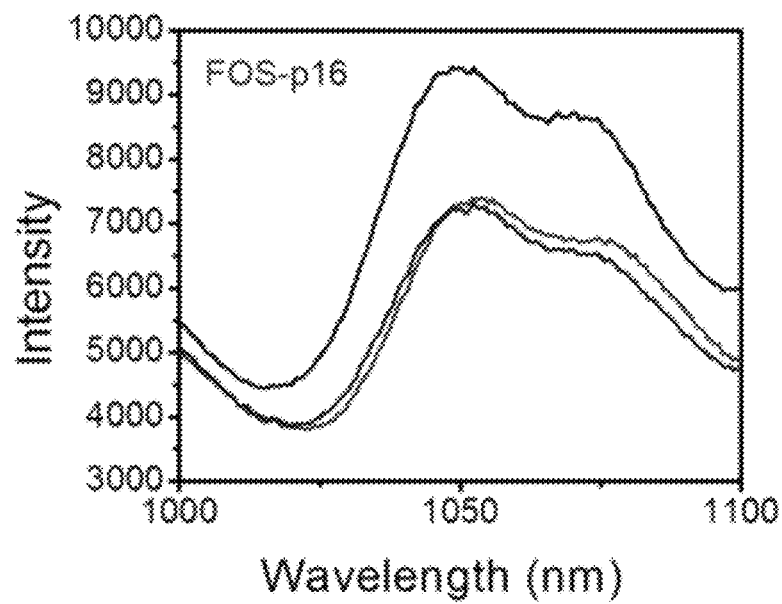
Figure 10F:
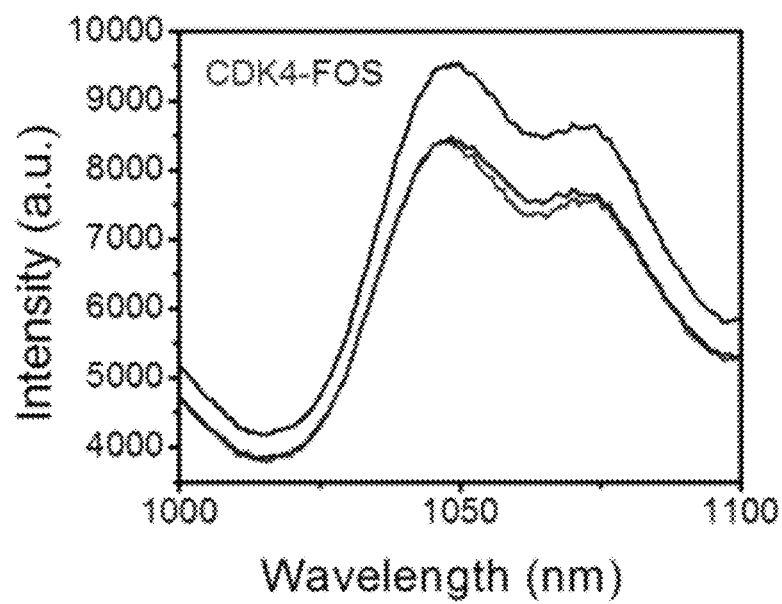
Figure 10G:
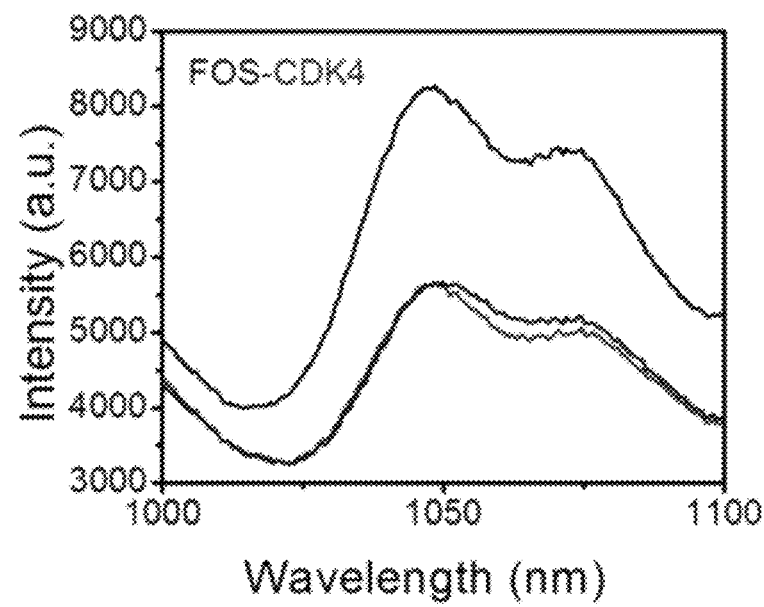
Figure 10H:
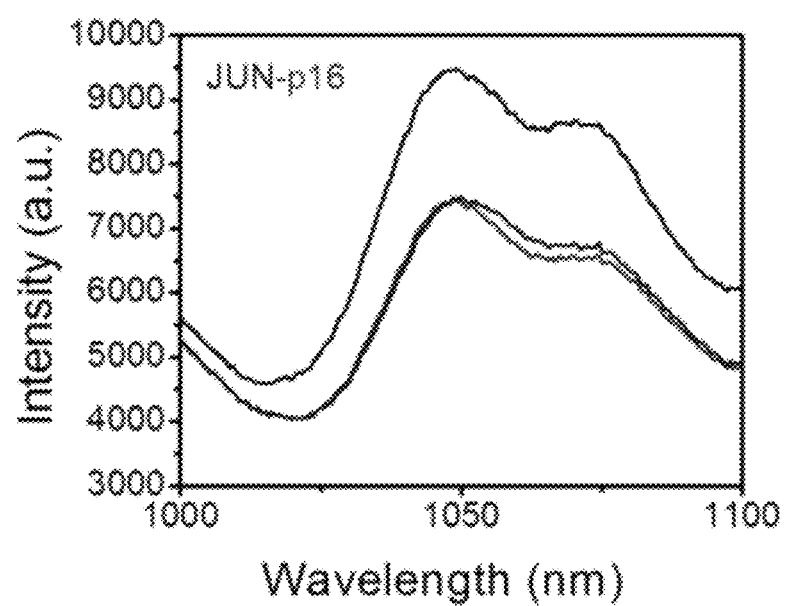
Figure 10I:
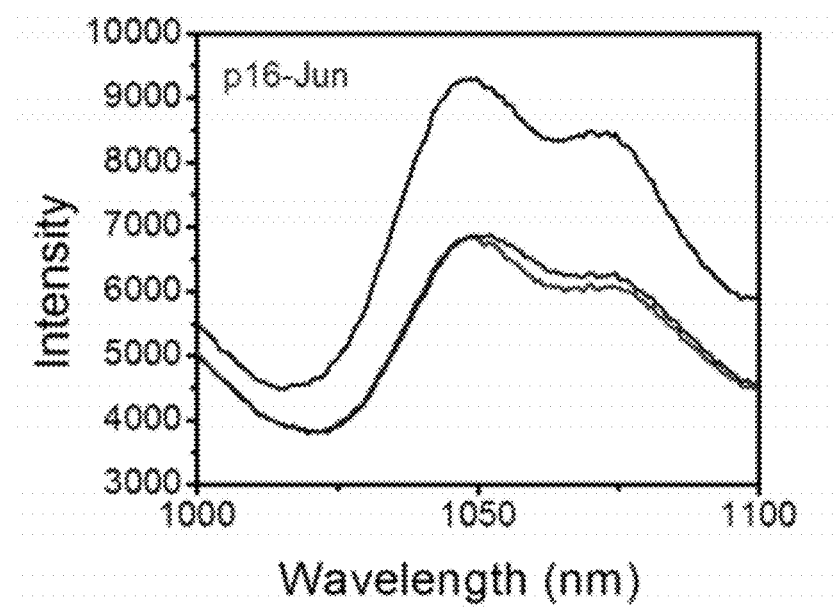
Figure 11:
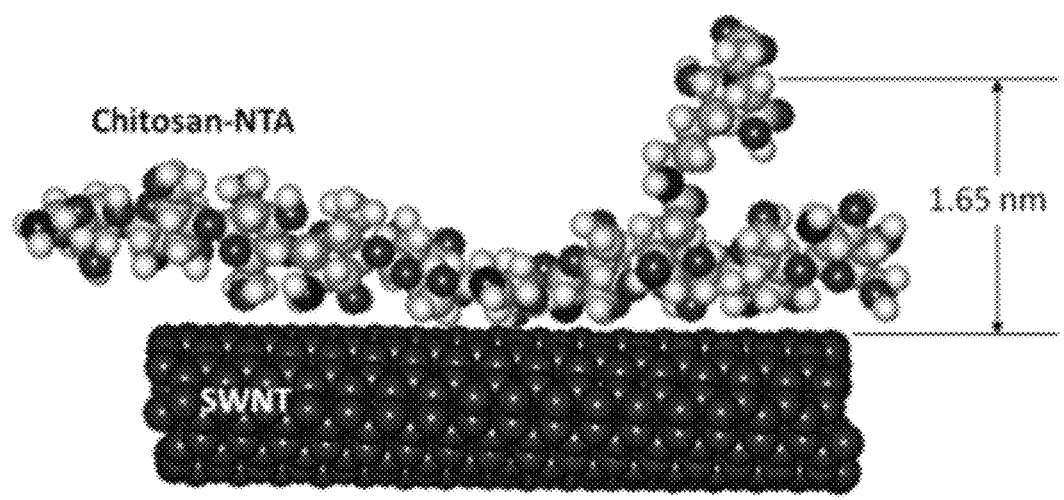
FIG. 11 is a schematic of the distance calculation between a nanostructure and an ion.
Figure 12:
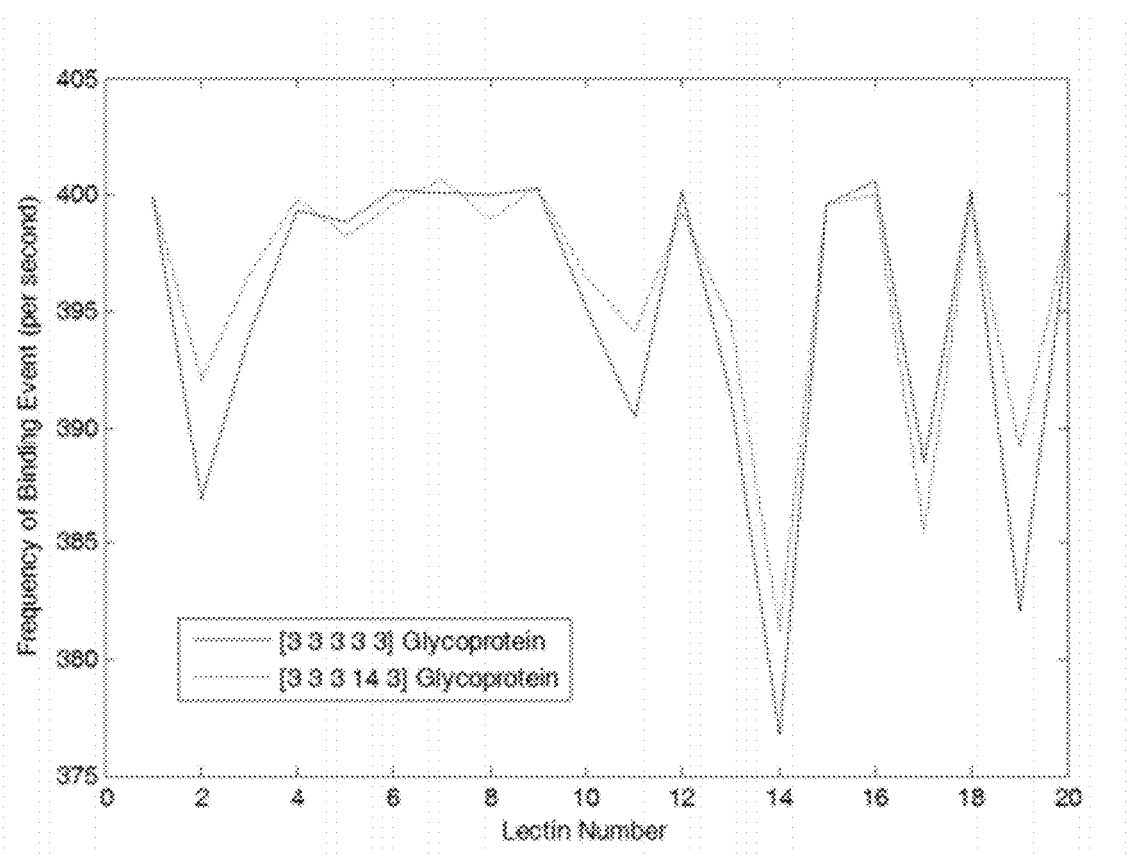
FIG. 12 is a graph showing simulated frequency responses of a lectin protein array showing detection of a glycan group.

To further demonstrate the detection of protein-protein interactions using this mechanism, human derived His-tag proteins were produced by on-chip cell-free expression and then, upon addition of their known binding partner, the resulting protein-protein interactions were investigated (FIG. 9). Two binary protein interactions were tested using well-known interacting pairs, CDK4-p16 and Jun-Fos. The first capture proteins were expressed by adding PCR DNA with a His-tag sequence to the cell-free lysate (FIG. 9a). After in situ expression of the capture protein containing the His-tag, the second query protein, without the His-tag sequence, was added to the capture protein bound spots, and the fluorescence response was monitored. As shown in FIG. 9, the fluorescence was diminished after expression of the capture proteins with His-tag on the SWNT/CHI array. In addition, after treatment of the analyte proteins with the query proteins, the fluorescence further decreased. This was the opposite of the results observed from the His-tag protein and anti-His-tag antibody interaction, which may suggest that the specific interactions between p16 and CDK4 (or Jun and Fos) can cause further fluorescence decrease (FIG. 9b and FIG. 10). Additionally, these results suggested that the SWNT/CHI array system can report the specific interactions between proteins without additional labeling (FIG. 9c). The fluorescence response for these protein interactions, compared to the His-tag protein and anti-His-tag antibody pair described above, was consistent with the proposed mechanism of detection described below. For p16-CDK4 and Jun-Fos interactions, recognition might occur via some peptide sequence instead of the Ni-NTA/His-tag region, which could push the $Ni^{2+}$ ion closer to the SWNT surface. For consistency, a Förster quenching model was used to calculate the distances between the $Ni^{2+}$ ion and the SWNT, based upon the observed fluorescence responses; the results are reported in Table 2 (see above). The magnitudes of these changes are consistent, and on average, less than a protein diameter. The distances corresponding to 10 monomer CHI units and the Ni-NTA moiety were estimated from a Hyperchem molecular model. Geometry optimization was performed in the presence of water at 300K for 1 ps resulting in a distance between SWNT and NTA of 1.65 nm (FIG. 11). The distance changes are also calculated after adding receptor protein and analyte protein based on the Förster resonance energy transfer to a non-emissive state (Table 2, see above).

The mechanism of detection involved the distance between the $Ni^{2+}$ and the nanotube fluorophore (FIGS. 9d, e, f). As with many divalent ions, $Ni^{2+}$ was an excited state quencher of the nanotube photoluminescence. (Brege, J. J. (2009); Brege, J. J., Gallaway, C. & Barron, A. R. Fluorescence quenching of single-walled carbon nanotubes in SDBS surfactant suspension by metal ions: Quenching efficiency as a function of metal and nanotube identity. *Journal of Physical Chemistry C* 111, 17812-17820 (2007), each of which is incorporated by reference in its entirety). The $Ni^{2+}$ bound to the CHI can be viewed as a freely diffusing entity constrained by the potential well created by the CHI tether. The equilibrium position, p, of the quencher can be found by integrating the sum of the random diffusive and restorative displacements over a series of simulated time steps ($\Delta\tau$)

$$\Delta p_i = \pm r_1 \sqrt{2D(\Delta\tau)} + \frac{Df(p_{i-1})}{kT}(\Delta\tau) \qquad \text{Eq. 1}$$

where D is the diffusivity of the complex ($10^{-10}$ m$^2$/s), $r_1$ is a uniform random number and f is the restorative force as a function of the current displacement, $p_i = p_{i-1} + \Delta p_i$ based on a Lennard-Jones 6-12 potential.

$$f(p) = -48\varepsilon \left[ \frac{p_t^6}{p^7} - \frac{p_t^{12}}{p^{13}} \right] \qquad \text{Eq. 2}$$

Here, $p_t$ is the location of vanishing restorative force (~1.65 nm). In this scheme, the $Ni^{2+}$, tethered to the CHI, can make periodic excursions biased towards $p > p_t$, and can return to the well minimum with a frequency that increases with the well depth, $\varepsilon$, as shown in FIG. 9d. A loosely bound $Ni^{2+}$ (small $\varepsilon$) can spend more time at the periphery of the potential well, causing minimal quenching. When a protein docks to the capture protein, it can increase the energy of the potential well via increases to electrostatic or van der Waals attractive forces to the complex. This can have the effect of decreasing the mean distance of the $Ni^{2+}$ to the nanotube, resulting in a quenching response. In this way, the probability distribution of position can tend to narrow with increasing well depth (FIG. 9e).

These transient changes in position can be related to the optical signal from the nanotube. The fluorescence efficiency, E, can be related to the displacement by assuming a Förster transfer mechanism to quenching states with Förster integral, $R_o$ (of order unity).

$$E = \frac{1}{1 + \left(\frac{R_o}{p}\right)^6} \qquad \text{Eq. 3}$$

Equations 1-3 simulate the dynamic trajectory of the $Ni^{1+}$ complex subjected to the potential well of depth $\varepsilon$. An asymmetric potential well, such as one formed from competing electrostatic and van der Waals attractive forces in DLVO theory can ensure that the mean $p > p_t$ for all cases. A decrease in E was observed when a captured protein increased the well depth, which the capture protein can do by either strengthening electrostatic or van der Waals forces. FIG. 9f displays a model calibration curve relating E with increasing well depth, $\varepsilon$. The magnitude of the decrease in E was similar to experimental observations. Conversely, it was consistent that subsequent docking to the complex also decreased $\varepsilon$, which may cause restoration. A more detailed knowledge of the potential well and protein contributions to it may allow responses to be predicted a priori.

In conclusion, a label-free SWNT/CHI protein array platform for detecting protein-protein interaction to a single protein molecular level was demonstrated. The array platform can include a composition including single walled carbon nanotubes (SWNT) embedded within a CHI matrix bearing an $N_\alpha,N_\alpha$-bis(carboxymethyl)-L-lysine (NTA) chelator bound to $Ni^{2+}$. $Ni^{2+}$ can bind and tether a hexa-histidine (SEQ ID NO: 37) tagged capture protein produced by the cell-free method. The binding event can be recorded directly as a modulation (increase or decrease) in the nIR fluorescence intensity without any prior processing of the analyte. The docking of the analyte protein to the capture site can cause a change in the intermolecular distance between the $Ni^{2+}$ and the SWNT, resulting in quenching. Using cell free synthesis this mechanism can be extended to a large array of 15 capture proteins, which can be queried with various interaction partners. Nascent proteins with C-terminal His tag can be directly immobilized on the SWNT/CHI array with the Ni-NTA functional group upon expression, and then protein-protein interactions can be detected via the nIR fluorescence change of SWNT in a label-free, real-time and high throughput. In addition, the SWNT-based protein array can enable detection of a single molecule binding events as stochastic fluctuations of nIR fluorescence, in a manner previously demonstrated for several small molecule analytes.

Combining a functional protein array with a label-free detection method would provide a more ideal platform technology to broaden our ability to understand protein-protein interactions. Moreover, the use of PCR-amplified linear DNA as a template for protein expression allowed for the translation of a large amount of genomic information into functional protein molecules, avoiding the need for DNA cloning steps. This could help to facilitate the high-throughput application of this technique. CHI hydrogel-encapsulated SWNT can transduce protein binding to its cognate interaction partner into an optical signal by perturbing the electronic structure of the nanotubes. Also, the extension of single molecule detection limits to protein quantification in the context of a microarray may significantly advance protein science.

Glycoprotein Profiling Using a Lectin Protein Array

Glycoproteins can be used as therapeutics due to their solubility and increased blood residence time. They can also show affinity to specialized in vitro targets, much like antibodies, but can have a wider range of interactions. Designers of protein therapeutics hope to protect valuable new therapies by decorating them with glycan groups while simultaneously giving them better targeting abilities. However, glycosylation of proteins may not be without a cost. It has been shown that certain glycans (like galactose—α-1, 3-galactose) can cause deleterious immunogenic responses (Chung C. H. *N. Engl. J. Med,* 2008, 358: 1109-1117). Most synthetic pathways for glycoproteins can result in varying degrees of glycosylation (many random chains of sugar groups attached to the protein).

Understanding the interactions between glycans and carbohydrate recognition domains (CRD) found on cellular and protein surfaces is vital to the fields of glycobiology, immunology, and pharmacology. Glycans decorating the surface of proteins substantially influence function, such as folding pathways, signaling, retention and pharmacokinetics.[1,2] The efficacy of protein-based therapeutics is largely dictated by their glycosylation[3], and thus design of drugs that interact with known CRD sites, such as cell-adhesion modulating galectins[4], requires a greater understanding of the kinetic parameters between glycans and CRDs. Despite this importance, robust assays of protein glycosylation are underdeveloped, with the dominant profiling technologies falling to frontal affinity chromatography[5] and mass spectrometry.[6] Recently, the concept of the lectin microarray has emerged as a promising approach to profiling glycans, except that lectin-glycan monovalent binding is generally far weaker ($10^{-7}$ M<Kd<$10^{-3}$ M) than typical antibody/antigen interactions.[5a,7] Hence conventional sandwich assay configurations that rely on strong binding are problematic for this approach. An emerging concept[5a,7a] is to use multivariate responses of glycans binding to a library of lectins to discern their identity, but this requires detection methods that are necessarily sensitive enough to transduce the presence of weakly bound proteins. Label free methods, which reduce sample volume requirements, have a distinct advantage in this approach by decreasing the absolute detection limit. Herein, a fluorescent single walled carbon nanotube sensor[8] for glycan-lectins interactions is described.

The approach described here couples band gap fluorescent SWNT to receptor lectins, which are a host of naturally occurring carbohydrate binding proteins.[9] Kinetic parameters between anti-His tag antibody were compared to literature surface plasmon resonance (SPR) parameters. The detection of fucose (Fuc) to PA-IIL lectin and N-acetylglucosamine (GlcNAc) to GafD lectin is also described. Kinetic parameters were obtained by first measuring the fluorescence intensity of a large spot of SWNT, and then it was shown how the same signal can be increased by probing individual SWNT sensors and determining which sensors were most responsive to glycosylated analyte addition. Glycan profiling is distinct from creating glycosolated carbon nanotubes for therapeutic purposes[10] and electronic FET sensors for lectin, but not glycan, binding[11].

Kinetic information between glycans and CRDs can be determined by two types of analytical methodology: equilibrium and non-equilibrium.[12] Non-equilibrium methods can yield relative binding information rather than physical kinetic rates; that is, they can specify which glycan-CRD combinations bind with greater affinity in reference to other pairs. These methods can include ELISA[13], glycan microarrays[14], agglutination[15], and electrophoresis[16]. Equilibrium methods can provide physical kinetic parameters, but can include certain limitations. Equilibrium dialysis can be used to determine the forward reaction rate ($k_f$) of glycan-CRD binding but at the cost of a lot of glycan reagent. Frontal affinity chromatography can be used to determine the affinity constant ($K_D$) but only for strong binding pairs ($K_D$>mM). Equilibrium titration calorimetry[17] is a delicate technique to determine kinetic parameters from thermodynamic information, but is rarely employed because of time and reagent expenses. Another equilibrium technique, frontal affinity chromatography[18], can be used to determine the affinity constant ($K_D$) for most glycan-CRD pairs ($K_D$>$10^{-7}$) however the glycan must be labeled for detection. The current standard for obtaining kinetic information from label-free groups is surface plasmon resonance (SPR) machines, such as the Biacore© systems. In the case of glycan-CRD interactions, SPR can detect both the forward and reverse kinetic rates for a wide range of affinities ($K_D$: mM-pM range). However, to induce a detectable signal the analyte must have significant mass. Thus glycans are typically immobilized on the gold surface (often using neoglycoproteins[19], i.e. glycans synthetically bound to a protein backbone) and the more substantial lectins are used as the binding analytes. This can bias the analysis of single lectin-glycan interactions as presentation and density of the glycan is a critical parameter in CRD binding and the immobilization methodology can alter this.[20]

The SWNT-based fluorescence sensors demonstrated loading curve signals competitive with SPR, both in shape and analysis technique, but they differed in a few significant ways. First, the detection scheme is reversed. The lectins are the tethered sensors and the glycans are the analyte in solution. This allows determination of the kinetics of free glycans as well as glycoproteins, giving control over carbohydrate presentation in the interaction. Second, the amount of analyte needed for each experiment (2 μg of glycosylated protein or 200 ng of free glycan) was smaller than what is necessary for SPR experiments, which require analyte flow to overcome mass-transport effects (often requiring milligrams of protein analyte[21]). Third, each SWNT-sensor spot can be bound to different lectins and illuminated simultaneously, creating the potential for a multiplexed detection of binding analogous to certain analogs of SPR.

Figure 25:
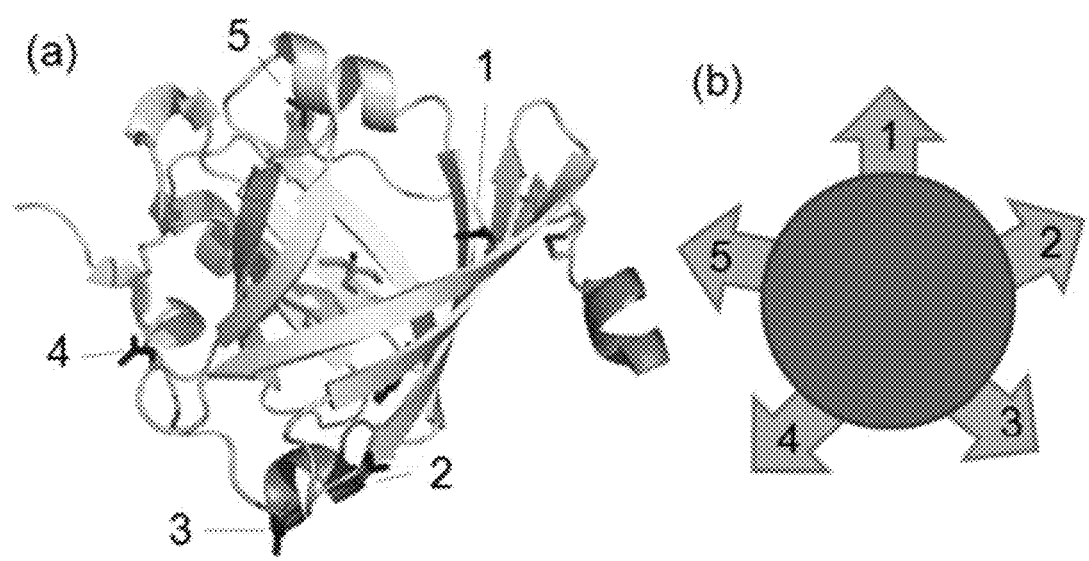
FIG. 25 includes two schematics of a glycoprotein for stochastic simulation.

A series of rough Kinetic Monte Carlo (KMC) simulations have shown that this data can be enough to differentiate between glycans by utilizing a pre-determined matrix of Lectin-Glycan dissociation constants (Kd). With one or two carefully-selected Lectins, glycoproteins can be screened for any harmful glycan group. The lectins used for detection can vary depending on the type of glycoproteins in solution. Using KMC models, the lectins which give the best response for differentiation of the target glycan can be predicted (FIG. 25). The simulation was done with a hypothetical dissociation matrix (Kd) of 20 lectins with 20 glycans. Differentiation was shown between a glycoprotein fully decorated with glycan group 3 (—) and a nearly identical protein with a 20% change of glycan group 3 to unwated group 14 (---). In this case lectins 2, 14, and 19 could be suitable candidates for clearer sensing. Utilizing a large enough array of lectins, the full glycan profile of an unknown glycoprotein can be determined without any a priori knowledge of its glycosynthesis route.

A SWNT-based sensors can have a loading curve signal very similar to SPR, both in shape and analysis technique, but they can differ in a few significant ways. First, the detection scheme can be reversed. The lectins can be the tethered sensors and the glycans can be the analyte in solution. This can allow us to determine the kinetics of free glycans, as well as glycoproteins. Secondly, the amount of glycans and lectins needed for each experiment (20 ng and 40 ng) can be smaller than SPR experiments, which can require flow to overcome mass-transport effects. Third, each spot of SWNT-sensors could be bound to different lectins and illuminated simultaneously, creating the potential for a multiplexed SPR-like detection of binding.

It can be advantageous to have a high-throughput platform in which protein therapeutics could be screened for known, harmful glycans. Such a device can be made with a label-free SWNT/CHI protein array platform. The protein array can detect single binding events of glycoproteins to the lectin-modified SWNT/CHI microarray. Both the frequency of binding/unbinding events and the average number of occupied SWNT at each time-point can be determined.

Figure 34A:
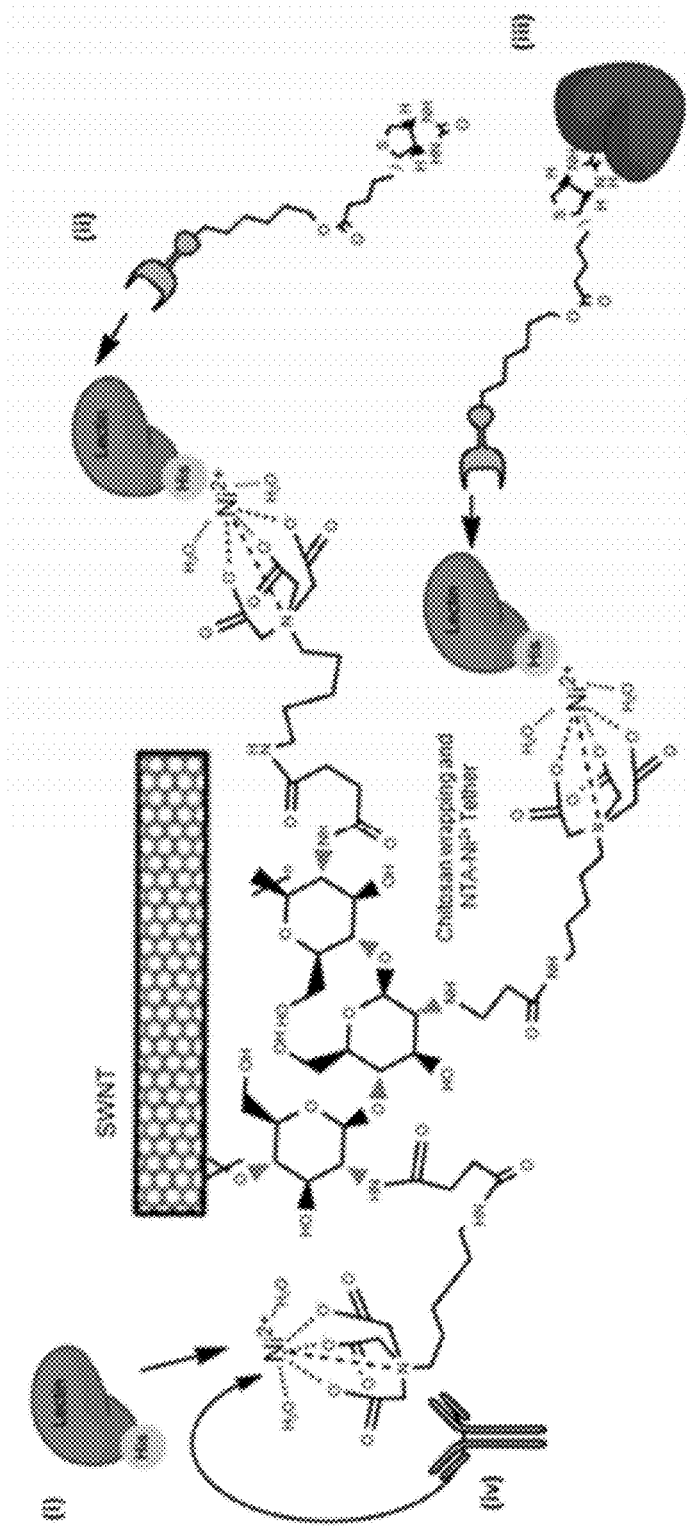
FIG. 34 includes a schematic of chitosan-SWNT sensors for determining kinetic parameters between lectins and glycans.
Figure 34B:
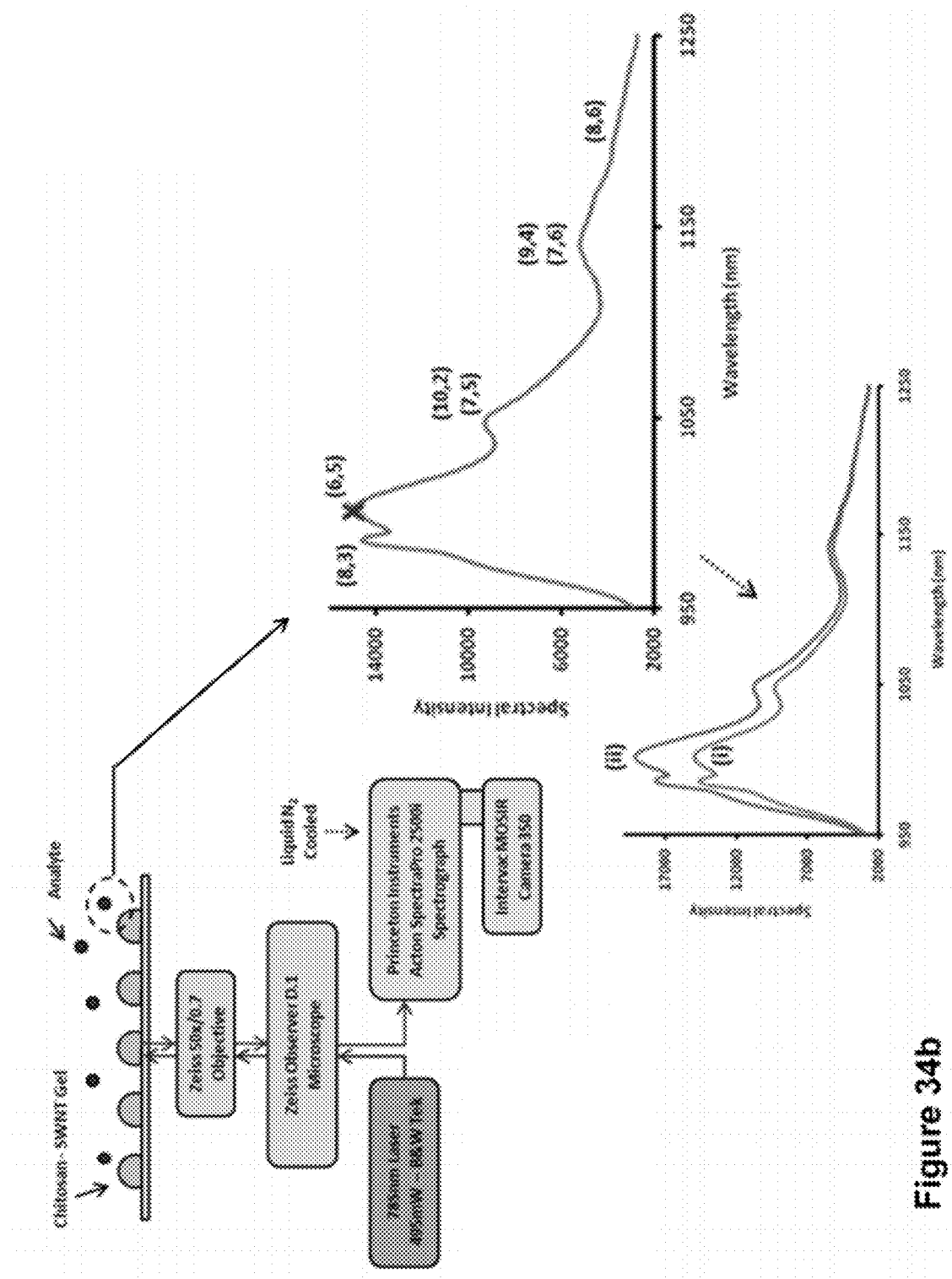

FIG. 34 describes ensemble measurements of chitosan-SWNT sensors for glycan lectin detection. FIG. 34a schemactically shows how the chistosan wrapped SWNT were processed (see text) to include tethered NTA groups and chelated $Ni^{2+}$ so that His-tagged lectins (i) would attach to the sensors. An analyte (anti His-tag antibody (iv), free biotinylated glycan (ii), or bound glycan to streptavidin (iii)) was added and the emission fluorescence was increased (FIG. 34b, spectra labeled (i) and (ii), respectively) due to the $Ni^{2+}$ group moving away from the SWNT, caused by steric loading of the sensor. FIG. 34b depicts the ensemble measurement setup: the chitosan-SWNT gel was spotted onto glass chips which were excited by a 785 nm laser in a custom inverted microscope setup. The resulting emission spectra were then analyzed looking at the intensity of the (6,5) nanotube peak over time.

Lectin Expression

The plasmid pET41GafD and pET41-PAIIL were transformed into BL21(DE3)™ Star (Invitrogen) according to standard procedures. (Ahmed, H., *Principles and reactions of protein extraction, purification, and characterization*. CRC Press: Boca Raton, 2005; p 387, which is incorporated by reference in its entirety). A single colony was used to inoculate 5 mL LB medium containing kanamycin (50 µg $mL^{-1}$). Three mL of the overnight culture at 37° C. was used as an inoculum to a 350 mL flask of LB containing 50 µg $mL^{-1}$ of kanamycin, and this was incubated again with shaking at 37° C. Heterologous protein was induced by the addition of isopropyl β-D-1-thiogalactopyranoside (IPTG, final concentration 1 mM) once this culture had reached log phase ($A_{600}$ of 0.6). Growth was continued for 6 h before the cells were harvested by centrifugation. For His-tag protein purification, harvested cell pellet was washed twice with phosphate-buffered saline, PBS (10 mM, pH 7.4) and then lysed with Complete Lysis-B (Roche Applied Science™). The crude lysate was clarified by centrifugation prior to application to a 3 mL Ni-NTA agarose column (Qiagen™). Non-specifically bound proteins were removed from the column with wash buffer (50 mM $NaH_2PO_4$, pH 8.0, 300 mM NaCl, 20 mM imidazole) and bound His-tag GafD and PAIIL were eluted with elution buffer (50 mM $NaH_2PO_4$, pH 8.0, 300 mM NaCl and 250 mM imidazole). Eluted samples were analyzed by 15% SDS-PAGE and protein concentration was determined with BCA assay kit according to manufacturer's instructions (Pierce™). To change the buffer with PBS (10 mM, pH 7.4), the eluted solution was centrifuged through a centrifugal filter with a molecular cutoff of 10 kDa (Millipore™) and the concentration of lectin was finally adjusted to 4 mg $mL^{-1}$.

Glycan and Model Glycoprotein Probes

Biotinylated glycans were provided by the Consortium of Functional Glycomics—Scripps Institute Group. Glycans B121 (GlcNAcβ-SpNH-LC-LC-Biotin) and B158 were used (Fucα1-2Galβ1-4Glcβ-SpNH-LC-LC-Biotin), where LC and Sp were $C_6H_{11}N$ and $C_2H_4N_3$ spacer groups, respectively. The lyophilized sugars were dissolved in 3 mL of 1×PBS to create stock solutions and stored at −20° C. To construct model glycoprotein probes, the biotinylated glycans were incubated with streptavidin (Sigma Aldrich $SO_{677}$™) for 1 hour at 20° C. in a 6:1 molar ratio to allow maximum binding to the four biotin binding sites on each streptavidin. Excess biotinylated glycans were filtered away from the glycoproteins by centrifugation through an Amicon filter (16,300×g on Labnet Inc centrifuge, 10 min, 30,000 kDa cutoff, Milipore). The glycoproteins were washed on the filter 3× (400 µL PBS) and then resuspended in PBS at the desired concentrations.

Native PAGE Binding Analysis

The interaction between lection and glycan was analyzed by 15% native PAGE according to the method of Schagger and von Jagow with minor modifications. (Brege, J. J., et al., Fluorescence Quenching of Single-Walled Carbon Nanotubes with Transition-Metal Ions. *Journal of Physical Chemistry C* 2009, 113 (11), 4270-4276; Jin, H., et al., Divalent ion and thermally induced DNA conformational polymorphism on single-walled carbon nanotubes. *Macromolecules* 2007, 40 (18), 6731-6739, each of which is incorporated by reference in its entirety). Briefly, blectrophoresis was performed using Mini Protean Electrophoresis system (Bio-Rad, USA™) for molecular interaction under nondenaturing conditions. Nonreduced protein/glycan samples in the sample buffer (20% glycerol, 200 mM Tris-HCl, pH 6.8, 0.05% bromophenol blue) were applied to the gel (gel buffer: 25 mM Tris-HCl, 200 mM glycine). Electrophoresis was performed at 80 V for 120 min. After electrophoresis, the protein bands were visualized by staining with Coomassie Brilliant Blue R-250.

Construction of Chitosan-SWNT Sensor Chips

Figure 35:
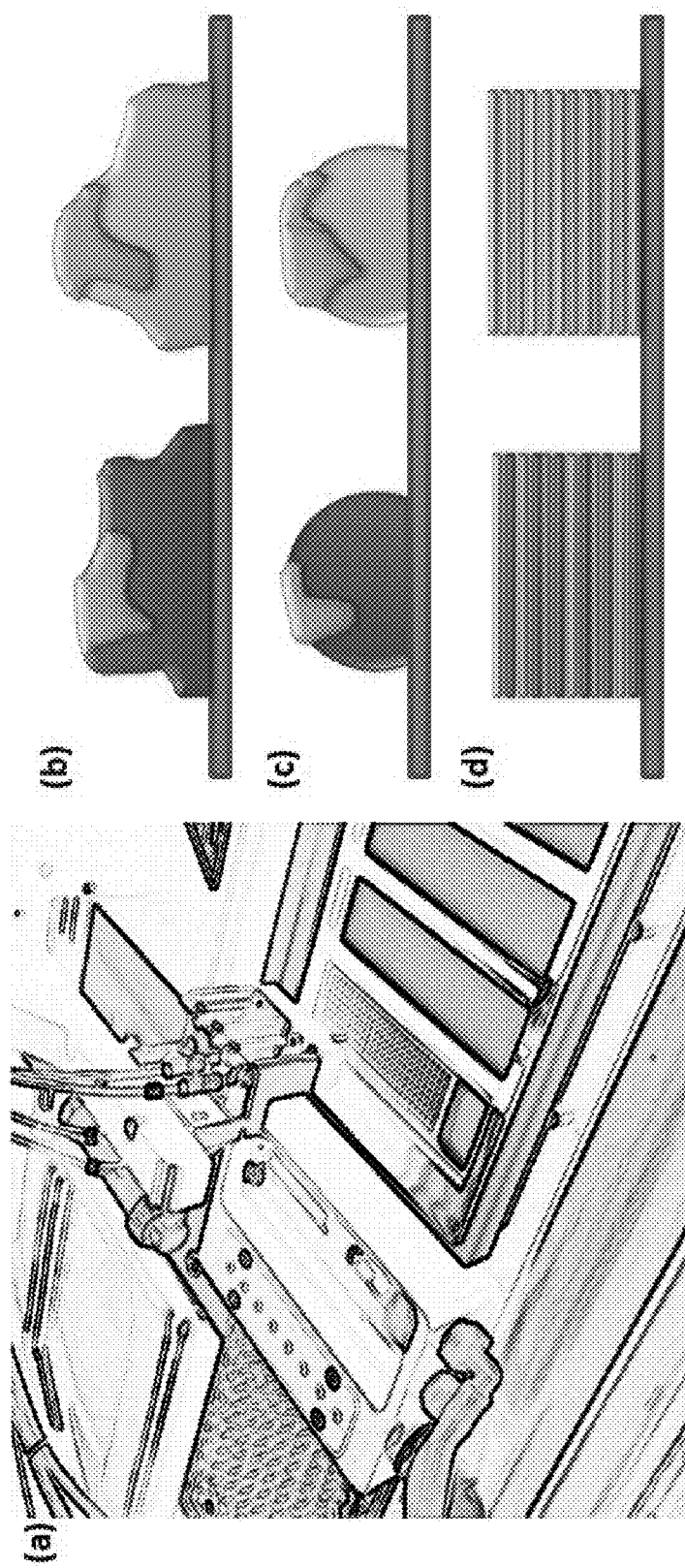
FIG. 35 includes an automated printer for printing the SWNT-chitosan gel (FIG. 35a) and includes schematics of gel morphology and crosslinking (FIG. 35b-d).

To increase the reproducibility of these sensors, an automated printing method of the chitosan gel was introduced (FIG. 35). Patterned glass microscope slides (Tekdon™) were inserted in a microarray printer (Digilab MicroSys System™), where the robotic head was programmed to dispense alternating layers of chitosan-SWNT (0.25 wt % chitosan (CHI), 1 vol % acetic acid, 30 ug/ml suspended (6,5) SWNT) and crosslinker (10 vol % glutaraldehyde). The suspended SWNT was made from Southwest Nanotechnologies, Inc. CoMoCAT® nanotubes sonicated in 0.25 wt % chitosan (CHI) and 1 vol % acetic acid for 45 minutes at 40% amplitude with a probe-tip sonicator (Cole Parmer, Model CV18). For each sensor spot ten alternating layers of SWNT-CHI and cross-linker were printed at 100 mL per layer, resulting in a highly-uniform gel of 1 ul SWNT-CHI material. The chips were printed in a humidified enclosure (85% RH) at 25° C. and allowed to cross-link overnight in the same environment. Nickel-NTA groups were introduced as previously reported[8]; see FIG. 3. Briefly, the chips were washed with a dilute basic buffer (0.01 M NaOH) and water three times. Carboxylic acid groups were introduced to the chitosan wrapped SWNT by bathing the chips in succinic anhydride (0.1 M) overnight. The chips were then washed three times with water and the carboxylic acid groups were activated via N-(3-dimethylaminopropyl)-N'-ethylcarbo diimide hydrochloride (EDC-0.1M) and N-hydroxysuccinimide (NHS-0.1M). The chips were bathed in this solution for 2 hours at 25° C. and examined for the expected formation of bubbles. The chips were again washed and allowed to bathe in a solution of a linked tricarboxylic acid group (Nα,Nα-bis(carboxymethyl)-L-lysine a.k.a. NTA-33 mM) overnight. The chips were washed in water again and stored in a 100 mM solution of $NiSO_4$ to allow maximum binding of nickel to the NTA chelating groups.

Ensemble Measurements of Sensors

Figure 26:
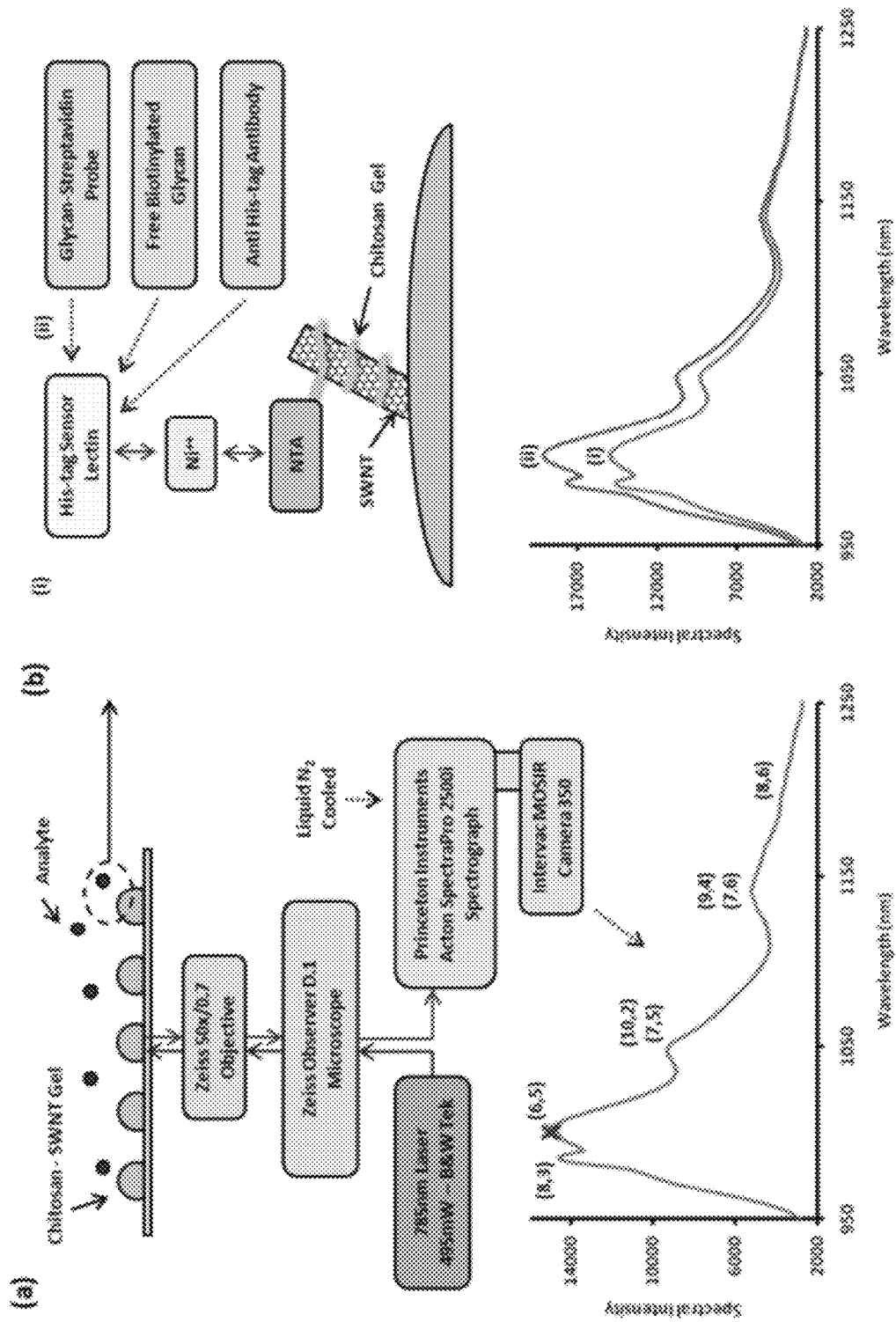
FIG. 26 includes ensemble measurements of chitosan-SWNT sensors for glycan lectin detection.

A custom-made near infrared inverted microscope (Zeiss D.1 Observer™) setup allowed us to probe the fluorescent emissions of our SWNT sensors (FIG. 26a). The chips were secured on the microscope stage and the objective (50×/0.7 Zeiss™) was pushed in contact with a blank portion of the glass slide (no SWNT-CHI) to obtain a 5 second background spectrum, which was subtracted from the response spectra. The objective was then moved under a SWNT-CHI gel spot and again pushed in contact with the glass slide. By placing the objective in the maximum z-axis position, the microscope imaged a higher plane of the SWNT-CHI gel where more analyte response was observed. The SWNT were excited by a 785 nm laser (B&W Tek™—495 mW) and the emission was sent to a spectrometer (Princeton Instruments Acton SpectraPro 2500i Spectrograph™) and accompanying nIR camera (Intervac MOSIR Camera 350™) The spectra were collected via WinSpec software (Princeton Instruments™) and analyzed with custom Matlab (Mathworks™) code. To maximize signal stability, the spectrometer was cooled with liquid nitrogen two hours prior to experimentation and the laser was allowed to reach peak stability for two hours. The SWNT-CHI gel has a small transient region when first exposed to the laser due to local heating and further permeation of $Ni^{2+}$ in the gel; thus each spot was exposed to the laser for 5 minutes before data was gathered. Data was gathered in the form of emission intensity spectra (950-1250 nm) integrated for 5 seconds.

A typical experiment was run for approximately 1000 frames (at 5 seconds each) and included a few addition and washing steps to detect lectin-glycan binding (FIG. 26b). First $NiSO_4$ was again added to ensure that the SWNT sensors were responsive and that the NTA chelating groups were fully loaded with $Ni^{++}$ groups. The nickel was then washed away with PBS three times, leaving 20 ul of PBS on the sensors. The His-tag lectin was then added to the sensor (20 μl at 2 mg/ml) and allowed to bind for 300 seconds. The excess lectin was again washed by PBS three times and 20±1 μl was left on the sensor. The sensor was allowed to equilibrate for 100 seconds and then 20 μl of analyte was added. The analytes tested include free biotinylated glycans, glycans bound to streptavidin, and anti His-tag antibody. Each of these, upon binding, can cause an increase in SWNT luminescence (FIG. 26b). The sensor response was recorded for 500 seconds and then data collection was terminated. Stabilization frames were recorded before and after the analyte addition in order to correct for any focus drift caused by the tension of the objective in contact with the glass slide (see below).

Single SWNT Sensor Measurements

Figure 27:
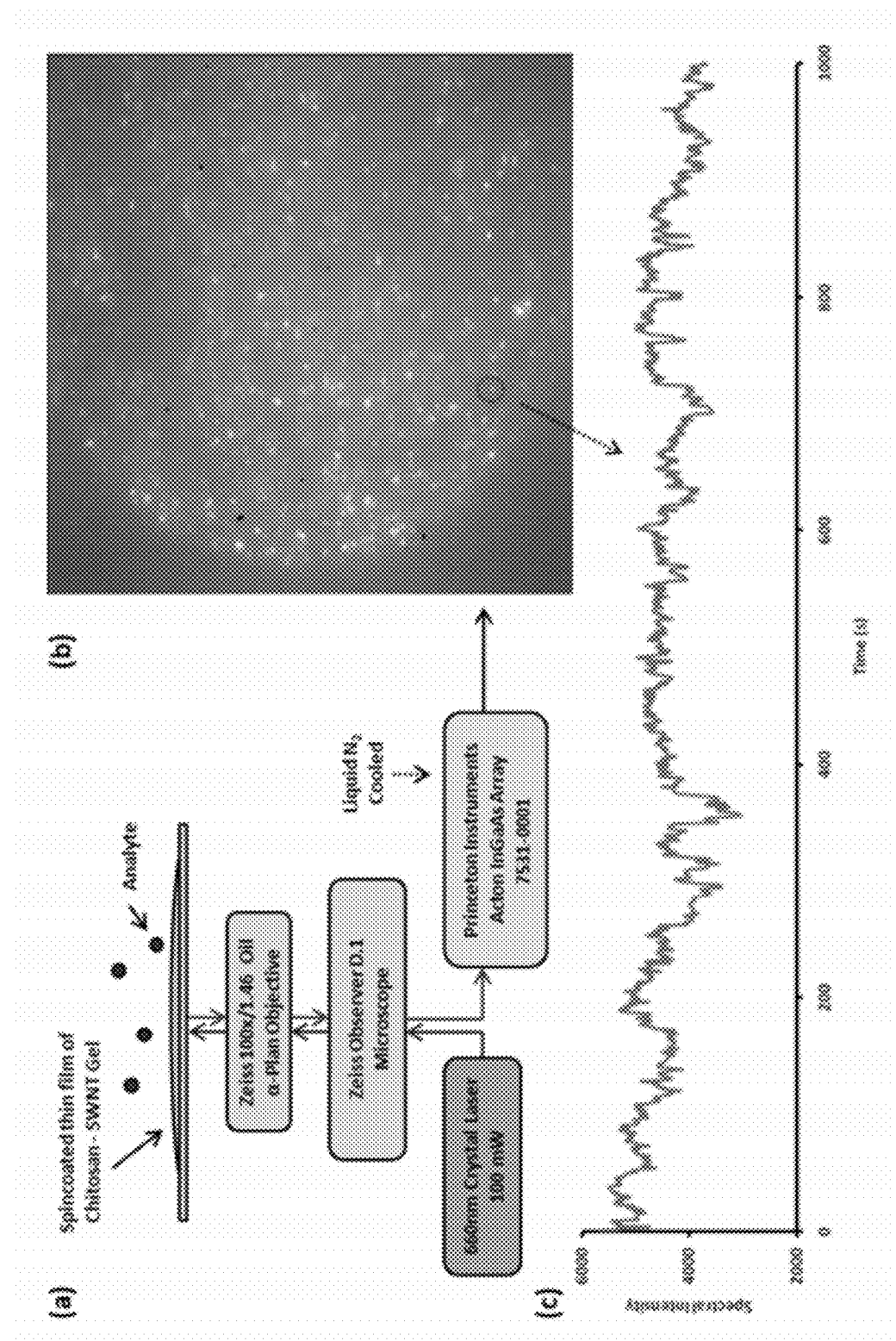
FIG. 27 includes single SWNT sensor measurements.

A second custom microscope was used to collect emission intensities of single SWNT sensors (FIG. 27a). The SWNT-CHI gel was diluted to 3 μg/ml of SWNT and spin-coated (3000 rpm for 30 s on Make of SpinCoater™) on glass-bottom petridishes (MarTec Corp™). The petri-dishes were then placed on the microscope platform (Zeiss D.1 Observer) and the oil-immersed objective (Zeiss™ 100×/1.46) was focused on the SWNT sensors on the glass surface. The SWNT were excited by a 660 nm laser (Crystal Laser—100 mW) and the emission intensities were recorded by a nitrogen-cooled InGaAs array (Princeton Instruments™). Again WinSpec software (Princeton Intsruments™) was used to collect the data in the form of a stacked Tiff image where pixel values corresponded to spectral intensity (FIG. 27b). These Tiff images were then analyzed using custom Matlab code (Mathworks™) to construct a intensity versus time trace for each SWNT sensor (FIG. 27c).

Figure 28:
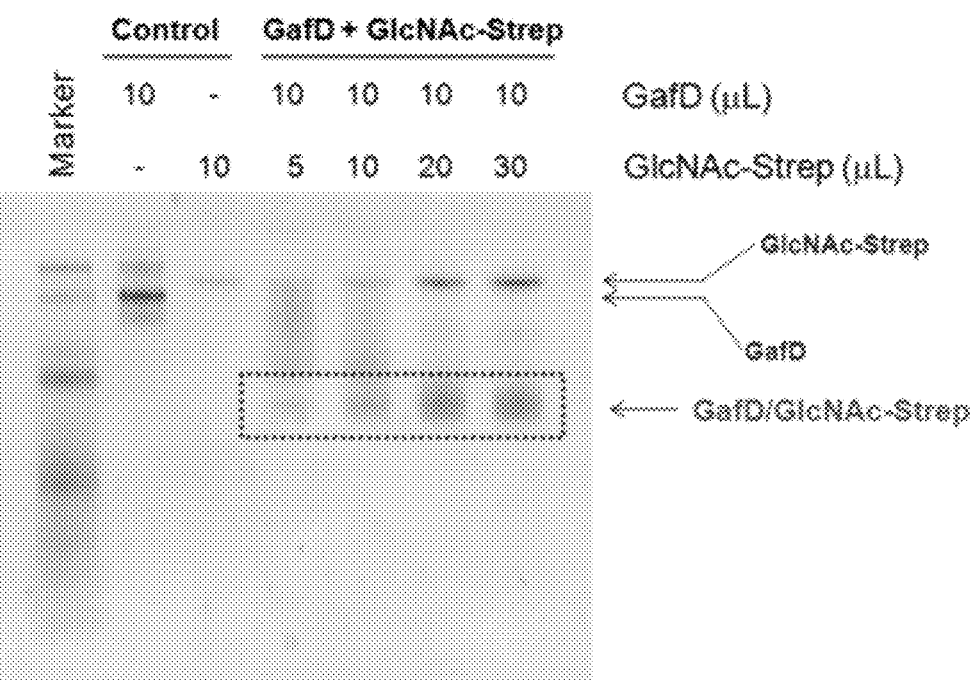
FIG. 28 includes native PAGE gel of GlcNAc-Streptavidin to GafD lectin in solution.

Binding of streptavidin-based model glycoproteins to expressed His-tag lectins was confirmed using native PAGE gel analysis, which allowed the protein-protein complex to remain in its native, non-denatured from. Separation was dictated by native complex charge and morphology, not strictly by molecular weight as in SDS-PAGE[25]. The resulting gel (FIG. 28) clearly indicated a bound complex that arises when GlcNAc-streptavidin probe (1 mg/ml) is added in solution with GafD lectin, a lectin from *Escherichia coli*, which binds 13-GlcNAc (3 mg/ml).

Figure 29:
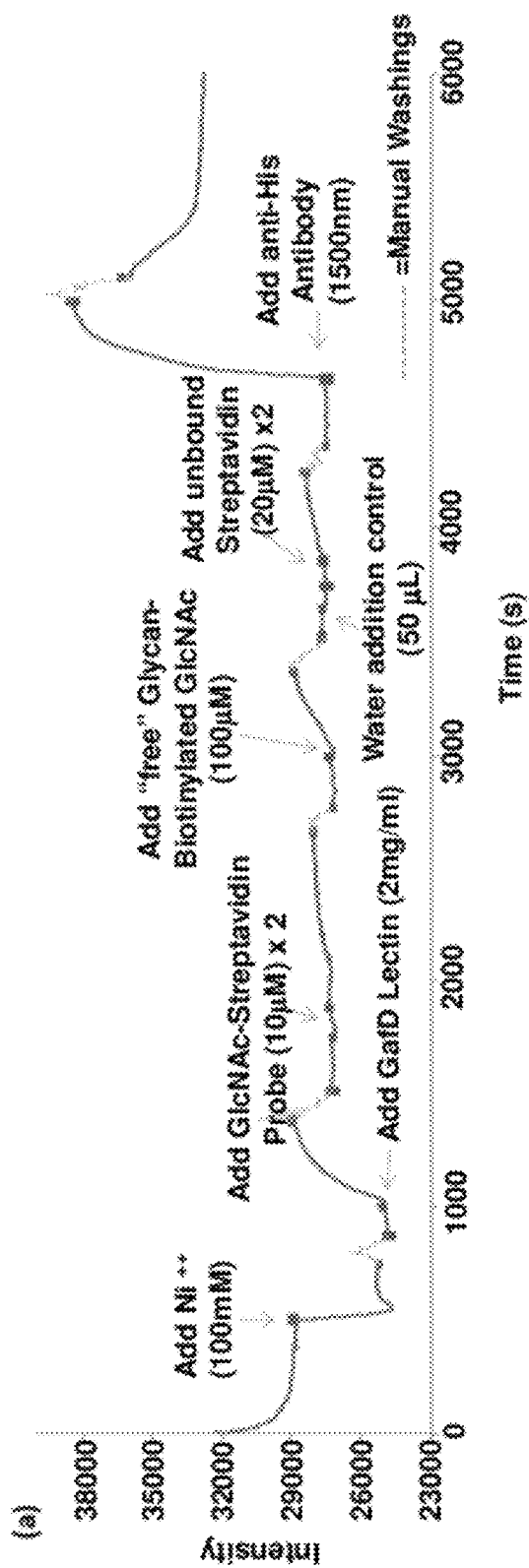
FIG. 29 includes time response curves of sensor chemistry steps and analyte additions.
Figure 29:
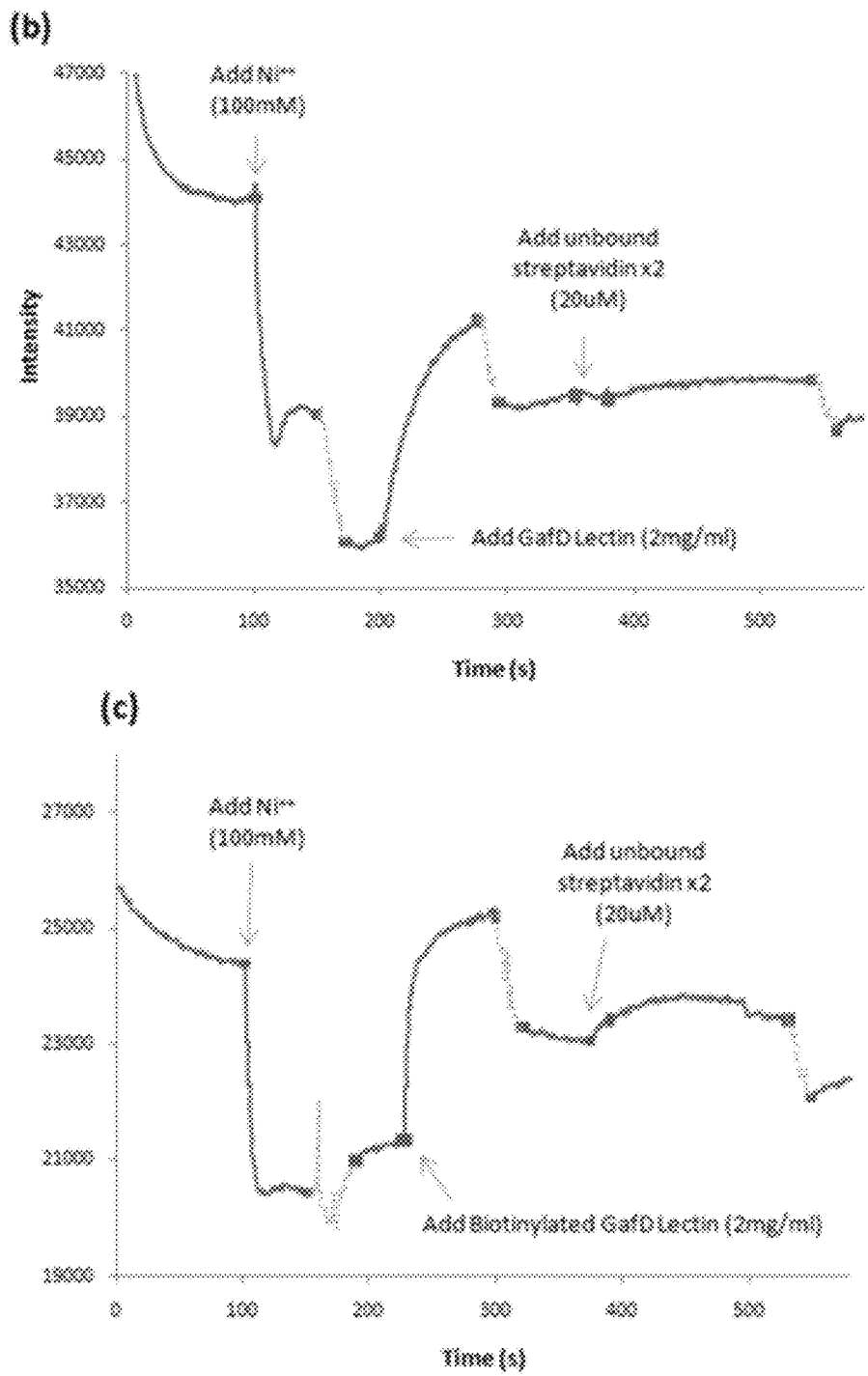
Figure 36:
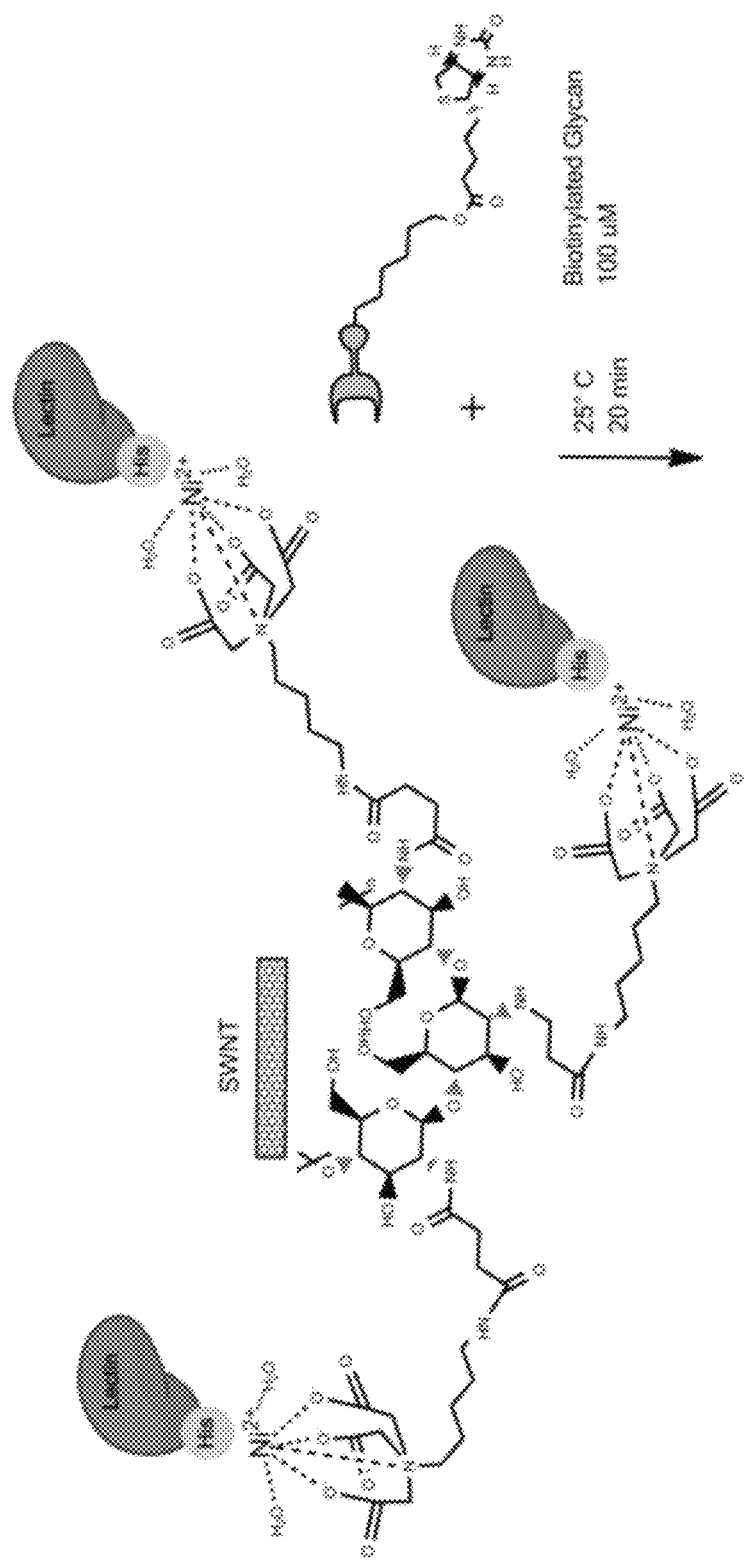
FIG. 36 is a schematic depiction of binding of biotinylated glycan to lectin and blank streptavidin to exposed biotin ends.
Figure 36:
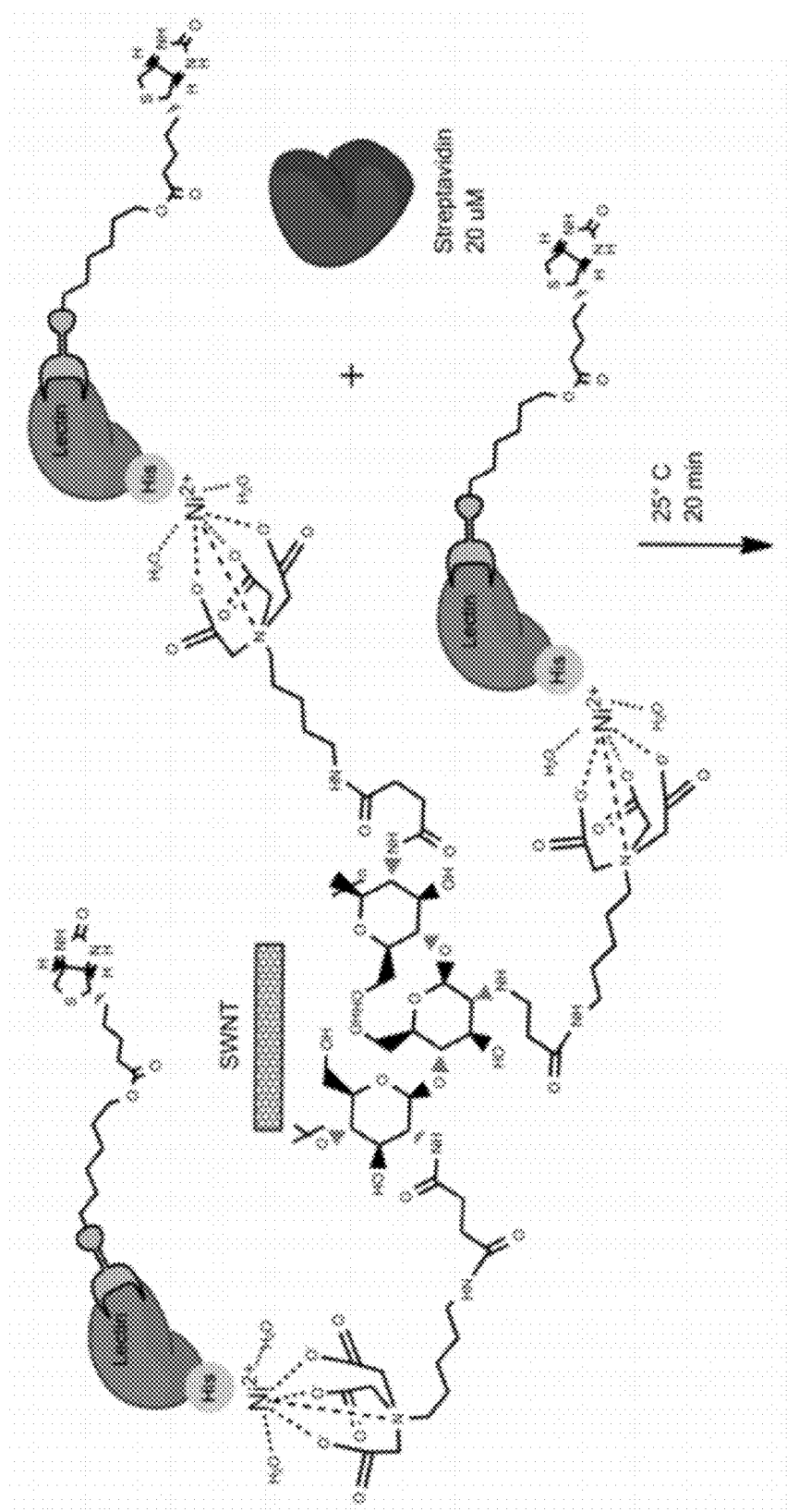
Figure 36:
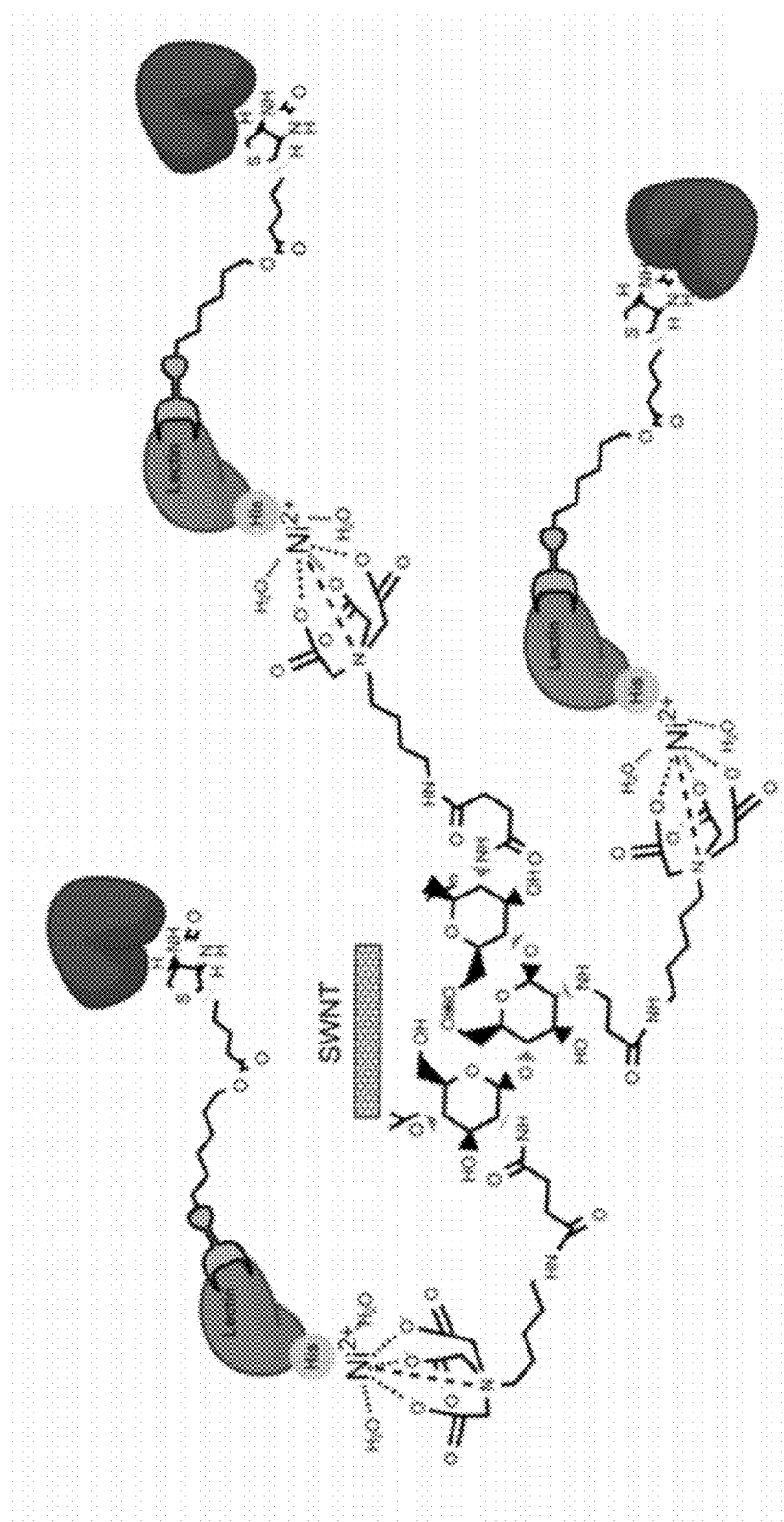

Next, the time response of the sensor during construction and various analyte additions was analyzed using the ensemble measurement technique. In the first test, $Ni^{2+}$ was added (100 mM) which caused a clear quenching response as the $Ni^{2+}$ interacted with the exposed SWNT decreasing their fluorescence (FIG. 29a). The effect of divalent cation quenching of nanotubes is established in the literature. (Nieba, L., et al., BIACORE analysis of histidine-tagged proteins using a chelating NTA sensor chip. *Analytical Biochemistry* 1997, 252 (2), 217-228, which is incorporated by reference in its entirety). The excess $Ni^{2+}$ was then washed away and the His-tag lectin GafD was added (40 μg in 20 μl). A loading curve (much like that observed in SPR assays) was observed as the lectin bound to the NTA-$Ni^{2+}$ complexes. The increase in SWNT fluorescence was with a mechanism based on an increase in the distance between the $Ni^{2+}$ complex, lessening its proximity quenching effect.[8] The excess lectin was washed away and the Streptavidin-GlcNAc probe was added (40 μg in 40 μl), in two steps. Again, an SPR-like loading curve was observed, except with slower kinetics and less overall response. The excess Streptavidin-GlcNAc probe was washed away and free biotinylated GlcNAc was added (20 μl of 100 μM). Again, the loading curve was observed. After washing away the excess free glycan, 40 μl of PBS was added to the system to ensure that the loading responses were due to the analyte and not some focal change due to increased mass on the sensor. We then checked to see if the biotinylated glycans, now bound to the sensor, were accessible to blank streptavidin (FIG. 36). Upon streptavidin addition, another loading curve with slower kinetics was observed, confirming binding of streptavidin to the biotin ends of glycans decorated on the SWNT-Lectin sensors. As a positive control, an anti His-tag antibody was used, [8] to verify the integrity of His-tag binding at the end of the experiment. Here, binding to the His-tagged lectin displaced it and increased the distance between the SWNT and $Ni^{2+}$, causing the observed increase.

Two other time-series analyses were conducted as a negative and positive control. In the negative control, blank streptavidin was added to the sensor, after $Ni^{++}$ and GafD lectin loading (FIG. 29b). No loading curve was observed. In the positive control blank streptavidin was again used as the analyte but this time the GafD lectin was biotinylated (Pierce™ Kit 21455). Upon addition of streptavidin, the expected loading curve was observed (FIG. 29c).

The time-series analyses revealed the potential activation limited kinetic responses from our free glycan and bound glycan probes. To obtain forward and reverse kinetic rates of the system, the loading curves of the sensors at varying analyte concentrations were analyzed. Assuming the reaction model is that of a Langmuir surface absorption:

$$G + L \leftrightarrow GL \quad (1)$$

Where G can be the glycosylated analyte, L can be the lectin binding sites and GL can be the bound complex, then the following kinetic model would be expected to express the rate of change of bound complex:

$$\frac{d[GL]}{dt} = k_f[G][L] - k_r[GL] \quad (2)$$

The concentration of the free lectin sites at a given time can be expressed as:

$$[L]_t = [L]_{to} - [GL]_t \quad (3)$$

Thus, equation 2 can be rewritten as:

$$\frac{d[GL]}{dt} = k_f[G]([L]_{to} - [GL]_t) - k_r[GL] \quad (4)$$

It was assumed that the analyte concentration, [G], was constant (as the bulk of fluid above the sensor was large in comparison to the number of lectin binding sites). The change in the fluorescent intensity (I) can be a measure of the change in bound complex [GL], so an analogous form of equation 4 for the sensor system would be:

$$\frac{dI}{dt} = k_f C_g (I_{max} - I_t) - k_r(I_t) \quad (5)$$

This equation can be rearranged as to lump the kinetic parameters together into one kinetic variable ($k_s$) as is done in fitting SPR data[12]:

$$\frac{dI}{dt} = k_f C_g I_{max} - k_s(I_t) \quad (6)$$

$$k_s = k_f C_g + k_r \quad (7)$$

Integrating equation (6) yields the equation for the absorption curve:

$$I_t = M(1 - e^{-k_s t}) + I_o \quad (8)$$

$$M = \frac{k_f C_g I_m}{k_f C_g + k_d} \quad (9)$$

Thus, by obtaining absorption curves at three to four different concentrations of glycosylated analytes ($C_g$) and fitting them to equation 8, a plot $k_s$ versus $C_g$ can be created. If this kinetic model accurately describes the binding of this system, a line can be fitted to this plot. As equation 7 shows, the slope and y-intercept of this line correspond to $k_f$ and $k_r$, respectively.

Concentration dependent absorption curves were obtained for controls, anti His-tag antibody, free biotinylated glycans (Fuc and GlcNAc), and glycans bound to streptavidin (Fuc and GlcNAc). The controls (FIG. 30a) revealed a positive response for Fuc-Streptavidin probe to PA-IIL lectin and GlcNAc-Streptavidin probe to GafD lectin. It also revealed a negligible response to blank streptavidin, as well as biotin. The first 20 frames of the absorption curve can contain artifacts due to the manual additions of analyte (pipette tip to edge of spot). Thus, in fitting the absorption curves to equation 8, the fit parameters have been set to optimize the fit on the curved portion of the isotherm rather than the artifacts at the beginning of the curve. Also, the absorption curves have been linearly corrected for focus drift caused by tension on the z-axis focus due to direct contact with the glass. This small correction (less than 0.05% of the signal) was made by linearly fitting the end of the absorption curve when the system was again at equilibrium.

The curves for antiHis-tag antibody (FIG. 30b) were obtained for 1500 nM, 500 nM, 166 nM, and 55 nM concentrations interacting with bound GafD lectin. The resulting $k_s$ fit was highly linear ($R^2=0.971$) and resulting $k_f$, $k_r$, and $K_D$ values are tabulated in Table 3. The $K_D$ of 4 µM found for our murine produced anti His-tag antibody (Sigma™ H1029) correlates well with the 1 µM found by Biacore SPR studies. (Saarela, S., et al., *Infection and Immunity* 1996, 64 (7), 2857-2860; Tanskanen, J., et al., *Journal of Bacteriology* 2001, 183 (2), 512-519; Merckel, M. C., et al., *Journal of Molecular Biology* 2003, 331 (4), 897-905; Carrillo, L. D., et al., *Journal of the American Chemical Society* 2006, 128 (46), 14768-14769, each of which is incorporated by reference in its entirety). The concentration-dependent curves for free biotinylated fucose (40, 13.3, 4.4, and 1.5 µM) to PA-IIL lectin (FIG. 30c) and bound fucose-streptavidin probes (10, 3.3, 1.1, and 0.4 µM) to PA-IIL lectin (FIG. 30d) also fit the SPR-like kinetic model well and their kinetic parameters are reported in Table 3. The $K_D$ of 106 and 142 µM found by our sensor for unbound and bound fucose to PA-IIL was weaker than the previously reported 3 µM found by isothermal titration microcalorimetry (ITC).[29] However, the discrepancy likely arose from the difference in measurement technique, as the method more closely resembled a surface bound technique, like SPR, whereas the thermodynamics of binding were measured in solution phase during ITC. The binding of free biotinylated GlcNAc (50, 16.6, and 5.5 µM) and GlcNAc-streptavidin probe (10, 3.3, 1.1 µM) to GafD lectin (FIG. 5e-f) also followed the model. The fitted kinetic parameters are reported in Table 3. This may be the first measurement of GlcNAc to GafD kinetics; although there are many glycan-array studies showing a high relative affinity of GlcNAc to GafD over other glycans.

TABLE 3

Kinetic parameters found from concentration dependent curves.

| Experiment | $R^2$ Val | $K_f$ (µM·s)$^{-1}$ | $k_r$ (s)$^{-1}$ | $K_D$ (µM) |
|---|---|---|---|---|
| ATB to GafD | 0.9707 | 2.00E−06 | 0.0082 | 4 |
| Fuc-Biotin to PA-IIL | 0.8649 | 7.00E−05 | 0.0074 | 106 |
| Fuc-Strept to PA-IIL | 0.9367 | 0.0001 | 0.0142 | 142 |
| GlcNAc-Biotin to GafD | 0.941 | 0.0002 | 0.0037 | 19 |
| GlcNAc-Strept to GafD | 0.99 | 0.0003 | 0.015 | 50 |

Figure 31:
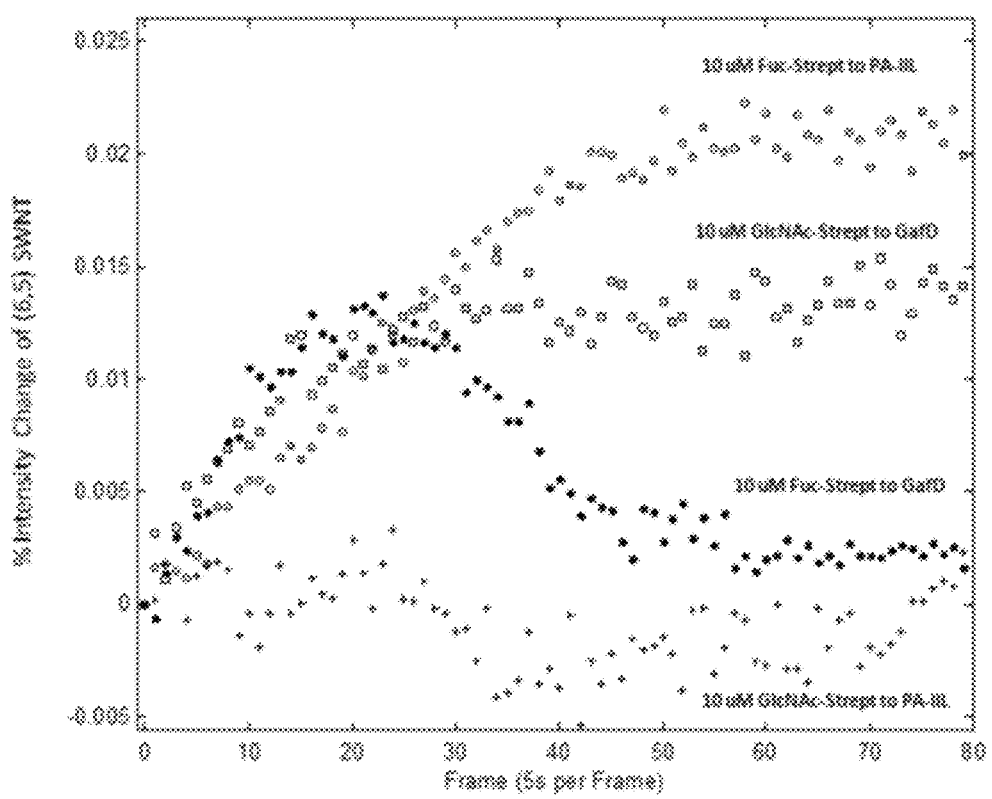
FIG. 31 includes selectivity of SWNT-lectin sensors.

The selectivity of the SWNT-Lectin sensors was also checked by measuring the cross response of the glycans and lectins (FIG. 31). The PA-IIL lectin showed negligible binding to GlcNAc-Streptavidin probe, whereas the GafD lectin exhibited a small affinity for Fuc-Streptavidin. However, the cross affinity of Fuc-Streptavidin to GafD was much smaller than the known strong-binding combination of fucose to PA-IIL. This demonstrated that the SWNT-lectin sensors could be used to distinguish between sugar groups, especially as the sensor signal is optimized.

Figure 30:
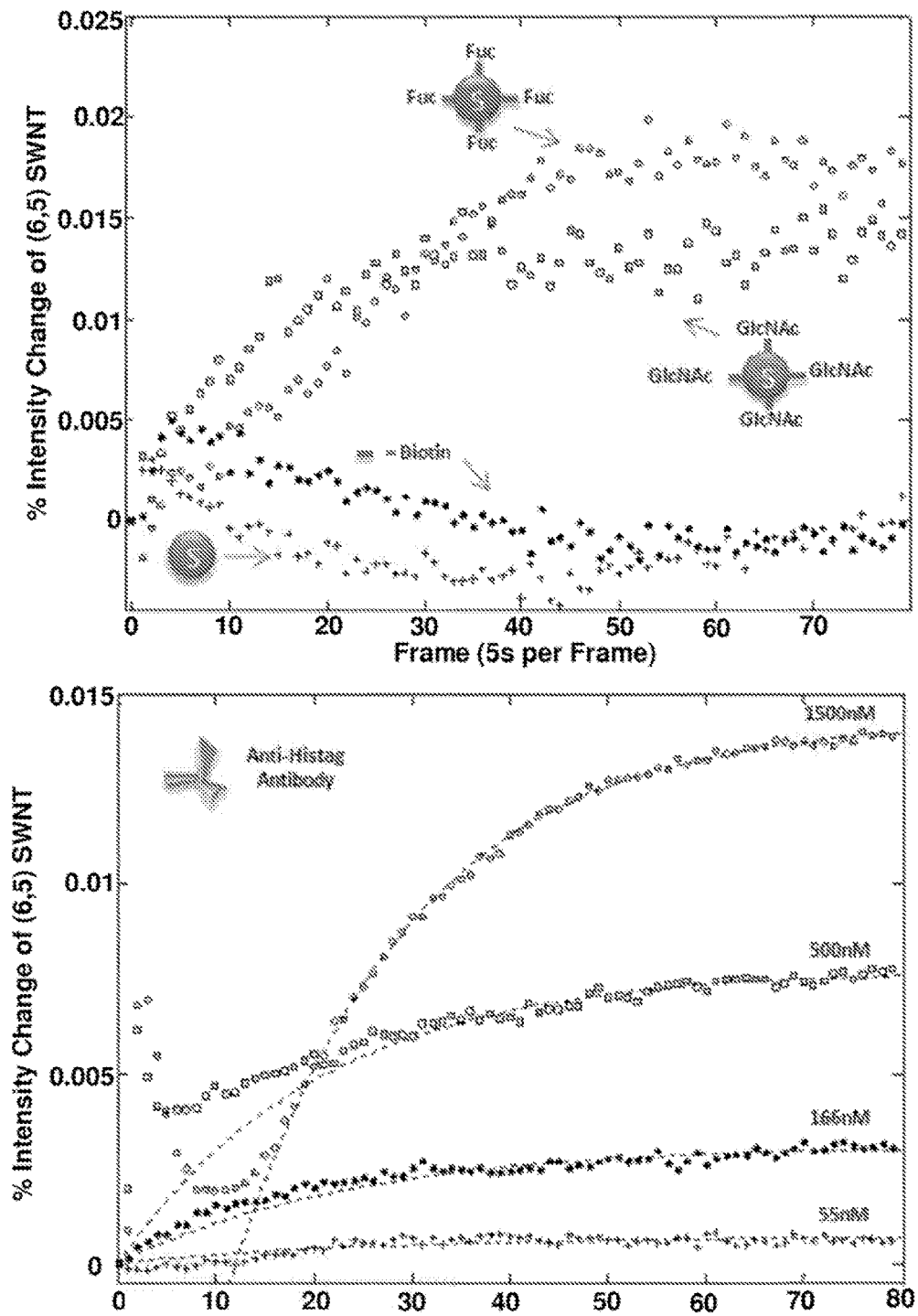
FIG. 30 includes concentration dependent curves loading curves of various analytes to SWNT-Chitosan sensors.
Figure 30:
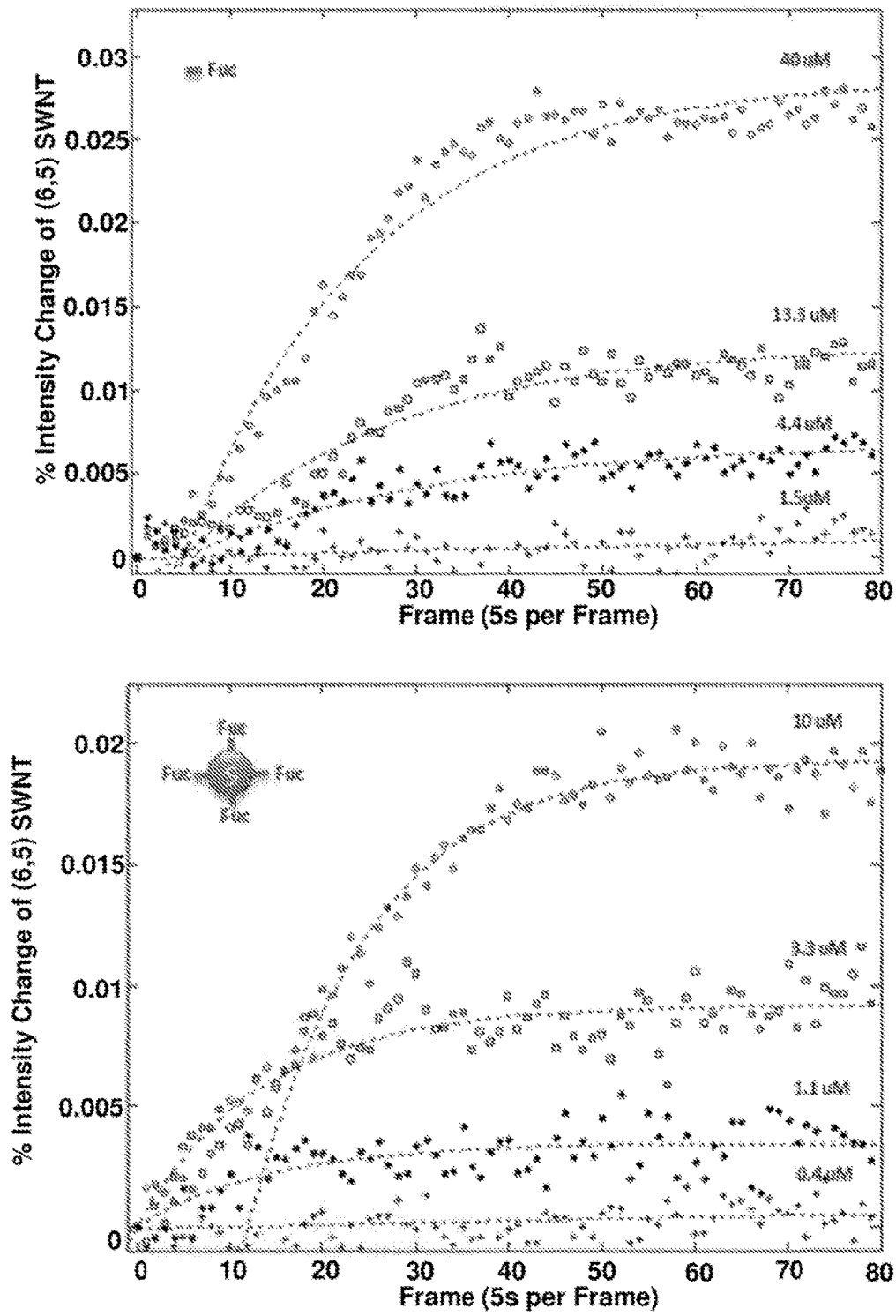
Figure 30:
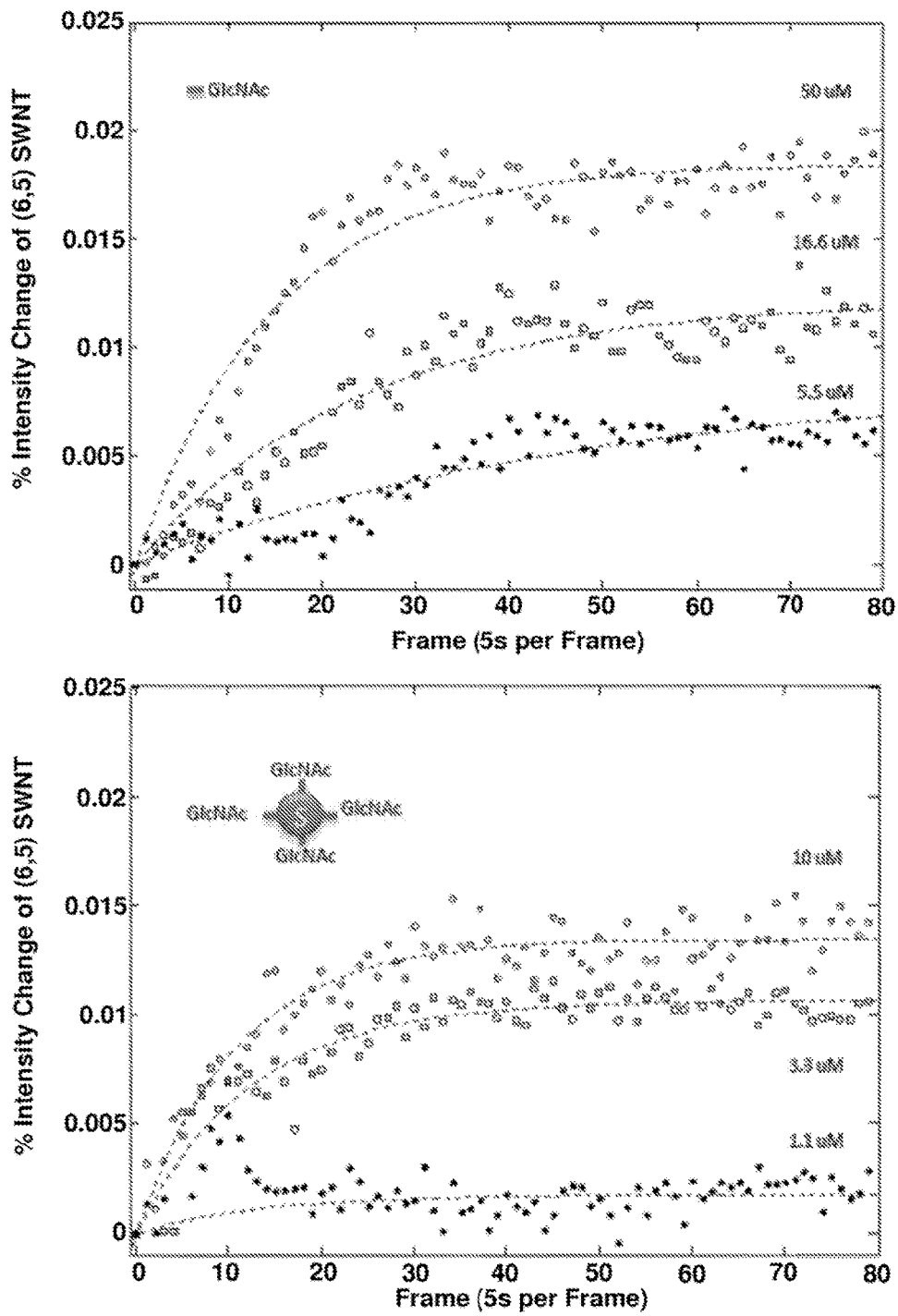
Figure 32:
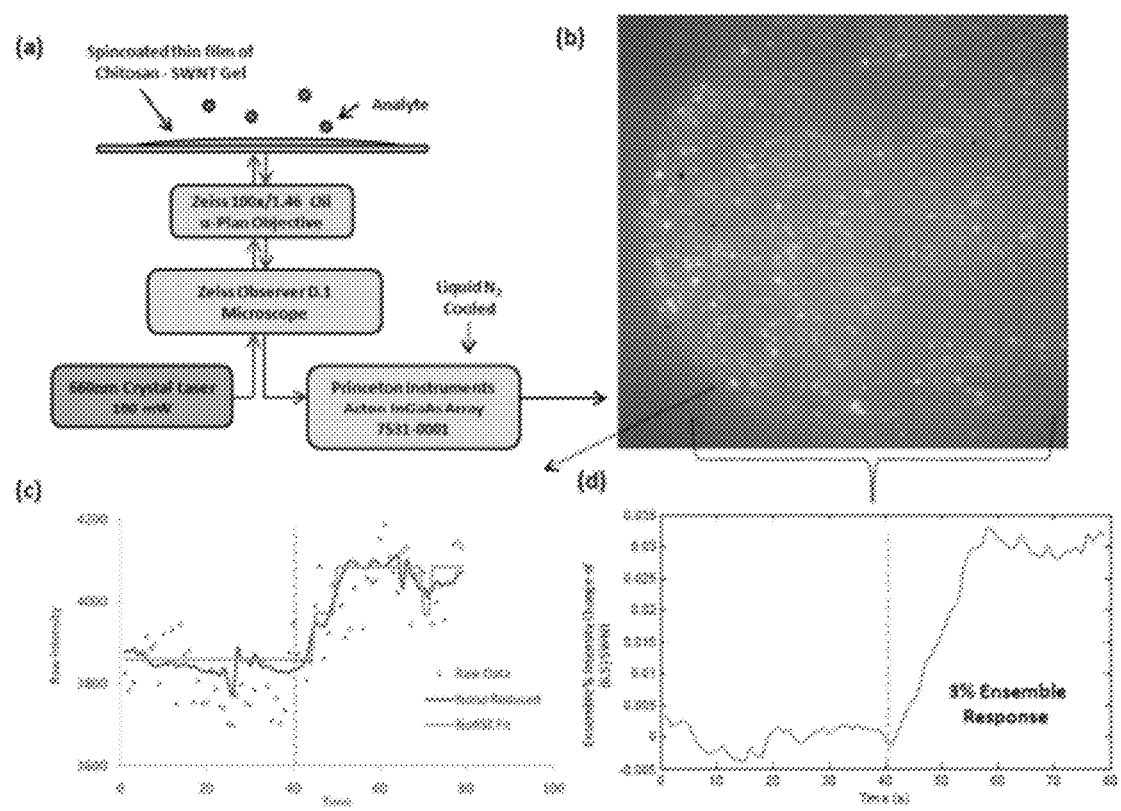
FIG. 32 shows results of single SWNT sensor measurements.
Figure 37:
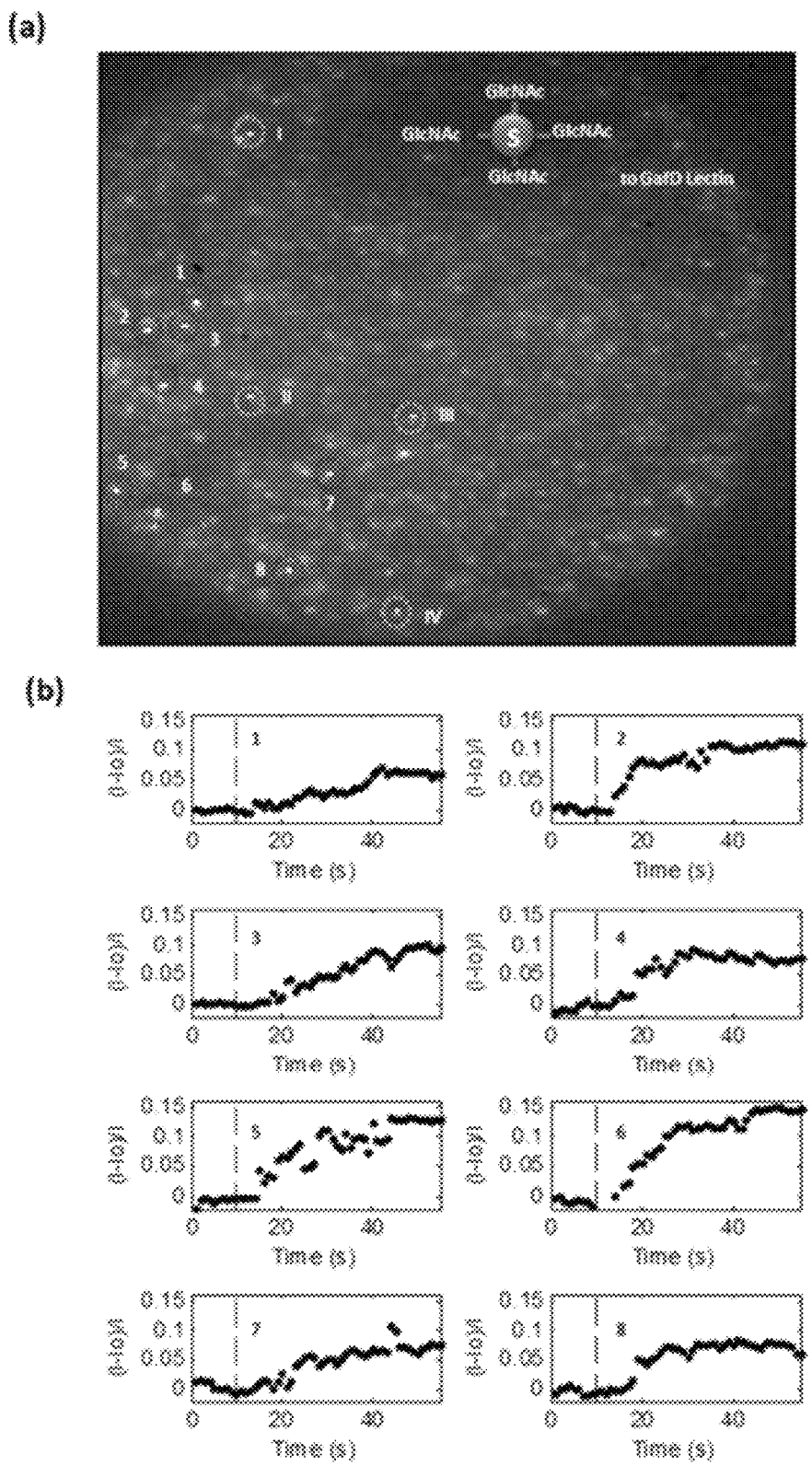
FIG. 37 shows single SWNT sensor measurement results.
Figure 37:
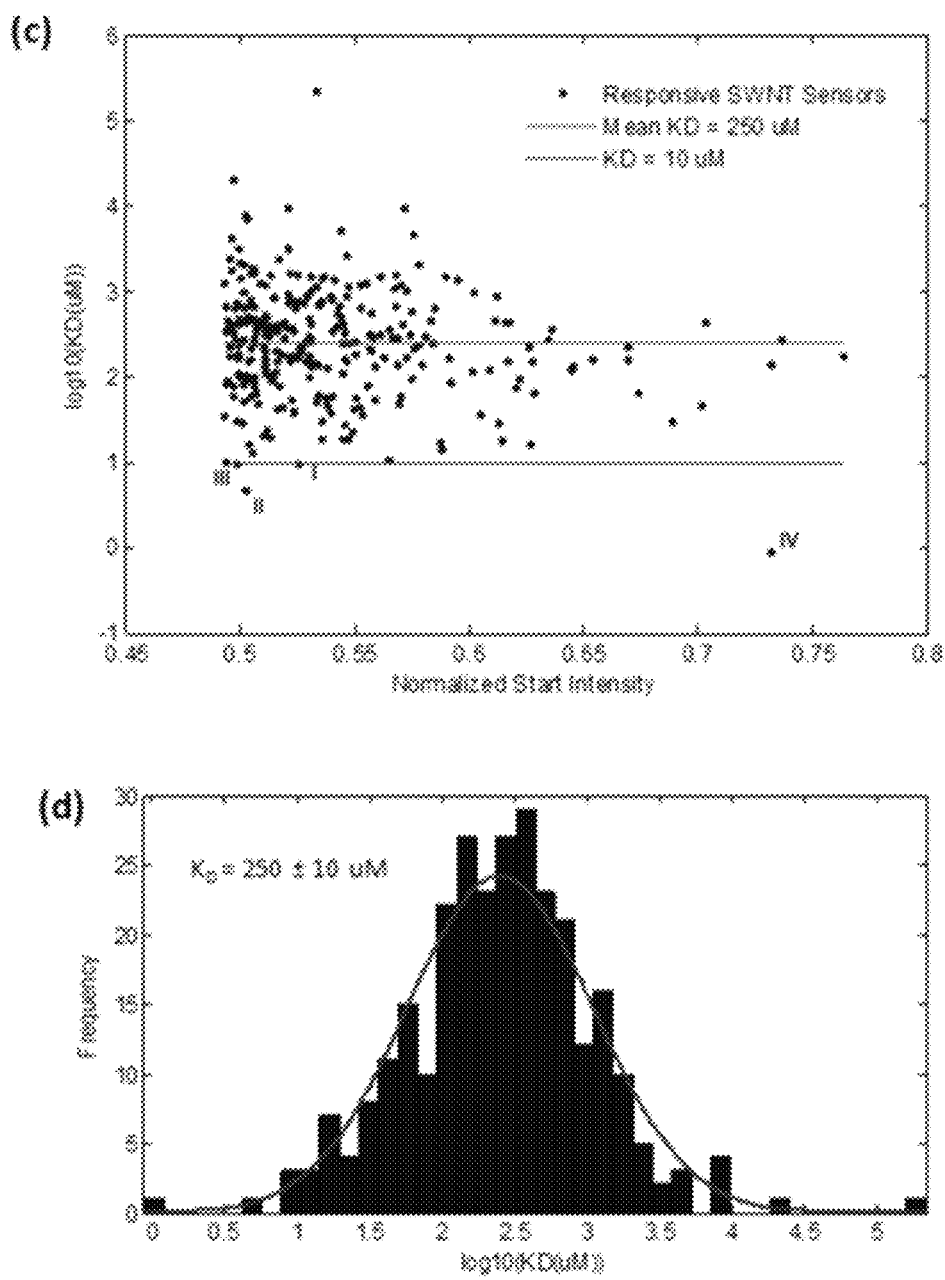

The overall change in signal intensity was small (3-5%) for ensemble measurements of glycan-lectin binding for this system (FIG. 30). If the observed response were homogeneous, that would mean that each SWNT responded to this small degree, or, if inhomogeneous, then that would mean that a subset of SWNT modulate to a much greater extent. The use of single nanotube spectroscopy allowed this question to be addressed (FIG. 32). This approach has been used for other single molecule sensitive platforms using SWNT-based sensors for $H_2O_2$[32], $NO^{24a, 33}$, glucose[30], and nitroaromatics.[34] The resulting thin film of chitosan wrapped SWNT (FIG. 32b) was imaged at a frequency of 1 frame per second using our InGaAs array setup. Using software developed in house, the movies of SWNT fluorescence were analyzed and intensity time traces were extracted for each of the individual SWNT sensors (FIG. 37).[24b] An efficient algorithm for fitting large quantities of these time traces to embedded fluorescent levels was used.[35] Briefly, the algorithm used an optimized form of an established noise-reduction algorithm for biological experiments[36] to clean the traces (FIG. 37c). It then evaluated all-points histograms of each trace to determine the unique fluorescent states of each trace. The resulting step traces (FIG. 37c) were then used to determine the forward and reverse kinetics of each SWNT sensor. Before analyzing the kinetics of each individual trace, the prior ensemble experiments were approximated by summing the intensity values of noise-reduced traces from 150 individual SWNT sensors (FIG. 37d). The resulting signal modulation of GlcNAc-Streptavidin probe (10 µM) to GafD was nearly identical to that of ensemble measurements (~3.5% response).

Figure 33:
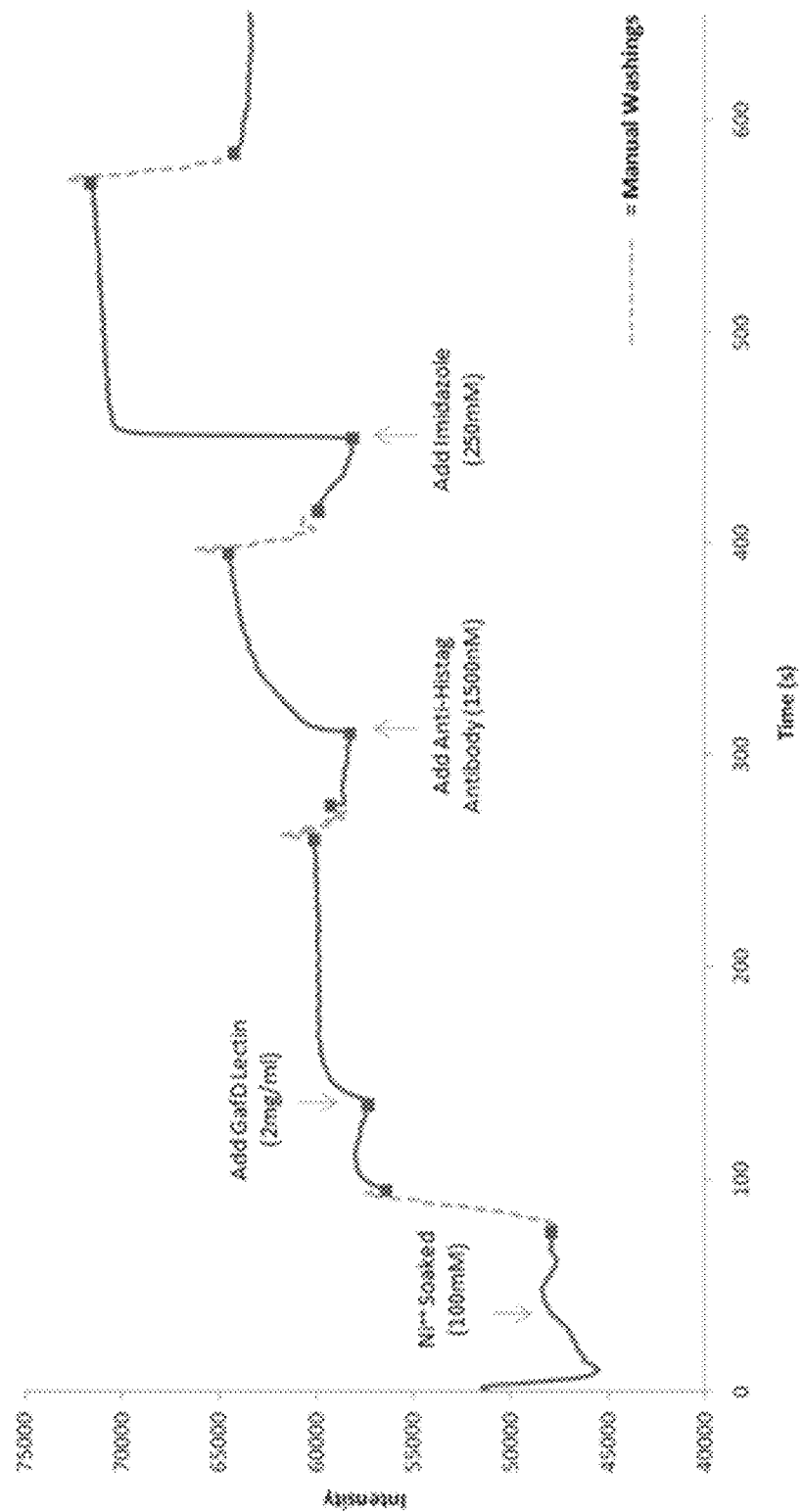
FIG. 33 includes time response curve showing increased fluorescence response upon addition of all analytes, including imidazole.

The kinetic analysis of individual SWNT sensors helped determine the locations of "strong-transducers" based on overall signal modulation and kinetic strength. Intensity versus time traces are extracted from the brightest 1000 SWNT sensors (FIG. 33), and analyzed for a time period of 40 seconds before and after glycan addition. The location of the eight top SWNT sensors based on signal modulation (each greater than 5%) was easily determined. To determine the $K_D$ of each SWNT sensor, the traces were noise-reduced and fitted by the NoRSE algorithm[35] and then kinetic parameters were found with the previously reported Birth-Death kinetic model.[24] The first 40 seconds of the trace (before glycan addition) were used to determine the background $k_f$ and $k_r$ rates for each SWNT sensor (due to intrinsic fluctuations of the tethered group) and then subtracted from the $k_f$ and $k_r$ rates found after glycan addition. Of the 1000 traces analyzed, 289 traces had sufficient signal over the background fluctuations to determine the $K_D$ upon glycan addition. Locations of the four strongest transducers, with $K_D$ values less than 10 µM, were determined These strong kinetic transducers were not the brightest SWNT traces but rather traces with 50 to 75% the intensity of the brightest recorded. This may have reflected the insensitivity of small SWNT bundles to this sensing mechanism. Bundles appeared brighter as a composite fluorescent spot, and their construction would necessarily shield the interior SWNT from modulation. The population of 289 SWNT transducers was analyzed to find a $K_D$ of 250±9 µM (FIG. 7d).

The SWNT may differ in their ability report the Glycan-Lectin binding events due to accessibility to analyte in the gel, inhomogeneous chemistry modifications (more or less NTA groups per SWNT), SWNT defects, and the influence of multivalent binding. Single molecule steps associated with discrete adsorption steps were not observed, as in the case of other, small molecule quenchers[24a, 34]. In this case, the interaction of the analyte with the SWNT was indirect, through the spacer chemistry that adjusted the $Ni^{2+}$ distance to the SWNT. This mechanism need not be discretized as in the case of adsorption/desorption of a molecular quencher directly on the SWNT surface. In the glycan/lectin system, the quenching distance was continuous. Nevertheless, single SWNT did respond and contributed to the ensemble response. The fact that the response was monitored in a single 2×2 pixel spot offers possibilities to dramatically decrease required analyte mass. Even the current responses were an improvement over SPR (which can require 1-5 mg of analyte depending on run conditions[21]); here, less than 2 µg of glycosylated protein or 100 ng of free glycan was used as the analyte probe. The amount of lectin (20 µg) used for the SWNT sensors can be dramatically reduced be microprinting smaller volumes of protein directly on an array of optimally responding SWNT sensors.

Finally, these data sets revealed more about the response mechanism of our Ni-NTA tethered SWNT sensor. As demonstrated previously[8], the $Ni^{2+}$ appeared to act as a proximity quencher[26a] to the SWNT, in the careful time-series analyses used here, and in static before-and-after measurements used previously. In each case of analyte binding, the fluorescent signal increased, consistent with the $Ni^{2+}$ group moving further away from the SWNT group. According to this model, the higher the affinity an analyte has for the sensor protein, the larger the observed increase. To demonstrate this, another time trace of anti His-tag antibody response to GafD (FIG. 33) was recorded, which included an addition of imidazole (250 mM). Imidazole exhibits a higher affinity for $Ni^{2+}$ than a His-tag group and is often used in protein purification to elute proteins bound in a Ni-agarose column. The time trace showed that for each of the additions (His-tag lectin, antibody, and imidazole) an increase in SWNT intensity was observed. This suggested that the increase in tether length was due to "steric-loading" of the NTA-$Ni^{2+}$-sensor protein complex. As more analyte bound to the complex, the required space increases and the tethered group's fluctuations tend to be further from the nanotube. Multivalency of the analyte may also play a role (as in the case of glycan-streptavidin addition) as multiple NTA-$Ni^{2+}$-sensor protein complexes stretch to meet a single, multivalent analyte.

Here, a recently reported SWNT-based sensor was extended to the measuring of kinetic parameters between lectins and glycans. (Ahn, et al., (2011)). The sensor was calibrated by measuring the kinetics between anti His-tag antibody to a His-tag lectin and comparing it to the literature. Lectin-glycan binding with two glycans (Fucose and N-Acetylglucosamine) was demonstrated, as bound and unbound probes to two lectins (PA-IIL and GafD). The response found from illuminating large gel spots (1 µl) can be approximated by an ensemble average of 1000 single SWNT sensors, and furthermore, the single sensors can be analyzed to determine which ones are maximum signal reporters. Optimization of these single-SWNT measurements of glycan-lectin binding can be done by: 1) creating regular arrays of single SWNT sensors, so that the positions of best sensors can be recorded, and 2) increasing the sampling frequency of the emission detection, as the current frequency of one frame per second would lose a lot of binding event information for weak glycan-lection combinations. In its current state, the platform can readily measure kinetic parameters between glycans and lectins (or other analytes to proteins) that have $K_D$ in the pM to high µM range. Further optimization of these sensors may extend them to all glycan-lectin combinations, which often interact monovalently in the mM range.

In some embodiments, an automated printer can be used to print a nanostructure, as previously described, on a surface (FIG. 35a), for example as a gel, more specifically a SWNT-Chitosan gel. When the gel is printed by hand, the gel morphology can be irregular and the crosslinking can be inhomogenous leading to different spot sizes and intensities after subsequent chemistry steps (FIG. 35b). Automated printing of large spots with subsequent addition of crosslinker on top of the gel can also lead to inhomogenous spots (FIG. 35c). By printing many alternating layers of SWNT-Chitosan gel and crosslinker, a spot can be built that can be homogenous in shape and signal (FIG. 35d).

REFERENCES

1. Ohtsubo, K.; Marth, J. D., Glycosylation in cellular mechanisms of health and disease. *Cell* 2006, 126 (5), 855-867.
2. Gamblin, D. P.; Scanlan, E. M.; Davis, B. G., Glycoprotein Synthesis: An Update. *Chemical Reviews* 2009, 109 (1), 131-163.
3. Li, H. J.; d'Anjou, M., Pharmacological significance of glycosylation in therapeutic proteins. *Current Opinion in Biotechnology* 2009, 20 (6), 678-684.
4. Elola, M. T.; Wolfenstein-Todel, C.; Troncoso, M. F.; Vasta, G. R.; Rabinovich, G. A., Galectins: matricellular glycan-binding proteins linking cell adhesion, migration, and survival. *Cellular and Molecular Life Sciences* 2007, 64 (13), 1679-1700.
5. (a) Hirabayashi, J., Concept, strategy and realization of lectin-based glycan profiling. *Journal of Biochemistry* 2008, 144 (2), 139-147; (b) Hirabayashi, J.; Kuno, A.; Tateno, H., Lectin-based structural glycomics: A practical approach to complex glycans. *Electrophoresis* 2011, 32 (10), 1118-1128.
6. (a) Harvey, D. J., Identification of protein-bound carbohydrates by mass spectrometry. *Proteomics* 2001, 1 (2), 311-328; (b) Cortes, D. F.; Kabulski, J. L.; Lazar, A. C.; Lazar, I. M., Recent advances in the MS analysis of glycoproteins: Capillary and microfluidic workflows. *Electrophoresis* 2011, 32 (1), 14-29; (c) Lazar, I. M.; Lazar, A. C.; Cortes, D. F.; Kabulski, J. L., Recent advances in the MS analysis of glycoproteins: Theoretical considerations. *Electrophoresis* 2011, 32 (1), 3-13.
7. (a) Pilobello, K. T.; Krishnamoorthy, L.; Slawek, D.; Mahal, L. K., Development of a lectin microarray for the rapid analysis of protein glycopatterns. *Chembiochem* 2005, 6 (6), 985-989; (b) Zheng, T.; Peelen, D.; Smith, L. M., Lectin arrays for profiling cell surface carbohydrate expression. *Journal of the American Chemical Society* 2005, 127 (28), 9982-9983; (c) Rosenfeld, R.; Bangio, H.; Gerwig, G. J.; Rosenberg, R.; Aloni, R.; Cohen, Y.; Amor, Y.; Plaschkes, I.; Kamerling, J. P.; Maya, R. B. Y., A lectin array-based methodology for the analysis of protein glycosylation. *J. Biochem. Biophys. Methods* 2007, 70 (3), 415-426; (d) Tao, S. C.; Li, Y.; Zhou, J. B.; Qian, J.; Schnaar, R. L.; Zhang, Y.; Goldstein, I. J.; Zhu, H.; Schneck, J. P., Lectin microarrays identify cell-specific and functionally significant cell surface glycan markers. *Glycobiology* 2008, 18 (10), 761-769.
8. Ahn, J. H.; Kim, J. H.; Reuel, N. F.; Barone, P. W.; Boghossian, A. A.; Zhang, J.; Yoon, H.; Chang, A. C.; Hilmer, A. J.; Strano, M. S., Label-Free, Single Protein Detection on a Near-Infrared Fluorescent Single-Walled Carbon Nanotube/Protein Microarray Fabricated by Cell-Free Synthesis. *Nano Lett* 2011.
9. Weis, W. I.; Drickamer, K., Structural basis of lectin-carbohydrate recognition. *Annual Review of Biochemistry* 1996, 65, 441-473.
10. (a) Wijagkanalan, W.; Kawakami, S.; Hashida, M., Glycosylated carriers for cell-selective and nuclear delivery of nucleic acids. *Frontiers in bioscience: a journal and virtual library* 2011, 17, 2970-87; (b) Hong, S. Y.; Tobias, G.; Al-Jamal, K. T.; Ballesteros, B.; Ali-Boucetta, H.; Lozano-Perez, S.; Nellist, P. D.; Sim, R. B.; Finucane, C.; Mather, S. J.; Green, M. L. H.; Kostarelos, K.; Davis, B. G., Filled and glycosylated carbon nanotubes for in vivo radioemitter localization and imaging. *Nature Materials* 2010, 9 (6), 485-490.
11. (a) Vedala, H.; Chen, Y. A.; Cecioni, S.; Imberty, A.; Vidal, S.; Star, A., Nanoelectronic Detection of Lectin-Carbohydrate Interactions Using Carbon Nanotubes. *Nano Letters* 2011, 11 (1), 170-175; (b) Nagaraj, V. J.; Aithal, S.; Eaton, S.; Bothara, M.; Wiktor, P.; Prasad, S., Nano Monitor: a miniature electronic biosensor for glycan biomarker detection. *Nanomedicine* 2010, 5 (3), 369-378; (c) Xue, Y.; Bao, L.; Xiao, X.; Ding, L.; Lei, J.; Ju, H., Noncovalent functionalization of carbon nanotubes with lectin for label-free dynamic monitoring of cell-surface glycan expression. *Analytical Biochemistry* 2011, 410 (1), 92-97.
12. Varki, A., *Essentials of glycobiology*. 2nd ed.; Cold Spring Harbor Laboratory Press: Cold Spring Harbor, N.Y., 2009; p xxix, 784 p.
13. Larsen, K.; Thygesen, M. B.; Guillaumie, F.; Willats, W. G. T.; Jensen, K. J., Solid-phase chemical tools for glycobiology. *Carbohydrate Research* 2006, 341 (10), 1209-1234.
14. Stevens, J.; Blixt, O.; Paulson, J. C.; Wilson, I. A., Glycan microarray technologies: tools to survey host specificity of influenza viruses. *Nature Reviews Microbiology* 2006, 4 (11), 857-864.
15. Hagiwara, K.; Colletcassart, D.; Kobayashi, K.; Vaerman, J. P., JACALIN-ISOLATION, CHARACTERIZATION, AND INFLUENCE OF VARIOUS FACTORS ON ITS INTERACTION WITH HUMAN IGA1, AS ASSESSED BY PRECIPITATION AND LATEX AGGLUTINATION. *Molecular Immunology* 1988, 25 (1), 69-83.
16. Bao, Y.; Newburg, D. S., Capillary electrophoresis of acidic oligosaccharides from human milk. *Electrophoresis* 2008, 29 (12), 2508-2515.
17. (a) Gupta, G.; Gemma, E.; Oscarson, S.; Surolia, A., Defining substrate interactions with calreticulin: an isothermal titration calorimetric study. *Glycoconjugate Journal* 2008, 25 (8), 797-802; (b) Tomme, P.; Creagh, A. L.; Kilburn, D. G.; Haynes, C. A., Interaction of polysaccharides with the N-terminal cellulose-binding domain of Cellulomonas fimi CenC 0.1. Binding specificity and calorimetric analysis. *Biochemistry* 1996, 35 (44), 13885-13894.
18. Tateno, H.; Nakamura-Tsuruta, S.; Hirabayashi, J., Frontal affinity chromatography: sugar-protein interactions. *Nature Protocols* 2007, 2 (10), 2529-2537.
19. Zhang, Y. L.; Li, Q. A.; Rodriguez, L. G.; Gildersleeve, J. C., An Array-Based Method To Identify Multivalent Inhibitors. *Journal of the American Chemical Society* 2010, 132 (28), 9653-9662.
20. Oyelaran, O.; Li, Q.; Farnsworth, D.; Gildersleeve, J. C., Microarrays with Varying Carbohydrate Density Reveal Distinct Subpopulations of Serum Antibodies. *Journal of Proteome Research* 2009, 8 (7), 3529-3538.
21. Karamanska, R.; Clarke, J.; Blixt, O.; MacRae, J. I.; Zhang, J. Q.; Crocker, P. R.; Laurent, N.; Wright, A.; Flitsch, S. L.; Russell, D. A.; Field, R. A., Surface plasmon resonance imaging for real-time, label-free analysis of protein interactions with carbohydrate microarrays. *Glycoconjugate Journal* 2008, 25 (1), 69-74.
22. Hsu, K. L.; Gildersleeve, J. C.; Mahal, L. K., A simple strategy for the creation of a recombinant lectin microarray. *Molecular Biosystems* 2008, 4 (6), 654-662.
23. Wittig, I.; Schagger, H., Advantages and limitations of clear-native PAGE. *Proteomics* 2005, 5 (17), 4338-4346.
24. (a) Zhang, J. Q.; Boghossian, A. A.; Barone, P. W.; Rwei, A.; Kim, J. H.; Lin, D. H.; Heller, D. A.; Hilmer, A. J.; Nair, N.; Reuel, N. F.; Strano, M. S., Single Molecule Detection of Nitric Oxide Enabled by d(AT)(15) DNA Adsorbed to Near Infrared Fluorescent Single-Walled Carbon Nanotubes. *Journal of the American Chemical Society* 2011, 133 (3), 567-581; (b) Boghossian, A. A.; Zhang, J.; Floch, F. T. L.; Ulissi, Z. W.; Bojo, P.; Han, J.-H.; Kim, J.-H.; Arkalgud, J. R.; Reuel, N. F.; Braatz, R.; Strano, M. S., The chemical dynamics of nanosensors capable of single molecule detection. *J Chem Phys* 2011, 135.
25. Ahmed, H., *Principles and reactions of protein extraction, purification, and characterization*. CRC Press: Boca Raton, 2005; p 387 p.
26. (a) Brege, J. J.; Gallaway, C.; Barron, A. R., Fluorescence Quenching of Single-Walled Carbon Nanotubes with Transition-Metal Ions. *Journal of Physical Chemistry C* 2009, 113 (11), 4270-4276; (b) Jin, H.; Jeng, E. S.; Heller, D. A.; Jena, P. V.; Kirmse, R.; Langowski, J.; Strano, M. S., Divalent ion and thermally induced DNA conformational polymorphism on single-walled carbon nanotubes. *Macromolecules* 2007, 40 (18), 6731-6739.
27. Oshannessy, D. J.; Brighamburke, M.; Soneson, K. K.; Hensley, P.; Brooks, I., Determination of rate and equilibrium binding constants for macromolecular interactions using surface-plasmon resonance: use of non-linear least-squares analysis methods *Analytical Biochemistry* 1993, 212 (2), 457-468.
28. Nieba, L.; NiebaAxmann, S. E.; Persson, A.; Hamalainen, M.; Edebratt, F.; Hansson, A.; Lidholm, J.; Magnusson, K.; Karlsson, A. F.; Pluckthun, A., BIACORE analysis of histidine-tagged proteins using a chelating NTA sensor chip. *Analytical Biochemistry* 1997, 252 (2), 217-228.
29. Perret, S.; Sabin, C.; Dumon, C.; Pokorna, M.; Gautier, C.; Galanina, O.; Ilia, S.; Bovin, N.; Nicaise, M.; Desmadril, M.; Gilboa-Garber, N.; Wimmerova, M.; Mitchell, E. P.; Imberty, A., Structural basis for the interaction between human milk oligosaccharides and the bacterial lectin PA-IIL of *Pseudomonas aeruginosa*. *Biochem. J.* 2005, 389, 325-332.
30. Yoon, H.; Ahn, J. H.; Barone, P. W.; Yum, K.; Sharma, R.; Boghossian, A. A.; Han, J. H.; Strano, M. S., Periplasmic Binding Proteins as Optical Modulators of Single-Walled Carbon Nanotube Fluorescence: Amplifying a Nanoscale Actuator. *Angewandte Chemie-International Edition* 2011, 50 (8), 1828-1831.
31. (a) Saarela, S.; WesterlundWikstrom, B.; Rhen, M.; Korhonen, T. K., The GafD protein of the G (F17) fimbrial complex confers adhesiveness of *Escherichia coli* to laminin. *Infection and Immunity* 1996, 64 (7), 2857-2860; (b) Tanskanen, J.; Saarela, S.; Tankka, S.; Kalkkinen, N.; Rhen, M.; Korhonen, T. K.; Westerlund-Wikstrom, B., The gaf fimbrial gene cluster of *Escherichia coli* expresses a full-size and a truncated soluble adhesin protein. *Journal of Bacteriology* 2001, 183 (2), 512-519; (c) Merckel, M. C.; Tanskanen, J.; Edelman, S.; Westerlund-Wikstrom, B.; Korhonen, T. K.; Goldman, A., The structural basis of receptor-binding by *Escherichia coli* associated with diarrhea and septicemia. *Journal of Molecular Biology* 2003, 331 (4), 897-905; (d) Carrillo, L. D.; Krishnamoorthy, L.; Mahal, L. K., A cellular FRET-based sensor for beta-O-GlcNAc, a dynamic carbohydrate modification involved in signaling. *Journal of the American Chemical Society* 2006, 128 (46), 14768-14769.
32. (a) Jin, H.; Heller, D. A.; Kim, J. H.; Strano, M. S., Stochastic Analysis of Stepwise Fluorescence Quenching Reactions on Single-Walled Carbon Nanotubes: Single Molecule Sensors. *Nano Letters* 2008, 8 (12), 4299-4304; (b) Jin, H.; Heller, D. A.; Kalbacova, M.; Kim, J. H.; Zhang, J. Q.; Boghossian, A. A.; Maheshri, N.; Strano, M. S., Detection of single-molecule H(2)O(2) signalling from epidermal growth factor receptor using fluorescent single-walled carbon nanotubes. *Nature Nanotechnology* 2010, 5 (4), 302-U81.
33. Kim, J. H.; Heller, D. A.; Jin, H.; Barone, P. W.; Song, C.; Zhang, J.; Trudel, L. J.; Wogan, G. N.; Tannenbaum, S. R.; Strano, M. S., The rational design of nitric oxide selectivity in single-walled carbon nanotube near-infrared fluorescence sensors for biological detection. *Nature Chemistry* 2009, 1 (6), 473-481.
34. Heller, D. A.; Pratt, G. W.; Zhang, J. Q.; Nair, N.; Hansborough, A. J.; Boghossian, A. A.; Reuel, N. F.; Barone, P. W.; Strano, M. S., Peptide secondary structure modulates single-walled carbon nanotube fluorescence as a chaperone sensor for nitroaromatics. *Proceedings of the National Academy of Sciences of the United States of America* 2011, 108 (21), 8544-8549.
35. Reuel, N. F.; Bojo, P.; Zhang, J.; Boghossian, A. A.; Ahn, J.-H.; Kim, J.-H.; Strano, M. S., NoRSE: Noise Reduction and State Evaluator for High-Frequency Single Event Traces. *Bioinformatics submitted* 2011.
36. Chung, S. H.; Kennedy, R. A., FORWARD-BACKWARD NONLINEAR FILTERING TECHNIQUE FOR EXTRACTING SMALL BIOLOGICAL SIGNALS FROM NOISE. *Journal of Neuroscience Methods* 1991, 40 (1), 71-86.

A number of embodiments of the invention have been described. Nevertheless, it will be understood that various modifications may be made without departing from the spirit and scope of the invention. Accordingly, other embodiments are within the scope of the following claims.

What is claimed is:

1. An array comprising a plurality of analysis regions on a substrate, at least one analysis region including a composition comprising:
   a nanostructure wherein the nanostructure is a carbon nanotube having photoluminescence in near infrared wavelengths, wherein the photoluminescence in the near infrared wavelengths of the carbon nanotube is subject to quenching;
   a linker associated with the nanostructure, wherein the linker has the formula A-L-C, wherein A is a polymer and the nanostructure is wrapped with the polymer, wherein the polymer is chitosan having carboxylic groups provided by activating the chitosan with succinic anhydride, wherein L-C is $N_\alpha,N_\alpha$-bis(carboxymethyl)-L-Lysine and the $N_\alpha,N_\alpha$-bis(carboxymethyl)-L-Lysine is directly linked via its amino group to the carboxylic group of the chitosan through an amide bond, wherein the carboxylic group containing portion of the $N_\alpha,N_\alpha$-bis(carboxymethyl)-L-Lysine is a chelating region capable of associating with a nickel ion, wherein the $N_\alpha,N_\alpha$-bis(carboxymethyl)-L-lysine is associated with a first binding partner through the chelating region, wherein the first binding partner is a quencher including a nickel ion; and
   an analyte-interacting capture protein including a second binding partner that binds to the first binding partner.

2. The array of claim 1, wherein the second binding partner is a protein tag.

3. The array of claim 1, wherein the capture protein is a lectin and the analyte includes a glycan.

4. The array of claim 1, wherein at least one analysis region further comprises a sample.

5. The array of claim 4, wherein the sample includes a protein.

6. The array of claim 4, the plurality of analysis regions comprising two or more subsets of analysis regions.

7. The array of claim 6, wherein an Nth subset of analysis regions includes an Nth composition including an Nth capture protein, wherein N is an integer between 1 and 5000.

8. The array of claim 6, wherein the composition further comprises a capture protein and an Nth subset of analysis regions includes an Nth sample, wherein N is an integer between 1 and 5000.

9. The array of claim 6, wherein the composition further comprises a capture protein and an Nth subset of analysis regions includes an Nth analyte, wherein N is an integer between 1 and 5000.

10. A composition comprising:
    a nanostructure wherein the nanostructure is a carbon nanotube having photoluminescence in near infrared wavelengths, wherein the photoluminescence in the near infrared wavelengths of the carbon nanotube is subject to quenching;

a linker associated with the nanostructure, wherein the linker has the formula A-L-C, wherein A is a polymer and the nanostructure is wrapped with the polymer, wherein the polymer is chitosan having carboxylic groups provided by activating the chitosan with succinic anhydride, wherein L-C is $N_\alpha,N_\alpha$-bis(carboxymethyl)-L-Lysine and the $N_\alpha,N_\alpha$-bis(carboxymethyl)-L-Lysine is directly linked via its amino group to the carboxylic group of the chitosan through an amide bond, wherein the carboxylic group containing portion of the $N_\alpha,N_\alpha$-bis(carboxymethyl)-L-Lysine is a chelating region capable of associating with a nickel ion, wherein the $N_\alpha,N_\alpha$-bis(carboxymethyl)-L-lysine is associated with a first binding partner through the chelating region, wherein the first binding partner is a quencher including a nickel on; and an analyte-interacting capture protein including a second binding partner that binds to the first binding partner.

* * * * *

SEQUENCE LISTING

```
<160> NUMBER OF SEQ ID NOS: 40

<210> SEQ ID NO 1
<211> LENGTH: 40
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 1
aagaaggaga tatacatatg tcgagtaagt tagtactggt                                 40

<210> SEQ ID NO 2
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ttaatgatga tgatgatgat gggcagtcag gcggctcgcg t                               41

<210> SEQ ID NO 3
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
aagaaggaga tatacatatg ggtaaaataa ttggtatcga                                 40

<210> SEQ ID NO 4
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ttaatgatga tgatgatgat gtttttttgtc tttgacttct t                              41

<210> SEQ ID NO 5
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aagaaggaga tatacatatg tctaagattt ttgatttcgt                                 40

<210> SEQ ID NO 6
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ttaatgatga tgatgatgat gcagaacgtc gatcgcgttc a                               41

<210> SEQ ID NO 7
<211> LENGTH: 40
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 7
aagaaggaga tatacatatg ttaaagcgtg aaatgaacat                40

<210> SEQ ID NO 8
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ttaatgatga tgatgatgat gtgcgtaaac cgggtaacgt g              41

<210> SEQ ID NO 9
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aagaaggaga tatacatatg agtactgaaa tcaaaactca                40

<210> SEQ ID NO 10
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ttaatgatga tgatgatgat gcttcttctt cgctttcggg t              41

<210> SEQ ID NO 11
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aagaaggaga tatacatatg cagggttctg tgacagagtt                40

<210> SEQ ID NO 12
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ttaatgatga tgatgatgat gctcgtcagc gatgcttgcc g              41

<210> SEQ ID NO 13
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
aagaaggaga tatacatatg gcagttgtta aatgtaaacc                        40

<210> SEQ ID NO 14
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ttaatgatga tgatgatgat gtttgctacg gcgacgtacg a                      41

<210> SEQ ID NO 15
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
aagaaggaga tatacatatg gcaactgttt ccatgcgcga                        40

<210> SEQ ID NO 16
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ttaatgatga tgatgatgat gctcagcttc tacgaagctt t                      41

<210> SEQ ID NO 17
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
aagaaggaga tatacatatg gctgaaatta ccgcatccct                        40

<210> SEQ ID NO 18
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ttaatgatga tgatgatgat gagactgctt ggacatcgca g                      41

<210> SEQ ID NO 19
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
aagaaggaga tatacatatg aaaaaagcca catgcttaac     40

<210> SEQ ID NO 20
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ttaatgatga tgatgatgat gcctctcctc attttcagct t     41

<210> SEQ ID NO 21
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
aagaaggaga tatacatatg catccacgtt ttcaaaccgc     40

<210> SEQ ID NO 22
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ttaatgatga tgatgatgat gagcgagaag cactcggtcg a     41

<210> SEQ ID NO 23
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
aagaaggaga tatacatatg gctacctctc gatatga     37

<210> SEQ ID NO 24
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ttaatgatga tgatgatgat gcaactccgg attaccttca t     41

<210> SEQ ID NO 25
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25

```
atgatgatga tgatgatgtt acaactccgg attaccttca t                    41
```

<210> SEQ ID NO 26
<211> LENGTH: 37
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 26

```
aagaaggaga tatacatatg gtgcgcaggt tcttggt                         37
```

<210> SEQ ID NO 27
<211> LENGTH: 41
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 27

```
ttaatgatga tgatgatgat gcaagccagg tccacgggca g                    41
```

<210> SEQ ID NO 28
<211> LENGTH: 41
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 28

```
atgatgatga tgatgatgtt acaagccagg tccacgggca g                    41
```

<210> SEQ ID NO 29
<211> LENGTH: 37
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 29

```
aagaaggaga tatacatatg actgcaaaga tggaaac                         37
```

<210> SEQ ID NO 30
<211> LENGTH: 41
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 30

```
ttaatgatga tgatgatgat ggtcaaatgt ttgcaactgc t                    41
```

<210> SEQ ID NO 31
<211> LENGTH: 41
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 31
atgatgatga tgatgatgtt agtcaaatgt tgcaactgc t                   41

<210> SEQ ID NO 32
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
aagaaggaga tatacatatg atgttctcgg gcttcaa                       37

<210> SEQ ID NO 33
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ttaatgatga tgatgatgat gcaacagggc cagcagcgtg g                  41

<210> SEQ ID NO 34
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
atgatgatga tgatgatgtt acaacagggc cagcagcgtg g                  41

<210> SEQ ID NO 35
<211> LENGTH: 98
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tcgatcccgc gaaattaata cgactcacta tagggagacc acaacggttt ccctctagaa   60
ataattttgt ttaactttaa gaaggagata tacatatg                     98

<210> SEQ ID NO 36
<211> LENGTH: 99
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
caaaaaaccc ctcaagaccc gtttagaggc cccaaggggt tatgctagct cgagaagctt   60
gtcgacgaat tcggatcctt aatgatgatg atgatgatg                    99

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 37

His His His His His His
1               5

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
aagaaggaga tatacatatg                                              20

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
ttaatgatga tgatgatgat g                                            21

<210> SEQ ID NO 40
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
catcatcatc atcatcatta aggatccgaa ttcgtcgaca agcttctcga gctagcataa    60
ccccttgggg cctctaaacg ggtcttgagg ggttttttg                           99